US007888374B2

(12) United States Patent
Liu et al.

(10) Patent No.: US 7,888,374 B2
(45) Date of Patent: Feb. 15, 2011

(54) INHIBITORS OF C-JUN N-TERMINAL KINASES

(75) Inventors: Gang Liu, Libertyville, IL (US); Hing L. Sham, Vernon Hills, IL (US); Bruce G. Szczepankiewicz, Lake Villa, IL (US); Zhili Xin, Lake Bluff, IL (US); Hongyu Zhao, Buffalo Grove, IL (US); Michael D. Serby, Mundelein, IL (US); Bo Liu, Waukegan, IL (US); Mei Liu, Gurnee, IL (US)

(73) Assignee: Abbott Laboratories, Abbott Park, IL (US)

( * ) Notice: Subject to any disclaimer, the term of this patent is extended or adjusted under 35 U.S.C. 154(b) by 1107 days.

(21) Appl. No.: 11/337,862

(22) Filed: Jan. 23, 2006

(65) Prior Publication Data

US 2006/0173050 A1  Aug. 3, 2006

Related U.S. Application Data

(60) Provisional application No. 60/648,298, filed on Jan. 28, 2005.

(51) Int. Cl.
*C07D 213/84* (2006.01)
*A61K 31/44* (2006.01)

(52) U.S. Cl. .................... 514/332; 546/255; 546/268.1; 546/288; 546/309; 546/314; 514/340; 514/344; 514/352; 514/354

(58) Field of Classification Search ........................ None
See application file for complete search history.

(56) References Cited

U.S. PATENT DOCUMENTS 2,790,806 A    4/1957  Middleton
5,294,597 A *  3/1994  Foster et al. ................ 504/255

FOREIGN PATENT DOCUMENTS

WO         02/083667        10/2002
WO    WO 03/011853 A1 *    2/2003
WO         2005/003123      1/2005

OTHER PUBLICATIONS

Kotera et al, Tetrahedron (1995), 51(7), pp. 1953-1972.*
Otsuka et al, Journal of Organometallic Chemistry (2000), 611(1-2), pp. 577-585.*
Hirosumi, J., et la., "A central role for JNK in obesity and insulin resistance", *Nature*, 420:333-336 (2002).
Ho, F.M., et al., "High Glucose-Induced Apoptosis in Human Endothelial Cells Is Mediated by Sequential Activations of c-Jun NH$_2$-Terminal Kinase and Caspase-3", *Circulation*, 101:2618-2624 (2000).
Kaneto, H., et al., "Involvement of c-Jun N-terminal Kinase in Oxidative Stress-mediated Suppression of Insulin Gene Expression", *J. of Biol. Chem.*, 277(33):30010-30018 (2002).

Katsura, Y., et al., "Studies on Antiulcer Drugs. 7. 2-Guanidino-4-pyriylthiazoles as Histamine H$_2$-Receptor Antagonists with Potent Gastroprotective Effects against Nonsteroidal Antiinflammatory Drug-Induced Injury", *J. Med. Chem.*, 37:57-66 (1993).
Kuan, C.-Y., et al., "A critical role of neural-specific JNK3 for ischemic apoptosis", *Proc. Natl. Acad. Sci. USA*, 100(25):15184-15189 (2003).
Kuman, D. et al., "Effect of angiotensin II type 2 receptor blockae on mitogen activated protein kinases during myocardian ischemia-reperfusion", *Mol. & Cell. Biochem.*, 258:211-218 (2004).
Kyriakis, J.M. & Avruch, J., "Mammalian Mitogen-Activated Protein Kinase Signal Transduction Pathways Activated by Stress and Inflammation", *Physiol. Rev.*, 81(2):807-869 (2001).
Mahata, P.K., et al., "1-Bis(methoxy)-4-bis(methylthio)-3-buten-2-one: useful three carbon synthon for synthesis of five and six membered heterocycles with masked (or unmasked) aldehyde functionality", *Tetrahedron*, 59:2631-2639 (2003).
Mariella, R.P. & Belcher, E.P., "α-Oxygenated Pyridines. III. The Reaction of N-Bromosuccinimide with Some Pyridine Derivatives", *J. of the Amer. Chem. Soc.*, 74(8):1916-1919 (1952).
Meyer, E.V., "Untersuchungen aus dem organ.-chem. Laboratorium der Technischen Hochschule zu Dresden", *Database Beilstein*, 78:497-534 (1908).
Sabapathy, K., et al., "JNK2 is required for efficient T-cell activation and apoptosis but not for normal lymphocyte development", *Curr. Biol.*, 9(3):116-125 (1999).
Samuel, V.T., et al., "Mechanism of Hepatic Insulin Resistance in Non-alcoholic Fatty Liver Disease", *J. of Biol. Chem.*, 279(31):32345-32553 (2004).
Miyamoto, T., et al., "Pyridonecarboxylic Acids as Antibacterial Agents. VIII. An Alternative Synthesis of Enoxacin via Fluoronicotinic Acid Derivatives", *chem.. Pharm. Bull.*, 35(6):2280-2285 (1987).
Waeber, G., et al., "The gene *MAPK8IP1*, encoding islet-brain-1, is a candidate for type 2 diabetes", *Nature Genetics*, 24:291-295 (2000).
Yan, D.D., et al., "Differentiation of CD4+ T Cells to Th1 Cells Required MAP Kinase JNK2", *Immunity*, 9:575-585 (1998).
Ueda, E., et al., "Potential Insulinominetic Agents of Zinc(II) Complexes with Picolinamide Derivatives: Preparation of Complexes, in Vitro and in Vivo Studies", *Chem. Pharm. Bull.*, 50(3):337-340 (2002).
Zafar, A., et al., "Hydrogen Bonding Control of Molecular Self-Assembly: Aggregation Behavior of Acylaminopyridine-Carboxylic Acid Derivatives in Solution and the Solid State", *Tetrahedron*, 56:8419-8427 (2000).
Zhang, H., et al., "Nocodazole-induced p53-dependent c-Jun N-terminal Kinase Activation Reduces Apoptosis in Human Colon Carcinoma HCT116 Cells", *J. of Biol. Chem.*, 277(46):43648-43658 (2002).

(Continued)

*Primary Examiner*—Zinna N Davis
(74) *Attorney, Agent, or Firm*—Lisa V. Mueller; Polsinelli Shughart PC

(57) ABSTRACT

The present invention relates to compounds that are inhibitors of c-jun N-terminal kinase 1, 2, or 3 (JNK1, JNK2, or JNK3), compositions containing the compounds and the use of the compounds in the prevention or treatment of disorders regulated by the activation of JNK1, JNK2 and JNK3.

23 Claims, No Drawings

OTHER PUBLICATIONS

Zhuang, L., et al., "Design and Synthesis of 8-Hydroxy-[1-6]Naphthridines as Novel Inhibitors of HIV-1 Integrase in vitro and in Infected Cells", *J. Med. Chem.*, 46:453-456 (2003).

Zimmet, P., "Global and societal implications of the diabetes epidemic", Nature, 414:782-787 (2001).

International Search Report for PCT/US2006/002789 dated Oct. 27, 2006.

Aguirre, V., et al., "The c-Jun $NH_2$-terminal Kinase Promotes Insulin Resistance during Associatoin with Insulin Receptor Substrate-1 and Phosphorylation of $Ser^{307}$", *The J. of Biol. Chem.*, 275(12):9047-9054 (2000).

Balode, D.E., "Ring-Chain Isomerism of N-Monosubstituted 2-Cyanobenzenesulfonamides", *Chem. Heterocycl. Compd.*, 14:1632-1635 (1978).

Beilstein Database, "n-(5-Cyano-4,6-DI-Methyl-Pyrid-2-YL)Acetamide", *Beilstein Inst. Zur Forderung der Chemischen Wissenschaft*, BRN 176822; CAS RN 24200-11-1, cited by J. Prakt. Chem (1908).

Birch, A.M., et al., "N-Substituted (2,3-Dihydro-1,4-benzodioxin-2-yl)methylamine Derivatives as $D_2$ Antagonists/5-$HT_{1A}$ Partial Agonists with Potential as Atypical Antipsychotic Agents",*J. Med. Chem.*, 42:3342-3355 (1999).

Chang, L. & Karin, M., "Mitogen-activated protein kinases (MAPKs) are important signal transducing enzymes, unique to eukaryotes, that are involved in many facets of cellular regulation. . . .",*Nature*, 410:37-40 (2001).

Cignarella, G. & Teotino, U., "Synthesis of a New Heterocyclic Ring—2,5-Dihydro-1,2,4-benzothiadiazepine 1,1-Dioxide and its Intermediates", *JACS*, 82:1594-1596 (1960).

Dol, G.C., et al., "Synthesis of 5-Substituted Resorcinol Derivatives Via Cross-Coupling Reactions", *Eur. J. Org. Chem.*, 26:359-364 (1998).

Eliel, E. & Nelson, K.W., "Reactions of *p*-Chlorobenzenesulfonic Acid and Derivatives. . . . ", *JOC*, 20:1657-1665 (1955).

Gu, Y.G., et al., "*trans*-2,6-, 3,6- and 4,6-Diaza-5,6,6a,7,8,12b-Hexahydro-Benzo[*C*]Phenanthrene-10,11-Diols as Dopamine Agonists", *Bioorg. & Medic. Chem. Ltrs.*, 9:1341-1346 (1999).

Han, Z., et al., "Joint Damage and Inflammation in c-Jun N-terminal Kinase 2 Knockout Mice With Passive Murine Collagen-Induced Arthritis", *Arthritis & Theumatism*, 46(3):818-823 (2002).

* cited by examiner

INHIBITORS OF C-JUN N-TERMINAL KINASES

This application claims priority from U.S. Provisional Patent Application Ser. No. 60/648,298, filed Jan. 28, 2005 and is incorporated herein by reference.

FIELD OF THE INVENTION

The present invention relates to compounds that are inhibitors of c-jun N-terminal kinase 1, 2, or 3 (JNK1, JNK2, or JNK3), compositions containing the compounds and the use of the compounds in the prevention or treatment of disorders regulated by the activation of JNK1, JNK2 and JNK3.

BACKGROUND OF THE INVENTION

Type 2 diabetes afflicts over 130 million people worldwide, and the incidence is expected to grow steadily over the next several years (Zimmet, P., et al. *Nature*, (2001) 414, 782). Current treatments are not completely successful in ameliorating Type 2 diabetes for many patients, and more efficacious agents are needed. A major goal of new therapies for Type 2 diabetes is to potentiate the action of insulin.

Insulin signaling is impaired in Type 2 diabetes patients. Although, factors leading to the downregulated insulin signaling pathway is not completely understood, one biochemical event known to disrupt insulin signaling involves the serine phosphorylation of IRS-1 by c-jun N-terminal Kinase 1 (JNK-1). Phosphorylation of IRS-1 at Serine$^{307}$ greatly reduces the binding affinity of IRS-1 for the insulin receptor (Aguirre, V., et al. *J. Biol. Chem.* (2000) 275: 9047-9054). This event inhibits IRS-1 tyrosine phosphorylation, and consequently prevents further insulin signal transduction from occuring. A JNK-1 inhibitor could therefore be expected to enhance insulin signaling by preventing the inactivation of IRS-1.

JNK-1 is a member of the mitogen activated protein kinase (MAP kinase) family of enzymes responsible for the serine/threonine phosphorylation of intracellular targets (Kyriakis, J., et al., *Physiol. Rev.* (2001) 81: 807-869). JNK-1 along with other JNK isoforms, JNK-2 and JNK-3, are activated in response to cellular stresses such as irradiation, hypoxia, chemotoxins, and peroxides. They are also activated in response to various cytokines and participate in the onset of apoptosis. In addition to IRS-1 and IRS-2, other cellular proteins phosphorylated by JNK enzymes include Shc, and Gab-1, and the gene transcription factors Jun, ATF2, Elk-1. JNK-1 and -2 are ubiquitously expressed in human tissues, while JNK-3 is restricted to the brain, heart, and testis, and each isoform is expressed in multiple splice variants. JNK enzymes themselves must be phosphorylated to carry out their functions. The enzymes MKK-4 and MKK-7 are known to phosphorylate and activate JNK-1 and -2.

There is substantial experimental evidence that JNK-1 activity is involved in the pathology of Type 2 diabetes mellitus. Inflammatory cytokines and free fatty acids have been implicated in the development of Type 2 diabetes, and both classes stimulate JNK activation (Chang, L. et al., *Nature* (2001) 410: 37-40). Insulin gene expression is reduced, while JNK is activated under conditions of oxidative stress. Furthermore, suppression of the JNK pathway protects pancreatic β-cells from oxidative stress (Kaneto, H., et al., J Biol Chem (2002) 277:30010-8). JNK may also mediate endothelial cell apoptosis caused by diabetes-associated hyperglycemia, and pancreatic β-cell apoptosis associated with diabetes (Ho, F. M. et al., *Circulation* (2000) 101:2618-2624). Activation of JNK is involved in tumor necrosis factor (TNF) induced lipolysis in adipocytes. Human genetic evidence shows that increased JNK activity caused by loss-of-function mutations in the JNK scaffold protein JIP1 is causal to Type 2 diabetes (Waeber G. et al. Nature Genet. (2000) 24: 291-295). JNK-1 is also involved in the mechanism of hepatic insulin resistance caused by liver steatosis (Samuel V T, et al. J. Biol. Chem. 2004, 279:32345-32353).

The most compelling data supporting an integral role for JNK-1 in insulin action and obesity comes from the targeted disruption of the JNK-1 gene in mice (Hirosumi J, Nature (2002) 420:333-336). Absence of JNK-1 protects mice from diet-induced obesity, and results in decreased adiposity and enhanced secretion of adiponectin. The JNK-1 null mice maintain lower fasting plasma glucose and insulin levels compared to their wild type littermates when they are high fat fed, indicating that these animals are protected from the development of obesity-induced insulin resistance. They also demonstrate greater insulin sensitivity in both oral glucose and intraperitoneal insulin tolerance tests. In addition, heterozygous animals show a partial phenotype. Moreover, genetically obese mice (ob/ob) with targeted mutations in JNK-1 were leaner and maintained lower blood glucose and insulin levels compared with the ob/ob mice expressing fuctional JNK-1. JNK-1 phosphorylation of IRS-1 at Ser$^{307}$ has been shown to downregulate insulin signaling in vitro. The extent of IRS-1 Ser$^{307}$ phosphorylation is markedly decreased in obese JNK-1 null mice, while the insulin-induced IRS-1 tyrosine phosphorylation is strongly enhanced in livers of those mice. Interestingly, ablation of the JNK-1 gene generates a phenotype of increased insulin sensitivity that is not mimicked by deficiency of JNK-2.

There is potential for JNK inhibitors to treat human diseases besides Type 2 diabetes. JNK-2 null mice have been produced by two different laboratories, and there is a clear role for JNK-2 in immunological function (Yang, D. D., et al., Immunity, (1998) 9: 575-585; Sabapathy, L. et al., Curr. Biol. (1999) 9:116-125). JNK-2, often in concert with JNK-1, has been implicated in the pathology of autoimmune disorders such as rheumatoid arthritis (Han, Z., et al., Arthritis & Rheumatism (2002) 46: 818-823), and asthma. It also may play a role in cancer (Zhang, H., et al., J. Biol. Chem. (2002) 277: 43648-43658), as well as ischemia-reperfusion injury following myocardial infarction (Kumar, D., et al., Mol. Cell. Biochem. (2004) 258: 211-218) or stroke. Inhibitors of JNK-1 and JNK-2 could be useful for treating these diseases, as well as a broad range of other diseases with an inflammatory component.

Human JNK-3 expression is limited to the brain, heart, and testis. JNK-3 has been shown to mediate neuronal apoptosis and may therefore be involved in the pathology of neurodegenerative diseases. Inhibitors of JNK-3 could be useful for treating Parkinson's disease, Alzheimer's disease, epilepsy, stroke, and other diseases of the central nervous system as JNK3 knockout mouse studies suggest the role of JNK-3 in neurological disorders (Kuan, C-Y., et al., PNAS, USA. (2003) 100:15184-15189).

SUMMARY OF THE INVENTION

In its principle embodiment, the present invention discloses compounds of the formula (I), or a pharmaceutically acceptable salt, prodrug, salt of a prodrug, or a combination thereof

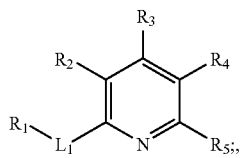

wherein

L₁ is selected from the group consisting of —C(O)—NH—, —C(NH)—NH—, —NH—C(O)— and —NH—C(NH)—;

R₁ is selected from the group consisting of alkenyl, alkenyloxyalkyl, alkoxyalkoxyalkyl, alkoxyalkyl, alkoxycarbonylalkyl, alkyl, alkylcarbonylalkyl, alkylsulfinylalkyl, alkylsulfonylalkyl, alkylthioalkyl, alkynyl, alkynylalkyl, alkynylalkoxyalkyl, aryl, arylalkenyl, arylalkenyloxyalkyl, arylalkoxyalkyl, arylalkyl, arylalkylsulfonylalkyl, arylalkylthioalkyl, arylcarbonylalkyl, aryloxyalkyl, arylthioalkyl, arylsulfinylalkyl, arylsulfonylalkyl, carboxyalkyl, cyanoalkyl, cycloalkenyl, cycloalkenylalkoxyalkyl, cycloalkenylalkyl, cycloalkenylalkylthioalkyl, cycloalkenyloxy, cycloalkenyloxyalkyl, cycloalkenylsulfinylalkyl, cycloalkenylsulfonylalkyl, cycloalkenylthioalkyl, cycloalkyl, cycloalkylalkoxyalkyl, cycloalkylalkyl, cycloalkylalkylthioalkyl, cycloalkylcarbonylalkyl, cycloalkyloxyalkyl, cycloalkylsulfinylalkyl, cycloalkylsulfonylalkyl, cycloalkylthioalkyl, haloalkyl, heteroaryl, heteroarylalkoxyalkyl, heteroarylalkyl, heteroarylalkylsulfonylalkyl, heteroarylalkylthioalkyl, heteroarylcarbonylalkyl, heteroaryloxy, heteroaryloxyalkyl, heteroarylsulfinylalkyl, heteroarylsulfonylalkyl, heteroarylthioalkyl, heterocycle, heterocyclealkoxyalkyl, heterocyclealkyl, heteroarylalkylsulfonylalkyl, heterocyclealkylthioalkyl, heterocyclecarbonylalkyl, heterocyclecarbonylalkenyl, heterocycleoxyalkyl, heterocyclesulfinylalkyl, heterocyclesulfonylalkyl, heterocyclethioalkyl, hydroxyalkyl, ($R_aR_b$N)alkyl, ($R_aR_b$N)carbonylalkenyl, ($R_aR_b$N)carbonylalkyl and ($R_aR_b$N)sulfonylalkyl;

R₂ and R₄ are independently selected from the group consisting of hydrogen, alkyl, alkylcarbonyl, alkylsulfonyl, alkenyl, alkynyl, aryl, arylcarbonyl, arylsulfonyl, cycloalkyl, cycloalkylcarbonyl, cycloalkylsulfonyl, cycloalkenyl, cyano, halo, haloalkyl, heteroaryl, heterocycle, nitro, formyl and alkynylalkenyl;

R₃ is selected from the group consisting of hydrogen, alkyl, azido, halo, heterocycle, hydroxy and $R_cR_d$N—;

R₅ is selected from the group consisting of alkenyl, alkoxy, alkoxyalkoxy, alkoxyalkoxyalkyl, alkoxyalkyl, alkyl, alkylcarbonylalkyl, alkylsulfonylalkyl, alkylthioalkyl, alkynyl, aryl, arylalkoxy, arylalkoxyalkyl, arylalkyl, aryloxy, aryloxyalkyl, arylthioalkyl, cyanoalkyl, cycloalkenyl, cycloalkenylalkoxy, cycloalkenylalkoxyalkyl, cycloalkenylalkyl, cycloalkyl, cycloalkylalkoxy, cycloalkylalkoxyalkyl, cycloalkylalkyl, cycloalkylalkylthioalkyl, cycloalkyloxy, cycloalkyloxyalkyl, cycloalkylthioalkyl, haloalkoxy, haloalkyl, heteroaryl, heteroarylalkoxy, heteroarylalkoxyalkyl, heteroarylalkyl, heteroarylalkylthioalkyl, heteroaryloxy, heteroaryloxyalkyl, heteroarylthioalkyl, heterocycle, heterocyclealkoxy, heterocyclealkoxyalkyl, heterocyclealkyl, heterocyclealkylthioalkyl, heterocycleoxy, heterocycleoxyalkyl, heterocyclethioalkyl, hydroxyalkyl, hydroxyalkoxy, $R_eR_fN$—, ($R_eR_f$N)alkyl, ($R_eR_f$N)alkoxy, -alkenyl-C(O)OH and —C(O)NR_eR_f;

R_a and R_b are independently selected from the group consisting of hydrogen, alkoxyalkyl, alkoxyalkylcarbonyl, alkoxycarbonyl, alkyl, alkylcarbonyl, alkylsulfonyl, alkylthioalkyl, alkylthioalkylcarbonyl, alkylthiocarbonyl, aryl, arylalkoxyalkyl, arylalkyl, arylcarbonyl, cycloalkyl, cycloalkylalkoxyalkyl, cycloalkylalkyl, cycloalkylcarbonyl, formyl, heteroaryl, heteroarylalkyl, heteroarylcarbonyl, heterocycle, heterocyclealkyl, heterocyclealkoxyalkyl, heterocyclecarbonyl, ($R_gR_h$N)alkyl and ($R_gR_h$N)carbonyl;

R_c and R_d are independently selected from the group consisting of hydrogen, alkyl, alkoxyalkyl, alkylcarbonyl, alkylsulfonyl, aryl, arylalkyl, arylalkylcarbonyl, arylalkylsulfonyl, arylcarbonyl, arylsulfonyl, cycloalkyl, cycloalkylcarbonyl, cycloalkylsulfonyl, formyl, heteroaryl, heteroarylalkyl, heteroarylcarbonyl, heteroarylsulfonyl, heterocycle, heterocyclealkyl, heterocyclecarbonyl and heterocyclesulfonyl;

R_e and R_f are independently selected from the group consisting of hydrogen, alkoxyalkyl, alkoxyalkylcarbonyl, alkoxycarbonyl, alkoxysulfonyl, alkyl, alkylcarbonyl, alkylsulfonyl, alkylthioalkyl, alkylthioalkylcarbonyl, alkylthiocarbonyl, aryl, arylalkoxyalkyl, arylalkyl, arylcarbonyl, cycloalkyl, cycloalkylalkoxyalkyl, cycloalkylalkyl, cycloalkylcarbonyl, formyl, heteroaryl, heteroarylalkoxyalkyl, heteroarylalkyl, heteroarylcarbonyl, heterocycle, heterocyclealkoxyalkyl, heterocyclealkyl, heterocyclecarbonyl, hydroxyalkyl, ($R_jR_k$N)alkyl and ($R_jR_k$N)carbonyl;

R_g and R_h are independently selected from the group consisting of hydrogen, alkoxycarbonyl, alkyl, alkylcarbonyl, alkoxysulfonyl, alkylsulfonyl, aryl, arylalkyl, arylcarbonyl, cycloalkyl, cycloalkylalkyl, cycloalkylcarbonyl, formyl, heteroaryl, heteroarylalkyl, heteroarylcarbonyl, heterocycle, heterocyclealkyl and heterocyclecarbonyl;

R_j and R_k are independently selected from the group consisting of hydrogen, alkoxycarbonyl, alkyl, alkylcarbonyl, alkylsulfonyl, aryl, arylalkyl, arylcarbonyl, cycloalkyl, cycloalkylalkyl, cycloalkylcarbonyl, formyl, heteroaryl, heteroarylalkyl, heteroarylcarbonyl, heterocycle, heterocyclealkyl and heterocyclecarbonyl.

According to another embodiment, the present invention is directed to a pharmaceutical composition comprising a therapeutically effective amount of a compound of formula (I) in combination with a pharmaceutically suitable carrier.

According to another embodiment, the present invention is directed to a method of treating a disorder regulated by c-jun N-terminal kinase 1, 2, or 3 (JNK1, JNK2, or JNK3) in a mammal, comprising administrating a therapeutically effective amount of a compound of formula (I).

According to another embodiment, the present invention is directed to a method of treating or lessening the severity of a disease or condition in a patient selected from impaired glucose tolerance, insulin resistance, Type 2 diabetes, obesity, and diabetes mellitus, comprising administrating a therapeutically effective amount of a compound of formula (I).

According to another embodiment, the present invention is directed to a method of treating or lessening the severity of a disease or condition in a patient selected from hypercalcemia, osteoporosis, osteoarthritis, symptomatic treatment of bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obtructive pulmonary disorder, contact dermatitis, Paget's disease, asthma, ischemic or reperfusion injury, allergic disease, atopic dermatitis, allergic rhinitis, Crohn's disease, or psorasis, comprising administrating a therapeutically effective amount of a compound of formula (I).

According to another embodiment, the present invention is directed to a method of treating or lessening the severity of a disease or condition in a patient selected from Alzheimer's disease, Huntington's, Parkinson's, AIDS associated dementia, amyotrophic lateral sclerosis (AML), epilepsy, stroke, multiple sclerosis (MS), schizophrenia, cardiomycete hypertrophy, or baldness, comprising administrating a therapeutically effective amount of a compound of formula (I).

According to another embodiment, the present invention is directed to the use of the compounds of formula (I), or a pharmaceutically acceptable salt, prodrug, salt of a prodrug, or a combination thereof, to prepare a medicament for treating a disorder or a disease that is regulated by c-jun N-terminal kinase 1, 2, or 3 (JNK1, JNK2, or JNK3) in a mammal. Diseases or disorders that are regulated by c-jun N-terminal kinase 1, 2, or 3 (JNK1, JNK2, or JNK3) are listed above.

DETAILED DESCRIPTION OF THE INVENTION

The principle embodiment of the present invention is directed to a compound of the formula (I),

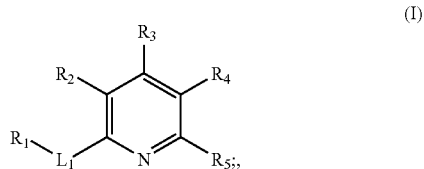

(I)

wherein $L_1$ is selected from the group consisting of —C(O)—NH—, —C(NH)—NH—, —NH—C(O)— and —NH—C(NH)—;

$R_1$ is selected from the group consisting of alkenyl, alkenyloxyalkyl, alkoxyalkoxyalkyl, alkoxyalkyl, alkoxycarbonylalkyl, alkyl, alkylcarbonylalkyl, alkylsulfinylalkyl, alkylsulfonylalkyl, alkylthioalkyl, alkynyl, alkynylalkyl, alkynylalkoxyalkyl, aryl, arylalkenyl, arylalkenyloxyalkyl, arylalkoxyalkyl, arylalkyl, arylalkylsulfonylalkyl, arylalkylthioalkyl, arylcarbonylalkyl, aryloxyalkyl, arylthioalkyl, arylsulfinylalkyl, arylsulfonylalkyl, carboxyalkyl, cyanoalkyl, cycloalkenyl, cycloalkenylalkoxyalkyl, cycloalkenylalkyl, cycloalkenylalkylthioalkyl, cycloalkenyloxy, cycloalkenyloxyalkyl, cycloalkenylsulfinylalkyl, cycloalkenylsulfonylalkyl, cycloalkenylthioalkyl, cycloalkyl, cycloalkylalkoxyalkyl, cycloalkylalkyl, cycloalkylalkylthioalkyl, cycloalkylcarbonylalkyl, cycloalkyloxyalkyl, cycloalkylsulfinylalkyl, cycloalkylsulfonylalkyl, cycloalkylthioalkyl, haloalkyl, heteroaryl, heteroarylalkoxyalkyl, heteroarylalkyl, heteroarylalkylsulfonylalkyl, heteroarylalkylthioalkyl, heteroarylcarbonylalkyl, heteroaryloxy, heteroaryloxyalkyl, heteroarylsulfinylalkyl, heteroarylsulfonylalkyl, heteroarylthioalkyl, heterocycle, heterocyclealkoxyalkyl, heterocyclealkyl, heteroarylalkylsulfonylalkyl, heterocyclealkylthioalkyl, heterocyclecarbonylalkyl, heterocyclecarbonylalkenyl, heterocycleoxyalkyl, heterocyclesulfinylalkyl, heterocyclesulfonylalkyl, heterocyclethioalkyl, hydroxyalkyl, $(R_aR_b N)$alkyl, $(R_aR_b N)$carbonylalkenyl, $(R_aR_b N)$carbonylalkyl and $(R_aR_b N)$sulfonylalkyl;

$R_2$ and $R_4$ are independently selected from the group consisting of hydrogen, alkyl, alkylcarbonyl, alkylsulfonyl, alkenyl, alkynyl, aryl, arylcarbonyl, arylsulfonyl, cycloalkyl, cycloalkylcarbonyl, cycloalkylsulfonyl, cycloalkenyl, cyano, halo, haloalkyl, heteroaryl, heterocycle, nitro, formyl and alkynylalkenyl;

$R_3$ is selected from the group consisting of hydrogen, alkyl, azido, halo, heterocycle, hydroxy and $R_cR_d N$—;

$R_5$ is selected from the group consisting of alkenyl, alkoxy, alkoxyalkoxy, alkoxyalkoxyalkyl, alkoxyalkyl, alkyl, alkylcarbonylalkyl, alkylsulfonylalkyl, alkylthioalkyl, alkynyl, aryl, arylalkoxy, arylalkoxyalkyl, arylalkyl, aryloxy, aryloxyalkyl, arylthioalkyl, cyanoalkyl, cycloalkenyl, cycloalkenylalkoxy, cycloalkenylalkoxyalkyl, cycloalkenylalkyl, cycloalkyl, cycloalkylalkoxy, cycloalkylalkoxyalkyl, cycloalkylalkyl, cycloalkylalkylthioalkyl, cycloalkyloxy, cycloalkyloxyalkyl, cycloalkylthioalkyl, haloalkoxy, haloalkyl, heteroaryl, heteroarylalkoxy, heteroarylalkoxyalkyl, heteroarylalkyl, heteroarylalkylthioalkyl, heteroaryloxy, heteroaryloxyalkyl, heteroarylthioalkyl, heterocycle, heterocyclealkoxy, heterocyclealkoxyalkyl, heterocyclealkyl, heterocyclealkylthioalkyl, heterocycleoxy, heterocycleoxyalkyl, heterocyclethioalkyl, hydroxyalkyl, hydroxyalkoxy, $R_eR_f N$—, $(R_eR_f N)$alkyl, $(R_eR_f N)$alkoxy, -alkenyl-C(O)OH and —C(O)NR$_e$R$_f$;

$R_a$ and $R_b$ are independently selected from the group consisting of hydrogen, alkoxyalkyl, alkoxyalkylcarbonyl, alkoxycarbonyl, alkyl, alkylcarbonyl, alkylsulfonyl, alkylthioalkyl, alkylthioalkylcarbonyl, alkylthiocarbonyl, aryl, arylalkoxyalkyl, arylalkyl, arylcarbonyl, cycloalkyl, cycloalkylalkyl, cycloalkylalkoxyalkyl, cycloalkylcarbonyl, formyl, heteroaryl, heteroarylalkyl, heteroarylcarbonyl, heterocycle, heterocyclealkyl, heterocyclealkoxyalkyl, heterocyclecarbonyl, $(R_gR_h N)$alkyl and $(R_gR_h N)$carbonyl;

$R_c$ and $R_d$ are independently selected from the group consisting of hydrogen, alkyl, alkoxyalkyl, alkylcarbonyl, alkylsulfonyl, aryl, arylalkyl, arylalkylcarbonyl, arylalkylsulfonyl, arylcarbonyl, arylsulfonyl, cycloalkyl, cycloalkylcarbonyl, cycloalkylsulfonyl, formyl, heteroaryl, heteroarylalkyl, heteroarylcarbonyl, heteroarylsulfonyl, heterocycle, heterocyclealkyl, heterocyclecarbonyl and heterocyclesulfonyl;

$R_e$ and $R_f$ are independently selected from the group consisting of hydrogen, alkoxyalkyl, alkoxyalkylcarbonyl, alkoxycarbonyl, alkoxysulfonyl, alkyl, alkylcarbonyl, alkylsulfonyl, alkylthioalkyl, alkylthioalkylcarbonyl, alkylthiocarbonyl, aryl, arylalkoxyalkyl, arylalkyl, arylcarbonyl, cycloalkyl, cycloalkylalkoxyalkyl, cycloalkylalkyl, cycloalkylcarbonyl, formyl, heteroaryl, heteroarylalkoxyalkyl, heteroarylalkyl, heteroarylcarbonyl, heterocycle, heterocyclealkoxyalkyl, heterocyclealkyl, heterocyclecarbonyl, hydroxyalkyl, $(R_jR_k N)$alkyl and $(R_jR_k N)$carbonyl;

$R_g$ and $R_h$ are independently selected from the group consisting of hydrogen, alkoxycarbonyl, alkyl, alkylcarbonyl, alkoxysulfonyl, alkylsulfonyl, aryl, arylalkyl, arylcarbonyl, cycloalkyl, cycloalkylalkyl, cycloalkylcarbonyl, formyl, heteroaryl, heteroarylalkyl, heteroarylcarbonyl, heterocycle, heterocyclealkyl and heterocyclecarbonyl;

$R_j$ and $R_k$ are independently selected from the group consisting of hydrogen, alkoxycarbonyl, alkyl, alkylcarbonyl, alkylsulfonyl, aryl, arylalkyl, arylcarbonyl, cycloalkyl, cycloalkylalkyl, cycloalkylcarbonyl, formyl, heteroaryl, heteroarylalkyl, heteroarylcarbonyl, heterocycle, heterocyclealkyl and heterocyclecarbonyl.

According to another embodiment of the present invention, there is disclosed a compound of formula (I), wherein $L_1$ is selected from the group consisting of —C(O)—NH— and —NH—C(O)—; and $R_1$, $R_2$, $R_3$, $R_4$ and $R_5$ are as described in the principal embodiment.

According to another embodiment of the present invention, there is disclosed a compound of formula (I), wherein $L_1$ is selected from the group consisting of —C(O)—NH— and —NH—C(O)—;

$R_3$ is selected from the group consisting of azido and $R_cR_dN$—; wherein $R_c$ and $R_d$ are as described in the principal embodiment; and $R_1$, $R_2$, $R_4$ and $R_5$ are as described in the principal embodiment.

According to another embodiment of the present invention, there is disclosed a compound of formula (I), wherein $L_1$ is selected from the group consisting of —C(O)—NH— and —NH—C(O)—;

$R_2$ is hydrogen;

$R_4$ is cyano or halo;

$R_3$ is selected from the group consisting of azido and $R_cR_dN$—; and $R_c$, $R_d$, $R_1$ and $R_5$ are as described in the principal embodiment.

According to another embodiment of the present invention, there is disclosed a compound of formula (I), wherein $L_1$ is selected from the group consisting of —C(O)—NH— and —NH—C(O)—;

$R_1$ is selected from the group consisting of alkoxyalkyl, alkoxycarbonylalkyl, alkyl, alkylsulfonylalkyl, aryl, arylalkenyl, arylalkoxyalkyl, arylalkyl, aryloxyalkyl, arylsulfonylalkyl, carboxyalkyl, cyanoalkyl, cycloalkyl, cycloalkylalkyl, haloalkyl, heteroaryl, heteroarylalkyl, heteroaryloxyalkyl, heterocycle, heterocyclealkyl, heterocycleoxyalkyl, hydroxyalkyl and $(R_aR_bN)$alkyl; wherein $R_a$ and $R_b$ are as described in the principal embodiment;

$R_2$ is hydrogen;

$R_4$ is cyano or halo;

$R_3$ is selected from the group consisting of azido and $R_cR_dN$—; wherein $R_c$ and $R_d$ are as described in the principal embodiment;

$R_5$ is selected from the group consisting of alkenyl, alkoxy, alkoxyalkoxy, alkoxyalkyl, alkyl, aryl, arylalkoxy, aryloxy, cycloalkyl, cycloalkylalkoxy, cycloalkyloxy, haloalkoxy, haloalkyl, heteroaryl, heteroarylalkoxy, heteroaryloxy, heterocycle, heterocyclealkoxy, heterocycleoxy, hydroxyalkyl, hydroxyalkoxy, $R_eR_fN$, $(R_eR_fN)$alkyl, $(R_eR_fN)$alkoxy, -alkenyl-COOH and —C(O)$NR_eR_f$; wherein $R_e$ and $R_f$ are as described in the principal embodiment; and the aryl, aryl moiety of the arylalkoxy, aryloxy, arylalkenyl, arylalkoxyalkyl, arylalkyl, aryloxyalkyl, and arylsulfonylalkyl, cycloalkyl, cycloalkyl moiety of cycloalkylalkoxy, cycloalkyloxy, and cycloalkylalkyl, heteroaryl, heteroaryl moiety of the heteroarylalkoxy, heteroaryloxy, heteroarylalkyl, and heteroaryloxyalkyl, heterocycle, heterocycle moiety of heterocyclealkoxy, heterocycleoxy, heterocyclealkyl, and heterocycleoxyalkyl as represented by $R_1$ and $R_5$ are each independently unsubstituted or substituted with substituents as described in the definition of terms.

According to another embodiment of the present invention, there is disclosed a compound of formula (I), wherein $L_1$ is selected from the group consisting of —C(O)—NH— and —NH—C(O)—;

$R_1$ is selected from the group consisting of alkoxyalkyl, alkyl, alkylsulfonylalkyl, aryl, arylalkyl, arylsulfonylalkyl, cycloalkyl, cycloalkylalkyl, heterocyclealkyl, heteroarylalkyl and $(R_aR_bN)$alkyl-;

$R_2$ is hydrogen;

$R_3$ is selected from the group consisting of azido and $R_cR_dN$—;

$R_4$ is cyano or halo;

$R_5$ is selected from the group consisting of alkenyl, alkoxy, alkoxyalkoxy, alkyl, aryl, aryloxy, cycloalkylalkoxy, haloalkoxy, heteroaryl, hydroxyalkyl, $R_eR_fN$, -alkenyl-COOH and —C(O)$NR_eR_f$;

$R_a$, $R_b$, $R_e$ and $R_f$ are as described in the principal embodiment; and the aryl, aryl moiety of the arylalkyl, aryloxy, and arylsulfonylalkyl, cycloalkyl, cycloalkyl moiety of the cycloalkylalkyl and cycloalkylalkoxy, heterocycle moiety of the heterocylealkyl, heteroaryl and the heteroaryl moiety of the heteroarylalkyl as represented by $R_1$ and $R_5$ are each independently unsubstituted or substituted with substituents as defined in the principal embodiment and the definition of terms.

According to another embodiment of the present invention, there is disclosed a compound of formula (I), wherein $L_1$ is selected from the group consisting of —C(O)—NH—;

$R_1$ is selected from the group consisting of methoxymethyl, $C_1$-$C_6$ alkyl, ($C_1$-alkyl)-sulfonyl-($C_2$-$C_3$ alkyl)-, phenyl, aryl-($C_1$-$C_3$ alkyl)-, aryl-sulfonyl-($C_3$ alkyl)-, $C_3$-$C_6$ cycloalkyl, ($C_3$-$C_6$ cycloalkyl)($C_1$-$C_3$ alkyl)-, heterocycle-($C_1$-$C_3$ alkyl)-, heteroaryl-($C_1$-$C_3$ alkyl)- and $(R_aR_bN)$($C_1$-$C_3$ alkyl)- wherein $R_a$ is hydrogen and $R_b$ is monocyclic heteroaryl; and wherein the phenyl, aryl moiety of aryl-($C_1$-$C_3$ alkyl)- and aryl-sulfonyl-($C_3$ alkyl)-, the $C_3$-$C_6$ cycloalkyl, the cycloalkyl moiety of ($C_3$-$C_6$ cycloalkyl)($C_1$-$C_3$ alkyl)-, the heterocycle moiety of heterocycle-($C_1$-$C_3$ alkyl)-, the heteroaryl moiety of heteroaryl-($C_1$-$C_3$ alkyl)-, and the mocyclic heteroaryl represented by $R_b$ are each independently unsubstituted or substituted with substituents as described in the principal embodiment and the definition of terms;

$R_2$ is hydrogen;

$R_3$ is selected from the group consisting of azido and —$NH_2$;

$R_4$ is cyano or halo; and $R_5$ is selected from the group consisting of $C_3$ alkenyl, $C_1$ alkoxy, $C_2$ alkoxy, $C_3$ alkoxy, $C_4$ alkoxy, 2-methoxyethoxy, $C_2$ alkyl, $C_3$ alkyl, $C_4$ alkyl, —$C_2$ alkenyl-COOH, —C(O)N(H)($C_3$ alkyl), 2-hydroxyethoxy, phenyl, bicyclic aryl, phenoxy, ($C_3$-$C_6$ cycloalkyl)methoxy-, 2,2,2-trifluoro-1-methylethoxy, monocyclic or bicyclic heteroaryl and $R_eR_fN$— wherein $R_e$ is hydrogen and $R_f$ is selected from the group consisting of $C_3$ alkyl, $C_3$-$C_5$ cycloalkyl, 2-hydroxy-1-methylethyl, —($C_3$ alkyl)-S-methyl, and monocyclic heterocycle; and wherein the phenyl, bicyclic aryl, phenyl moiety of the phenoxy, cycloalkyl moiety of the ($C_3$-$C_6$ cycloalkyl)methoxy-, monocyclic heteroaryl, bicyclic heteroaryl, and the monocyclic heterocycle as represented by $R_f$ are each independently unsubstituted or substituted as described in the principal embodiment and definition of terms.

According to another embodiment of the present invention, there is disclosed a compound of formula (I), wherein $L_1$ is selected from the group consisting of —C(O)—NH—;

$R_1$ is selected from the group consisting of methoxymethyl, methyl, ethyl, 1-methylethyl, propyl, 1,1-dimethylethyl, 2-methylpropyl, butyl, 2,2-dimethylpropyl, pentyl, methylsulfonylethyl-, methylsulfonylpropyl-, phenyl, benzyl, 1-phenylethyl-, 2-phenylethyl-, naphthylmethyl-, phenysulfonylpropyl-, cyclobutyl, cyclopentyl, cyclopentylmethyl-, cyclohexylmethyl-, piperidinylmethyl-, pyrrolidinylmethyl-, piperazinylethyl-, pyridinylmethyl-, 1H-benzimidazoylmethyl-, thienylmethyl-, 1,3-thiazolylmethyl-, 1H-imidazolylmethyl-, 1H-indolylethyl-, 1H-imidazolylpropyl-, and $(R_aR_bN)$ethyl- wherein $R_a$ is hydrogen and $R_b$ is pyridinyl; and wherein the phenyl, phenyl moiety of benzyl, 1-phenylethyl-, 2-phenylethyl-, and phenysulfonylpropyl-, naphthyl moiety of the naphthylmethyl-, cyclobutyl, cyclopentyl, cyclopentyl moiety of the cyclopentylmethyl-, cyclohexyl moiety of the cyclohexylmethyl-, piperidinyl moiety of the piperidinylmethyl-, pyrrolidinyl moiety of the pyrrolidinylmethyl-, piperazinyl moiety of the piperazinylethyl-, pyridinyl moiety of the pyridinylmethyl-, 1H-benzimidazoyl moiety of the 1H-benzimidazoylmethyl-, thienyl moiety of the thienylmethyl-, 1,3-thiazolyl moiety of the 1,3-thiazolylmethyl-, 1H-imidazolyl moiety of the 1H-imidazolylmethyl-, 1H-indolyl moiety of the 1H-indolylethyl-, 1H-imidazolyl moiety of the 1H-imidazolylpropyl-, and the pyridinyl represented by $R_b$ are each independently unsubstituted or substituted with substituents as described in the principal embodiment and the definition of terms;

$R_2$ is hydrogen;

$R_3$ is selected from the group consisting of azido and —$NH_2$;

$R_4$ is cyano or halo; and $R_5$ is selected from the group consisting of prop-1-enyl, methoxy, ethoxy, isopropoxy, isobutoxy, butoxy, 2-methoxyethoxy, ethyl, propyl, isobutyl, -ethenyl-COOH, —C(O)N(H)(isopropyl), 2-hydroxyethoxy, phenyl, naphthyl, phenoxy, cyclopentylmethoxy, cyclopropylmethoxy, 2,2,2-trifluoro-1-methylethoxy, thienyl, benzo furanyl, pyridinyl, and $R_eR_fN$— wherein $R_e$ is hydrogen and $R_f$ is selected from the group consisting of isopropyl, cyclopropyl, cyclobutyl, cyclopentyl, 2-hydroxy-1-methylethyl, -(propyl)-S-methyl, and pyrrolidinyl; and wherein the phenyl, naphthyl, phenyl moiety of phenoxy, cyclopentyl moiety of the cyclopentylmethoxy, cyclopropyl moiety of the cyclopropylmethoxy, thienyl, benzofuranyl, pyridinyl, and the cyclopropyl, cyclobutyl, cyclopentyl and pyrrolidinyl as represented by $R_f$, are each independently unsubstituted or substituted as described in the principal embodiment and definition of terms. According to another embodiment of the present invention, there is disclosed a compound of formula (I), wherein $L_1$ is selected from the group consisting of —NH—C(O)—;

$R_1$ is selected from the group consisting of methoxymethyl, $C_1$-$C_6$ alkyl, ($C_1$-alkyl)-sulfonyl-($C_2$-$C_3$ alkyl)-, phenyl, aryl-($C_1$-$C_3$ alkyl)-, aryl-sulfonyl-($C_3$ alkyl)-, $C_3$-$C_6$ cycloalkyl, ($C_3$-$C_6$ cycloalkyl)($C_1$-$C_3$ alkyl)-, heterocycle-($C_1$-$C_3$ alkyl)-, heteroaryl-($C_1$-$C_3$ alkyl)- and ($R_aR_bN$)($C_1$-$C_3$ alkyl)- wherein $R_a$ is hydrogen and $R_b$ is monocyclic heteroaryl; and wherein the phenyl, aryl moiety of aryl-($C_1$-$C_3$ alkyl)- and aryl-sulfonyl-($C_3$ alkyl)-, the $C_3$-$C_6$ cycloalkyl, the cycloalkyl moiety of ($C_3$-$C_6$ cycloalkyl)($C_1$-$C_3$ alkyl)-, the heterocycle moiety of heterocycle-($C_1$-$C_3$ alkyl)-, the heteroaryl moiety of heteroaryl-($C_1$-$C_3$ alkyl)-, and the mocyclic heteroaryl represented by $R_b$ are each independently unsubstituted or substituted with substituents as described in the principal embodiment and the definition of terms;

$R_2$ is hydrogen;

$R_3$ is selected from the group consisting of azido and —$NH_2$, $R_4$ is cyano or halo; and $R_5$ is selected from the group consisting of $C_3$ alkenyl, $C_1$ alkoxy, $C_2$ alkoxy, $C_3$ alkoxy, $C_4$ alkoxy, 2-methoxyethoxy, $C_2$ alkyl, $C_3$ alkyl, $C_4$ alkyl, —$C_2$ alkenyl-COOH, —C(O)N(H)($C_3$ alkyl), 2-hydroxyethoxy, phenyl, bicyclic aryl, phenoxy, ($C_3$-$C_6$ cycloalkyl)methoxy-, 2,2,2-trifluoro-1-methylethoxy, monocyclic or bicyclic heteroaryl and $R_eR_fN$— wherein $R_e$ is hydrogen and $R_f$ is selected from the group consisting of $C_3$ alkyl, $C_3$-$C_5$ cycloalkyl, 2-hydroxy-1-methylethyl, —($C_3$ alkyl)-S-methyl, and monocyclic heterocycle; and wherein the phenyl, bicyclic aryl, phenyl moiety of the phenoxy, cycloalkyl moiety of the ($C_3$-$C_6$ cycloalkyl)methoxy-, monocyclic heteroaryl, bicyclic heteroaryl, and the monocyclic heterocycle as represented by $R_f$, are each independently unsubstituted or substituted as described in the principal embodiment and definition of terms.

According to another embodiment of the present invention, there is disclosed a compound of formula (I), wherein $L_1$ is selected from the group consisting of —NH—C(O)—;

$R_1$ is selected from the group consisting of methoxymethyl, methyl, ethyl, 1-methylethyl, propyl, 1,1-dimethylethyl, 2-methylpropyl, butyl, 2,2-dimethylpropyl, pentyl, methylsulfonylethyl-, methylsulfonylpropyl-, phenyl, benzyl, 1-phenylethyl-, 2-phenylethyl-, naphthylmethyl-, phenysulfonylpropyl-, cyclobutyl, cyclopentyl, cyclopentylmethyl-, cyclohexylmethyl-, piperidinylmethyl-, pyrrolidinylmethyl-, piperazinylethyl-, pyridinylmethyl-, 1H-benzimidazoylmethyl-, thienylmethyl-, 1,3-thiazolylmethyl-, 1H-imidazolylmethyl-, 1H-indolylethyl-, 1H-imidazolylpropyl-, and ($R_aR_bN$)ethyl- wherein $R_a$ is hydrogen and $R_b$ is pyridinyl; and wherein the phenyl, phenyl moiety of 1-phenylethyl-, 2-phenylethyl-, benzyl and phenysulfonylpropyl-, the naphthyl moiety of the naphthylmethyl-, cyclobutyl, cyclopentyl, cyclopentyl moiety of the cyclopentylmethyl-, cyclohexyl moiety of the cyclohexylmethyl-, piperidinyl moiety of the piperidinylmethyl-, pyrrolidinyl moiety of the pyrrolidinylmethyl-, piperazinyl moiety of the piperazinylethyl-, pyridinyl moiety of the pyridinylmethyl-, 1H-benzimidazoyl moiety of the 1H-benzimidazoylmethyl-, thienyl moiety of the thienylmethyl-, 1,3-thiazolyl moiety of the 1,3-thiazolylmethyl-, 1H-imidazolyl moiety of the 1H-imidazolylmethyl-, 1H-indolyl moiety of the 1H-indolylethyl-, 1H-imidazolyl moiety of the 1H-imidazolylpropyl-, and the pyridinyl represented by $R_b$ are each independently unsubstituted or substituted with substituents as described in the principal embodiment and the definition of terms;

$R_2$ is hydrogen;

$R_3$ is selected from the group consisting of azido and —$NH_2$;

$R_4$ is cyano or halo; and $R_5$ is selected from the group consisting of prop-1-enyl, methoxy, ethoxy, isopropoxy, isobutoxy, butoxy, 2-methoxyethoxy, ethyl, propyl, isobutyl, -ethenyl-COOH, —C(O)N(H)(isopropyl), 2-hydroxyethoxy, phenyl, naphthyl, phenoxy, cyclopentylmethoxy, cyclopropylmethoxy, 2,2,2-trifluoro-1-methylethoxy, thienyl, benzofuranyl, pyridinyl, and $R_eR_fN$— wherein $R_e$ is hydrogen and $R_f$ is selected from the group consisting of isopropyl, cyclopropyl, cyclobutyl, cyclopentyl, 2-hydroxy-1-methylethyl, -(propyl)-S-methyl, and pyrrolidinyl; and wherein the phenyl, naphthyl, phenyl moiety of phenoxy, cyclopentyl moiety of the cyclopentylmethoxy, cyclopropyl moiety of the cyclopropylmethoxy, thienyl, benzofuranyl, pyridinyl, and the cyclopropyl, cyclobutyl, cyclopentyl and pyrrolidinyl as represented by $R_f$, are each independently unsubstituted or substituted as described in the principal embodiment and definition of terms. According to another embodiment of the present invention, there is disclosed a compound of formula (I), or a pharmaceutically acceptable salt, prodrug, salt of a prodrug, or a combination thereof, wherein $L_1$ is selected from the group consisting of —C(O)—NH— and —NH—C(O)—;

$R_3$ is selected from the group consisting of azido and $R_cR_dN$—;

$R_2$ is hydrogen;

$R_4$ is hydrogen, heteroaryl, formyl or alkynylalkenyl;

$R_5$ is selected from the group consisting of alkenyl, alkoxy, alkoxyalkoxy, alkyl, aryl, aryloxy, cycloalkylalkoxy, haloalkoxy, heteroaryl, hydroxyalkoxy, $R_eR_fN$, -alkenyl-COOH and —C(O)$NR_eR_f$;

$R_1$ is selected from the group consisting of alkoxyalkyl, alkyl, alkylsulfonylalkyl, aryl, arylalkyl, arylsulfonylalkyl, cycloalkyl, cycloalkylalkyl, heterocyclealkyl, heteroarylalkyl and $(R_aR_bN)$alkyl-; $R_a$, $R_b$, $R_e$, and $R_f$ are as described in the principal embodiment; and the aryl, aryl moiety of the arylalkyl, aryloxy, and arylsulfonylalkyl, cycloalkyl, cycloalkyl moiety of the cycloalkylalkyl and cycloalkylalkoxy, heterocycle moiety of the heterocylealkyl, heteroaryl and the heteroaryl moiety of the heteroarylalkyl as represented by $R_1$ and $R_5$ are each independently unsubstituted or substituted with substituents as defined in the principal embodiment and the definition of terms.

According to another embodiment of the present invention, there is disclosed a compound of formula (I), wherein $L_1$ is selected from the group consisting of —C(O)—NH—;

$R_1$ is selected from the group consisting of methoxymethyl, $C_1$-$C_6$ alkyl, ($C_1$-alkyl)-sulfonyl-($C_2$-$C_3$ alkyl)-, phenyl, aryl-($C_1$-$C_3$ alkyl)-, aryl-sulfonyl-($C_3$ alkyl)-, $C_3$-$C_6$ cycloalkyl, ($C_3$-$C_6$ cycloalkyl)($C_1$-$C_3$ alkyl)-, heterocycle-($C_1$-$C_3$ alkyl)-, heteroaryl-($C_1$-$C_3$ alkyl)- and $(R_aR_bN)(C_1$-$C_3$ alkyl)- wherein $R_a$ is hydrogen and $R_b$ is monocyclic heteroaryl; and wherein the phenyl, aryl moiety of aryl-($C_1$-$C_3$ alkyl)- and aryl-sulfonyl-($C_3$ alkyl)-, the $C_3$-$C_6$ cycloalkyl, the cycloalkyl moiety of ($C_3$-$C_6$ cycloalkyl)($C_1$-$C_3$ alkyl)-, the heterocycle moiety of heterocycle-($C_1$-$C_3$ alkyl)-, the heteroaryl moiety of heteroaryl-($C_1$-$C_3$ alkyl)-, and the mocyclic heteroaryl represented by $R_b$ are each independently unsubstituted or substituted with substituents as described in the principal embodiment and the definition of terms;

$R_2$ is hydrogen;

$R_3$ is selected from the group consisting of azido and —$NH_2$;

$R_4$ is hydrogen, formyl or but-1-en-3-ynyl or monocyclic heteroaryl which is unsubstituted or substituted with one or two substituents selected from the group consisting of $C_1$-$C_6$ alkyl, halo and haloalkyl; and $R_5$ is selected from the group consisting of $C_3$ alkenyl, $C_1$ alkoxy, $C_2$ alkoxy, $C_3$ alkoxy, $C_4$ alkoxy, 2-methoxyethoxy, $C_2$ alkyl, $C_3$ alkyl, $C_4$ alkyl, —$C_2$ alkenyl-COOH, —C(O)N(H)($C_3$ alkyl), 2-hydroxyethoxy, phenyl, bicyclic aryl, phenoxy, ($C_3$-$C_6$ cycloalkyl)methoxy-, 2,2,2-trifluoro-1-methylethoxy, monocyclic or bicyclic heteroaryl and $R_eR_fN$— wherein $R_e$ is hydrogen and $R_f$ is selected from the group consisting of $C_3$ alkyl, $C_3$-$C_5$ cycloalkyl, 2-hydroxy-1-methylethyl, —($C_3$ alkyl)-S-methyl, and monocyclic heterocycle; and wherein the phenyl, bicyclic aryl, phenyl moiety of the phenoxy, cycloalkyl moiety of the ($C_3$-$C_6$ cycloalkyl)methoxy-, monocyclic heteroaryl, bicyclic heteroaryl, and the monocyclic heterocycle as represented by $R_f$, are each independently unsubstituted or substituted as described in the principal embodiment and definition of terms.

According to another embodiment of the present invention, there is disclosed a compound of formula (I), wherein $L_1$ is selected from the group consisting of —C(O)—NH—, $R_1$ is selected from the group consisting of methoxymethyl, methyl, ethyl, 1-methylethyl, propyl, 1,1-dimethylethyl, 2-methylpropyl, butyl, 2,2-dimethylpropyl, pentyl, methylsulfonylethyl-, methylsulfonylpropyl-, phenyl, benzyl, 1-phenylethyl-, 2-phenylethyl-, naphthylmethyl-, phenysulfonylpropyl-, cyclobutyl, cyclopentyl, cyclopentylmethyl-, cyclohexylmethyl-, piperidinylmethyl-, pyrrolidinylmethyl-, piperazinylethyl-, pyridinylmethyl-, 1H-benzimidazoylmethyl-, thienylmethyl-, 1,3-thiazolylmethyl-, 1H-imidazolylmethyl-, 1H-indolylethyl-, 1H-imidazolylpropyl-, and $(R_aR_bN)$ethyl- wherein $R_a$ is hydrogen and $R_b$ is pyridinyl; and wherein the phenyl, phenyl moiety of 1-phenylethyl-, 2-phenylethyl-, benzyl and phenysulfonylpropyl-, the naphthyl moiety of the naphthylmethyl-, cyclobutyl, cyclopentyl, cyclopentyl moiety of the cyclopentylmethyl-, cyclohexyl moiety of the cyclohexylmethyl-, piperidinyl moiety of the piperidinylmethyl-, pyrrolidinyl moiety of the pyrrolidinylmethyl-, piperazinyl moiety of the piperazinylethyl-, pyridinyl moiety of the pyridinylmethyl-, 1H-benzimidazoyl moiety of the 1H-benzimidazoylmethyl-, thienyl moiety of the thienylmethyl-, 1,3-thiazolyl moiety of the 1,3-thiazolylmethyl-, 1H-imidazolyl moiety of the 1H-imidazolylmethyl-, 1H-indolyl moiety of the 1H-indolylethyl-, 1H-imidazolyl moiety of the 1H-imidazolylpropyl-, and the pyridinyl represented by $R_b$ are each independently unsubstituted or substituted with substituents as described in the principal embodiment and the definition of terms;

$R_2$ is hydrogen;

$R_3$ is selected from the group consisting of azido and —$NH_2$;

$R_4$ is hydrogen, formyl, but-1-en-3-ynyl, unsubstituted pyridinyl, or pyridinyl substituted with one or two substituents selected from the group consisting of methyl, ethyl, propyl and trifluoromethyl; and $R_5$ is selected from the group consisting of prop-1-enyl, methoxy, ethoxy, isopropoxy, isobutoxy, butoxy, 2-methoxyethoxy, ethyl, propyl, isobutyl, -ethenyl-COOH, —C(O)N(H)(isopropyl), 2-hydroxyethoxy, phenyl, naphthyl, phenoxy, cyclopentylmethoxy, cyclopropylmethoxy, 2,2,2-trifluoro-1-methylethoxy, thienyl, benzofuranyl, pyridinyl, and $R_eR_fN$— wherein $R_e$ is hydrogen and $R_f$ is selected from the group consisting of isopropyl, cyclopropyl, cyclobutyl, cyclopentyl, 2-hydroxy-1-methylethyl, -(propyl)-S-methyl, and pyrrolidinyl; and wherein the phenyl, naphthyl, phenyl moiety of phenoxy, cyclopentyl moiety of the cyclopentylmethoxy, cyclopropyl moiety of the cyclopropylmethoxy, thienyl, benzofuranyl, pyridinyl, and the cyclopropyl, cyclobutyl, cyclopentyl and pyrrolidinyl as represented by $R_f$, are each independently unsubstituted or substituted as described in the principal embodiment and definition of terms. According to another embodiment of the present invention, there is disclosed a compound of formula (I), wherein $L_1$ is selected from the group consisting of —NH—C(O)—;

$R_1$ is selected from the group consisting of methoxymethyl, $C_1$-$C_6$ alkyl, ($C_1$-alkyl)-sulfonyl-($C_2$-$C_3$ alkyl)-, phenyl, aryl-($C_1$-$C_3$ alkyl)-, aryl-sulfonyl-($C_3$ alkyl)-, $C_3$-$C_6$ cycloalkyl, ($C_3$-$C_6$ cycloalkyl)($C_1$-$C_3$ alkyl)-, heterocycle-($C_1$-$C_3$ alkyl)-, heteroaryl-($C_1$-$C_3$ alkyl)- and $(R_aR_bN)(C_1$-$C_3$ alkyl)- wherein $R_a$ is hydrogen and $R_b$ is monocyclic heteroaryl; and wherein the phenyl, aryl moiety of aryl-($C_1$-$C_3$ alkyl)- and aryl-sulfonyl-($C_3$ alkyl)-, the $C_3$-$C_6$ cycloalkyl, the cycloalkyl moiety of ($C_3$-$C_6$ cycloalkyl)($C_1$-$C_3$ alkyl)-, the heterocycle moiety of heterocycle-($C_1$-$C_3$ alkyl)-, the heteroaryl moiety of heteroaryl-($C_1$-$C_3$ alkyl)-, and the mocyclic heteroaryl represented by $R_b$ are each independently unsubstituted or substituted with substituents as described in the principal embodiment and the definition of terms;

$R_2$ is hydrogen;

$R_3$ is selected from the group consisting of azido and —$NH_2$;

$R_4$ is hydrogen, formyl or but-1-en-3-ynyl or monocyclic heteroaryl which is unsubstituted or substituted with one or two substituents selected from the group consisting of $C_1$-$C_6$ alkyl, halo and haloalkyl; and $R_5$ is selected from the group consisting of $C_3$ alkenyl, $C_1$ alkoxy, $C_2$ alkoxy, $C_3$ alkoxy, $C_4$ alkoxy, 2-methoxyethoxy, $C_2$ alkyl, $C_3$ alkyl, $C_4$ alkyl, —$C_2$ alkenyl-COOH, —C(O)N(H)($C_3$ alkyl), 2-hydroxyethoxy, phenyl, bicyclic aryl, phenoxy, ($C_3$-$C_6$ cycloalkyl)methoxy-, 2,2,2-trifluoro-1-methylethoxy, monocyclic or bicyclic heteroaryl and $R_eR_fN$— wherein $R_e$ is hydrogen and $R_f$ is selected from the group consisting of $C_3$ alkyl, $C_3$-$C_5$ cycloalkyl, 2-hydroxy-1-methylethyl, —($C_3$ alkyl)-S-methyl, and monocyclic heterocycle; and wherein the phenyl, bicyclic aryl, phenyl moiety of the phenoxy, cycloalkyl moiety of the ($C_3$-$C_6$ cycloalkyl)methoxy-, monocyclic heteroaryl, bicyclic heteroaryl, and the monocyclic heterocycle as represented by $R_f$, are each independently unsubstituted or substituted as described in the principal embodiment and definition of terms.

According to another embodiment of the present invention, there is disclosed a compound of formula (I), or a pharmaceutically acceptable salt, prodrug, salt of a prodrug, or a combination thereof,

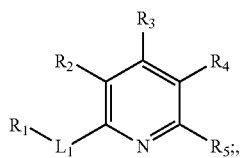

(I)

wherein $L_1$ is selected from the group consisting of —C(O)—NH—, and —NH—C(O)—;

$R_1$ is selected from the group consisting of alkoxyalkyl, alkyl, alkylsulfinylalkyl, aryl, arylalkyl, arylsulfinylalkyl, cycloalkyl, cycloalkylalkyl, heteroarylalkyl, and heterocyclealkyl;

$R_2$ and $R_4$ are independently selected from the group consisting of hydrogen, cyano, halo, and heteroaryl;

$R_3$ is selected from the group consisting of hydrogen, azido, and $R_cR_dN$—;

$R_5$ is selected from the group consisting of alkenyl, alkoxy, alkoxyalkoxy, alkyl, aryl, aryloxy, cycloalkyloxy, haloalkoxy, heteroaryl, heterocycle, hydroxyalkoxy, and $R_eR_fN$—;

$R_c$ and $R_d$ are hydrogen; and $R_e$ and $R_f$ are independently selected from the group consisting of hydrogen, alkylthioalkyl, and cycloalkyl.

According to another embodiment of the present invention, there is disclosed a compound of formula (I), wherein $L_1$ is selected from the group consisting of —NH—C(O)—;

$R_1$ is selected from the group consisting of methoxymethyl, methyl, ethyl, 1-methylethyl, propyl, 1,1-dimethylethyl, 2-methylpropyl, butyl, 2,2-dimethylpropyl, pentyl, methylsulfonylethyl-, methylsulfonylpropyl-, phenyl, benzyl, 1-phenylethyl-, 2-phenylethyl-, naphthylmethyl-, phenysulfonylpropyl-, cyclobutyl, cyclopentyl, cyclopentylmethyl-, cyclohexylmethyl-, piperidinylmethyl-, pyrrolidinylmethyl-, piperazinylethyl-, pyridinylmethyl-, 1H-benzimidazoylmethyl-, thienylmethyl-, 1,3-thiazolylmethyl-, 1H-imidazolylmethyl-, 1H-indolylethyl-, 1H-imidazolylpropyl-, and ($R_aR_bN$)ethyl- wherein $R_a$ is hydrogen and $R_b$ is pyridinyl; and wherein the phenyl, phenyl moiety of 1-phenylethyl-, 2-phenylethyl-, benzyl, and phenysulfonylpropyl-, the naphthyl moiety of the naphthylmethyl-, cyclobutyl, cyclopentyl, cyclopentyl moiety of the cyclopentylmethyl-, cyclohexyl moiety of the cyclohexylmethyl-, piperidinyl moiety of the piperidinylmethyl-, pyrrolidinyl moiety of the pyrrolidinylmethyl-, piperazinyl moiety of the piperazinylethyl-, pyridinyl moiety of the pyridinylmethyl-, 1H-benzimidazoyl moiety of the 1H-benzimidazoylmethyl-, thienyl moiety of the thienylmethyl-, 1,3-thiazolyl moiety of the 1,3-thiazolylmethyl-, 1H-imidazolyl moiety of the 1H-imidazolylmethyl-, 1H-indolyl moiety of the 1H-indolylethyl-, 1H-imidazolyl moiety of the 1H-imidazolylpropyl-, and the pyridinyl represented by $R_b$ are each independently unsubstituted or substituted with substituents as described in the principal embodiment and the definition of terms;

$R_2$ is hydrogen;

$R_3$ is selected from the group consisting of azido and —$NH_2$;

$R_4$ is hydrogen, formyl, but-1-en-3-ynyl, unsubstituted pyridinyl, or pyridinyl substituted with one or two substituents selected from the group consisting of methyl, ethyl, propyl and trifluoromethyl; and $R_5$ is selected from the group consisting of prop-1-enyl, methoxy, ethoxy, isopropoxy, isobutoxy, butoxy, 2-methoxyethoxy, ethyl, propyl, isobutyl, -ethenyl-COOH, —C(O)N(H)(isopropyl), 2-hydroxyethoxy, phenyl, naphthyl, phenoxy, cyclopentylmethoxy, cyclopropylmethoxy, 2,2,2-trifluoro-1-methylethoxy, thienyl, benzofuranyl, pyridinyl, and $R_eR_fN$— wherein $R_e$ is hydrogen and $R_f$ is selected from the group consisting of isopropyl, cyclopropyl, cyclobutyl, cyclopentyl, 2-hydroxy-1-methylethyl, -(propyl)-S-methyl, and pyrrolidinyl; and wherein the phenyl, naphthyl, phenyl moiety of phenoxy, cyclopentyl moiety of the cyclopentylmethoxy, cyclopropyl moiety of the cyclopropylmethoxy, thienyl, benzofuranyl, pyridinyl, and the cyclopropyl, cyclobutyl, cyclopentyl and pyrrolidinyl as represented by $R_f$, are each independently unsubstituted or substituted as described in the principal embodiment and definition of terms. According to another embodiment of the present invention, there is disclosed a compound of formula (I), or a pharmaceutically acceptable salt, prodrug, salt of a prodrug, or a combination thereof, wherein $L_1$ is selected from the group consisting of —C(O)—NH— and —NH—C(O)—;

$R_2$ is hydrogen;

$R_3$ is hydrogen;

$R_4$ is cyano or halo;

$R_5$ is selected from the group consisting of alkenyl, alkoxy, alkoxyalkoxy, alkyl, aryl, aryloxy, cycloalkylalkoxy, haloalkoxy, heteroaryl, hydroxyalkoxy, $R_eR_fN$, -alkenyl-COOH and —C(O)$NR_eR_f$;

$R_1$ is selected from the group consisting of alkoxyalkyl, alkyl, alkylsulfonylalkyl, aryl, arylalkyl, arylsulfonylalkyl, cycloalkyl, cycloalkylalkyl, heterocyclealkyl, heteroarylalkyl and ($R_aR_bN$)alkyl-; $R_a$, $R_b$, $R_e$, and $R_f$ are as described in the principal embodiment; and the aryl, aryl moiety of the arylalkyl, aryloxy, and arylsulfonylalkyl, cycloalkyl, cycloalkyl moiety of the cycloalkylalkyl and cycloalkylalkoxy, heterocycle moiety of the heterocylealkyl, heteroaryl and the heteroaryl moiety of the heteroarylalkyl as represented by $R_1$ and $R_5$ are each independently unsubstituted or substituted with substituents as defined in the principal embodiment and the definition of terms.

According to another embodiment of the present invention, there is disclosed a compound of formula (I), wherein $L_1$ is selected from the group consisting of —C(O)—NH—;

$R_1$ is selected from the group consisting of methoxymethyl, $C_1$-$C_6$ alkyl, ($C_1$-alkyl)-sulfonyl-($C_2$-$C_3$ alkyl)-, phenyl, aryl-($C_1$-$C_3$ alkyl)-, aryl-sulfonyl-($C_3$ alkyl)-, $C_3$-$C_6$ cycloalkyl, ($C_3$-$C_6$ cycloalkyl)($C_1$-$C_3$ alkyl)-, heterocycle-($C_1$-$C_3$ alkyl)-, heteroaryl-($C_1$-$C_3$ alkyl)- and ($R_aR_bN$)($C_1$-$C_3$ alkyl)- wherein $R_a$ is hydrogen and $R_b$ is monocyclic heteroaryl; and wherein the phenyl, aryl moiety of aryl-($C_1$-$C_3$ alkyl)- and aryl-sulfonyl-($C_3$ alkyl)-, the $C_3$-$C_6$ cycloalkyl, the cycloalkyl moiety of $(C_3-C_6$ cycloalkyl$)(C_1-C_3$ alkyl$)$-, the heterocycle moiety of heterocycle-$(C_1-C_3$ alkyl$)$-, the heteroaryl moiety of heteroaryl-$(C_1-C_3$ alkyl$)$-, and the mocyclic heteroaryl represented by $R_b$ are each independently unsubstituted or substituted with substituents as described in the principal embodiment and the definition of terms;

$R_2$ is hydrogen;

$R_3$ is hydrogen;

$R_4$ is cyano or halo; and $R_5$ is selected from the group consisting of $C_3$ alkenyl, $C_1$ alkoxy, $C_2$ alkoxy, $C_3$ alkoxy, $C_4$ alkoxy, 2-methoxyethoxy, $C_2$ alkyl, $C_3$ alkyl, $C_4$ alkyl, —$C_2$ alkenyl-COOH, —C(O)N(H)($C_3$ alkyl), 2-hydroxyethoxy, phenyl, bicyclic aryl, phenoxy, $(C_3-C_6$ cycloalkyl)methoxy-, 2,2,2-trifluoro-1-methylethoxy, monocyclic or bicyclic heteroaryl and $R_eR_fN$— wherein $R_e$ is hydrogen and $R_f$ is selected from the group consisting of $C_3$ alkyl, $C_3-C_5$ cycloalkyl, 2-hydroxy-1-methylethyl, —($C_3$ alkyl)-S-methyl, and monocyclic heterocycle; and wherein the phenyl, bicyclic aryl, phenyl moiety of the phenoxy, cycloalkyl moiety of the $(C_3-C_6$ cycloalkyl)methoxy-, monocyclic heteroaryl, bicyclic heteroaryl, and the monocyclic heterocycle as represented by $R_f$ are each independently unsubstituted or substituted as described in the principal embodiment and definition of terms.

According to another embodiment of the present invention, there is disclosed a compound of formula (I), wherein $L_1$ is selected from the group consisting of —C(O)—NH—;

$R_1$ is selected from the group consisting of methoxymethyl, methyl, ethyl, 1-methylethyl, propyl, 1,1-dimethylethyl, 2-methylpropyl, butyl, 2,2-dimethylpropyl, pentyl, methylsulfonylethyl-, methylsulfonylpropyl-, phenyl, benzyl, 1-phenylethyl-, 2-phenylethyl-, naphthylmethyl-, phenysulfonylpropyl-, cyclobutyl, cyclopentyl, cyclopentylmethyl-, cyclohexylmethyl-, piperidinylmethyl-, pyrrolidinylmethyl-, piperazinylethyl-, pyridinylmethyl-, 1H-benzimidazoylmethyl-, thienylmethyl-, 1,3-thiazolylmethyl-, 1H-imidazolylmethyl-, 1H-indolylethyl-, 1H-imidazolylpropyl-, and $(R_aR_bN)$ethyl- wherein $R_a$ is hydrogen and $R_b$ is pyridinyl; and wherein the phenyl, phenyl moiety of 1-phenylethyl-, 2-phenylethyl-, benzyl and phenysulfonylpropyl-, the naphthyl moiety of the naphthylmethyl-, cyclobutyl, cyclopentyl, cyclopentyl moiety of the cyclopentylmethyl-, cyclohexyl moiety of the cyclohexylmethyl-, piperidinyl moiety of the piperidinylmethyl-, pyrrolidinyl moiety of the pyrrolidinylmethyl-, piperazinyl moiety of the piperazinylethyl-, pyridinyl moiety of the pyridinylmethyl-, 1H-benzimidazoyl moiety of the 1H-benzimidazoylmethyl-, thienyl moiety of the thienylmethyl-, 1,3-thiazolyl moiety of the 1,3-thiazolylmethyl-, 1H-imidazolyl moiety of the 1H-imidazolylmethyl-, 1H-indolyl moiety of the 1H-indolylethyl-, 1H-imidazolyl moiety of the 1H-imidazolylpropyl-, and the pyridinyl represented by $R_b$ are each independently unsubstituted or substituted with substituents as described in the principal embodiment and the definition of terms;

$R_2$ is hydrogen;

$R_3$ is hydrogen;

$R_4$ is cyano or halo; and $R_5$ is selected from the group consisting of prop-1-enyl, methoxy, ethoxy, isopropoxy, isobutoxy, butoxy, 2-methoxyethoxy, ethyl, propyl, isobutyl, -ethenyl-COOH, —C(O)N(H)(isopropyl), 2-hydroxyethoxy, phenyl, naphthyl, phenoxy, cyclopentylmethoxy, cyclopropylmethoxy, 2,2,2-trifluoro-1-methylethoxy, thienyl, benzofuranyl, pyridinyl, and $R_eR_fN$— wherein $R_e$ is hydrogen and $R_f$ is selected from the group consisting of isopropyl, cyclopropyl, cyclobutyl, cyclopentyl, 2-hydroxy-1-methylethyl, -(propyl)-S-methyl, and pyrrolidinyl; and wherein the phenyl, naphthyl, phenyl moiety of phenoxy, cyclopentyl moiety of the cyclopentylmethoxy, cyclopropyl moiety of the cyclopropylmethoxy, thienyl, benzofuranyl, pyridinyl, and the cyclopropyl, cyclobutyl, cyclopentyl and pyrrolidinyl as represented by $R_f$ are each independently unsubstituted or substituted as described in the principal embodiment and definition of terms; According to another embodiment of the present invention, there is disclosed a compound of formula (I), wherein $L_1$ is selected from the group consisting of —NH—C(O)—;

$R_1$ is selected from the group consisting of methoxymethyl, $C_1-C_6$ alkyl, ($C_1$-alkyl)-sulfonyl-($C_2-C_3$ alkyl)-, phenyl, aryl-($C_1-C_3$ alkyl)-, aryl-sulfonyl-($C_3$ alkyl)-, $C_3-C_6$ cycloalkyl, ($C_3-C_6$ cycloalkyl)($C_1-C_3$ alkyl)-, heterocycle-($C_1-C_3$ alkyl)-, heteroaryl-($C_1-C_3$ alkyl)- and $(R_aR_bN)(C_1-C_3$ alkyl)- wherein $R_a$ is hydrogen and $R_b$ is monocyclic heteroaryl; and wherein the phenyl, aryl moiety of aryl-($C_1-C_3$ alkyl)- and aryl-sulfonyl-($C_3$ alkyl)-, the $C_3-C_6$ cycloalkyl, the cycloalkyl moiety of ($C_3-C_6$ cycloalkyl)($C_1-C_3$ alkyl)-, the heterocycle moiety of heterocycle-($C_1-C_3$ alkyl)-, the heteroaryl moiety of heteroaryl-($C_1-C_3$ alkyl)-, and the mocyclic heteroaryl represented by $R_b$ are each independently unsubstituted or substituted with substituents as described in the principal embodiment and the definition of terms;

$R_2$ is hydrogen;

$R_3$ is hydrogen;

$R_4$ is cyano or halo; and $R_5$ is selected from the group consisting of $C_3$ alkenyl, $C_1$ alkoxy, $C_2$ alkoxy, $C_3$ alkoxy, $C_4$ alkoxy, 2-methoxyethoxy, $C_2$ alkyl, $C_3$ alkyl, $C_4$ alkyl, —$C_2$ alkenyl-COOH, —C(O)N(H)($C_3$ alkyl), 2-hydroxyethoxy, phenyl, bicyclic aryl, phenoxy, $(C_3-C_6$ cycloalkyl)methoxy-, 2,2,2-trifluoro-1-methylethoxy, monocyclic or bicyclic heteroaryl and $R_eR_fN$— wherein $R_e$ is hydrogen and $R_f$ is selected from the group consisting of $C_3$ alkyl, $C_3-C_5$ cycloalkyl, 2-hydroxy-1-methylethyl, —($C_3$ alkyl)-S-methyl, and monocyclic heterocycle; and wherein the phenyl, bicyclic aryl, phenyl moiety of the phenoxy, cycloalkyl moiety of the $(C_3-C_6$ cycloalkyl)methoxy-, monocyclic heteroaryl, bicyclic heteroaryl, and the monocyclic heterocycle as represented by $R_f$ are each independently unsubstituted or substituted as described in the principal embodiment and definition of terms.

According to another embodiment of the present invention, there is disclosed a compound of formula (I), wherein $L_1$ is selected from the group consisting of —NH—C(O)—;

$R_1$ is selected from the group consisting of methoxymethyl, methyl, ethyl, 1-methylethyl, propyl, 1,1-dimethylethyl, 2-methylpropyl, butyl, 2,2-dimethylpropyl, pentyl, methylsulfonylethyl-, methylsulfonylpropyl-, phenyl, benzyl, 1-phenylethyl-, 2-phenylethyl-, naphthylmethyl-, phenysulfonylpropyl-, cyclobutyl, cyclopentyl, cyclopentylmethyl-, cyclohexylmethyl-, piperidinylmethyl-, pyrrolidinylmethyl-, piperazinylethyl-, pyridinylmethyl-, 1H-benzimidazoylmethyl-, thienylmethyl-, 1,3-thiazolylmethyl-, 1H-imidazolylmethyl-, 1H-indolylethyl-, 1H-imidazolylpropyl-, and $(R_aR_bN)$ethyl- wherein $R_a$ is hydrogen and $R_b$ is pyridinyl; and wherein the phenyl, phenyl moiety of 1-phenylethyl-, 2-phenylethyl-, benzyl and phenysulfonylpropyl-, the naphthyl moiety of the naphthylmethyl-, cyclobutyl, cyclopentyl, cyclopentyl moiety of the cyclopentylmethyl-, cyclohexyl moiety of the cyclohexylmethyl-, piperidinyl moiety of the piperidinylmethyl-, pyrrolidinyl moiety of the pyrrolidinylmethyl-, piperazinyl moiety of the piperazinylethyl-, pyridinyl moiety of the pyridinylmethyl-, 1H-benzimidazoyl moiety of the 1H-benzimidazoylmethyl-, thienyl moiety of the thienylmethyl-, 1,3-thiazolyl moiety of the 1,3-thiazolylmethyl-, 1H-imidazolyl moiety of the 1H-imidazolylmethyl-, 1H-indolyl moiety of the 1H-indolylethyl-, 1H-imidazolyl moiety of the 1H-imidazolylpropyl-, and the pyridinyl represented by $R_b$ are each independently unsubstituted or substituted with substituents as described in the principal embodiment and the definition of terms;

$R_2$ is hydrogen;

$R_3$ is hydrogen;

$R_4$ is cyano or halo; and $R_5$ is selected from the group consisting of prop-1-enyl, methoxy, ethoxy, isopropoxy, isobutoxy, butoxy, 2-methoxyethoxy, ethyl, propyl, isobutyl, -ethenyl-COOH, —C(O)N(H)(isopropyl), 2-hydroxyethoxy, phenyl, naphthyl, phenoxy, cyclopentylmethoxy, cyclopropylmethoxy, 2,2,2-trifluoro-1-methylethoxy, thienyl, benzofuranyl, pyridinyl, and $R_eR_fN$— wherein $R_e$ is hydrogen and $R_f$ is selected from the group consisting of isopropyl, cyclopropyl, cyclobutyl, cyclopentyl, 2-hydroxy-1-methylethyl, -(propyl)-S-methyl, and pyrrolidinyl; and wherein the phenyl, naphthyl, phenyl moiety of phenoxy, cyclopentyl moiety of the cyclopentylmethoxy, cyclopropyl moiety of the cyclopropylmethoxy, thienyl, benzofuranyl, pyridinyl, and the cyclopropyl, cyclobutyl, cyclopentyl and pyrrolidinyl as represented by $R_f$, are each independently unsubstituted or substituted as described in the principal embodiment and definition of terms. According to another embodiment of the present invention, there is disclosed a compound of formula (I), or a pharmaceutically acceptable salt, prodrug, salt of a prodrug, or a combination thereof, wherein $L_1$ is selected from the group consisting of —C(O)—NH— and —NH—C(O)—;

$R_2$ is hydrogen;

$R_3$ is hydrogen;

$R_4$ is hydrogen, heteroaryl, formyl, or alkynylalkenyl;

$R_5$ is selected from the group consisting of alkenyl, alkoxy, alkoxyalkoxy, alkyl, aryl, aryloxy, cycloalkylalkoxy, haloalkoxy, heteroaryl, hydroxyalkyl, $R_eR_fN$, -alkenyl-COOH and —C(O)$NR_eR_f$, $R_1$ is selected from the group consisting of alkoxyalkyl, alkyl, alkylsulfonylalkyl, aryl, arylalkyl, arylsulfonylalkyl, cycloalkyl, cycloalkylalkyl, heterocyclealkyl, heteroarylalkyl and ($R_aR_bN$)alkyl-; $R_a$, $R_b$, $R_e$, and $R_f$ are as described in the principal embodiment; and the aryl, aryl moiety of the arylalkyl, aryloxy, and arylsulfonylalkyl, cycloalkyl, cycloalkyl moiety of the cycloalkylalkyl and cycloalkylalkoxy, heterocycle moiety of the heterocylealkyl, heteroaryl and the heteroaryl moiety of the heteroarylalkyl as represented by $R_1$ and $R_5$ are each independently unsubstituted or substituted with substituents as defined in the principal embodiment and the definition of terms.

According to another embodiment of the present invention, there is disclosed a compound of formula (I), wherein $L_1$ is selected from the group consisting of —C(O)—NH—;

$R_1$ is selected from the group consisting of methoxymethyl, $C_1$-$C_6$ alkyl, ($C_1$-alkyl)-sulfonyl-($C_2$-$C_3$ alkyl)-, phenyl, aryl-($C_1$-$C_3$ alkyl)-, aryl-sulfonyl-($C_3$ alkyl)-, $C_3$-$C_6$ cycloalkyl, ($C_3$-$C_6$ cycloalkyl)($C_1$-$C_3$ alkyl)-, heterocycle-($C_1$-$C_3$ alkyl)-, heteroaryl-($C_1$-$C_3$ alkyl)- and ($R_aR_bN$)($C_1$-$C_3$ alkyl)- wherein $R_a$ is hydrogen and $R_b$ is monocyclic heteroaryl; and wherein the phenyl, aryl moiety of aryl-($C_1$-$C_3$ alkyl)- and aryl-sulfonyl-($C_3$ alkyl)-, the $C_3$-$C_6$ cycloalkyl, the cycloalkyl moiety of ($C_3$-$C_6$ cycloalkyl)($C_1$-$C_3$ alkyl)-, the heterocycle moiety of heterocycle-($C_1$-$C_3$ alkyl)-, the heteroaryl moiety of heteroaryl-($C_1$-$C_3$ alkyl)-, and the mocyclic heteroaryl represented by $R_b$ are each independently unsubstituted or substituted with substituents as described in the principal embodiment and the definition of terms;

$R_2$ is hydrogen;

$R_3$ is hydrogen;

$R_4$ is hydrogen, formyl or but-1-en-3-ynyl, or monocyclic heteroaryl which is unsubstituted or substituted with one or two substituents selected from the group consisting of $C_1$-$C_6$ alkyl, halo and haloalkyl; and $R_5$ is selected from the group consisting of $C_3$ alkenyl, $C_1$ alkoxy, $C_2$ alkoxy, $C_3$ alkoxy, $C_4$ alkoxy, 2-methoxyethoxy, $C_2$ alkyl, $C_3$ alkyl, $C_4$ alkyl, —$C_2$ alkenyl-COOH, —C(O)N(H)($C_3$ alkyl), 2-hydroxyethoxy, phenyl, bicyclic aryl, phenoxy, ($C_3$-$C_6$ cycloalkyl)methoxy-, 2,2,2-trifluoro-1-methylethoxy, monocyclic or bicyclic heteroaryl and $R_eR_fN$— wherein $R_e$ is hydrogen and $R_f$ is selected from the group consisting of $C_3$ alkyl, $C_3$-$C_5$ cycloalkyl, 2-hydroxy-1-methylethyl, —($C_3$ alkyl)-S-methyl, and monocyclic heterocycle; and wherein the phenyl, bicyclic aryl, phenyl moiety of the phenoxy, cycloalkyl moiety of the ($C_3$-$C_6$ cycloalkyl)methoxy-, monocyclic heteroaryl, bicyclic heteroaryl, and the monocyclic heterocycle as represented by $R_f$, are each independently unsubstituted or substituted as described in the principal embodiment and definition of terms.

According to another embodiment of the present invention, there is disclosed a compound of formula (I), wherein $L_1$ is selected from the group consisting of —C(O)—NH—;

$R_1$ is selected from the group consisting of methoxymethyl, methyl, ethyl, 1-methylethyl, propyl, 1,1-dimethylethyl, 2-methylpropyl, butyl, 2,2-dimethylpropyl, pentyl, methylsulfonylethyl-, methylsulfonylpropyl-, phenyl, benzyl, 1-phenylethyl-, 2-phenylethyl-, naphthylmethyl-, phenysulfonylpropyl-, cyclobutyl, cyclopentyl, cyclopentylmethyl-, cyclohexylmethyl-, piperidinylmethyl-, pyrrolidinylmethyl-, piperazinylethyl-, pyridinylmethyl-, 1H-benzimidazoylmethyl-, thienylmethyl-, 1,3-thiazolylmethyl-, 1H-imidazolylmethyl-, 1H-indolylethyl-, 1H-imidazolylpropyl-, and ($R_aR_bN$)ethyl- wherein $R_a$ is hydrogen and $R_b$ is pyridinyl; and wherein the phenyl, phenyl moiety of 1-phenylethyl-, 2-phenylethyl-, benzyl and phenysulfonylpropyl-, the naphthyl moiety of the naphthylmethyl-, cyclobutyl, cyclopentyl, cyclopentyl moiety of the cyclopentylmethyl-, cyclohexyl moiety of the cyclohexylmethyl-, piperidinyl moiety of the piperidinylmethyl-, pyrrolidinyl moiety of the pyrrolidinylmethyl-, piperazinyl moiety of the piperazinylethyl-, pyridinyl moiety of the pyridinylmethyl-, 1H-benzimidazoyl moiety of the 1H-benzimidazoylmethyl-, thienyl moiety of the thienylmethyl-, 1,3-thiazolyl moiety of the 1,3-thiazolylmethyl-, 1H-imidazolyl moiety of the 1H-imidazolylmethyl-, 1H-indolyl moiety of the 1H-indolylethyl-, 1H-imidazolyl moiety of the 1H-imidazolylpropyl-, and the pyridinyl represented by $R_b$ are each independently unsubstituted or substituted with substituents as described in the principal embodiment and the definition of terms;

$R_2$ is hydrogen;

$R_3$ is hydrogen;

$R_4$ is hydrogen, formyl, but-1-en-3-ynyl, unsubstituted pyridinyl or pyridinyl substituted with one or two substituents selected from the group consisting of methyl, ethyl, propyl and trifluoromethyl; and $R_5$ is selected from the group consisting of prop-1-enyl, methoxy, ethoxy, isopropoxy, isobutoxy, butoxy, 2-methoxyethoxy, ethyl, propyl, isobutyl, -ethenyl-COOH, —C(O)N(H)(isopropyl), 2-hydroxyethoxy, phenyl, naphthyl, phenoxy, cyclopentylmethoxy, cyclopropylmethoxy, 2,2,2-trifluoro-1-methylethoxy, thienyl, benzofuranyl, pyridinyl, and R$_e$R$_f$N— wherein R$_e$ is hydrogen and R$_f$ is selected from the group consisting of isopropyl, cyclopropyl, cyclobutyl, cyclopentyl, 2-hydroxy-1-methylethyl, -(propyl)-S-methyl, and pyrrolidinyl; and wherein the phenyl, naphthyl, phenyl moiety of phenoxy, cyclopentyl moiety of the cyclopentyl-methoxy, cyclopropyl moiety of the cyclopropylmethoxy, thienyl, benzofuranyl, pyridinyl, and the cyclopropyl, cyclobutyl, cyclopentyl and pyrrolidinyl as represented by R$_f$, are each independently unsubstituted or substituted as described in the principal embodiment and definition of terms.

According to another embodiment of the present invention, there is disclosed a compound of formula (I), wherein L$_1$ is selected from the group consisting of —NH—C(O)—;

R$_1$ is selected from the group consisting of methoxymethyl, C$_1$-C$_6$ alkyl, (C$_1$-alkyl)-sulfonyl-(C$_2$-C$_3$ alkyl)-, phenyl, aryl-(C$_1$-C$_3$ alkyl)-, aryl-sulfonyl-(C$_3$ alkyl)-, C$_3$-C$_6$ cycloalkyl, (C$_3$-C$_6$ cycloalkyl)(C$_1$-C$_3$ alkyl)-, heterocycle-(C$_1$-C$_3$ alkyl)-, heteroaryl-(C$_1$-C$_3$ alkyl)- and (R$_a$R$_b$N)(C$_1$-C$_3$ alkyl)- wherein R$_a$ is hydrogen and R$_b$ is monocyclic heteroaryl; and wherein the phenyl, aryl moiety of aryl-(C$_1$-C$_3$ alkyl)- and aryl-sulfonyl-(C$_3$ alkyl)-, the C$_3$-C$_6$ cycloalkyl, the cycloalkyl moiety of (C$_3$-C$_6$ cycloalkyl)(C$_1$-C$_3$ alkyl)-, the heterocycle moiety of heterocycle-(C$_1$-C$_3$ alkyl)-, the heteroaryl moiety of heteroaryl-(C$_1$-C$_3$ alkyl)-, and the mocyclic heteroaryl represented by R$_b$ are each independently unsubstituted or substituted with substituents as described in the principal embodiment and the definition of terms;

R$_2$ is hydrogen;

R$_3$ is hydrogen;

R$_4$ is hydrogen, formyl or but-1-en-3-ynyl or monocyclic heteroaryl which is unsubstituted or substituted with one or two substituents selected from the group consisting of C$_1$-C$_6$ alkyl, halo and haloalkyl; and R$_5$ is selected from the group consisting of C$_3$ alkenyl, C$_1$ alkoxy, C$_2$ alkoxy, C$_3$ alkoxy, C$_4$ alkoxy, 2-methoxyethoxy, C$_2$ alkyl, C$_3$ alkyl, C$_4$ alkyl, —C$_2$ alkenyl-COOH, —C(O)N(H)(C$_3$ alkyl), 2-hydroxyethoxy, phenyl, bicyclic aryl, phenoxy, (C$_3$-C$_6$ cycloalkyl)methoxy-, 2,2,2-trifluoro-1-methylethoxy, monocyclic or bicyclic heteroaryl and R$_e$R$_f$N— wherein R$_e$ is hydrogen and R$_f$ is selected from the group consisting of C$_3$ alkyl, C$_3$-C$_5$ cycloalkyl, 2-hydroxy-1-methylethyl, —(C$_3$ alkyl)-S-methyl, and monocyclic heterocycle; and wherein the phenyl, bicyclic aryl, phenyl moiety of the phenoxy, cycloalkyl moiety of the (C$_3$-C$_6$ cycloalkyl)methoxy-, monocyclic heteroaryl, bicyclic heteroaryl, and the monocyclic heterocycle as represented by R$_f$, are each independently unsubstituted or substituted as described in the principal embodiment and definition of terms.

According to another embodiment of the present invention, there is disclosed a compound of formula (I), wherein L$_1$ is selected from the group consisting of —NH—C(O)—;

R$_1$ is selected from the group consisting of methoxymethyl, methyl, ethyl, 1-methylethyl, propyl, 1,1-dimethylethyl, 2-methylpropyl, butyl, 2,2-dimethylpropyl, pentyl, methylsulfonylethyl-, methylsulfonylpropyl-, phenyl, benzyl, 1-phenylethyl-, 2-phenylethyl-, naphthylmethyl-, phenysulfonylpropyl-, cyclobutyl, cyclopentyl, cyclopentylmethyl-, cyclohexylmethyl-, piperidinylmethyl-, pyrrolidinylmethyl-, piperazinylethyl-, pyridinylmethyl-, 1H-benzimidazoylmethyl-, thienylmethyl-, 1,3-thiazolylmethyl-, 1H-imidazolylmethyl-, 1H-indolylethyl-, 1H-imidazolylpropyl-, and (R$_a$R$_b$N)ethyl- wherein R$_a$ is hydrogen and R$_b$ is pyridinyl; and wherein the phenyl, phenyl moiety of 1-phenylethyl-, 2-phenylethyl-, benzyl and phenysulfonylpropyl-, the naphthyl moiety of the naphthylmethyl-, cyclobutyl, cyclopentyl, cyclopentyl moiety of the cyclopentylmethyl-, cyclohexyl moiety of the cyclohexylmethyl-, piperidinyl moiety of the piperidinylmethyl-, pyrrolidinyl moiety of the pyrrolidinylmethyl-, piperazinyl moiety of the piperazinylethyl-, pyridinyl moiety of the pyridinylmethyl-, 1H-benzimidazoyl moiety of the 1H-benzimidazoylmethyl-, thienyl moiety of the thienylmethyl-, 1,3-thiazolyl moiety of the 1,3-thiazolylmethyl-, 1H-imidazolyl moiety of the 1H-imidazolylmethyl-, 1H-indolyl moiety of the 1H-indolylethyl-, 1H-imidazolyl moiety of the 1H-imidazolylpropyl-, and the pyridinyl represented by R$_b$ are each independently unsubstituted or substituted with substituents as described in the principal embodiment and the definition of terms;

R$_2$ is hydrogen;

R$_3$ is hydrogen;

R$_4$ is hydrogen, formyl, but-1-en-3-ynyl, unsubstituted pyridinyl, or pyridinyl substituted with one or two substituents selected from the group consisting of methyl, ethyl, propyl and trifluoromethyl; and R$_5$ is selected from the group consisting of prop-1-enyl, methoxy, ethoxy, isopropoxy, isobutoxy, butoxy, 2-methoxyethoxy, ethyl, propyl, isobutyl, -ethenyl-COOH, —C(O)N(H)(isopropyl), 2-hydroxyethoxy, phenyl, naphthyl, phenoxy, cyclopentylmethoxy, cyclopropylmethoxy, 2,2,2-trifluoro-1-methylethoxy, thienyl, benzofuranyl, pyridinyl, and R$_e$R$_f$N— wherein R$_e$ is hydrogen and R$_f$ is selected from the group consisting of isopropyl, cyclopropyl, cyclobutyl, cyclopentyl, 2-hydroxy-1-methylethyl, -(propyl)-S-methyl, and pyrrolidinyl; and wherein the phenyl, naphthyl, phenyl moiety of phenoxy, cyclopentyl moiety of the cyclopentylmethoxy, cyclopropyl moiety of the cyclopropylmethoxy, thienyl, benzofuranyl, pyridinyl, and the cyclopropyl, cyclobutyl, cyclopentyl and pyrrolidinyl as represented by R$_f$, are each independently unsubstituted or substituted as described in the principal embodiment and definition of terms. Exemplary compounds of formula (I) include, but are not limited to, N-(4-Amino-5-cyano-6-ethoxy-pyridin-2-yl)-acetamide;
N-(4-amino-5-cyano-6-ethoxypyridin-2-yl)cyclopentanecarboxamide;
N-(4-amino-5-cyano-6-ethoxypyridin-2-yl)pentanamide;
N-(4-amino-5-cyano-6-ethoxypyridin-2-yl)benzamide;
N-(4-amino-5-cyano-6-ethoxypyridin-2-yl)cyclobutanecarboxamide;
N-(4-amino-5-cyano-6-ethoxypyridin-2-yl)butanamide;
N-(4-amino-5-cyano-6-ethoxypyridin-2-yl)-3-methylbutanamide;
N-(4-amino-5-cyano-6-ethoxypyridin-2-yl)hexanamide;
N-(4-amino-6-butoxy-5-cyanopyridin-2-yl)acetamide;
N-(4-amino-5-cyano-6-methoxypyridin-2-yl)acetamide;
N-(4-amino-5-cyano-6-ethoxypyridin-2-yl)-2-phenylacetamide;
N-(4-amino-5-cyano-6-ethoxypyridin-2-yl)-3-phenylpropanamide;
N-(4-amino-5-cyano-6-ethoxypyridin-2-yl)propanamide;
N-(4-amino-5-cyano-6-ethoxypyridin-2-yl)-2-methylpropanamide;
N-(4-amino-5-cyano-6-ethoxypyridin-2-yl)-2,2-dimethylpropanamide;
N-(4-amino-5-cyano-6-phenoxypyridin-2-yl)acetamide;
N-(4-amino-5-cyano-6-isopropoxypyridin-2-yl)acetamide;
N-(4-amino-5-cyano-6-ethoxypyridin-2-yl)-2-methoxyacetamide;
N-(4-amino-5-cyano-6-ethoxypyridin-2-yl)-2-(3-methoxyphenyl)acetamide;

N-(4-amino-5-cyano-6-ethoxypyridin-2-yl)-2-(4-methoxyphenyl)acetamide;
N-(4-amino-5-cyano-6-ethoxypyridin-2-yl)-2-(2-fluorophenyl)acetamide;
N-(4-amino-5-cyano-6-ethoxypyridin-2-yl)-2-(4-fluorophenyl)acetamide;
N-(4-amino-5-cyano-6-ethoxypyridin-2-yl)-2-(2-chlorophenyl)acetamide;
N-(4-amino-5-cyano-6-ethoxypyridin-2-yl)-2-(4-chlorophenyl)acetamide;
N-(4-amino-5-cyano-6-ethoxypyridin-2-yl)-2-(2-bromophenyl)acetamide;
N-(4-amino-5-cyano-6-ethoxypyridin-2-yl)-2-(3-bromophenyl)acetamide;
N-(4-amino-5-cyano-6-ethoxypyridin-2-yl)-2-(4-bromophenyl)acetamide;
N-(4-amino-5-cyano-6-ethoxypyridin-2-yl)-2-(2-methylphenyl)acetamide;
N-(4-amino-5-cyano-6-ethoxypyridin-2-yl)-2-(3-methylphenyl)acetamide;
N-(4-amino-5-cyano-6-ethoxypyridin-2-yl)-2-(4-methylphenyl)acetamide;
N-(4-amino-5-cyano-6-ethoxypyridin-2-yl)-2-(2-methoxyphenyl)acetamide;
N-(4-amino-5-cyano-6-ethoxypyridin-2-yl)-2-(2,5-difluorophenyl)acetamide;
N-(4-amino-5-cyano-6-ethoxypyridin-2-yl)-2-(3-fluorophenyl)acetamide;
N-(4-amino-5-cyano-6-ethoxypyridin-2-yl)-2-(3-chlorophenyl)acetamide;
N-(4-amino-5-cyano-6-ethoxypyridin-2-yl)-2-(2-nitrophenyl)acetamide;
N-(4-amino-5-cyano-6-ethoxypyridin-2-yl)-2-(2,4-dichlorophenyl)acetamide;
N-(4-amino-5-cyano-6-ethoxypyridin-2-yl)-2-(3-nitrophenyl)acetamide;
N-(4-amino-5-cyano-6-ethoxypyridin-2-yl)-2-(4-nitrophenyl)acetamide;
N-(4-amino-5-cyano-6-ethoxypyridin-2-yl)-2-[3-(trifluoromethyl)phenyl]acetamide;
N-(4-amino-5-cyano-6-ethoxypyridin-2-yl)-2-[4-(benzyloxy)phenyl]acetamide;
N-(4-amino-5-cyano-6-ethoxypyridin-2-yl)-2-(1-naphthyl)acetamide;
N-(4-amino-5-cyano-6-ethoxypyridin-2-yl)-2-(2-naphthyl)acetamide;
N-(4-amino-5-cyano-6-ethoxypyridin-2-yl)-2-(2,5-dimethylphenyl)acetamide;
N-(4-amino-5-cyano-6-ethoxypyridin-2-yl)-2-(3,5-dimethylphenyl)acetamide;
N-(4-amino-5-cyano-6-ethoxypyridin-2-yl)-2-(2,4-dimethoxyphenyl)acetamide;
N-(4-amino-5-cyano-6-ethoxypyridin-2-yl)-2-(2,5-dimethoxyphenyl)acetamide;
N-(4-amino-5-cyano-6-ethoxypyridin-2-yl)-2-(3,4-dimethoxyphenyl)acetamide;
N-(4-amino-5-cyano-6-ethoxypyridin-2-yl)-2-(3,5-dimethoxyphenyl)acetamide;
N-(4-amino-5-cyano-6-ethoxypyridin-2-yl)-2-(1,3-benzodioxol-5-yl)acetamide;
N-(4-amino-5-cyano-6-ethoxypyridin-2-yl)-2-(2,3-difluorophenyl)acetamide;
N-(4-amino-5-cyano-6-ethoxypyridin-2-yl)-2-(1,1'-biphenyl-4-yl)acetamide;
N-(4-amino-5-cyano-6-ethoxypyridin-2-yl)-2-[4-(dimethylamino)phenyl]acetamide;
N-(4-amino-5-cyano-6-ethoxypyridin-2-yl)-2-[4-(trifluoromethyl)phenyl]acetamide;
N-(4-amino-5-cyano-6-ethoxypyridin-2-yl)-2-[4-(trifluoromethoxy)phenyl]acetamide;
N-(4-amino-5-cyano-6-ethoxypyridin-2-yl)-2-(4-phenoxyphenyl)acetamide;
N-(4-amino-5-cyano-6-ethoxypyridin-2-yl)-2-(3,4,5-trimethoxyphenyl)acetamide;
N-(4-amino-5-cyano-6-ethoxypyridin-2-yl)-3,3-dimethylbutanamide;
N-(4-amino-5-cyano-6-ethoxypyridin-2-yl)-2-(2,3-dimethoxyphenyl)acetamide;
N-(4-amino-5-cyano-6-ethoxypyridin-2-yl)-2-thien-2-ylacetamide;
N-(4-amino-5-cyano-6-isopropoxypyridin-2-yl)-2-(2,5-dimethoxyphenyl)acetamide;
N-[4-amino-5-cyano-6-(2-methoxyethoxy)pyridin-2-yl]-2-(2,5-dimethoxyphenyl)acetamide;
N-[4-amino-5-cyano-6-(2-hydroxyethoxy)pyridin-2-yl]-2-(2,5-dimethoxyphenyl)acetamide;
N-(4-amino-5-cyano-6-ethoxypyridin-2-yl)-2-cyclohexylacetamide;
N-(4-amino-5-cyano-6-ethoxypyridin-2-yl)-2-cyclopentylacetamide;
N-(4-amino-5-cyano-6-phenylpyridin-2-yl)acetamide;
N-(4-amino-5-cyano-6-propylpyridin-2-yl)acetamide;
N-(4-amino-5-cyano-6-isobutylpyridin-2-yl)-2-(3-methoxyphenyl)acetamide;
N-(4-amino-5-cyano-6-propylpyridin-2-yl)-2-(2,5-dimethoxyphenyl)acetamide;
N-(4-amino-5-cyano-6-phenylpyridin-2-yl)-2-(2,5-dimethoxyphenyl)acetamide;
N-[4-amino-5-cyano-6-(4-methylphenoxy)pyridin-2-yl]acetamide;
N-[4-amino-5-cyano-6-(4-phenoxyphenoxy)pyridin-2-yl]acetamide;
N-{4-amino-5-cyano-6-[4-(1H-pyrrol-1-yl)phenoxy]pyridin-2-yl}acetamide;
N-[4-amino-6-(4-benzylphenoxy)-5-cyanopyridin-2-yl]acetamide;
N-[4-amino-6-(4-tert-butylphenoxy)-5-cyanopyridin-2-yl]acetamide;
N-(4-{[6-(acetylamino)-4-amino-3-cyanopyridin-2-yl]oxy}phenyl)acetamide;
N-[4-amino-5-cyano-6-(4-propoxyphenoxy)pyridin-2-yl]acetamide;
N-[4-amino-5-cyano-6-(4-ethoxyphenoxy)pyridin-2-yl]acetamide;
N-[4-amino-5-cyano-6-(3-methylphenyl)pyridin-2-yl]acetamide;
methyl 4-[6-(acetylamino)₄-amino-3-cyanopyridin-2-yl]benzoate;
N-[4-amino-5-cyano-6-(3-methoxyphenyl)pyridin-2-yl]acetamide;
N-[4-amino-5-cyano-6-(4-methoxyphenyl)pyridin-2-yl]acetamide;
N-[4-amino-6-(3-chlorophenyl)-5-cyanopyridin-2-yl]acetamide;
N-[4-amino-6-(4-chlorophenyl)-5-cyanopyridin-2-yl]acetamide;
N-[4-amino-5-cyano-6-(3-cyanophenyl)pyridin-2-yl]acetamide;
N-[4-amino-5-cyano-6-(4-cyanophenyl)pyridin-2-yl]acetamide;
N-[6-(3-acetylphenyl)-4-amino-5-cyanopyridin-2-yl]acetamide;

N-[4-amino-5-cyano-6-(4-phenoxyphenyl)pyridin-2-yl]acetamide;
N-[6-(4-acetylphenyl)-4-amino-5-cyanopyridin-2-yl]acetamide;
N-{4-amino-5-cyano-6-[4-(trifluoromethoxy)phenyl]pyridin-2-yl}acetamide;
N-[4-amino-5-cyano-6-(3,4-dimethylphenyl)pyridin-2-yl]acetamide;
N-[4-amino-5-cyano-6-(3,5-dimethylphenyl)pyridin-2-yl]acetamide;
N-[4-amino-5-cyano-6-(2,4-dimethoxyphenyl)pyridin-2-yl]acetamide;
N-(4-amino-5-cyano-6-thien-2-ylpyridin-2-yl)acetamide;
N-(4-amino-5-cyano-6-thien-3-ylpyridin-2-yl)acetamide;
N-[4-amino-6-(1-benzofuran-2-yl)-5-cyanopyridin-2-yl]acetamide;
N-[6-(5-acetylthien-2-yl)-4-amino-5-cyanopyridin-2-yl]acetamide;
N-[4-amino-5-cyano-6-(2-naphthyl)pyridin-2-yl]acetamide;
N-(4-amino-3-cyano-2,3'-bipyridin-6-yl)acetamide;
N-[4-amino-5-cyano-6-(3,4-dihydro-2H-1,5-benzodioxepin-7-yl)pyridin-2-yl]acetamide;
N-{4-amino-5-cyano-6-[4-(methylsulfonyl)phenyl]pyridin-2-yl}acetamide;
N-(4-amino-5-cyano-6-ethylpyridin-2-yl)acetamide;
4-azido-5-cyano-N-(2,5-dimethoxybenzyl)-6-isopropoxy-pyridine-2-carboxamide;
4-amino-5-cyano-N-(2,5-dimethoxybenzyl)-6-isopropoxy-pyridine-2-carboxamide;
4-amino-5-cyano-N-(2,5-dimethoxybenzyl)-6-ethoxypyridine-2-carboxamide;
4-amino-5-cyano-6-ethoxy-N-(1-phenylethyl)pyridine-2-carboxamide;
4-amino-5-cyano-6-ethoxy-N-(pyridin-4-ylmethyl)pyridine-2-carboxamide;
4-amino-5-cyano-6-ethoxy-N-(pyridin-3-ylmethyl)pyridine-2-carboxamide;
4-amino-5-cyano-6-ethoxy-N-(pyridin-2-ylmethyl)pyridine-2-carboxamide;
4-amino-N-benzyl-5-cyano-6-ethoxypyridine-2-carboxamide;
4-amino-5-cyano-6-ethoxy-N-(2-methylbenzyl)pyridine-2-carboxamide;
4-amino-5-cyano-6-ethoxy-N-(3-methylbenzyl)pyridine-2-carboxamide;
4-amino-5-cyano-6-ethoxy-N-(4-methylbenzyl)pyridine-2-carboxamide;
4-amino-N-(2-aminobenzyl)-5-cyano-6-ethoxypyridine-2-carboxamide;
4-amino-N-(3-aminobenzyl)-5-cyano-6-ethoxypyridine-2-carboxamide;
4-amino-N-(4-aminobenzyl)-5-cyano-6-ethoxypyridine-2-carboxamide;
4-amino-5-cyano-6-ethoxy-N-{4-[(trifluoromethyl)thio]benzyl}pyridine-2-carboxamide;
4-amino-5-cyano-6-ethoxy-N-[3-fluoro-5-(trifluoromethyl)benzyl]pyridine-2-carboxamide;
methyl 4-({[(4-amino-5-cyano-6-ethoxypyridin-2-yl)carbonyl]amino}methyl)benzoate;
4-amino-5-cyano-6-ethoxy-N-(2-methoxybenzyl)pyridine-2-carboxamide;
4-amino-5-cyano-6-ethoxy-N-(3-methoxybenzyl)pyridine-2-carboxamide;
4-amino-5-cyano-6-ethoxy-N-(4-methoxybenzyl)pyridine-2-carboxamide;
4-amino-5-cyano-6-ethoxy-N-(2-fluorobenzyl)pyridine-2-carboxamide;
4-amino-5-cyano-6-ethoxy-N-(3-fluorobenzyl)pyridine-2-carboxamide;
4-amino-5-cyano-6-ethoxy-N-(4-fluorobenzyl)pyridine-2-carboxamide;
4-amino-N-(2-chlorobenzyl)-5-cyano-6-ethoxypyridine-2-carboxamide;
4-amino-N-(3-chlorobenzyl)-5-cyano-6-ethoxypyridine-2-carboxamide;
4-amino-N-(4-chlorobenzyl)-5-cyano-6-ethoxypyridine-2-carboxamide;
4-amino-N-(2-bromobenzyl)-S-cyano-6-ethoxypyridine-2-carboxamide;
4-amino-N-(3-bromobenzyl)-5-cyano-6-ethoxypyridine-2-carboxamide;
4-Amino-5-cyano-6-ethoxy-pyridine-2-carboxylic acid 3-nitro-benzylamide;
4-Amino-5-cyano-6-ethoxy-pyridine-2-carboxylic acid 4-nitro-benzylamide;
4-amino-5-cyano-6-ethoxy-N-[4-(trifluoromethoxy)benzyl]pyridine-2-carboxamide;
4-amino-5-cyano-N-[4-(dimethylamino)benzyl]-6-ethoxypyridine-2-carboxamide;
4-amino-5-cyano-6-ethoxy-N-[3-(trifluoromethyl)benzyl]pyridine-2-carboxamide;
4-amino-5-cyano-6-ethoxy-N-[4-(trifluoromethyl)benzyl]pyridine-2-carboxamide;
4-amino-5-cyano-6-ethoxy-N-[3-(trifluoromethoxy)benzyl]pyridine-2-carboxamide;
4-amino-5-cyano-6-ethoxy-N-(1-naphthylmethyl)pyridine-2-carboxamide;
4-amino-N-(4-tert-butylbenzyl)-S-cyano-6-ethoxypyridine-2-carboxamide;
4-amino-5-cyano-N-(2,3-dimethylbenzyl)-6-ethoxypyridine-2-carboxamide;
4-amino-5-cyano-N-(2,4-dimethylbenzyl)-6-ethoxypyridine-2-carboxamide;
4-amino-5-cyano-N-(2,5-dimethylbenzyl)-6-ethoxypyridine-2-carboxamide;
4-amino-5-cyano-N-(3,4-dimethylbenzyl)-6-ethoxypyridine-2-carboxamide;
4-amino-5-cyano-N-(3,5-dimethylbenzyl)-6-ethoxypyridine-2-carboxamide;
4-amino-5-cyano-N-(2,3-dimethoxybenzyl)-6-ethoxypyridine-2-carboxamide;
4-amino-5-cyano-N-(2,4-dimethoxybenzyl)-6-ethoxypyridine-2-carboxamide;
4-amino-5-cyano-N-(3,4-dimethoxybenzyl)-6-ethoxypyridine-2-carboxamide;
4-amino-5-cyano-N-(3,5-dimethoxybenzyl)-6-ethoxypyridine-2-carboxamide;
4-amino-N-(1,3-benzodioxol-5-ylmethyl)-5-cyano-6-ethoxypyridine-2-carboxamide;
4-amino-5-cyano-6-ethoxy-N-(3,4,5-trimethoxybenzyl)pyridine-2-carboxamide;
4-amino-5-cyano-N-(2,3-dichlorobenzyl)-6-ethoxypyridine-2-carboxamide;
4-amino-5-cyano-N-(2,4-dichlorobenzyl)-6-ethoxypyridine-2-carboxamide;
4-amino-5-cyano-N-(2,5-dichlorobenzyl)-6-ethoxypyridine-2-carboxamide;
4-amino-5-cyano-N-(3,5-dichlorobenzyl)-6-ethoxypyridine-2-carboxamide;
5-cyano-N-(2,5-dimethoxybenzyl)-6-ethoxypyridine-2-carboxamide;
4-amino-N-[2-(aminosulfonyl)benzyl]-5-cyano-6-ethoxypyridine-2-carboxamide;

4-amino-5-cyano-N-{2-[(dimethylamino)sulfonyl]benzyl}-6-ethoxypyridine-2-carboxamide;
methyl 3-[5-({[(4-amino-5-cyano-6-ethoxypyridin-2-yl)carbonyl]amino}methyl)pyridin-2-yl]benzoate;
4-amino-5-cyano-6-ethoxy-N-[4-(phenylsulfinyl)benzyl]pyridine-2-carboxamide;
4-amino-5-cyano-6-ethoxy-N-[(6-{4-[(methylamino)carbonyl]phenyl}pyridin-3-yl)methyl]pyridine-2-carboxamide;
4-amino-5-cyano-6-isopropoxy-N-[4-(methylsulfonyl)benzyl]pyridine-2-carboxamide;
methyl 4-[5-({[(4-amino-5-cyano-6-ethoxypyridin-2-yl)carbonyl]amino}methyl)pyridin-2-yl]benzoate;
4-amino-N-[2-(aminosulfonyl)benzyl]-5-chloro-6-ethoxypyridine-2-carboxamide;
4-amino-5-cyano-6-ethoxy-N-[4-(1,2,3-thiadiazol-5-yl)benzyl]pyridine-2-carboxamide;
4-amino-5-cyano-N-(4-cyanobenzyl)-6-ethoxypyridine-2-carboxamide;
N-(4-amino-5-cyano-6-ethoxypyridin-2-yl)-2-(4-amino-2,5-dimethoxyphenyl)acetamide;
4-amino-5-cyano-6-ethoxy-N-[(6-methoxypyridin-3-yl)methyl]pyridine-2-carboxamide;
N-(4-amino-5-cyano-6-ethoxypyridin-2-yl)-2-[2-methoxy-5-(methylthio)phenyl]acetamide;
4-amino-5-cyano-6-ethoxy-N-{4-[(2-hydroxyethyl)sulfonyl]benzyl}pyridine-2-carboxamide;
4-amino-N-[2-(aminosulfonyl)benzyl]-5-chloro-6-isopropoxypyridine-2-carboxamide;
4-amino-5-cyano-6-ethoxy-N-[4-(phenylsulfonyl)benzyl]pyridine-2-carboxamide;
4-amino-5-cyano-6-ethoxy-N-[(6-piperidin-1-ylpyridin-3-yl)methyl]pyridine-2-carboxamide;
4-amino-5-cyano-6-ethoxy-N-[4-(isopropylsulfonyl)benzyl]pyridine-2-carboxamide;
4-amino-5-cyano-6-ethoxy-N-[4-(methylsulfonyl)benzyl]pyridine-2-carboxamide;
2-[4-(acetylamino)-2,5-dimethoxyphenyl]-N-(4-amino-5-cyano-6-ethoxypyridin-2-yl)acetamide;
4-amino-5-cyano-N-{4-[(dimethylamino)sulfonyl]benzyl}-6-ethoxypyridine-2-carboxamide;
4-amino-5-cyano-N-{[6-(3,5-dimethoxyphenyl)pyridin-3-yl]methyl}-6-ethoxypyridine-2-carboxamide;
4-amino-5-cyano-6-ethoxy-N-[4-(methylsulfonyl)-3-(trifluoromethyl)benzyl]pyridine-2-carboxamide;
4-amino-5-cyano-6-(cyclopentylmethoxy)-N-[4-(methylsulfonyl)benzyl]pyridine-2-carboxamide;
4-amino-5-cyano-6-(isopropylamino)-N-[4-(methylsulfonyl)benzyl]pyridine-2-carboxamide;
4-amino-5-cyano-6-ethoxy-N-[4-(ethylsulfonyl)benzyl]pyridine-2-carboxamide;
4-amino-5-chloro-6-ethoxy-N-[4-(methylsulfonyl)benzyl]pyridine-2-carboxamide;
4-amino-N-[(6-chloropyridin-3-yl)methyl]-5-cyano-6-ethoxypyridine-2-carboxamide;
4-amino-5-cyano-6-(cyclopropylmethoxy)-N-[4-(methylsulfonyl)benzyl]pyridine-2-carboxamide;
4-amino-5-chloro-6-isopropoxy-N-[4-(methylsulfonyl)benzyl]pyridine-2-carboxamide;
4-amino-5-cyano-6-ethoxy-N-{4-[2-(methylamino)-2-oxoethoxy]benzyl}pyridine-2-carboxamide;
4-amino-5-cyano-6-(cyclopentylamino)-N-[4-(methylsulfonyl)benzyl]pyridine-2-carboxamide;
4-amino-N-(1H-benzimidazol-2-ylmethyl)-5-cyano-6-ethoxypyridine-2-carboxamide;
4-amino-5-cyano-6-ethoxy-N-(4-morpholin-4-ylbenzyl)pyridine-2-carboxamide;
4-amino-5-cyano-N-[4-(methylsulfonyl)benzyl]-6-thien-3-ylpyridine-2-carboxamide;
4-amino-5-cyano-6-(cyclobutylamino)-N-[4-(methylsulfonyl)benzyl]pyridine-2-carboxamide;
methyl 4-{[4-({[(4-amino-5-cyano-6-ethoxypyridin-2-yl)carbonyl]amino}methyl)piperidin-1-yl]carbonyl}benzoate;
4-amino-5-cyano-6-ethoxy-N-{[6-(trifluoromethyl)pyridin-3-yl]methyl}pyridine-2-carboxamide;
methyl 1-[5-({[(4-amino-5-cyano-6-ethoxypyridin-2-yl)carbonyl]amino}methyl)pyridin-2-yl]piperidine-4-carboxylate;
N-(4-amino-5-cyano-6-isopropoxypyridin-2-yl)-2-[2,5-dimethoxy-4-(methylsulfonyl)phenyl]acetamide;
4-amino-5-cyano-6-ethoxy-N-(4-fluoro-3-methoxybenzyl)pyridine-2-carboxamide;
4-amino-5-cyano-6-ethoxy-N-[4-({[4-(methylsulfonyl)phenyl]amino}methyl)benzyl]pyridine-2-carboxamide;
N-[4-({[(4-amino-5-cyano-6-ethoxypyridin-2-yl)carbonyl]amino}methyl)phenyl]glycinamide;
4-amino-5-cyano-6-isobutoxy-N-[4-(methylsulfonyl)benzyl]pyridine-2-carboxamide;
N-[4-(acetylamino)benzyl]-4-amino-5-cyano-6-ethoxypyridine-2-carboxamide;
4-amino-5-cyano-6-ethoxy-N-[2-methoxy-4-(methylsulfonyl)benzyl]pyridine-2-carboxamide;
4-amino-N-[4-(aminosulfonyl)benzyl]-5-cyano-6-ethoxypyridine-2-carboxamide;
4-amino-5-cyano-6-ethoxy-N-{2-[(S-nitropyridin-2-yl)amino]ethyl}pyridine-2-carboxamide;
4-amino-5-cyano-6-ethoxy-N-({6-[3-(methylsulfonyl)phenyl]pyridin-3-yl}methyl)pyridine-2-carboxamide;
4-amino-5-cyano-6-ethoxy-N-[2-(methylthio)benzyl]pyridine-2-carboxamide;
methyl N-{[4-({[(4-amino-5-cyano-6-ethoxypyridin-2-yl)carbonyl]amino}methyl)phenyl]sulfonyl}glycinate;
4-amino-5-cyano-6-ethoxy-N-(4-hydroxybenzyl)pyridine-2-carboxamide;
4-amino-5-cyano-6-ethoxy-N-[(1-pyrimidin-2-ylpiperidin-4-yl)methyl]pyridine-2-carboxamide;
4-amino-5-cyano-6-ethoxy-N-{[6-(methylsulfonyl)pyridin-3-yl]methyl}pyridine-2-carboxamide;
4-amino-5-cyano-6-ethoxy-N-{[6-(methylthio)pyridin-3-yl]methyl}pyridine-2-carboxamide;
4-amino-5-cyano-6-ethoxy-N-[4-(isopropylsulfinyl)benzyl]pyridine-2-carboxamide;
4-amino-5-cyano-N-[4-(methylsulfonyl)benzyl]-6-[(1E)-prop-1-enyl]pyridine-2-carboxamide;
tert-butyl N-{[4-({[(4-amino-5-cyano-6-ethoxypyridin-2-yl)carbonyl]amino}methyl)phenyl]sulfonyl}-β-alaninate;
4-amino-5-cyano-6-ethoxy-N-[(6-methylpyridin-3-yl)methyl]pyridine-2-carboxamide;
4-amino-N-{2-[(tert-butylamino)sulfonyl]benzyl}-5-cyano-6-ethoxypyridine-2-carboxamide;
N-(4-amino-5-cyano-6-ethoxypyridin-2-yl)-2-{2,5-dimethoxy-4-[(methylsulfonyl)amino]phenyl}acetamide;
4-amino-5-cyano-6-ethoxy-N-[2-(methylsulfonyl)benzyl]pyridine-2-carboxamide;
4-amino-5-cyano-6-ethoxy-N-(4-propionylbenzyl)pyridine-2-carboxamide;
4-amino-5-cyano-6-ethoxy-N-[(5-methylpyridin-3-yl)methyl]pyridine-2-carboxamide;
4-amino-5-cyano-N-{4-[2-(dimethylamino)-2-oxoethoxy]benzyl}-6-ethoxypyridine-2-carboxamide;
4-amino-5-cyano-N-[4-(phenylsulfonyl)benzyl]-6-thien-3-ylpyridine-2-carboxamide;

4-amino-5-bromo-6-ethoxy-N-[4-(methylsulfonyl)benzyl]pyridine-2-carboxamide;
4-amino-5-cyano-6-ethoxy-N-(3-hydroxybenzyl)pyridine-2-carboxamide;
4-amino-N-[4-(2-amino-2-oxoethoxy)benzyl]-5-cyano-6-ethoxypyridine-2-carboxamide;
N-(4-amino-5-cyano-6-ethoxypyridin-2-yl)-2-[2-methoxy-5-(methylsulfonyl)phenyl]acetamide;
4-amino-5-cyano-6-ethoxy-N-[3-(methylsulfonyl)benzyl]pyridine-2-carboxamide;
benzyl 4-({[(4-amino-5-cyano-6-ethoxypyridin-2-yl)carbonyl]amino}methyl)piperidine-1-carboxylate;
4-amino-5-cyano-6-ethoxy-N-(4-ethoxybenzyl)pyridine-2-carboxamide;
4-amino-5-cyano-6-ethoxy-N-{4-[(methylamino)carbonyl]benzyl}pyridine-2-carboxamide;
4-[5-({[(4-amino-5-cyano-6-ethoxypyridin-2-yl)carbonyl]amino}methyl)pyridin-2-yl]benzoic acid;
4-amino-5-cyano-6-ethoxy-N-[(6-{3-[(methylamino)carbonyl]phenyl}pyridin-3-yl)methyl]pyridine-2-carboxamide;
4-amino-5-cyano-6-ethoxy-N-[(6-phenylpyridin-3-yl)methyl]pyridine-2-carboxamide;
4-amino-5-cyano-6-ethoxy-N-({6-[4-(methylsulfonyl)phenyl]pyridin-3-yl}methyl)pyridine-2-carboxamide;
methyl 3-{[4-({[(4-amino-5-cyano-6-ethoxypyridin-2-yl)carbonyl]amino}methyl)piperidin-1-yl]carbonyl}benzoate;
4-amino-N-[(5-chlorothien-2-yl)methyl]-5-cyano-6-ethoxypyridine-2-carboxamide;
4-amino-5-cyano-6-(cyclopropylamino)-N-[4-(methylsulfonyl)benzyl]pyridine-2-carboxamide;
4-amino-6-ethoxy-5-iodo-N-[4-(methylsulfonyl)benzyl]pyridine-2-carboxamide;
tert-butyl 3-{[4-amino-3-cyano-6-({[4-(methylsulfonyl)benzyl]amino}carbonyl)pyridin-2-yl]amino}pyrrolidine-1-carboxylate;
4-amino-5-cyano-6-ethoxy-N-(2-hydroxybenzyl)pyridine-2-carboxamide;
4-amino-5-cyano-6-ethoxy-N-(4-pentanoylbenzyl)pyridine-2-carboxamide;
4-amino-5-cyano-6-ethoxy-N-[3-methoxy-4-(methylsulfonyl)benzyl]pyridine-2-carboxamide;
4-amino-5-cyano-6-ethoxy-N-[(5-pyridin-2-ylthien-2-yl)methyl]pyridine-2-carboxamide;
4-amino-5-cyano-6-ethoxy-N-[(6-fluoropyridin-3-yl)methyl]pyridine-2-carboxamide;
4-amino-N-[(1-benzylpiperidin-4-yl)methyl]-5-cyano-6-ethoxypyridine-2-carboxamide;
4-amino-N-[(2-chloropyridin-3-yl)methyl]-5-cyano-6-ethoxypyridine-2-carboxamide;
N-(4-amino-5-cyano-6-ethoxypyridin-2-yl)-2-[2,5-dimethoxy-4-(methylsulfonyl)phenyl]acetamide;
4-amino-5-cyano-6-ethoxy-N-[4-(morpholin-4-ylcarbonyl)benzyl]pyridine-2-carboxamide;
ethyl 2-[5-({[(4-amino-5-cyano-6-ethoxypyridin-2-yl)carbonyl]amino}methyl)pyridin-2-yl]benzoate;
Trans-4-amino-5-cyano-6-ethoxy-N-({4-[(methylsulfonyl)amino]cyclohexyl}methyl)pyridine-2-carboxamide;
isobutyl 4-({[(4-amino-5-cyano-6-ethoxypyridin-2-yl)carbonyl]amino}methyl)piperidine-1-carboxylate;
2-(4-acetyl-4-phenylpiperidin-1-yl)-N-(4-amino-5-cyano-6-ethoxypyridin-2-yl)acetamide;
4-amino-5-cyano-6-ethoxy-N-[(1-pyridin-2-ylpiperidin-4-yl)methyl]pyridine-2-carboxamide;
4-amino-5-cyano-6-ethoxy-N-{4-[(methylamino)sulfonyl]benzyl}pyridine-2-carboxamide;
methyl 1-{2-[(4-amino-5-cyano-6-ethoxypyridin-2-yl)amino]-2-oxoethyl}piperidine-4-carboxylate;
4-amino-5-cyano-6-ethoxy-N-(4-heptanoylbenzyl)pyridine-2-carboxamide;
4-amino-5-cyano-6-ethoxy-N-[4-(pyridin-2-yloxy)benzyl]pyridine-2-carboxamide;
4-amino-5-cyano-6-ethoxy-N-(1,3-thiazol-5-ylmethyl)pyridine-2-carboxamide;
N-(4-amino-5-cyano-6-ethoxypyridin-2-yl)-2-[2-(methylthio)phenyl]acetamide;
4-amino-5-cyano-6-(3-methoxyphenyl)-N-[4-(methylsulfonyl)benzyl]pyridine-2-carboxamide;
methyl trans-N-{[4-({[(4-amino-5-cyano-6-ethoxypyridin-2-yl)carbonyl]amino}methyl)cyclohexyl]carbonyl}-L-norleucinate;
4-amino-5-cyano-6-ethoxy-N-[(4-methyl-1H-imidazol-2-yl)methyl]pyridine-2-carboxamide;
4-amino-5-cyano-N-(pyridin-3-ylmethyl)-6-thien-3-ylpyridine-2-carboxamide;
methyl 4-({[(4-amino-5-cyano-6-ethoxypyridin-2-yl)carbonyl]amino}methyl)piperidine-1-carboxylate;
4-amino-5-bromo-N-(2,5-dimethoxybenzyl)-6-ethoxypyridine-2-carboxamide;
4-amino-5-cyano-6-ethoxy-N-[(2-fluoropyridin-3-yl)methyl]pyridine-2-carboxamide;
4-amino-6-ethoxy-5-fluoro-N-[4-(methylsulfonyl)benzyl]pyridine-2-carboxamide;
N-(4-amino-5-cyano-6-ethoxypyridin-2-yl)-2-[4-(methylsulfonyl)phenyl]acetamide;
4-amino-5-cyano-6-ethoxy-N-[2-(methylsulfonyl)ethyl]pyridine-2-carboxamide;
4-amino-5-cyano-N-[4-(methylsulfonyl)benzyl]-6-{[3-(methylthio)propyl]amino}pyridine-2-carboxamide;
methyl trans-4-({[(4-amino-5-cyano-6-ethoxypyridin-2-yl)carbonyl]amino}methyl)cyclohexanecarboxylate;
1-{2-[(4-amino-5-cyano-6-isopropoxypyridin-2-yl)amino]-2-oxoethyl}piperidine-4-carboxamide;
4-amino-5-cyano-6-ethoxy-N-{4-[(trifluoromethyl)sulfonyl]benzyl}pyridine-2-carboxamide;
4-amino-5-cyano-6-ethoxy-N-{3-[(4-methylphenyl)sulfonyl]propyl}pyridine-2-carboxamide;
(2E)-3-[4-amino-3-cyano-6-({[4-(methylsulfonyl)benzyl]amino}carbonyl)pyridin-2-yl]acrylic acid;
4-amino-5-cyano-6-{[(1R)-2-hydroxy-1-methylethyl]amino}-N-[4-(methylsulfonyl)benzyl]pyridine-2-carboxamide;
4-amino-5-cyano-6-ethoxy-N-[2-(6-methoxy-1H-indol-3-yl)ethyl]pyridine-2-carboxamide;
4-azido-5-cyano-6-isopropoxy-N-[4-(methylsulfonyl)benzyl]pyridine-2-carboxamide;
4-amino-3-cyano-$N^2$-isopropyl-$N^6$-[4-(methylsulfonyl)benzyl]pyridine-2,6-dicarboxamide;
N-(4-amino-5-cyano-6-ethoxypyridin-2-yl)-2-[2-methoxy-5-(methylsulfinyl)phenyl]acetamide;
4-amino-5-cyano-6-ethoxy-N-[3-(1H-imidazol-2-yl)propyl]pyridine-2-carboxamide;
4-amino-5-cyano-6-ethoxy-N-({1-[(isopropylamino)carbonyl]piperidin-4-yl}methyl)pyridine-2-carboxamide;
4-amino-5-cyano-6-ethoxy-N-{[(3S)-1-(methylsulfonyl)pyrrolidin-3-yl]methyl}pyridine-2-carboxamide;
Trans-tert-butyl 4-({[(4-amino-5-cyano-6-ethoxypyridin-2-yl)carbonyl]amino}methyl)cyclohexylcarbamate;
N-[4-amino-5-cyano-6-(2,2,2-trifluoro-1-methylethoxy)pyridin-2-yl]acetamide;
4-amino-5-cyano-6-ethoxy-N-[3-(methylsulfonyl)propyl]pyridine-2-carboxamide;

N-(4-amino-5-cyano-6-ethoxypyridin-2-yl)-2-(4-cyanopiperidin-1-yl)acetamide;
4-amino-N-[2-(4-benzylpiperazin-1-yl)ethyl]-5-cyano-6-ethoxypyridine-2-carboxamide;
4-amino-5-cyano-6-ethoxy-N-({6-[4-(methylsulfonyl)piperazin-1-yl]pyridin-3-yl}methyl)pyridine-2-carboxamide;
N-(4-amino-5-chloro-6-ethoxypyridin-2-yl)-2-[2,5-dimethoxy-4-(methylsulfonyl)phenyl]acetamide;
N-[4-({[(4-amino-5-cyano-6-ethoxypyridin-2-yl)carbonyl]amino}methyl)phenyl]glycine;
[4-({[(4-amino-5-cyano-6-ethoxypyridin-2-yl)carbonyl]amino}methyl)piperidin-1-yl](oxo)acetic acid;
4-amino-N-{2-[4-(aminosulfonyl)phenyl]ethyl}-5-cyano-6-ethoxypyridine-2-carboxamide;
4'-amino-2'-ethoxy-N-[4-(methylsulfonyl)benzyl]-2,3'-bipyridine-6'-carboxamide;
4-amino-5-[(1E)-but-1-en-3-ynyl]-6-ethoxy-N-[4-(methylsulfonyl)benzyl]pyridine-2-carboxamide;
4-amino-6-ethoxy-5-formyl-N-[4-(methylsulfonyl)benzyl]pyridine-2-carboxamide;
5-cyano-N-(2,5-dimethoxybenzyl)-6-isopropoxypyridine-2-carboxamide;
5-chloro-6-ethoxy-N-[4-(methylsulfonyl)benzyl]pyridine-2-carboxamide;
N-(2,5-dimethoxybenzyl)-6-ethoxypyridine-2-carboxamide; and
6-ethoxy-N-(pyridin-3-ylmethyl)pyridine-2-carboxamide.

According to another embodiment, the present invention is directed to a pharmaceutical composition comprising a therapeutically effective amount of a compound of formula (I) in combination with a pharmaceutically suitable carrier.

According to another embodiment, the present invention is directed to a method of treating a disorder regulated by c-jun N-terminal kinase 1, 2, or 3 (JNK1, JNK2, or JNK3) in a mammal, comprising administrating a therapeutically effective amount of a compound of formula (I), or a pharmaceutically acceptable salt, prodrug, salt of a prodrug, or a combination thereof.

According to another embodiment, the present invention is directed to a method of treating or lessening the severity of a disease or condition in a patient selected from impaired glucose intolerance, insulin resistance, Type 2 diabetes, obesity, and diabetes mellitus, comprising administrating a therapeutically effective amount of a compound of formula (I)), or a pharmaceutically acceptable salt, prodrug, salt of a prodrug, or a combination thereof.

According to another embodiment, the present invention is directed to a method of treating or lessening the severity of a disease or condition in a patient selected from hypercalcemia, osteoporosis, osteoarthritis, symptomatic treatment of bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obtructive pulmonary disorder, contact dermatitis, Paget's disease, asthma, ischemic or reperfusion injury, allergic disease, atopic dermatitis, or allergic rhinitis, comprising administrating a therapeutically effective amount of a compound of formula (I)), or a pharmaceutically acceptable salt, prodrug, salt of a prodrug, or a combination thereof. According to another embodiment, the present invention is directed to a method of treating or lessening the severity of a disease or condition in a patient selected from Alzheimer's disease, Huntington's, Parkinson's, AIDS associated dementia, amyotrophic lateral sclerosis (AML), epilepsy, stroke, multiple sclerosis (MS), schizophrenia, cardiomycete hypertrophy, or baldness, comprising administrating a therapeutically effective amount of a compound of formula (I)), or a pharmaceutically acceptable salt, prodrug, salt of a prodrug, or a combination thereof.

DEFINITIONS

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl and 3-decenyl.

The term "alkenyloxy" as used herein, means an alkenyl group, as defined herein, appended to the parent molecular moiety through an oxygen atom.

The term "alkenyloxyalkyl" as used herein, means an alkenyloxy group, as defined herein, appended to the parent molecular moiety through an alkyl group, as defined herein.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, n-butoxy, tert-butoxy, pentyloxy and hexyloxy.

The term "alkoxyalkoxy" as used herein, means an alkoxy group, as defined herein, appended to the parent molecular moiety through an alkoxy group. Representative example of alkoxyalkoxy include, but are not limited to, 2-(methoxy)ethoxy, 2-(ethoxy)ethoxy, 3-(methoxy)propoxy and 2-(n-butoxy)ethoxy.

The term "alkoxyalkoxyalkyl" as used herein, means an alkoxyalkoxy group, as defined herein, appended to the parent molecular moiety through an alkyl group, as defined herein. Representative examples of alkoxyalkoxyalkyl include, but are not limited to, 2-(methoxy)ethoxymethyl, 2-(ethoxy)ethoxymethyl, 3-(methoxy)propoxymethyl, 2-(n-butoxy)ethoxymethyl and 2-(tert-butoxy)ethoxymethyl.

The term "alkoxyalkyl" as used herein, means an alkoxy group, as defined herein, appended to the parent molecular moiety through an alkyl group, as defined herein. Representative examples of alkoxyalkyl include, but are not limited to, n-butoxymethyl, tert-butoxymethyl, 2-(ethoxy)ethyl, 2-methoxyethyl and methoxymethyl.

The term "alkoxyalkylcarbonyl" as used herein, means an alkoxyalkyl group, as defined herein, appended to the parent molecular moiety through a carbonyl group, as defined herein. Representative examples of alkoxyalkylcarbonyl include, but are not limited to, n-butoxymethylcarbonyl, tert-butoxymethylcarbonyl, 2-(ethoxy)ethylcarbonyl, 2-methoxyethylcarbonyl and methoxymethylcarbonyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl and tert-butoxycarbonyl.

The term "alkoxycarbonylalkyl" as used herein, means an alkoxycarbonyl group, as defined herein, appended to the parent molecular moiety through a alkyl group, as defined herein.

The term "alkoxysulfonyl" as used herein, means an alkoxy group, as defined herein, appended to the parent molecular moiety through a sulfonyl group, as defined herein.

Representative examples of alkoxysulfonyl include, but are not limited to, methoxysulfonyl, ethoxysulfonyl and tert-butoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3-oxobutyl, 3-oxopentyl and 4-oxopentyl.

The term "alkylcarbonyloxy" as used herein, means an alkylcarbonyl group, as defined herein, appended to the parent molecular moiety through an oxygen atom, as defined herein. Representative examples of alkylcarbonyloxy include, but are not limited to, acetyloxy, propionyloxy, 3-oxobutyl and butyryloxy.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" as used herein, means an alkylsulfinyl group, as defined herein, appended to the parent molecular moiety through an alkyl group, as defined herein. Representative examples of alkylsulfinylalkyl include, but are not limited to, methylsulfinylmethyl and ethylsulfinylmethyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl" as used herein, means an alkylsulfonyl group, as defined herein, appended to the parent molecular moiety through an alkyl group, as defined herein. Representative examples of alkylsulfonyl include, but are not limited to, methylsulfonylmethyl and ethylsulfonylmethyl.

The term "alkylthio" as used herein, means an alkyl group, as defined herein, appended to the parent molecular moiety through a sulfur atom. Representative examples of alkylthio include, but are not limited to, methylthio and ethylthio.

The term "alkylthioalkyl" as used herein, means an alkylthio group, as defined herein, appended to the parent molecular moiety through an alkyl group, as defined herein. Representative examples of alkylthioalkyl include, but are not limited to, methylthiomethyl and ethylthiomethyl.

The term "alkylthioalkylcarbonyl" as used herein, means an alkylthioalkyl group, as defined herein, appended to the parent molecular moiety through a carbonyl group, as defined herein. Representative examples of alkylthioalkylcarbonyl include, but are not limited to, methylthiomethylcarbonyl and ethylthiomethylcarbonyl.

The term "alkylthiocarbonyl" as used herein, means an alkylthio group, as defined herein, appended to the parent molecular moiety through a carbonyl group, as defined herein. Representative examples of alkylthiocarbonyl include, but are not limited to, methylthiocarbonyl and ethylthiocarbonyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl and 1-butynyl.

The term "alkynylalkenyl" as used herein, means an alkynyl group, as defined herein, appended to the parent molecular moiety through an alkenyl group, as defined herein. Representative example of alkynylalkenyl includes, but not limited to, but-1-en-3-ynyl.

The term, "alkynylalkoxy" as used herein, means an alkynyl group, as defined herein, appended to the parent molecular moiety through an alkoxy group, as defined herein.

The term, "alkynylalkoxyalkyl" as used herein, refers to an alkynylalkoxy group, as defined herein, appended to the parent molecular moiety through an alkyl group, as defined herein.

The term, "alkynylalkyl" as used herein, refers to an alkynyl group, as defined herein, appended to the parent molecular moiety through an alkyl group, as defined herein.

The term "aryl" as used herein, means a phenyl, a bicyclic aryl or a tricyclic aryl. The bicyclic aryl is naphthyl, or a phenyl fused to a monocyclic cycloalkyl, as defined herein, or a phenyl fused to a monocyclic cycloalkenyl, as defined herein. Tricyclic aryl is a bicyclic aryl fused to a monocyclic cycloalkyl group, as defined herein, a bicyclic aryl fused to a monocyclic cycloalkenyl, as defined herein, or a bicyclic aryl fused to another phenyl group. Representative examples of aryl include, but are not limited to, anthracenyl, fluorenyl, indanyl, indenyl, naphthyl, phenyl and tetrahydronaphthyl. The bicyclic aryls and the tricyclic aryls are attached to the parent molecular moiety through any substitutable carbon atom contained within the bicyclic aryls and the tricyclic aryls.

The aryl groups of this invention can be optionally substituted with 1, 2, 3, 4, or 5 substituents independently selected from the group consisting of alkenyl, alkoxy, alkoxyalkyl, alkoxyalkylcarbonyl, alkoxyalkylsulfonyl, alkoxycarbonyl, alkoxycarbonylalkyl, alkyl, alkylcarbonyl, alkylcarbonylalkyl, alkylcarbonyloxy, alkylsulfinyl, alkylsulfonyl, alkylthio, alkynyl, aryl, arylalkoxy, arylalkoxycarbonyl, arylalkyl, arylcarbonyl, aryloxy, arylsulfinyl, arylsulfonyl, carboxy, carboxyalkyl, carboxycarbonyl, cyano, cyanoalkyl, cycloalkyl, cycloalkylalkoxy, cycloalkylcarbonyl, cycloalkyloxy, cycloalkylsulfonyl, formyl, haloalkoxy, haloalkyl, haloalkylthio, haloalkylcarbonyl, haloalkylsulfonyl, halogen, heteroaryl, heteroarylalkyl, heteroaryloxy, heteroarylcarbonyl, heteroarylsulfinyl, heteroarylsulfonyl, heterocycle, heterocyclealkyl, heterocyclecarbonyl, heterocyclesulfinyl, heterocyclesulfonyl, hydroxy, hydroxyalkyl, hydroxyalkylsulfonyl, hydroxyhaloalkyl, mercapto, nitro, $R_mR_n$—, $R_mR_nN$—C(O)—, $R_mR_n$—S(O$_2$)—, $(R_mR_nN)$alkyl, $R_mR_nN$—C(O)-alkyl-O—, and —O—(CH$_2$)$_n$—O— wherein the oxygen atoms are attached to two adjacent carbon atoms of aryl, and n is 1, 2 or 3, and wherein the substituent aryl, the aryl of arylalkoxy, the aryl of arylalkoxycarbonyl, the aryl of arylalkyl, the aryl of arylcarbonyl, the aryl of aryloxy, the aryl of arylsulfinyl, the aryl of arylsulfonyl, the substituent cycloalkyl, the cycloalkyl of cycloalkylalkoxy, the cycloalkyl of cycloalkylcarbonyl, the cycloalkyl of cycloalkylsulfonyl, the heteroaryl, the heteroaryl of heteroarylalkyl, the heteroaryl of heteroarylcarbonyl, the heteroaryl of heteroaryloxy, the heteroaryl of heteroarylsulfinyl, the heteroaryl of heteroarylsulfonyl, the heterocycle, the heterocycle of heterocyclealkyl, the heterocycle of heterocyclecarbonyl, the heterocycle of heterocyclesulfinyl and the heterocycle of heterocyclesulfonyl can be optionally substituted with 1, or 2 substitutents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, formyl, haloalkoxy, haloalkyl, haloalkylcarbonyl, haloalkylsulfonyl, halogen, hydroxy, hydroxyalkyl, and $R_pR_qN$—C(O)—. $R_m$ at each occurrence is hydrogen or alkyl, $R_n$ at each occurrence is independently selected from the group consisting of hydrogen, alkyl, alkoxyalkyl, alkoxycarbonyl, alkoxycarbonylalkyl, alkylcarbonyl, alkylsulfonyl, carboxyalkyl, $(R_pR_qN)$—C(O)-alkyl-, $(R_pR_qN)$—S(O)$_2$-alkyl-, phenyl and phenylalkyl wherein the phenyl and the phenyl moiety of the phenylalkyl are each independently unsubstituted or substituted with one or two substituents selected from the group consisting of alkyl, halogen, haloalkyl, alkylcarbonyl, and alkylsulfonyl. $R_p$ and $R_q$, at each occurrence, are each independently hydrogen or alkyl.

Representative examples of substituted aryls include, but are not limited to, 2-bromophenyl, 2-chlorophenyl, 3-chlorophenyl, 4-chlorophenyl, 3-cyanophenyl, 4-cyanophenyl, 2,3-dichlorophenyl, 3,4-dichlorophenyl, 2,5-dichlorophenyl, 2,4-dimethylphenyl, 3,5-dimethylphenyl, 2-fluoro-3-methylphenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-(methylthio)phenyl, 4-nitrophenyl, 1,3-benzodioxol-5-yl, 1,5-benzodioxepin-7-yl, 4-(trifluoromethoxy)phenyl and 3-(trifluoromethyl)phenyl.

The term "arylalkenyl" as used herein, means an aryl group, as defined herein, appended to the parent molecular moiety through an alkenyl group, as defined herein.

The term "arylalkenyloxy" as used herein, means an arylalkenyl group, as defined herein, appended to the parent molecular moiety through an oxygen atom.

The term "arylalkenyloxyalkyl" as used herein, means an arylalkenyoxy group, as defined herein, appended to the parent molecular moiety through an alkyl group, as defined herein.

The term "arylalkoxy" as used herein, means an aryl group, as defined herein, appended to the parent molecular moiety through an alkoxy group, as defined herein. Representative examples of arylalkoxy include, but are not limited to, benzyloxy, 2-bromobenzyloxy, 2-chlorobenzyloxy, 3-chlorobenzyloxy, 4-chlorobenzyloxy, 2-(4-chlorophenyl)ethoxy, 3-cyanobenzyloxy, 4-cyanobenzyloxy, 2,3-dichlorobenzyloxy, 2,5-dichlorobenzyloxy, 2,4-dimethylbenzyloxy, 3,5-dimethylbenzyloxy, 2-fluoro-3-methylbenzyloxy, 2-fluorobenzyloxy, 4-fluorobenzyloxy, 2-methoxybenzyloxy, 3-methoxybenzyloxy, 4-methoxybenzyloxy, 2-methylbenzyloxy, 3-methylbenzyloxy, 4-(methylthio)benzyloxy, 4-nitrobenzyloxy, 4-(trifluoromethoxy)benzyloxy and 3-(trifluoromethyl)benzyloxy.

The term "arylalkoxycarbonyl" as used herein, means an arylalkoxy group, as defined herein, appended to the parent molecular moiety through a carbonyl group, as defined herein.

The term "arylalkoxyalkyl" as used herein, means an arylalkoxy group, as defined herein, appended to the parent molecular moiety through an alkyl group, as defined herein. Representative examples of arylalkoxyalkyl include, but are not limited to, benzyloxymethyl, 2-bromobenzyloxymethyl, 2-chlorobenzyloxymethyl, 3-chlorobenzyloxymethyl, 4-chlorobenzyloxymethyl, 4-cyanobenzyloxymethyl, 2,3-dichlorobenzyloxymethyl, 2,5-dichlorobenzyloxymethyl, 2,4-dimethylbenzyloxymethyl, 3,5-dimethylbenzyloxymethyl, 2-fluoro-3-methylbenzyloxymethyl, 2-fluorobenzyloxymethyl, 4-fluorobenzyloxymethyl, 2-methoxybenzyloxymethyl, 3-methoxybenzyloxymethyl, 4-methoxybenzyloxymethyl, 2-methylbenzyloxymethyl, 3-methylbenzyloxymethyl, 4-(methylthio)benzyloxymethyl, 4-nitrobenzyloxymethyl, 4-(trifluoromethoxy)benzyloxymethyl and 3-(trifluoromethyl)benzyloxymethyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 1-phenylethyl, 3-phenylpropyl, 4-phenylbutyl, 2-naphth-2-ylethyl, 2-bromobenzyl, 4-cyanobenzyl, 1-(4-cyanophenyl)ethyl, 2-chlorobenzyl, 3-chlorobenzyl, 4-chlorobenzyl, 1-(4-chlorophenyl)ethyl, 2-(4-chlorophenyl)ethyl, 2,3-dichlorobenzyl, 2,5-dichlorobenzyl, 2,4-dimethylbenzyl, 3,5-dimethylbenzyl, 2-fluoro-3-methylbenzyl, 2-fluorobenzyl, 4-fluorobenzyl, 2-methoxybenzyl, 3-methoxybenzyl, 4-methoxybenzyl, 2-methylbenzyl, 3-methylbenzyl, 4-(methylthio)benzyl, 4-nitrobenzyl, 1-(4-nitrophenyl)ethyl, 2-(4-chlorophenyl)ethyl, 4-(trifluoromethoxy)benzyl and 3-(trifluoromethyl)benzyl.

The term, "arylalkylcarbonyl" as used herein, refers to an arylalkyl group, as defined herein, appended to the parent molecular moiety through a carbonyl group, as defined herein.

The term, "arylalkylsulfonyl" as used herein, refers to an arylalkyl group, as defined herein, appended to the parent molecular moiety through a sulfonyl group, as defined herein.

The term, "arylalkylsulfonylalkyl" as used herein, refers to an arylalkylsulfonyl group, as defined herein, appended to the parent molecular moiety through an alkyl group, as defined herein.

The term "arylalkylthio" as used herein, means an arylalkyl group, as defined herein, appended to the parent molecular moiety through a sulfur atom. Representative examples of arylalkylthio include, but are not limited to, benzylthio, 2-phenylethylthio, 1-phenylethylthio, 3-phenylpropylthio, 4-phenylbutylthio, 2-naphth-2-ylethylthio, 2-bromobenzylthio, 4-cyanobenzylthio, 1-(4-cyanophenyl)ethyl, 2-chlorobenzylthio, 3-chlorobenzylthio, 4-chlorobenzylthio, 1-(4-chlorophenyl)ethylthio, 2-(4-chlorophenyl)ethylthio, 2,3-dichlorobenzylthio, 2,5-dichlorobenzylthio, 2,4-dimethylbenzylthio, 3,5-dimethylbenzylthio, 2-fluoro-3-methylbenzylthio, 2-fluorobenzylthio, 4-fluorobenzylthio, 2-methoxybenzylthio, 3-methoxybenzylthio, 4-methoxybenzylthio, 2-methylbenzylthio, 3-methylbenzylthio, 4-(methylthio)benzylthio, 4-nitrobenzylthio, 1-(4-nitrophenyl)ethylthio, 2-(4-chlorophenyl)ethylthio, 4-(trifluoromethoxy)benzylthio and 3-(trifluoromethyl)benzylthio.

The term "arylalkylthioalkyl" as used herein, means an arylalkylthio group, as defined herein, appended to the parent molecular moiety through an alkyl group, as defined herein. Representative examples of arylalkylthio include, but are not limited to, benzylthiomethyl, 2-phenylethylthiomethyl, 1-phenylethylthiomethyl, 3-phenylpropylthiomethyl, 4-phenylbutylthiomethyl, 2-naphth-2-ylethylthiomethyl, 2-bromobenzylthiomethyl, 4-cyanobenzylthiomethyl, 1-(4-cyanophenyl)ethylmethyl, 2-chlorobenzylthiomethyl, 3-chlorobenzylthiomethyl, 4-chlorobenzylthiomethyl, 1-(4-chlorophenyl)ethylthiomethyl, 2-(4-chlorophenyl)ethylthiomethyl, 2,3-dichlorobenzylthiomethyl, 2,5-dichlorobenzylthiomethyl, 2,4-dimethylbenzylthiomethyl, 3,5-dimethylbenzylthiomethyl, 2-fluoro-3- methylbenzylthiomethyl, 2-fluorobenzylthiomethyl, 4-fluorobenzylthiomethyl, 2-methoxybenzylthiomethyl, 3-methoxybenzylthiomethyl, 4-methoxybenzylthiomethyl, 2-methylbenzylthiomethyl, 3-methylbenzylthiomethyl, 4-(methylthio)benzylthiomethyl, 4-nitrobenzylthiomethyl, 1-(4-nitrophenyl)ethylthiomethyl, 2-(4-chlorophenyl)ethylthiomethyl, 4-(trifluoromethoxy)benzylthiomethyl and 3-(trifluoromethyl)benzylthiomethyl.

The term "arylcarbonyl" as used herein, means an aryl group, as defined herein, appended to the parent molecular moiety through a carbonyl group, as defined herein. Representative examples of arylcarbonyl include, but are not limited to, benzoyl, naphthoyl, 2-bromo benzoyl, 2-chlorobenzoyl, 3-chlorobenzoyl, 4-chlorobenzoyl, 3-cyanobenzoyl, 4-cyanobenzoyl, 2,3-dichlorobenzoyl, 3,4-dichlorobenzoyl, 2,5-dichlorobenzoyl, 2,4-dimethylbenzoyl, 3,5-dimethylbenzoyl, 2-fluoro-3-methylbenzoyl, 2-fluorobenzoyl, 3-fluorobenzoyl, 4-fluorobenzoyl, 2-methoxybenzoyl, 3-methoxybenzoyl, 4-methoxybenzoyl, 2-methylbenzoyl, 3-methylbenzoyl, 4-(methylthio)benzoyl, 4-nitrobenzoyl, 4-(trifluoromethoxy)benzoyl and 3-(trifluoromethyl)benzoyl.

The term "arylcarbonylalkyl" as used herein, means an arylcarbonyl group, as defined herein, appended to the parent molecular moiety through an alkyl group, as defined herein.

The term "aryloxy" as used herein, means an aryl group, as defined herein, appended to the parent molecular moiety through an oxygen atom. Representative examples of aryloxy include, but are not limited to, 2-bromophenoxy, 2-chlorophenoxy, 3-chlorophenoxy, 4-chlorophenoxy, 4-cyanophenoxy, 2,3-dichlorophenoxy, 3,4-dichlorophenoxy, 2,5-dichlorophenoxy, 2,4-dimethylphenoxy, 3,5-dimethylphenoxy, 2-fluoro-3-methylphenoxy, 2-fluorophenoxy, 3-fluorophenoxy, 4-fluorophenoxy, 2-methoxyphenoxy, 3-methoxyphenoxy, 4-methoxyphenoxy, 2-methylphenoxy, 3-methylphenoxy, 4-(methylthio)phenoxy, 3-nitrophenoxy, 4-nitrophenoxy, 4-(trifluoromethoxy)phenoxy and 3-(trifluoromethyl)phenoxy.

The term "aryloxyalkyl" as used herein, means an aryloxy group, as defined herein, appended to the parent molecular moiety through an alkyl group, as defined herein. Representative examples of aryloxyalkyl include, but are not limited to, 2-(2-bromophenoxy)ethyl, 2-(2-chlorophenoxy)ethyl, 3-chlorophenoxymethyl, 4-chlorophenoxymethyl, 4-cyanophenoxymethyl, 2,3-dichlorophenoxymethyl, 3,4-dichlorophenoxymethyl, 2,5-dichlorophenoxymethyl, 2,4-dimethylphenoxymethyl, 3,5-dimethylphenoxymethyl, 2-fluoro-3-methylphenoxymethyl, 2-fluorophenoxymethyl, 3-fluorophenoxymethyl, 4-fluorophenoxymethyl, 2-methoxyphenoxymethyl, 3-methoxyphenoxymethyl, 4-methoxyphenoxymethyl, 2-methylphenoxymethyl, 3-methylphenoxymethyl, 4-(methylthio)phenoxymethyl, 3-nitrophenoxymethyl, 4-nitrophenoxymethyl, 4-(trifluoromethoxy)phenoxymethyl and 3-(trifluoromethyl)phenoxymethyl.

The term "arylsulfinyl," as used herein, refers to an aryl group, as defined herein, appended to the parent molecular moiety through a sulfinyl group, as defined herein. Representative examples of arylsulfinyl include, but are not limited to, phenylsulfinyl and naphthylsulfinyl.

The term "arylsulfinylalkyl," as used herein, refers to an arylsulfinyl group, as defined herein, appended to the parent molecular moiety through an alkyl group, as defined herein. Representative examples of arylsulfinylalkyl include, but are not limited to, phenylsulfinylmethyl and naphthylsulfinylmethyl.

The term "arylsulfonyl" as used herein, means an aryl group, as defined herein, appended to the parent molecular moiety through a sulfonyl group, as defined herein. Representative examples of arylsulfonyl include, but are not limited to, phenylsulfonyl, naphthylsulfonyl, 2-bromophenylsulfonyl, 2-chlorophenylsulfonyl, 3-chlorophenylsulfonyl, 4-chlorophenylsulfonyl, 3-cyanophenylsulfonyl, 4-cyanophenylsulfonyl, 2,3-dichlorophenylsulfonyl, 3,4-dichlorophenylsulfonyl, 2,5-dichlorophenylsulfonyl, 2,4-dimethylphenylsulfonyl, 3,5-dimethylphenylsulfonyl, 2-fluoro-3-methylphenylsulfonyl, 2-fluorophenylsulfonyl, 3-fluorophenylsulfonyl, 4-fluorophenylsulfonyl, 2-methoxyphenylsulfonyl, 3-methoxyphenylsulfonyl, 4-methoxyphenylsulfonyl, 2-methylphenylsulfonyl, 3-methylphenylsulfonyl, 4-(methylthio)phenylsulfonyl, 4-nitrophenylsulfonyl, 4-(trifluoromethoxy)phenylsulfonyl and 3-(trifluoromethyl)phenylsulfonyl.

The term "arylsulfonylalkyl" as used herein, means an arylsulfonyl group, as defined herein, appended to the parent molecular moiety through an alkyl group, as defined herein.

The term "arylthio" as used herein, means an aryl group, as defined herein, appended to the parent molecular moiety through a sulfur atom. Representative examples of arylthio include, but are not limited to, 2-bromophenylthio, 2-chlorophenylthio, 3-chlorophenylthio, 4-chlorophenylthio, 4-cyanophenylthio, 2,3-dichlorophenylthio, 3,4-dichlorophenylthio, 2,5-dichlorophenylthio, 2,4-dimethylphenylthio, 3,5-dimethylphenylthio, 2-fluoro-3-methylphenylthio, 2-fluorophenylthio, 3-fluorophenylthio, 4-fluorophenylthio, 2-methoxyphenylthio, 3-methoxyphenylthio, 4-methoxyphenylthio, 2-methylphenylthio, 3-methylphenylthio, 4-(methylthio)phenylthio, 3-nitrophenylthio, 4-nitrophenylthio, 4-(trifluoromethoxy)phenylthio and 3-(trifluoromethyl)phenylthio.

The term "arylthioalkyl" as used herein, means an arylthio group, as defined herein, appended to the parent molecular moiety through an alkyl group, as defined herein. Representative examples of arylthioalkyl include, but are not limited to, 2-bromophenylthiomethyl, 2-chlorophenylthiomethyl, 3-chlorophenylthiomethyl, 4-chlorophenylthiomethyl, 4-cyanophenylthiomethyl, 2,3-dichlorophenylthiomethyl, 3,4-dichlorophenylthiomethyl, 2,5-dichlorophenylthiomethyl, 2,4-dimethylphenylthiomethyl, 3,5-dimethylphenylthiomethyl, 2-fluoro-3-methylphenylthiomethyl, 2-fluorophenylthiomethyl, 3-fluorophenylthiomethyl, 4-fluorophenylthiomethyl, 2-methoxyphenylthiomethyl, 3-methoxyphenylthiomethyl, 4-methoxyphenylthiomethyl, 2-methylphenylthiomethyl, 3-methylphenylthiomethyl, 4-(methylthio)phenylthiomethyl, 3-nitrophenylthiomethyl, 4-nitrophenylthiomethyl, 4-(trifluoromethoxy)phenylthiomethyl and 3-(trifluoromethyl)phenylthiomethyl.

The term "azido," as used herein, refers to a —$N_3$ group.

The term "carbonyl" as used herein, means a —C(=O)— group.

The term "carboxy" as used herein, means a —$CO_2H$ group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl and 3-carboxypropyl.

The term "carboxycarbonyl" as used herein, means a carboxy group, as defined herein, appended to the parent molecular moiety through a carbonyl group, as defined herein.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl and 3-cyanopropyl.

The term "cycloalkenyl" as used herein, means a monocyclic, a bicyclic or a tricyclic cycloalkenyl group. Monocyclic cycloalkenyls are exemplified by a 4 or 5 membered carbocyclic ring containing zero heteroatom and 1 double bond, a six-membered carbocyclic ring containing 1 or 2 double bonds and zero heteroatom, or a 7-8 membered hydrocarbon ring containing 1, 2 or 3 double bonds and zero heteroatom. Examples of monocyclic cycloalkenyls include cyclobutenyl, cyclopentenyl, cyclohexenyl, cycloheptenyl, and cyclooctenyl. Bicyclic cycloalkenyl is a monocyclic cycloalkenyl group fused to a monocyclic cycloalkenyl group, or a monocyclic cycloalkenyl group fused to a monocyclic cycloalkyl group, as defined herein. Bicyclic cycloalkenyls also include bridged monocyclic cycloalkenyl in which two non-adjacent carbon atoms of a monocyclic cycloalkenyl are linked by an alkylene bridge of between one and three additional carbon atoms. Representative examples of bicyclic cycloalkenyls include, but are not limited to, bicyclo[3.1.1]heptene, bicyclo[2.2.1]heptene, bicyclo[2.2.2]octene, bicyclo[3.2.2]nonene, bicyclo[3.3.1]nonene, and bicyclo[4.2.1]nonene. Tricyclic cycloalkenyl is a bicyclic cycloalkenyl fused to a monocyclic cycloalkenyl, or a bicyclic cycloalkenyl fused to a monocyclic cycloalkyl, as defined herein. Tricyclic cycloalkenyl also include a bicyclic cycloalkenyl in which two non-adjacent carbon atoms of the bicyclic ring are linked by an alkylene bridge of between one and three carbon atoms. Representative examples of tricyclic cycloalkenyls include, but are not limited to, tricyclo[3.3.1.0$^{3,7}$]nonene and tricyclo[3.3.1.1$^{3,7}$]decene. The monocyclic, bicyclic or tricyclic cycloalkenyls of this invention are attached to the molecular moiety through any substitutable atom within the monocyclic, bicyclic or tricyclic ring.

The monocyclic, bicyclic or tricyclic cycloalkenyls of this invention can be optionally substituted with 1, 2, 3, or 4 substituents independently selected from the group consisting of alkenyl, alkoxy, alkoxyalkyl, alkoxyalkylcarbonyl, alkoxyalkylsulfonyl, alkoxycarbonyl, alkoxycarbonylalkyl, alkyl, alkylcarbonyl, alkylcarbonylalkyl, alkylcarbonyloxy, alkylsulfinyl, alkylsulfonyl, alkylthio, alkynyl, aryl, arylalkoxy, arylalkyl, arylcarbonyl, aryloxy, arylsulfinyl, arylsulfonyl, carboxy, carboxyalkyl, cyano, cyanoalkyl, cycloalkyl, cycloalkoxy, cycloalkylcarbonyl, cycloalkylsulfonyl, formyl, haloalkoxy, haloalkyl, haloalkylthio, haloalkylcarbonyl, haloalkylsulfonyl, halogen, heteroaryl, heteroarylalkyl, heteroarylcarbonyl, heteroarylsulfinyl, heteroarylsulfonyl, heterocycle, heterocyclealkyl, heterocyclecarbonyl, heterocyclesulfinyl, heterocyclesulfonyl, hydroxy, hydroxyalkyl, hydroxyhaloalkyl, mercapto, oxo, nitro, $R_mR_nN$—, $R_mR_nN$—C(O)—, $R_mR_nN$—S(O$_2$)— and ($R_mR_nN$)alkyl, wherein the substituent aryl, the aryl of arylalkoxy, the aryl of arylalkyl, the aryl of arylcarbonyl, the aryl of aryloxy, the aryl of arylsulfinyl, the aryl of arylsulfonyl, the substituent cycloalkyl, the cycloalkyl of cycloalkylalkoxy, the cycloalkyl of cycloalkylcarbonyl, the cycloalkyl of cycloalkylsulfonyl, the heteroaryl, the heteroaryl of heteroarylalkyl, the heteroaryl of heteroarylcarbonyl, the heteroaryl of heteroarylsulfinyl, the heteroaryl of heteroarylsulfonyl, the heterocycle, the heterocycle of heterocyclealkyl, the heterocycle of heterocyclecarbonyl, the heterocycle of heterocyclesulfinyl and the heterocycle of heterocyclesulfonyl can be optionally substituted with 1, or 2 substitutents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, formyl, haloalkoxy, haloalkyl, haloalkylcarbonyl, haloalkylsulfonyl, halogen, hydroxy and hydroxyalkyl. $R_m$ and $R_n$ are independently selected from the group consisting of hydrogen, alkyl, alkoxyalkyl, alkylcarbonyl, phenyl and phenylalkyl.

The term "cycloalkenylalkoxy" as used herein, means a cycloalkenyl group, as defined herein, appended to the parent molecular moiety through an alkoxy group, as defined herein. Representative examples of cycloalkenylalkoxy include, but are not limited to, cyclopropenylmethoxy, cyclobutenylmethoxy, cyclopentenylmethoxy, cyclohexenylmethoxy, cycloheptenylmethoxy and cyclooctenylmethoxy.

The term "cycloalkenylalkoxyalkyl" as used herein, means a cycloalkenylalkoxy group, as defined herein, appended to the parent molecular moiety through an alkyl group, as defined herein. Representative examples of cycloalkenylalkoxyalkyl include, but are not limited to, cyclopropenylmethoxymethyl, cyclobutenylmethoxymethyl, cyclopentenylmethoxymethyl, cyclohexenylmethoxymethyl, cycloheptenylmethoxymethyl and cyclooctenylmethoxymethyl.

The term "cycloalkenylalkyl" as used herein, means a cycloalkenyl group, as defined herein, appended to the parent molecular moiety through an alkyl group, as defined herein. Representative examples of cycloalkenylalkyl include, but are not limited to, cyclopropenylmethyl, cyclobutenylmethyl, cyclopentenylmethyl, cyclohexenylmethyl, cycloheptenylmethyl and cyclooctenylmethyl.

The term "cycloalkenylalkylthio" as used herein, means a cycloalkenylalkyl group, as defined herein, appended to the parent molecular moiety through a sulfur atom. Representative examples of cycloalkenylalkylthio include, but are not limited to, cyclopropenylmethylthio, cyclobutenylmethylthio, cyclopentenylmethylthio, cyclohexenylmethylthio, cycloheptenylmethylthio and cyclooctenylmethylthio.

The term "cycloalkenylalkylthioalkyl" as used herein, means a cycloalkenylalkylthio group, as defined herein, appended to the parent molecular moiety through an alkyl group, as defined herein. Representative examples of cycloalkenylalkylthioalkyl include, but are not limited to, cyclopropenylmethylthiomethyl, cyclobutenylmethylthiomethyl, cyclopentenylmethylthiomethyl, cyclohexenylmethylthiomethyl, cycloheptenylmethylthiomethyl and cyclooctenylmethylthiomethyl.

The term "cycloalkenyloxy" as used herein, means a cycloalkenyl group, as defined herein, appended to the parent molecular moiety through an oxygen atom. Representative examples of cycloalkenyloxy include, but are not limited to, cyclopropenyloxy, cyclobutenyloxy, cyclopentenyloxy, cyclohexenyloxy, cycloheptenyloxy and cyclooctenyloxy.

The term "cycloalkenyloxyalkyl" as used herein, means a cycloalkenyloxy group, as defined herein, appended to the parent molecular moiety through an alkyl group, as defined herein. Representative examples of cycloalkenyloxyalkyl include, but are not limited to, cyclopropenyloxymethyl, cyclobutenyloxymethyl, cyclopentenyloxymethyl, cyclohexenyloxymethyl, cycloheptenyloxymethyl and cyclooctenyloxymethyl.

The term "cycloalkenylsulfinylalkyl," as used herein, means a cycloalkenyl group, as defined herein, appended to the parent molecular moiety through a sulfinyl group, as defined herein.

The term "cycloalkenylsulfonyl" as used herein, means a cycloalkenyl group, as defined herein, appended to the parent molecular moiety through a sulfonyl group, as defined herein.

The term "cycloalkenylsulfonylalkyl" as used herein, means a cycloalkenylsulfonyl group, as defined herein, appended to the parent molecular moiety through an alkyl group, as defined herein.

The term "cycloalkenylthio" as used herein, means a cycloalkenyl group, as defined herein, appended to the parent molecular moiety through a sulfur atom. Representative examples of cycloalkenylthio include, but are not limited to, cyclopropenylthio, cyclobutenylthio, cyclopentenylthio, cyclohexenylthio, cycloheptenylthio and cyclooctenylthio.

The term "cycloalkenylthioalkyl" as used herein, means a cycloalkenylthio group, as defined herein, appended to the parent molecular moiety through an alkyl group, as defined herein. Representative examples of cycloalkenylthioalkyl include, but are not limited to, cyclopropenylthiomethyl, cyclobutenylthiomethyl, cyclopentenylthiomethyl, cyclohexenylthiomethyl, cycloheptenylthiomethyl and cyclooctenylthiomethyl.

The term "cycloalkyl," as used herein, refers to a monocyclic, bicyclic, or tricyclic cycloalkyl. Monocyclic cycloalkyls are cyclic hydrocarbon ring containing from 3 to 8 carbon atoms and single carbon-carbon bonds within the ring. Examples of monocyclic cycloalkyls include cyclopropyl, cyclobutyl, cyclopentyl, cyclohexyl, cycloheptyl, and cyclooctyl. Bicyclic cycloalkyl is a monocyclic cycloalkyl fused to a monocyclic cycloalkyl group. Bicyclic cycloalkyls also include bridged monocyclic cycloalkyls wherein two non-adjacent carbon atoms of the monocyclic cycloalkyls are linked by an alkylene bridge of between one and three additional carbon atoms. Representative examples of bicyclic cycloalkyls include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are bicyclic cycloalkyls, as defined herein, fused to a monocyclic cycloalkyl group, as defined herein. Tricyclic cycloalkyls also include bicyclic cycloalkyls in which two non-adjacent carbon atoms of the bicyclic cycloalkyls are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane). The monocyclic, bicyclic or tricyclic cycloalkyls are appended to the molecular moiety through any substitutable atom within the monocyclic, bicyclic or tricyclic ring.

The monocyclic, bicyclic and tricyclic cycloalkyls of this invention can be optionally substituted with 1, 2, 3, or 4 substituents independently selected from the group consisting of alkenyl, alkoxy, alkoxyalkyl, alkoxyalkylcarbonyl, alkoxyalkylsulfonyl, alkoxycarbonyl, alkoxycarbonylalkyl, alkyl, alkylcarbonyl, alkylcarbonylalkyl, alkylcarbonyloxy, alkylsulfinyl, alkylsulfonyl, alkylthio, alkynyl, aryl, arylalkoxy, arylalkoxycarbonyl, arylalkyl, arylcarbonyl, aryloxy, arylsulfinyl, arylsulfonyl, carboxy, carboxyalkyl, carboxycarbonyl, cyano, cyanoalkyl, cycloalkyl, cycloalkoxy, cycloalkylcarbonyl, cycloalkylsulfonyl, formyl, haloalkoxy, haloalkyl, haloalkylthio, haloalkylcarbonyl, haloalkylsulfonyl, halogen, heteroaryl, heteroarylalkyl, heteroaryloxy, heteroarylcarbonyl, heteroarylsulfinyl, heteroarylsulfonyl, heterocycle, heterocyclealkyl, heterocyclecarbonyl, heterocyclesulfinyl, heterocyclesulfonyl, hydroxy, hydroxyalkyl, hydroxyalkylsulfonyl, hydroxyhaloalkyl, mercapto, oxo, nitro, $R_mR_nN$—, $R_mR_nN$—C(O)—, $R_mR_nN$—S(O$_2$)—, ($R_mR_nN$)alkyl, $R_mR_nN$—C(O)-alkyl-O—, and —O—(CH$_2$)$_n$—O— wherein the oxygen atoms are attached to two adjacent carbon atoms of the cycloalkyl, and n is 1, 2 or 3, and wherein the substituent aryl, the aryl of arylalkoxy, the aryl of arylalkoxycarbonyl, the aryl of arylalkyl, the aryl of arylcarbonyl, the aryl of aryloxy, the aryl of arylsulfinyl, the aryl of arylsulfonyl, the substituent cycloalkyl, the cycloalkyl of cycloalkylalkoxy, the cycloalkyl of cycloalkylcarbonyl, the cycloalkyl of cycloalkylsulfonyl, the heteroaryl, the heteroaryl of heteroarylalkyl, the heteroaryl of heteroarylcarbonyl, the heteroaryl of heteroaryloxy, the heteroaryl of heteroarysulfinyl, the heteroaryl of heteroarylsulfonyl, the heterocycle, the heterocycle of heterocyclealkyl, the heterocycle of heterocyclecarbonyl, the heterocycle of heterocyclesulfinyl and the heterocycle of heterocyclesulfonyl can be optionally substituted with 1, or 2 substituents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, formyl, haloalkoxy, haloalkyl, haloalkylcarbonyl, haloalkylsulfonyl, halogen, hydroxy, hydroxyalkyl, and $R_pR_qN$—C(O)—. $R_m$ at each occurrence is hydrogen or alkyl, $R_n$ at each occurrence is independently selected from the group consisting of hydrogen, alkyl, alkoxyalkyl, alkoxycarbonyl, alkoxycarbonylalkyl, alkylcarbonyl, alkylsulfonyl, carboxyalkyl, ($R_pR_qN$)—C(O)-alkyl-, ($R_pR_qN$)—S(O)$_2$-alkyl-, phenyl and phenylalkyl; wherein the phenyl and the phenyl moiety of the phenylalkyl are each independently unsubstituted or substituted with one or two substituents selected from the group consisting of alkyl, halogen, haloalkyl, alkylcarbonyl, and alkylsulfonyl. $R_p$ and $R_q$, at each occurrence, are each independently hydrogen or alkyl.

The term "cycloalkylalkoxy" as used herein, means a cycloalkyl group, as defined herein, appended to the parent molecular moiety through an alkoxy group, as defined herein. Representative examples of cycloalkylalkoxy include, but are not limited to, cyclopropylmethoxy, cyclobutylmethoxy, cyclopentylmethoxy, cyclohexylmethoxy, 2-cyclohexylethoxy, cycloheptylmethoxy and cyclooctylmethoxy.

The term "cycloalkylalkoxyalkyl" as used herein, means a cycloalkylalkoxy group, as defined herein appended to the parent molecular moiety through an alkyl group, as defined herein. Representative examples of cycloalkoxyalkyl include, but are not limited to, cyclopropylmethoxymethyl, cyclobutylmethoxymethyl, cyclopentylmethoxymethyl, cyclohexylmethoxymethyl, (2-cyclohexylethoxy)methyl, cycloheptylmethoxymethyl and cyclooctylmethoxymethyl.

The term "cycloalkylalkyl" as used herein, means a cycloalkyl group, as defined herein, appended to the parent molecular moiety through an alkyl group as defined herein. Representative examples of cycloalkylalkyl include, but are not limited to, cyclopropylmethyl, cyclobutylmethyl, cyclopentylmethyl, cyclohexylmethyl, 2-cyclohexylethyl, cycloheptylmethyl and cyclooctylmethyl.

The term "cycloalkylalkylthio" as used herein, means a cycloalkylalkyl group, as defined herein, appended to the parent molecular moiety through a sulfur atom. Representative examples of cycloalkylalkylthio include, but are not limited to, cyclopropylmethylthio, cyclobutylmethylthio, cyclopentylmethylthio, cyclohexylmethylthio, 2-cyclohexylethylthio, cycloheptylmethylthio and cyclooctylmethylthio.

The term "cycloalkylalkylthioalkyl" as used herein, means a cycloalkylalkylthio group, as defined herein, appended to the parent molecular moiety through an alkyl group, as defined herein. Representative examples of cycloalkylalkylthioalkyl include, but are not limited to, cyclopropylmethylthiomethyl, cyclobutylmethylthiomethyl, cyclopentylmethylthiomethyl, cyclohexylmethylthiomethyl, 2-cyclohexylethylthiomethyl, cycloheptylmethylthiomethyl and cyclooctylmethylthiomethyl.

The term "cycloalkylcarbonyl" as used herein, means a cycloalkyl group, as defined herein, appended to the parent molecular moiety through a carbonyl group as defined herein. Representative examples of cycloalkylcarbonyl include, but are not limited to, cyclopropylcarbonyl, cyclobutylcarbonyl, cyclopentylcarbonyl, cyclohexylcarbonyl, cycloheptylcarbonyl and cyclooctylcarbonyl.

The term "cycloalkylcarbonylalkyl," as used herein, means a cycloalkylcarbonyl group, as defined herein, appended to the parent molecular moiety through an alkyl group as defined herein.

The term "cycloalkyloxy" as used herein, means a cycloalkyl group, as defined herein, appended to the parent molecular moiety through an oxygen atom, examples of cycloalkyloxy include cyclopropyloxy, cyclobutyloxy, cyclopentyloxy, cyclohexyloxy, cycloheptyloxy and cyclooctyloxy.

The term "cycloalkyloxyalkyl" as used herein, means a cycloalkyloxy group, as defined herein, appended to the parent molecular moiety through an alkyl group, as defined herein. Representative examples of cycloalkyloxyalkyl include, but are not limited to, cyclopropyloxymethyl, cyclobutyloxymethyl, cyclopentyloxymethyl, cyclohexyloxymethyl, cycloheptyloxymethyl and cyclooctyloxymethyl.

The term "cycloalkylsulfinyl," as used herein, refers to a cycloalkyl group, as defined herein, appended to the parent molecular moiety through a sulfinyl group, as defined herein.

The term "cycloalkylsulfinylalkyl," as used herein, refers to a cycloalkylsulfinyl group, as defined herein, appended to the parent molecular moiety through an alkyl group, as defined herein.

The term "cycloalkylsulfonyl," as used herein, refers to a cycloalkyl group, as defined herein, appended to the parent molecular moiety through a sulfonyl group, as defined herein.

The term "cycloalkylsulfonylalkyl," as used herein, refers to a cycloalkylsulfonyl group, as defined herein, appended to the parent molecular moiety through an alkyl group, as defined herein.

The term "cycloalkylthio" as used herein, means a cycloalkyl group, as defined herein, appended to the parent molecular moiety through a sulfur atom, examples of cycloalkylthio include cyclopropylthio, cyclobutylthio, cyclopentylthio, cyclohexylthio, cycloheptylthio and cyclooctylthio.

The term "cycloalkylthioalkyl" as used herein, means a cycloalkylthio group, as defined herein, appended to the parent molecular moiety through an alkyl group, as defined herein. Representative examples of cycloalkylthioalkyl include cyclopropylthiomethyl, cyclobutylthiomethyl, cyclopentylthiomethyl, cyclohexylthiomethyl, cycloheptylthiomethyl and cyclooctylthiomethyl.

The term "formyl," as used herein, means a —C(O)H group.

The term "halo" or "halogen," as used herein, means —Cl, —Br, —I or —F.

The term "haloalkoxy," as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, pentafluoroethoxy and 2-chloro-3-fluoropentoxy.

The term "haloalkyl," as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl and 2-chloro-3-fluoropentyl.

The term "haloalkylcarbonyl," as used herein, means a haloalkyl group, as defined herein, appended to the parent molecular moiety through a carbonyl group, as defined herein. Representative examples of haloalkylcarbonyl include, but are not limited to, chloromethylcarbonyl, 2-fluoroethylcarbonyl, trifluoromethylcarbonyl, pentafluoroethylcarbonyl and 2-chloro-3-fluoropentylcarbonyl.

The term "haloalkylsulfonyl," as used herein, means a haloalkyl group, as defined herein, appended to the parent molecular moiety through a sulfonyl group, as defined herein. Representative examples of haloalkylsulfonyl include, but are not limited to, chloromethylsulfonyl, 2-fluoroethylsulfonyl, trifluoromethylsulfonyl, pentafluoroethylsulfonyl and 2-chloro-3-fluoropentylsulfonyl.

The term "heteroaryl," as used herein, means a monocyclic heteroaryl or a bicyclic heteroaryl. The monocyclic heteroaryls are five or six membered rings wherein 1, 2, 3, or 4 atoms are independently selected from the group consisting of N, O and S, and the others are carbon. The five membered monocyclic heteroaryls have two double bonds and the six membered monocyclic heteroaryls have three double bonds. Bicyclic heteroaryl is a monocyclic heteroaryl fused to a phenyl, a monocyclic heteroaryl fused to a monocyclic heteroaryl, a monocyclic heteroaryl fused to a monocyclic heterocycle, as defined herein, a monocyclic heteroaryl fused to a monocyclic cycloalkyl, as defined herein, or a monocyclic heteroaryl fused to a monocyclic cycloalkenyl, as defined herein. The monocyclic and the bicyclic heteroaryls are connected to the parent molecular moiety through any substitutable carbon or nitrogen atom within the monocyclic and the bicyclic ring. Representative examples of heteroaryl include, but are not limited to, benzimidazole, benzothienyl, benzoxadiazolyl, cinnolinyl, dibenzofuranyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, quinolinyl, tetrazolyl, thiadiazolyl, thiazolyl, thienopyridinyl, thienyl, triazolyl and triazinyl.

The monocyclic and the bicyclic heteroaryls of the present invention are optionally substituted with 1, 2, 3, or 4 substituents independently selected from the group consisting of alkenyl, alkoxy, alkoxyalkyl, alkoxyalkylcarbonyl, alkoxyalkylsulfonyl, alkoxycarbonyl, alkoxycarbonylalkyl, alkyl, alkylcarbonyl, alkylcarbonylalkyl, alkylcarbonyloxy, alkylsulfinyl, alkylsulfonyl, alkylthio, alkynyl, aryl, arylalkoxy, arylalkoxycarbonyl, arylalkyl, arylcarbonyl, aryloxy, arylsulfinyl, arylsulfonyl, carboxy, carboxyalkyl, carboxycarbonyl, cyano, cyanoalkyl, cycloalkyl, cycloalkoxy, cycloalkylcarbonyl, cycloalkylsulfonyl, formyl, haloalkoxy, haloalkyl, haloalkylthio, haloalkylcarbonyl, haloalkylsulfonyl, halogen, heteroaryl, heteroarylalkyl, heteroaryloxy, heteroarylcarbonyl, heteroarylsulfinyl, heteroarylsulfonyl, heterocycle, heterocyclealkyl, heterocyclecarbonyl, heterocyclesulfinyl, heterocyclesulfonyl, hydroxy, hydroxyalkyl, hydroxyalkylsulfonyl, hydroxyhaloalkyl, mercapto, nitro, oxo, $R_mR_nN$—, $R_mR_nN$—C(O)—, $R_mR_nN$—S(O$_2$)—, $(R_mR_nN)$alkyl, $R_mR_nN$—C(O)-alkyl-O—, and —O—(CH$_2$)$_n$—O— wherein the oxygen atoms are attached to two adjacent carbon atoms of the heteroaryl, and n is 1, 2 or 3, and wherein the substituent aryl, the aryl of arylalkoxy, the aryl of arylalkoxycarbonyl, the aryl of arylalkyl, the aryl of arylcarbonyl, the aryl of aryloxy, the aryl of arylsulfinyl, the aryl of arylsulfonyl, the substituent cycloalkyl, the cycloalkyl of cycloalkylalkoxy, the cycloalkyl of cycloalkylcarbonyl, the cycloalkyl of cycloalkylsulfonyl, the heteroaryl, the heteroaryl of heteroarylalkyl, the heteroaryl of heteroarylcarbonyl, the heteroaryl of heteroaryloxy, the heteroaryl of heteroarysulfinyl, the heteroaryl of heteroarylsulfonyl, the heterocycle, the heterocycle of heterocyclealkyl, the heterocycle of heterocyclecarbonyl, the heterocycle of heterocyclesulfinyl and the heterocycle of heterocyclesulfonyl can be optionally substituted with 1, or 2 substitutents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, formyl, haloalkoxy, haloalkyl, haloalkylcarbonyl, haloalkylsulfonyl, halogen, hydroxy, hydroxyalkyl, and $R_pR_qN$—C(O)—. $R_m$ at each occurrence is hydrogen or alkyl, $R_n$ at each occurrence is independently selected from the group consisting of hydrogen, alkyl, alkoxyalkyl, alkoxycarbonyl, alkoxycarbonylalkyl, alkylcarbonyl, alkylsulfonyl, carboxyalkyl, $(R_pR_qN)$—C(O)-alkyl-, $(R_pR_qN)$—S(O)$_2$-alkyl-, phenyl and phenylalkyl; wherein the phenyl and the phenyl moiety of the phenylalkyl are each independently unsubstituted or substituted with one or two substituents selected from the group consisting of alkyl, halogen, haloalkyl, alkylcarbonyl, and alkylsulfonyl. $R_p$ and $R_q$, at each occurrence, are each independently hydrogen or alkyl.

The term "heteroarylalkoxy" as used herein, means a heteroaryl group, as defined herein, appended to the parent molecular moiety through an alkoxy group, as defined herein. Representative examples of heteroarylalkoxy include, but are not limited to, fur-3-ylmethoxy, 1H-imidazol-2-ylmethoxy, 1H-imidazol-4-ylmethoxy, 1-(pyridin-4-yl)ethoxy, pyridin-3-ylmethoxy, 6-chloropyridin-3-ylmethoxy, pyridin-4-ylmethoxy, (6-(trifluoromethyl)pyridin-3-yl)methoxy, (6-(cyano)pyridin-3-yl)methoxy, (2-(cyano)pyridin-4-yl)methoxy, (5-(cyano)pyridin-2-yl)methoxy, (2-(chloro)pyridin-4-yl)methoxy, pyrimidin-5-ylmethoxy, 2-(pyrimidin-2-yl)propoxy, thien-2-ylmethoxy and thien-3-ylmethoxy.

The term "heteroarylalkoxyalkyl" as used herein, means a heteroarylalkoxy group, as defined herein, appended to the parent molecular moiety through an alkyl group, as defined herein. Representative examples of heteroarylalkoxyalkyl include, but are not limited to, fur-3-ylmethoxymethyl, 1H-imidazol-2-ylmethoxymethyl, 1H-imidazol-4-ylmethoxymethyl, pyridin-3-ylmethoxymethyl, 6-chloropyridin-3-ylmethoxymethyl, pyridin-4-ylmethoxymethyl, (6-(trifluoromethyl)pyridin-3-yl)methoxymethyl, (6-(cyano)pyridin-3-yl)methoxymethyl, (2-(cyano)pyridin-4-yl)methoxymethyl, (5-(cyano)pyridin-2-yl)methoxymethyl, (2-(chloro)pyridin-4-yl)methoxymethyl, pyrimidin-5-ylmethoxymethyl, 2-(pyrimidin-2-yl)propoxymethyl, thien-2-ylmethoxymethyl and thien-3-ylmethoxymethyl.

The term "heteroarylalkyl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl and thien-3-ylmethyl.

The term "heteroarylalkylsulfonyl" as used herein, means a heteroarylalkyl, as defined herein, appended to the parent molecular moiety through a sulfonyl group, as defined herein.

The term "heteroarylalkylsulfonylalkyl" as used herein, means a heteroarylalkylsulfonyl, as defined herein, appended to the parent molecular moiety through an alkyl group, as defined herein.

The term "heteroarylalkylthio" as used herein, means a heteroarylalkyl group, as defined herein, appended to the parent molecular moiety through a sulfur atom. Representative examples of heteroarylalkylthio include, but are not limited to, fur-3-ylmethylthio, 1H-imidazol-2-ylmethylthio, 1H-imidazol-4-ylmethylthio, pyridin-3-ylmethylthio, 6-chloropyridin-3-ylmethylthio, pyridin-4-ylmethylthio, (6-(trifluoromethyl)pyridin-3-yl)methylthio, (6-(cyano)pyridin-3-yl)methylthio, (2-(cyano)pyridin-4-yl)methylthio, (5-(cyano)pyridin-2-yl)methylthio, (2-(chloro)pyridin-4-yl)methylthio, pyrimidin-5-ylmethylthio, 2-(pyrimidin-2-yl)propylthio, thien-2-ylmethylthio and thien-3-ylmethylthio.

The term "heteroarylalkylthioalkyl" as used herein, means a heteroarylalkylthio group, as defined herein, appended to the parent molecular moiety through an alkyl group, as defined herein. Representative examples of heteroarylalkylthioalkyl include, but are not limited to, fur-3-ylmethylthiomethyl, 1H-imidazol-2-ylmethylthiomethyl, 1H-imidazol-4-ylmethylthiomethyl, pyridin-3-ylmethylthiomethyl, 6-chloropyridin-3-ylmethylthiomethyl, pyridin-4-ylmethylthiomethyl, (6-(trifluoromethyl)pyridin-3-yl)methylthiomethyl, (6-(cyano)pyridin-3-yl)methylthiomethyl, (2-(cyano)pyridin-4-yl)methylthiomethyl, (5-(cyano)pyridin-2-yl)methylthiomethyl, (2-(chloro)pyridin-4-yl)methylthiomethyl, pyrimidin-5-ylmethylthiomethyl, 2-(pyrimidin-2-yl)propylthiomethyl, thien-2-ylmethylthiomethyl and thien-3-ylmethylthiomethyl.

The term "heteroarylcarbonyl" as used herein, means a heteroaryl group, as defined herein, appended to the parent molecular moiety through a carbonyl group, as defined herein.

Representative examples of heteroarylcarbonyl include, but are not limited to, fur-3-ylcarbonyl, 1H-imidazol-2-ylcarbonyl, 1H-imidazol-4-ylcarbonyl, pyridin-3-ylcarbonyl, 6-chloropyridin-3-ylcarbonyl, pyridin-4-ylcarbonyl, (6-(trifluoromethyl)pyridin-3-yl)carbonyl, (6-(cyano)pyridin-3-yl)carbonyl, (2-(cyano)pyridin-4-yl)carbonyl, (5-(cyano)pyridin-2-yl)carbonyl, (2-(chloro)pyridin-4-yl)carbonyl, pyrimidin-5-ylcarbonyl, pyrimidin-2-ylcarbonyl, thien-2-ylcarbonyl and thien-3-ylcarbonyl.

The term "heteroarylcarbonylalkyl" as used herein, means a heteroarylcarbonyl group, as defined herein, appended to the parent molecular moiety through an alkyl group, as defined herein.

The term "heteroaryloxy" as used herein, means a heteroaryl group, as defined herein, appended to the parent molecular moiety through an oxygen atom. Representative examples of heteroaryloxy include, but are not limited to, fur-3-yloxy, 1H-imidazol-2-yloxy, 1H-imidazol-4-yloxy, pyridin-3-yloxy, 6-chloropyridin-3-yloxy, pyridin-4-yloxy, (6-(trifluoromethyl)pyridin-3-yl)oxy, (6-(cyano)pyridin-3-yl)oxy, (2-(cyano)pyridin-4-yl)oxy, (5-(cyano)pyridin-2-yl)oxy, (2-(chloro)pyridin-4-yl)oxy, pyrimidin-5-yloxy, pyrimidin-2-yloxy, thien-2-yloxy and thien-3-yloxy.

The term "heteroaryloxyalkyl" as used herein, means a heteroaryloxy group, as defined herein, appended to the parent molecular moiety through an alkyl group, as defined herein. Representative examples of heteroaryloxyalkyl include, but are not limited to, fur-3-yloxymethyl, 1H-imidazol-2-yloxymethyl, 1H-imidazol-4-yloxymethyl, pyridin-3- yloxymethyl, 6-chloropyridin-3-yloxymethyl, pyridin-4-yloxymethyl, (6-(trifluoromethyl)pyridin-3-yl)oxymethyl, (6-(cyano)pyridin-3-yl)oxymethyl, (2-(cyano)pyridin-4-yl)oxymethyl, (5-(cyano)pyridin-2-yl)oxymethyl, (2-(chloro)pyridin-4-yl)oxymethyl, pyrimidin-5-yloxymethyl, pyrimidin-2-yloxymethyl, thien-2-yloxymethyl and thien-3-yloxymethyl.

The term "heteroarylsulfinyl," as used herein, means a heteroaryl group, as defined herein, appended to the parent molecular moiety through a sulfinyl group, as defined herein.

The term "heteroarylsulfinylalkyl," as used herein, means a heteroarylsulfinyl group, as defined herein, appended to the parent molecular moiety through an alkyl group, as defined herein.

The term "heteroarylsulfonyl" as used herein, means a heteroaryl group, as defined herein, appended to the parent molecular moiety through a sulfonyl group, as defined herein.

The term "heteroarylsulfonylalkyl" as used herein, means a heteroarylsulfonyl group, as defined herein, appended to the parent molecular moiety through a alkyl group, as defined herein.

The term "heteroarylthio" as used herein, means a heteroaryl group, as defined herein, appended to the parent molecular moiety through a sulfur atom. Representative examples of heteroarylthio include, but are not limited to, fur-3-ylthio, 1H-imidazol-2-ylthio, 1H-imidazol-4-ylthio, pyridin-3-ylthio, 6-chloropyridin-3-ylthio, pyridin-4-ylthio, (6-(trifluoromethyl)pyridin-3-yl)thio, (6-(cyano)pyridin-3-yl)thio, (2-(cyano)pyridin-4-yl)thio, (5-(cyano)pyridin-2-yl)thio, (2-(chloro)pyridin-4-yl)thio, pyrimidin-5-ylthio, pyrimidin-2-ylthio, thien-2-ylthio and thien-3-ylthio.

The term "heteroarylthioalkyl" as used herein, means a heteroarylthio group, as defined herein, appended to the parent molecular moiety through an alkyl group, as defined herein. Representative examples of heteroarylthioalkyl include, but are not limited to, fur-3-ylthiomethyl, 1H-imidazol-2-ylthiomethyl, 1H-imidazol-4-ylthiomethyl, pyridin-3-ylthiomethyl, 6-chloropyridin-3-ylthiomethyl, pyridin-4-ylthiomethyl, (6-(trifluoromethyl)pyridin-3-yl)thiomethyl, (6-(cyano)pyridin-3-yl)thiomethyl, (2-(cyano)pyridin-4-yl)thiomethyl, (5-(cyano)pyridin-2-yl)thiomethyl, (2-(chloro)pyridin-4-yl)thiomethyl, pyrimidin-5-ylthiomethyl, pyrimidin-2-ylthiomethyl, thien-2-ylthiomethyl and thien-3-ylthiomethyl.

The term "heterocycle" as used herein, refers to a monocyclic heterocycle or a bicyclic heterocycle. The monocyclic heterocycle is a three, four, five, six, seven, or eight membered ring containing 1 or 2 heteroatoms independently selected from the group consisting of N, O and S, and the others are carbon. The three-membered heterocycles contain only single bonds. The four and five-membered monocyclic heterocycles have zero or 1 double bond. The six, seven, or eight membered heterocycles have zero, one or two double bonds. The bicyclic heterocycle is a monocyclic heterocycle fused to a phenyl group, a monocyclic heterocycle fused to another monocyclic heterocycle, a monocyclic heterocycle fused to a monocyclic cycloalkenyl, as defined herein, or a monocyclic heterocycle fused to a monocyclic cycloalkyl, as defined herein. The monocyclic and the bicyclic heterocycles of the present invention can be attached to the parent molecular moiety through any substitutable atom within the ring. Representative examples of heterocycle include, but are not limited to, azetidinyl, 1,3-benzodioxolyl, 1,3-benzodioxol-4-yl, hexahydro-1H-azepinyl, hexahydroazocin-(2H)-yl, morpholinyl, piperazinyl, piperidinyl, pyrrolidinyl, tetrahydrofuranyl, tetrahydrofuran-2-yl, tetrahydrofuran-3-yl, tetrahydro-2H-pyranyl, tetrahydro-2H-pyran-2-yl, tetrahydro-2H-pyran-4-yl, tetrahydrothienyl, tetrahydrothien-2-yl and tetrahydrothien-3-yl and thiomorpholinyl.

The monocyclic and the bicyclic heterocycles of the present invention are optionally substituted with 1, 2, 3 or 4 substituents independently selected from the group consisting of alkenyl, alkoxy, alkoxyalkyl, alkoxyalkylcarbonyl, alkoxyalkylsulfonyl, alkoxycarbonyl, alkoxycarbonylalkyl, alkyl, alkylcarbonyl, alkylcarbonylalkyl, alkylcarbonyloxy, alkylsulfinyl, alkylsulfonyl, alkylthio, alkynyl, aryl, arylalkoxy, arylalkoxycarbonyl, arylalkyl, arylcarbonyl, aryloxy, arylsulfinyl, arylsulfonyl, carboxy, carboxyalkyl, carboxycarbonyl, cyano, cyanoalkyl, cycloalkyl, cycloalkoxy, cycloalkylcarbonyl, cycloalkylsulfonyl, formyl, haloalkoxy, haloalkyl, haloalkylthio, haloalkylcarbonyl, haloalkylsulfonyl, halogen, heteroaryl, heteroarylalkyl, heteroaryloxy, heteroarylcarbonyl, heteroarylsulfinyl, heteroarylsulfonyl, heterocycle, heterocyclealkyl, heterocyclecarbonyl, heterocyclesulfinyl, heterocyclesulfonyl, hydroxy, hydroxyalkyl, hydroxyalkylsulfonyl, hydroxyhaloalkyl, mercapto, nitro, oxo, $R_mR_nN$—, $R_mR_nN$—C(O)—, $R_mR_nN$—S(O$_2$)—, $(R_mR_nN)$alkyl, $R_mR_nN$—C(O)-alkyl-O—, and —O—(CH$_2$)$_n$—O— wherein the oxygen atoms are attached to two adjacent carbon atoms of heterocycle, and n is 1, 2 or 3, and wherein the substituent aryl, the aryl of arylalkoxy, the aryl of arylalkoxycarbonyl, the aryl of arylalkyl, the aryl of arylcarbonyl, the aryl of aryloxy, the aryl of arylsulfinyl, the aryl of arylsulfonyl, the substituent cycloalkyl, the cycloalkyl of cycloalkylalkoxy, the cycloalkyl of cycloalkylcarbonyl, the cycloalkyl of cycloalkylsulfonyl, the heteroaryl, the heteroaryl of heteroarylalkyl, the heteroaryl of heteroarylcarbonyl, the heteroaryl of heteroaryloxy, the heteroaryl of heteroarylsulfinyl, the heteroaryl of heteroarylsulfonyl, the heterocycle, the heterocycle of heterocyclealkyl, the heterocycle of heterocyclecarbonyl, the heterocycle of heterocyclesulfinyl and the heterocycle of heterocyclesulfonyl can be optionally substituted with 1, or 2 substitutents independently selected from the group consisting of alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylsulfonyl, alkylthio, alkynyl, carboxy, carboxyalkyl, cyano, cyanoalkyl, formyl, haloalkoxy, haloalkyl, haloalkylcarbonyl, haloalkylsulfonyl, halogen, hydroxy, hydroxyalkyl, and $R_pR_qN$—C(O)—. $R_m$ at each occurrence is hydrogen or alkyl, $R_n$ at each occurrence is independently selected from the group consisting of hydrogen, alkyl, alkoxyalkyl, alkoxycarbonyl, alkoxycarbonylalkyl, alkylcarbonyl, alkylsulfonyl, carboxyalkyl, $(R_pR_qN)$—C(O)-alkyl-, $(R_pR_qN)$—S(O)$_2$-alkyl-, phenyl and phenylalkyl; wherein the phenyl and the phenyl moiety of the phenylalkyl are each independently unsubstituted or substituted with one or two substituents selected from the group consisting of alkyl, halogen, haloalkyl, alkylcarbonyl, and alkylsulfonyl. $R_p$ and $R_q$, at each occurrence, are each independently hydrogen or alkyl.

The term "heterocyclealkoxy" as used herein, means a heterocycle group, as defined herein, appended to the parent molecular moiety through an alkoxy group, as defined herein. Representative examples of heterocyclealkoxy include, but are not limited to, 1,3-benzodioxol-4-ylmethoxy, pyridin-3-ylmethoxy, 2-pyrimidin-2-ylpropoxy, tetrahydrofuran-2-ylmethoxy, tetrahydrofuran-3-ylmethoxy, tetrahydro-2H-pyran-2-ylmethoxy, tetrahydro-2H-pyran-4-ylmethoxy, tetrahydrothien-2-ylmethoxy and tetrahydrothien-3-ylmethoxy.

The term "heterocyclealkoxyalkyl" as used herein, means a heterocyclealkoxy group, as defined herein, appended to the parent molecular moiety through an alkyl group, as defined herein. Representative examples of heterocyclealkoxyalkyl include, but are not limited to, 1,3-benzodioxol-4-yl-methoxymethyl, pyridin-3-ylmethoxymethyl, 2-pyrimidin-2-ylpropoxymethyl, tetrahydrofuran-2-ylmethoxymethyl, tetrahydrofuran-3-ylmethoxymethyl, tetrahydro-2H-pyran-2-ylmethoxymethyl, tetrahydro-2H-pyran-4-ylmethoxymethyl, tetrahydrothien-2-ylmethoxymethyl and tetrahydrothien-3-ylmethoxymethyl.

The term "heterocyclealkyl" as used herein, means a heterocycle group, as defined herein, appended to the parent molecular moiety through an alkyl group, as defined herein. Representative examples of heterocyclealkyl include, but are not limited to, 1,3-benzodioxol-4-ylmethyl, pyridin-3-ylmethyl, 2-pyrimidin-2-ylpropyl, tetrahydrofuran-2-ylmethyl, tetrahydrofuran-3-ylmethyl, tetrahydro-2H-pyran-2-ylmethyl, tetrahydro-2H-pyran-4-ylmethyl, tetrahydrothien-2-ylmethyl and tetrahydrothien-3-ylmethyl.

The term "heterocyclealkylthio" as used herein, means a heterocyclealkyl group, as defined herein, appended to the parent molecular moiety through a sulfur atom. Representative examples of heterocyclealkylthio include, but are not limited to, 1,3-benzodioxol-4-ylmethylthio, pyridin-3-ylmethylthio, 2-pyrimidin-2-ylpropylthio, tetrahydrofuran-2-ylmethylthio, tetrahydrofuran-3-ylmethylthio, tetrahydro-2H-pyran-2-ylmethylthio, tetrahydro-2H-pyran-4-ylmethylthio, tetrahydrothien-2-ylmethylthio and tetrahydrothien-3-ylmethylthio.

The term "heterocyclealkylthioalkyl" as used herein, means a heterocyclealkylthio group, as defined herein, appended to the parent molecular moiety through an alkyl group, as defined herein. Representative examples of heterocyclealkylthioalkyl include, but are not limited to, 1,3-benzodioxol-4-ylmethylthiomethyl, pyridin-3-ylmethylthiomethyl, 2-pyrimidin-2-ylpropylthiomethyl, tetrahydrofuran-2-ylmethylthiomethyl, tetrahydrofuran-3-ylmethylthiomethyl, tetrahydro-2H-pyran-2-ylmethylthiomethyl, tetrahydro-2H-pyran-4-ylmethylthiomethyl, tetrahydrothien-2-ylmethylthiomethyl and tetrahydrothien-3-ylmethylthiomethyl.

The term "heterocyclecarbonyl" as used herein, means a heterocycle group, as defined herein, appended to the parent molecular moiety through a carbonyl group, as defined herein. Representative examples of heterocyclecarbonyl include, but are not limited to, 1,3-benzodioxol-4-ylcarbonyl, pyridin-3-ylcarbonyl, pyrimidin-2-ylcarbonyl, tetrahydrofuran-2-ylcarbonyl, tetrahydrofuran-3-ylcarbonyl, tetrahydro-2H-pyran-2-ylcarbonyl, tetrahydro-2H-pyran-4-ylcarbonyl, tetrahydrothien-2-ylcarbonyl and tetrahydrothien-3-ylcarbonyl.

The term "heterocyclecarbonylalkyl" as used herein, means a heterocyclecarbonyl group, as defined herein, appended to the parent molecular moiety through an alkyl group, as defined herein.

The term "heterocycleoxy" as used herein, means a heterocycle group, as defined herein, appended to the parent molecular moiety through an oxygen atom. Representative examples of heterocycleoxy include, but are not limited to, 1,3-benzodioxol-4-yloxy, pyridin-3-yloxy, 2-pyrimidin-2-yloxy, tetrahydrofuran-2-yloxy, tetrahydrofuran-3-yloxy, tetrahydro-2H-pyran-2-yloxy, tetrahydro-2H-pyran-4-yloxy, tetrahydrothien-2-yloxy and tetrahydrothien-3-yloxy.

The term "heterocycleoxyalkyl" as used herein, means a heterocycleoxy group, as defined herein, appended to the parent molecular moiety through an alkyl group, as defined herein. Representative examples of heterocycleoxyalkyl include, but are not limited to, 1,3-benzodioxol-4-yloxymethyl, pyridin-3-yloxymethyl, 2-pyrimidin-2-yloxymethyl, tetrahydrofuran-2-yloxymethyl, tetrahydrofuran-3-yloxymethyl, tetrahydro-2H-pyran-2-yloxymethyl, tetrahydro-2H-pyran-4-yloxymethyl, tetrahydrothien-2-yloxymethyl and tetrahydrothien-3-yloxymethyl.

The term "heterocyclesulfinyl," as used herein, means a heterocycle group, as defined herein, appended to the parent molecular moiety through a sulfinyl group, as defined herein.

The term "heterocyclesulfinylalkyl" as used herein, means a heterocyclesulfinyl group, as defined herein, appended to the parent molecular moiety through an alkyl group, as defined herein. The term "heterocyclesulfonyl" as used herein, means a heterocycle group, as defined herein, appended to the parent molecular moiety through a sulfonyl group, as defined herein.

The term "heterocyclesulfonylalkyl" as used herein, means a heterocyclesulfonyl group, as defined herein, appended to the parent molecular moiety through an alkyl group, as defined herein.

The term "heterocyclethio" as used herein, means a heterocycle group, as defined herein, appended to the parent molecular moiety through a sulfur atom. Representative examples of heterocyclethio include, but are not limited to, 1,3-benzodioxol-4-ylthio, pyridin-3-ylthio, 2-pyrimidin-2-ylthio, tetrahydrofuran-2-ylthio, tetrahydrofuran-3-ylthio, tetrahydro-2H-pyran-2-ylthio, tetrahydro-2H-pyran-4-ylthio, tetrahydrothien-2-ylthio and tetrahydrothien-3-ylthio.

The term "heterocyclethioalkyl" as used herein, means a heterocyclethio group, as defined herein, appended to the parent molecular moiety through an alkyl group, as defined herein. Representative examples of heterocyclethioalkyl include, but are not limited to, 1,3-benzodioxol-4-ylthiomethyl, pyridin-3-ylthiomethyl, 2-pyrimidin-2-ylthiomethyl, tetrahydrofuran-2-ylthiomethyl, tetrahydrofuran-3-ylthiomethyl, tetrahydro-2H-pyran-2-ylthiomethyl, tetrahydro-2H-pyran-4-ylthiomethyl, tetrahydrothien-2-ylthiomethyl and tetrahydrothien-3-ylthiomethyl.

The term "hydroxy" as used herein, means an —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, 2-hydroxyethyl, 2-hydroxypropyl, 1,2-dihydroxypropyl, 3-hydroxybutyl and the like.

The term "hydroxyhaloalkyl" as used herein, means at least one hydroxy group, as defined herein, appended to the parent molecular moiety through a haloalkyl group, as defined herein.

The term "hydroxyalkoxy" as used herein, means at least one hydroxy group, as defined herein, appended to the parent molecular moiety through an alkoxy group, as defined herein.

The term "hydroxyalkylsulfonyl" as used herein, means a hydroxyalkyl group, as defined herein, appended to the parent molecular moiety through a sulfonyl group, as defined herein.

The term "mercapto" as used herein, means a —SH group.

The term "nitro" as used herein, means a —NO$_2$ group.

The term "oxo" as used herein, means =O.

The term "sulfinyl" as used herein, means a —SO— group.

The term "sulfonyl" as used herein, means a —SO$_2$— group.

The present compounds can exist as therapeutically suitable salts. The term "pharmaceutically acceptable salt," refers to salts or zwitterions of the compounds which are water or oil-soluble or dispersible, suitable for treatment of disorders without undue toxicity, irritation and allergic response, commensurate with a reasonable benefit/risk ratio and effective for their intended use. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulfonate, undecanoate, hydrochloric, hydrobromic, sulfuric, phosphoric and the like. The amino groups of the compounds can also be quaternized with alkyl chlorides, bromides and iodides such as methyl, ethyl, propyl, isopropyl, butyl, lauryl, myristyl, stearyl and the like.

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine and the like, are contemplated as being within the scope of the present invention.

The present compounds can also exist as therapeutically suitable prodrugs. The term "therapeutically suitable prodrug," refers to those prodrugs which are suitable for use in contact with the tissues of patients without undue toxicity, irritation and allergic response, are commensurate with a reasonable benefit/risk ratio and are effective for their intended use. The term "prodrug," refers to compounds which are rapidly transformed in vivo to the parent compounds of the present invention for example, by hydrolysis in blood.

Asymmetric centers can exist in the present compounds. Individual stereoisomers of the compounds are prepared by synthesis from chiral starting materials or by preparation of racemic mixtures and separation by conversion to a mixture of diastereomers followed by separation or recrystallization, chromatographic teiques, or direct separation of the enantiomers on chiral chromatographic columns. Starting materials of particular stereochemistry are either commercially available or are made by the methods described hereinbelow and resolved by teiques well-known in the art.

Geometric isomers can exist in the present compounds. The invention contemplates the various geometric isomers and mixtures thereof resulting from the disposal of substituents around a carbon-carbon double bond, a cycloalkyl group, or a heterocycle group. Substituents around a carbon-carbon double bond are designated as being of Z or E configuration and substituents around a cycloalkyl or heterocycle are designated as being of cis or trans configuration.

Therapeutic compositions of the present compounds comprise an effective amount of the same formulated with one or more therapeutically suitable excipients. The term "therapeutically suitable excipient," as used herein, represents a non-toxic, solid, semi-solid or liquid filler, diluent, encapsulating material, or formulation auxiliary of any type. Examples of therapeutically suitable excipients include sugars; cellulose and derivatives thereof, oils; glycols; solutions; buffering, coloring, releasing, coating, sweetening, flavoring and perfuming agents; and the like. These therapeutic compositions can be administered parenterally, intracisternally, orally, rectally, or intraperitoneally.

Liquid dosage forms for oral administration of the present compounds comprise formulations of the same as emulsions, microemulsions, solutions, suspensions, syrups and elixirs. In addition to the compounds, the liquid dosage forms can contain diluents and/or solubilizing or emulsifying agents. Besides inert diluents, the oral compositions can include wetting, emulsifying, sweetening, flavoring and perfuming agents.

Injectable preparations of the present compounds comprise sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents which dissolve or disperse in the injectable media.

Regulation of the effects of ghrelin by the compounds of the present invention can be delayed by using a liquid suspension of crystalline or amorphous material with poor water solubility. The rate of absorption of the compounds depends upon their rate of dissolution which, in turn, depends on their crystalline form. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions which are compatible with body tissues.

Solid dosage forms for oral administration of the present compounds include capsules, tablets, pills, powders and granules. In such forms, the compound is mixed with at least one inert, therapeutically suitable excipient such as a carrier, filler, extender, disintegrating agent, solution retarding agent, wetting agent, absorbent, or lubricant. With capsules, tablets and pills, the excipient can also contain buffering agents. Suppositories for rectal administration can be prepared by mixing the compounds with a suitable non-irritating excipient which is solid at ordinary temperature but fluid in the rectum.

The present compounds can be micro-encapsulated with one or more of the excipients discussed previously. The solid dosage forms of tablets, dragees, capsules, pills and granules can be prepared with coatings and shells such as enteric and release-controlling. In these forms, the compounds can be mixed with at least one inert diluent and can optionally comprise tableting lubricants and aids. Capsules can also optionally contain opacifying agents which delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin and the rate of absorption can be controlled by providing a rate controlling membrane or by dispersing the compounds in a polymer matrix or gel.

Disorders that may be regulated by JNKs are treated or prevented in a patient by administering to the patient, a therapeutically effective amount of a compound of the present invention in such an amount and for such time as is necessary to achieve the desired result. The term "therapeutically effective amount," refers to a sufficient amount of a compound to effectively emeliorate disorders reglulated by ghrelin at a reasonable benefit/risk ratio applicable to any medical treatment. The specific therapeutically effective dose level for any particular patient will depend upon a variety of factors including the disorder being treated and the severity of the disorder, the activity of the compound employed; the specific composition employed; the age, body weight, general health, sex and diet of the patient; the time of administration, route of administration, rate of excretion; the duration of the treatment; and drugs used in combination or coincidental therapy.

The total daily dose of the present compounds in single or divided doses can be in amounts, for example, from 0.01 to 50 mg/kg body weight or more usually from 0.1 to 25 mg/kg body weight. In general, treatment regimens comprise administration to a patient in need of such treatment from about 10 mg to about 1000 mg of the compounds per day in single or multiple doses.

Determination of Biological Activity

Recombinant human JNK1 mediated phosphorylation reactions were performed in 50 µl volume containing 10 ng/well enzyme, 1 µM BT-GST-ATF2 substrate, and γ[$^{33}$P]-ATP (5 µM, 500 µCi/mmol) in a 96-well polypropylene plate. Enzyme, substrate and ATP were diluted in 20 mM MOPS, pH 7.2; 10 mM MgCl$_2$; 2 mM EGTA; 0.1% Triton ×100; 1 mM dTT. Test compounds were diluted in 100% DMSO with a final assay concentration of 1% DMSO. Reactions were carried out at room temperature and stopped after 60 minutes with the addition of EDTA. 30 µl aliquots of the quenched reactions were transferred to a Streptavidin Flashplate. The plate was incubated at room temperature for 30 minutes, washed and then counted in a Perkin-Elmer Micro-Beta plate counter. Sigmoidal curves were fitted for the six data points and IC$_{50}$ values were determined. The IC$_{50}$ for JNK2 was determined in the same fashion by using recombinant human JNK2. As shown in the table below, the compounds of the present invention were found to inhibit the activities of JNK1 and JNK2 with IC$_{50}$ in a range of about 0.001 µM to about 10 µM in the assays. In a preferred range, the compounds inhibit the activities of JNK1 and JNK2 with IC$_{50}$ in a range of about 0.001 µM to about 1.0 µM; In a more preferred range, the compounds inhibit the activities of JNK1 and JNK2 with IC$_{50}$ in a range of about 0.001 µM to about 0.1 µM.

TABLE 1

JNK-1 and JNK-2 inhibitory concentration

| Compound | JNK1 IC$_{50}$ (µM) | JNK2 IC$_{50}$ (µM) |
| --- | --- | --- |
| AA | 0.02 | |
| AB | 0.04 | |
| AC | 0.05 | 0.1255 |
| AD | 0.06 | |
| AE | 0.06 | |
| AF | 0.06 | |
| BA | 0.06 | |
| BB | 0.06 | |
| BC | 0.07 | |
| BD | 0.07 | |
| BE | 0.07 | |
| BF | 0.08 | |
| CA | 0.08 | 0.1676 |
| CB | 0.09 | |
| CC | 0.09 | 0.07821 |
| CD | 0.10 | 0.2611 |
| CE | 0.11 | |
| CF | 0.11 | |
| DA | 0.12 | |
| DB | 0.12 | |
| DC | 0.12 | |
| DD | 0.13 | |

TABLE 1-continued

JNK-1 and JNK-2 inhibitory concentration

| Compound | JNK1 IC$_{50}$ (µM) | JNK2 IC$_{50}$ (µM) |
| --- | --- | --- |
| DE | 0.13 | 0.1809 |
| DF | 0.13 | |
| EA | 0.14 | 0.06641 |
| EB | 0.14 | |
| EC | 0.15 | |
| ED | 0.15 | |
| EE | 0.15 | |
| EF | 0.15 | |
| FA | 0.16 | |
| FB | 0.16 | |
| FC | 0.18 | |
| FD | 0.18 | |
| FE | 0.19 | 0.3002 |
| FF | 0.19 | 0.06071 |
| GA | 0.19 | 0.07982 |
| GB | 0.19 | 2.359 |
| GC | 0.20 | |
| GD | 0.22 | |
| GE | 0.24 | |
| GF | 0.24 | |
| HA | 0.24 | |
| HB | 0.24 | |
| HC | 0.24 | |
| HD | 0.25 | |
| HE | 0.27 | |
| HF | 0.30 | 1.055 |
| IA | 0.31 | 2.702 |
| IB | 0.32 | |
| IC | 0.35 | |
| ID | 0.36 | |
| IE | 0.36 | |
| IF | 0.36 | |
| JA | 0.38 | 0.32 |
| JB | 0.38 | 0.2495 |
| JC | 0.40 | |
| JD | 0.40 | 0.2962 |
| JE | 0.42 | |
| JF | 0.45 | |
| KA | 0.45 | |
| KB | 0.49 | |
| KC | 0.49 | 0.802 |
| KD | 0.50 | 0.3393 |
| KE | 0.51 | 1.664 |
| KF | 0.51 | |
| LA | 0.51 | |
| LB | 0.54 | |
| LC | 0.56 | |
| LD | 0.56 | |
| LE | 0.57 | |
| LF | 0.59 | 0.7024 |
| MA | 0.61 | |
| MB | 0.64 | 0.3976 |
| MC | 0.64 | 7.299 |
| MD | 0.66 | 1.26 |
| ME | 0.67 | 1.459 |
| MF | 0.69 | |
| NA | 0.70 | 5.659 |
| NB | 0.70 | 1.379 |
| NC | 0.71 | |
| ND | 0.72 | |
| NE | 0.80 | 0.9313 |
| NF | 0.80 | |
| OA | 0.89 | |
| OB | 0.91 | 0.99755 |
| OC | 0.92 | 5.512 |
| OD | 0.93 | |
| OE | 1.05 | |
| OF | 1.10 | |
| PA | 1.12 | |
| PB | 1.17 | |
| PC | 1.18 | 3.883 |
| PD | 1.21 | |
| PE | 1.21 | |
| PF | 1.22 | |
| QA | 1.23 | |

TABLE 1-continued

JNK-1 and JNK-2 inhibitory concentration

| Compound | JNK1 IC$_{50}$ (μM) | JNK2 IC$_{50}$ (μM) |
|---|---|---|
| QB | 1.32 | |
| QC | 1.34 | |
| QD | 1.36 | |
| QE | 1.37 | |
| QF | 1.40 | |
| RA | 1.45 | |
| RB | 1.47 | |
| RC | 1.50 | |
| RD | 1.53 | |
| RE | 1.57 | |
| RF | 1.62 | |
| SA | 1.69 | |
| SB | 1.69 | |
| SC | 1.94 | |
| SD | 2.02 | |
| SE | 2.03 | |
| SF | 2.05 | |
| TA | 2.28 | |
| TB | 2.32 | |
| TC | 2.37 | |
| TD | 2.49 | |
| TE | 2.51 | |
| TF | 2.65 | |
| UA | 2.67 | |
| UB | 3.22 | |
| UC | 3.24 | |
| UD | 3.26 | |
| UE | 3.32 | |
| UF | 3.65 | |
| VA | 3.77 | |
| VB | 3.79 | |
| VC | 3.88 | |
| VD | 3.88 | |
| VE | 4.09 | |
| VF | 4.28 | |
| WA | 4.33 | |
| WB | 4.34 | |
| WC | 4.35 | |
| WD | 4.80 | |
| WE | 4.82 | |
| WF | 5.03 | |
| XA | 5.54 | |
| XB | 5.59 | |
| XC | 5.65 | |
| XD | 6.10 | |
| XE | 6.39 | |
| XF | 6.60 | |
| YA | 6.74 | |
| YB | 6.89 | |
| YC | 6.96 | |
| YD | 6.99 | |
| YE | 7.32 | |
| YF | 7.35 | |
| ZA | 7.70 | |
| ZB | 8.95 | |
| ZC | 8.99 | |
| ZD | 8.99 | |
| ZE | 9.70 | |
| ZF | 9.80 | |
| AAA | 9.90 | |
| A1 | 0.059 | 0.074 |
| A2 | 0.028 | 0.057 |
| A3 | 0.14 | 0.247 |
| A4 | 0.015 | 0.038 |
| A5 | 0.032 | 0.045 |
| A6 | 0.059 | |
| A7 | 0.028 | 0.116 |
| A8 | 0.049 | 0.065 |
| A9 | 0.012 | 0.053 |
| A10 | 0.057 | |
| A11 | 0.050 | 0.086 |
| A12 | 0.027 | 0.051 |
| A13 | 0.222 | |
| A14 | 0.016 | 0.023 |
| A15 | 0.024 | 0.049 |
| A16 | 0.150 | 0.478 |
| A17 | 0.039 | 0.049 |
| A18 | 0.016 | 0.026 |
| A19 | 0.036 | 0.051 |
| A20 | 0.029 | |
| A21 | 0.072 | 1.468 |
| A22 | 0.371 | 0.614 |
| A23 | 0.062 | 0.064 |
| A24 | 0.098 | |
| A25 | 0.058 | |
| A26 | 0.039 | 0.028 |
| A27 | 0.017 | 0.140 |
| A28 | 0.031 | 0.042 |
| A29 | 0.015 | |
| A30 | 0.035 | 0.041 |
| A31 | 0.036 | |
| A32 | 0.014 | 0.064 |
| A33 | 0.132 | 0.126 |
| A34 | 0.077 | |
| A35 | 0.052 | 0.180 |
| A36 | 0.098 | 0.372 |
| A37 | 0.047 | 0.064 |
| A38 | 0.037 | |
| A39 | 0.051 | 0.087 |
| A40 | 0.045 | 0.132 |
| A41 | 0.022 | |
| A42 | 0.154 | |
| A43 | 0.027 | 0.036 |
| A44 | 0.062 | 0.108 |
| A45 | 0.022 | |
| A46 | 0.053 | |
| A47 | 0.046 | |
| A48 | 0.022 | 0.043 |
| A49 | 0.049 | 0.232 |
| A50 | 0.135 | |
| A51 | 0.034 | 0.044 |
| A52 | 0.295 | 0.767 |
| A53 | 0.082 | 0.056 |
| A54 | 0.063 | |
| A55 | 0.071 | |
| A56 | 0.092 | |
| A57 | 0.097 | |
| A58 | 0.086 | 0.058 |
| A59 | 0.038 | |
| A60 | 0.089 | |
| A61 | 0.071 | 0.224 |
| A62 | 0.266 | |
| A63 | 0.048 | |
| A64 | 0.059 | 0.046 |
| A65 | 0.070 | 0.292 |
| A66 | 0.068 | |
| A67 | 0.107 | 0.294 |
| A68 | 0.029 | |
| A69 | 0.084 | |
| A70 | 0.070 | 0.079 |
| A71 | 0.178 | 0.280 |
| A72 | 0.045 | |
| A73 | 0.121 | 0.413 |
| A74 | 0.060 | 0.073 |
| A75 | 0.034 | 0.046 |
| A76 | 0.080 | 0.246 |
| A77 | 0.032 | 0.086 |
| A78 | 0.103 | |
| A79 | 0.191 | 0.393 |
| A80 | 0.496 | |
| A81 | 0.222 | |
| A82 | 0.032 | 0.069 |
| A83 | 0.118 | 0.160 |
| A84 | 0.039 | 0.115 |
| A85 | 0.041 | 0.187 |
| A86 | 0.262 | |
| A87 | 0.039 | 0.066 |
| A88 | 0.072 | |
| A89 | 0.254 | 1.500 |
| A90 | 0.097 | |

TABLE 1-continued

JNK-1 and JNK-2 inhibitory concentration

| Compound | JNK1 IC$_{50}$ (µM) | JNK2 IC$_{50}$ (µM) |
|---|---|---|
| A91 | 0.130 | |
| A92 | 0.089 | 0.096 |
| A93 | 0.042 | |
| A94 | 0.311 | 1.221 |
| A95 | 0.307 | 0.605 |
| A96 | 0.119 | |
| A97 | 0.234 | 0.533 |
| A98 | 0.200 | |
| A99 | 0.406 | |
| A100 | 0.113 | |
| A101 | 0.120 | 0.196 |
| A102 | 0.044 | 0.049 |
| A103 | 0.167 | 0.353 |
| A104 | 0.139 | |
| A105 | 0.077 | 0.210 |
| A106 | 0.204 | |
| A107 | 0.091 | 0.099 |
| A108 | 0.209 | 0.236 |
| A109 | 0.078 | 0.300 |
| A110 | 0.283 | 0.118 |
| A111 | 0.016 | 0.022 |
| A112 | 0.204 | |
| A113 | 0.022 | 0.043 |
| A114 | 0.282 | 0.430 |
| A115 | 0.161 | |
| A116 | 0.422 | 0.399 |
| A117 | 0.078 | 0.581 |
| A118 | 0.042 | 0.609 |
| A119 | 0.063 | 0.069 |
| A120 | 0.112 | |
| A121 | 0.156 | |
| A122 | 0.040 | 0.092 |
| A123 | 0.058 | 0.136 |
| A124 | 0.126 | 0.253 |
| A125 | 0.442 | |
| A126 | 0.051 | 0.138 |
| A127 | 0.349 | |
| A128 | 0.451 | |
| A129 | 0.234 | |
| A130 | 0.084 | |
| A131 | 0.047 | |
| A132 | 0.035 | |
| A133 | 0.307 | |

As shown Table 1, the compounds of the present invention demonstrate the ability to inhibit the activities of JNK1 and JNK2 in the assays. Therefore, the compounds of the present invention may be useful in treating disorders regulated by c-jun N-terminal kinase 1 (JNK1) such as impaired glucose intolerance, insulin resistance, Type 2 diabetes, obesity, and diabetes mellitus. Additionally, the compounds of the present invention may be useful in treating disorders regulated by c-jun N-terminal kinase 2 (JNK2), such as hypercalcemia, osteoporosis, osteoarthritis, symptomatic treatment of bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obtructive pulmonary disorder, contact dermatitis, Paget's disease, asthma, ischemic or reperfusion injury, allergic disease, atopic dermatitis, allergic rhinitis, Crohn's disease, or psorasis. Furthermore, the compounds of the present invention may be useful in treating disorders regulated by c-jun N-terminal kinase 3 (JNK3) such as Alzheimer's disease, Huntington's, Parkinson's, AIDS associated dementia, amyotrophic lateral sclerosis (AML), epilepsy, stroke, multiple sclerosis (MS), schizophrenia, cardiomycete hypertrophy, or baldness.

Synthetic Methods

Abbreviations which have been used in the descriptions of the scheme and the examples that follow are: BBr$_3$ for boron tribromide; m-CPBA for meta-chloroperoxy-benzoic acid; DMF for N,N-dimethylformamide; DMSO for dimethylsulfoxide; DEAD for diethyl azodicarboxylate; EDAC for 1-(3-dimethylaminopropyl)-3-ethylcarbodiimide hydrochloride; HATU for O-(7-azabenzotriazol-1-yl)-N,N,N'N'-tetramethyluronium hexafluorophosphate; HOBT for 1-hydroxybenzotriazole hydrate; HPLC for high pressure liquid chromatography; NMP for N-methylpyrrolidinone; NCS for N-chlorosuccinimide; MeONa for sodium methoxide; MeOH for methanol; MTBE for methyl tert butyl ether, THF for tetrahydrofuran; TFA for trifluoroacetic acid; TMS$_2$ for trimethylsilyldiazomethane; TBAF for tetra butylammonium fluoride; Pd(dppf)Cl$_2$ for (diphenylphospino)ferrocenyl palladium chloride; Ph$_3$P for triphenylphosphine; Pr$_2$Net for diisopropyl ethylamine; and TBTU for (benzotriazol-1-yloxy)-dimethylamino-methylene)-dimethyl-ammonium tetrafluoroborate.

The compounds and processes of the present invention will be better understood in connection with the following synthetic schemes which together with the experimentals section illustrate the methods by which the compounds of the invention may be prepared. Representative procedures and synthetic routes are shown in, but are not limited to, Scheme 1-10. Variables such as R$_1$, R$_2$, R$_3$, R$_4$, R$_5$, R$_e$ and R$_f$ are as defined in the principal embodiment unless otherwise noted below.

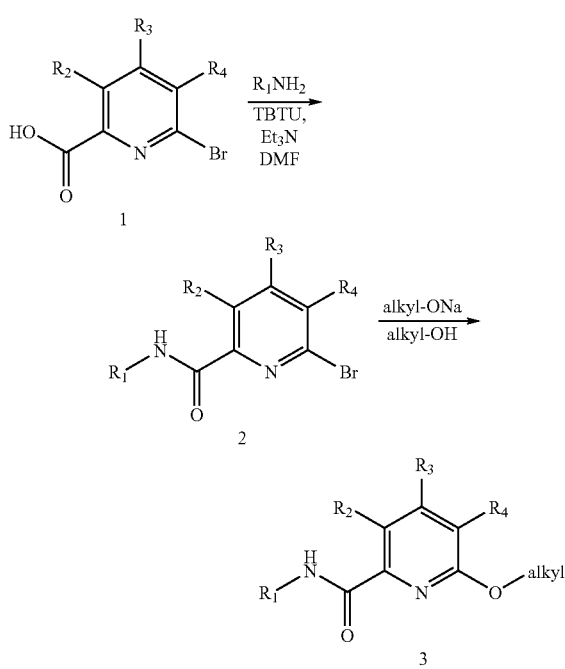

As outlined in Scheme 1, pyridines of formula 1 containing a carboxy group in the 5 position may be converted to amides of formula 2 utilizing conditions known to those skilled in the art or with reagents such as but not limited to TBTU (2-(1-

H-benzotriazol-1-yl)-1,1,3,3-tetramethyluronium tetrafluoroborate) and triethylamine and an amine $R_1NH_2$, in solvents such as DMF. Compounds of formula 2 containing a halogen in the 1 position may be treated with various nucleophiles such as but not limited to sodium alkoxides to provide compounds of formula 3 which are representative of compounds of the present invention.

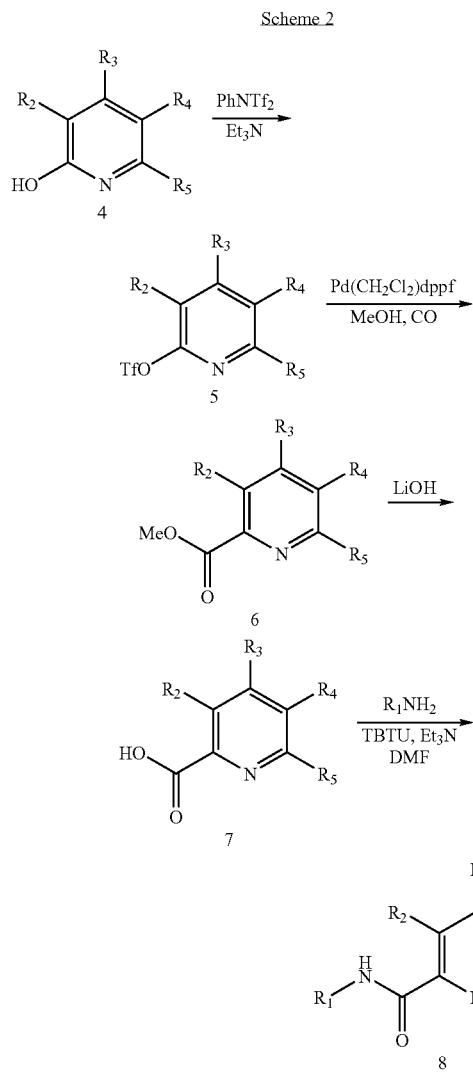

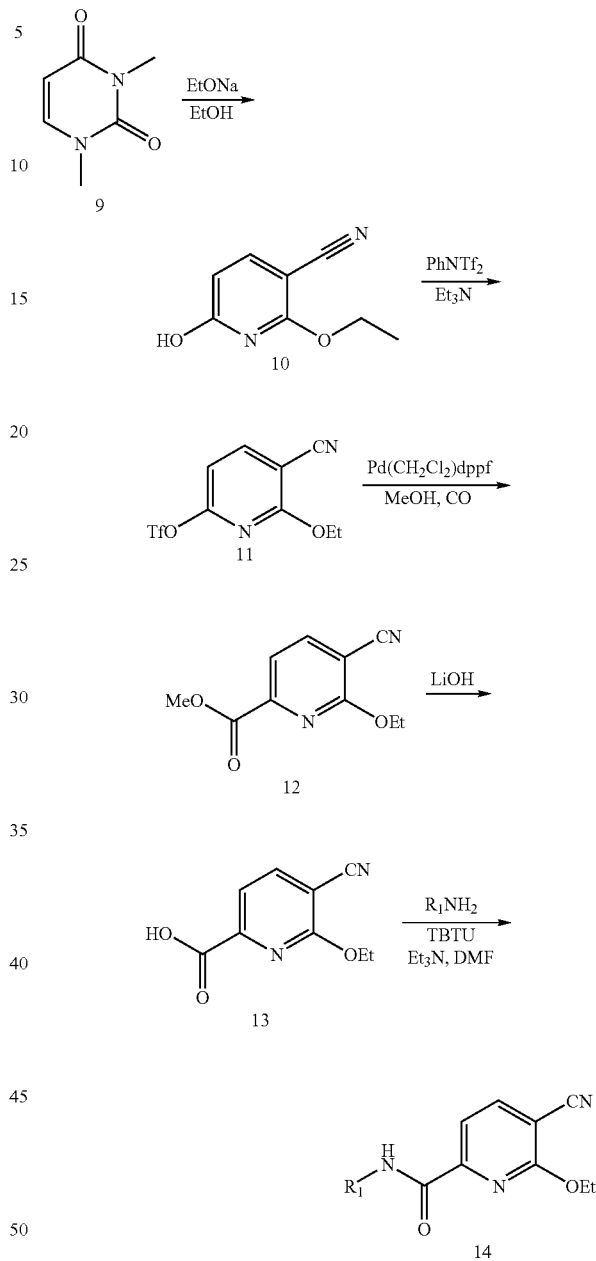

As outlined in Scheme 2, compounds of formula 4 may be treated with N-phenyltrifluoromethanesulfonimide and triethyamine to provide triflates of formula 5. Compounds of formula 5 which contain a triflate when treated with (1,1'-bis[diphenylphosphino]ferrocene)dichloropalladium (II) complexed with dichloromethane in methanol with an atmosphere of carbon monoxide will provide methyl esters of formula 6. The ester functional group of 6 when treated to hydrolysis conditions such as but not limited to lithium hydroxide will provide compounds of formula 7. The carboxylic acid of compounds 7 may be converted to amides as outlined in Scheme 1 to provide compounds of formula 8 which are representative of compounds of the present invention.

As outlined in Scheme 3, compounds of formula 9 when treated with sodium ethoxide in ethanol will provide compounds of formula 10. Compounds of formula 10 when treated with phenyltrifluoromethanesulfonimide and triethyamine will provide triflates of formula 11. The triflate 11 when treated with bis[diphenylphosphino]ferrocene)dichloropalladium (II) complexed with dichloromethane in methanol with an atmosphere of carbon monoxide will provide compounds of formula 12. The ester functionality when hydrolyzed according to conditions described in Scheme 2 will provide compounds of formula 13 which may be converted to compounds of formula 14 when treated with an amine $R_1NH_2$, TBTU and triethylamine in DMF.

Scheme 4

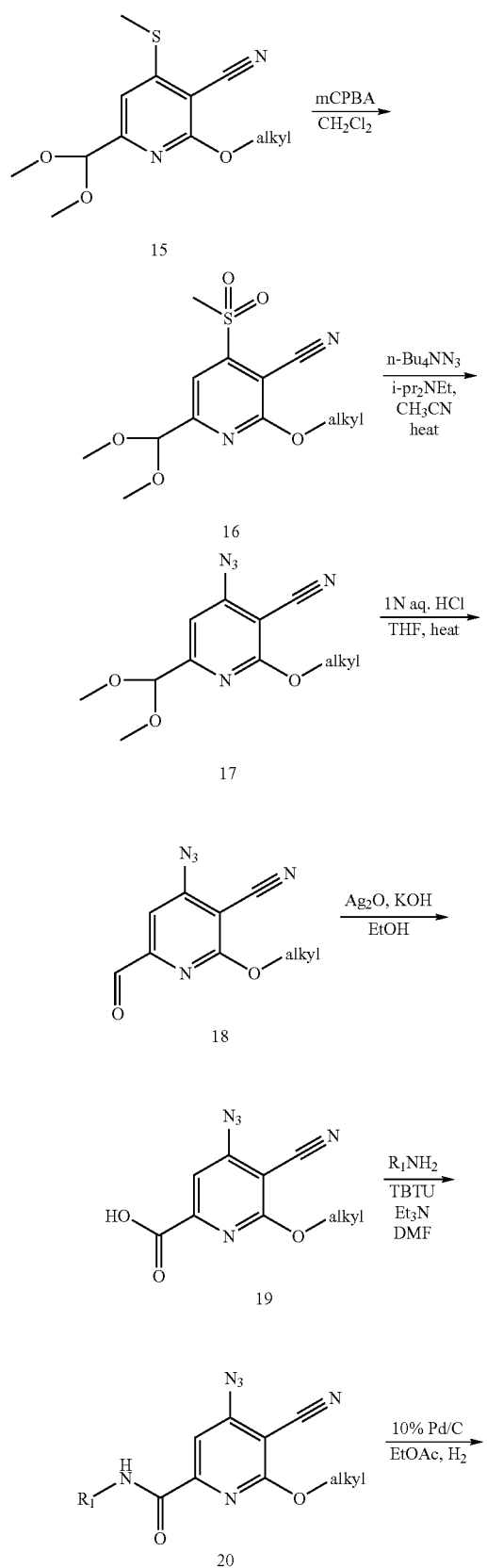

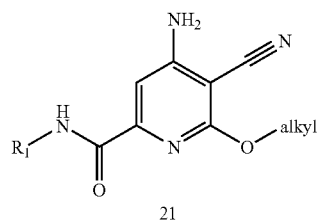

As outlined in Scheme 4, compounds of formula 15 when treated to oxidative conditions such as meta chloroperoxybenzoic acid in dichloromethane will provide compounds of formula 16. Compounds of formula 16 when treated with tetrabutylammonium azide and diisopropylethylamine in acetonitrile under heated conditions will provide compounds of formula 17. Compounds of formula 17 when subjected to hydrolyzing conditions will provide the aldehyde of formula 18. The aldehyde functional group may be oxidized with silver oxide to provide compounds of formula 19. The acid of compounds of formula 19 may be converted to the amide of formula 20 using the conditions describe above and the azide functional group may be hydrogenated to provide the amine of formula 21 which is representative of compounds of the present invention.

Scheme 5

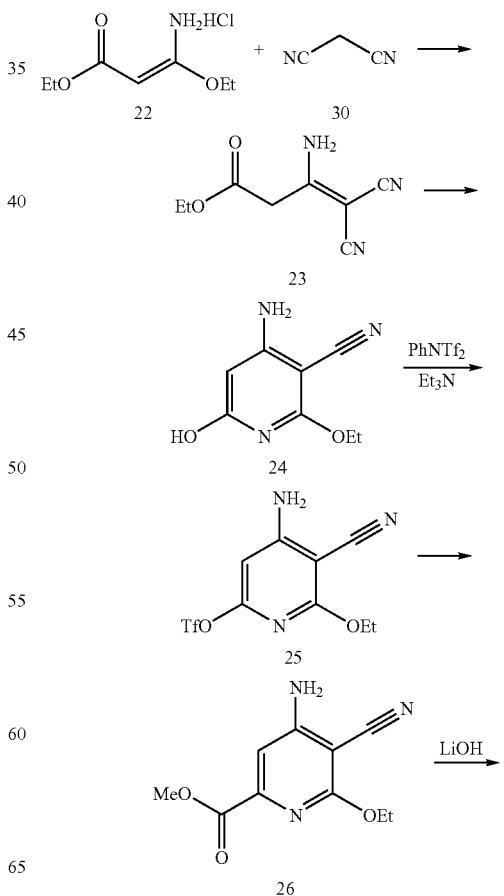

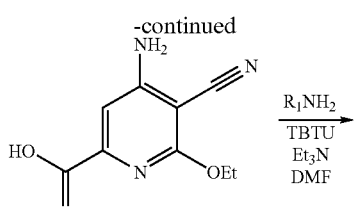

As outlined in Scheme 5, compounds of formula 22 when treated with malononitrile will provide compounds of formula 23. Compounds of formula 23 when treated with sodium ethoxide in ethanol will provide compounds of formula 24. The alcohol functional group of 24 when treated with phenyltrifluoromethanesulfonimide and triethyamine will provide triflates of formula 25. The triflate when treated with bis[diphenylphosphino]ferrocene)dichloropalladium (II) complexed with dichloromethane in methanol with an atmosphere of carbon monoxide will provide methyl esters of formula 26. The ester functional group may be hydrolyzed with lithium hydroxide and the corresponding acid converted to the amine of formula 28 using conditions outlined above.

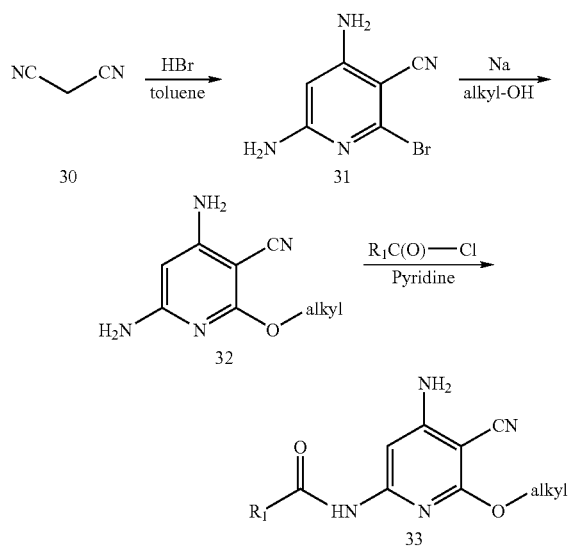

As outlined in Scheme 6, malononitrile 30 when treated with a stream of hydrogen bromide gas in toluene will provide compounds of formula 31. Compounds of formula 31 when treated with a freshly prepared solution of a sodium alkoxide in its parent alcohol or another inert solvent (such as dioxane, tetrahydrofuran, dimethoxyethane, or toluene) will provide compounds of formula 32. Compounds of formula 32 when treated with an acid chloride of formula $R_1C(O)$—Cl and a base such as but not limited to pyridine, will provide compounds of formula 33 which are representative of compounds of the present invention.

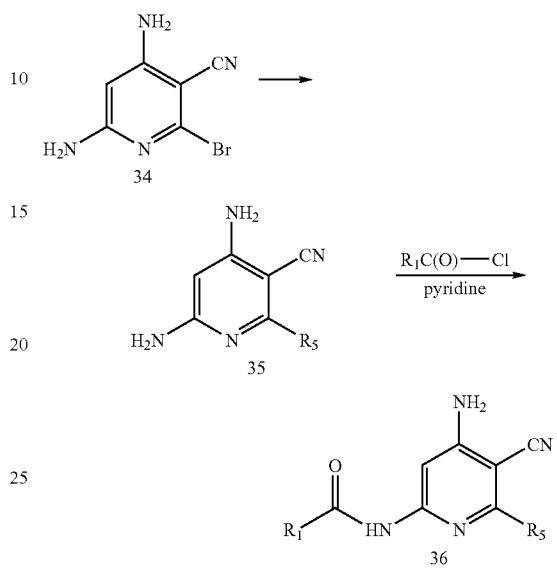

As outlined in Scheme 7, compounds of formula 34 may be treated with an alkyl or aryl boronic acid, a trialkyl borane or an alkyl zinc halide in the presence of a palladium caralust such as but not limited to a mixture of palladium (II) acetate and tri(o-tolyl)phosphine or (tetrakis(triphenylphosphino)) palladium in an inert solcent such as tetrahydrofuran, dimethoxyethane, dioxane, toluene, N,N-dimethylformamide and if necessary a base such as triethylamine, N,N-diisopropylethylamine, potassium carbonate or sodium carbonate and if necessary water as a cosolvent to provide compounds of formula 35. Compounds of formula 35 when treated with acid chlorides of formula $R_1C(O)$—Cl in the presence of pyridine will provide compounds of formula 36 which are representative of compounds of the present invention.

Scheme 8

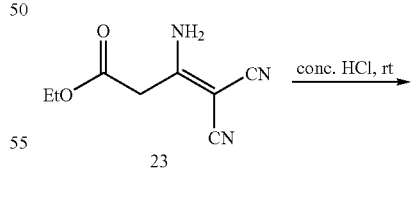

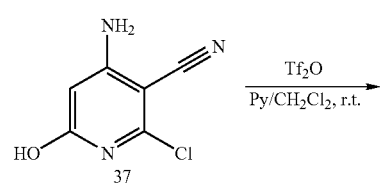

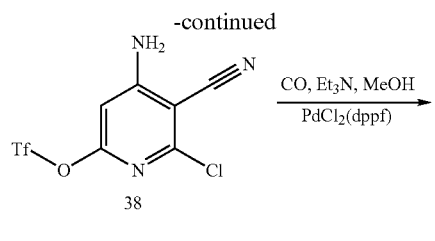

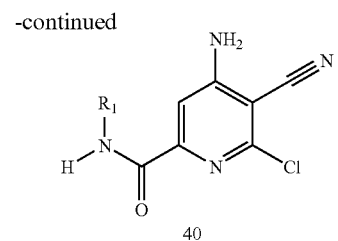

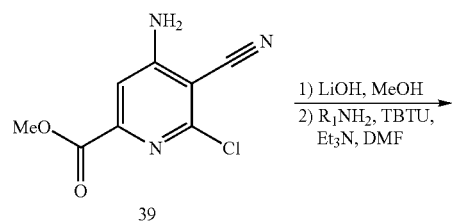

Compounds of formula 40 can be prepared using chemistry as outlined in Scheme 8.

Compounds of formula 23 when treated with concentrated hydrochloric acid at about room temperature provide nitriles of formula 37. Treatment of nitriles of formula 37 with triflate anhydride and a base such as, but not limited to, pyridine afford triflates of formula 38. The reaction can be conducted at about room temperature and in an aprotic solvent such as, but not limited to, dichloromethane. Conversion of compounds of formula 38 to compounds of formula 40 can be achieved using reaction conditions for the transformation of compounds of formula 5 to 8 as described in Scheme 2.

Scheme 9

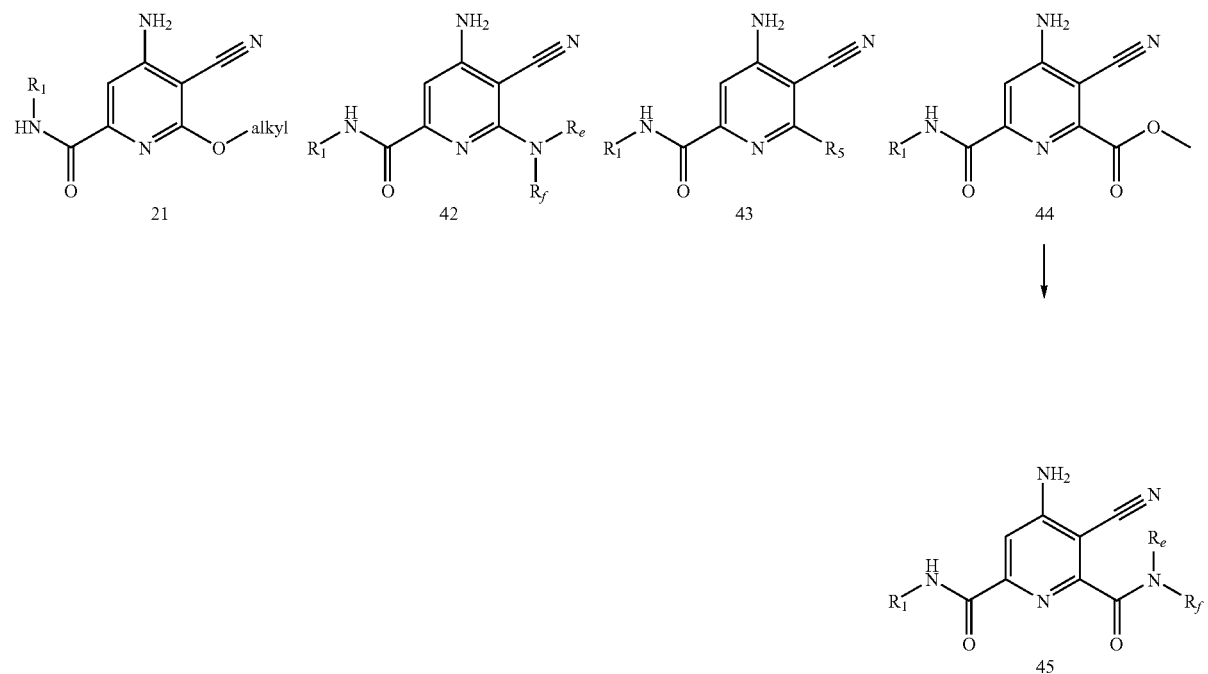

Compounds of formula 40 can be transformed to compounds of formula 21 using reaction conditions for the conversion of compounds of formula 31 to 32 as described in Scheme 6.

Compounds of formula 42 can be obtained from treatment of compounds of formula 40 with an amine of formula $R_eR_fNH$ in the presence of a base such as, but not limited to, diisopropylethyl amine. The reaction is generally conducted in a solvent such as, but not limited to, dimethyl acetamide or N,N-dimethyl formamide, and at a temperature from about 150° C. to about 200° C.

Compounds of formula 43 wherein $R_5$ is aryl or heteroaryl can be derived from reactions of compounds of formula 40 with boronic acid or ester of formula $R_5B(OR_{101})_2$ wherein $R_{101}$ is hydrogen or alkyl, in the presence of a palladium catalyst such as, but not limited to, bis(triphenylphospine) palladium (II) dichloride and a base such as triethylamine, diisopropylethyl amine or sodium carbonate. The reaction can be effected by heating from 50-90° C. in a solvent such as dimethyl acetamide, N,N-dimethyl formamide, isopropanol, ethanol, dimethoxyethane, water or dioxane. Alternatively, the transformation can also be accomplished by reaction of 40 with tin reagents of formula $R_5Sn(alkyl)_3$, a palladium catalyst such as, but not limited to, tetrakis(triphenylphospine) palladium (0) or tris(dibenzylideneacetone)dipalladium(0), optionally in the presence of a ligand such as, but not limited to, tri-tert-butylphosphine, cesium fluoride and heating (for example at about 50° C. to about 100° C.) in a solvent such as dioxane or N,N-dimethylformamide. These transformations can also be effected by heating in a microwave reactor.

Compounds of formula 45 can be obtained from stepwise reactions of (a) compounds of formula 40 with an atmosphere of carbon monoxide, a base such as, but not limited to, triethylamine, and (1,1'-bis[diphenylphosphino]ferrocene) dichloropalladium (II), (b) intermediate from step (a) with a base such as, but not limited to lithium hydroxide, in a solvent such as, but not limited to, methanol; and (c) intermediate from step (c) with an amine of formula $R_eR_fNH$, in the presence of a coupling reagent such as, but not limited to, O-benzotriazol-1-yl-N,N,N',N'-tetramethyluronium tetrafluoroborate and a base such as triethylamine and the like, and in a solvent such as N,N-dimethylformamide.

Scheme 10

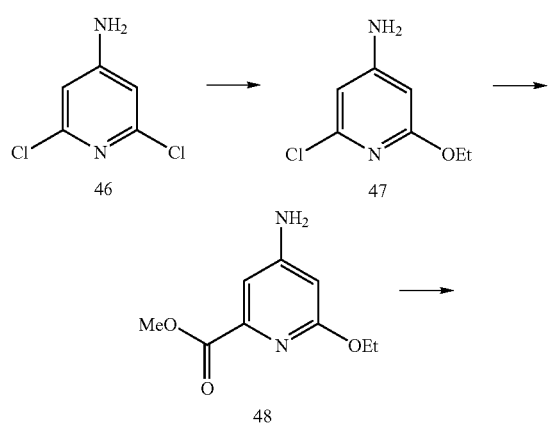

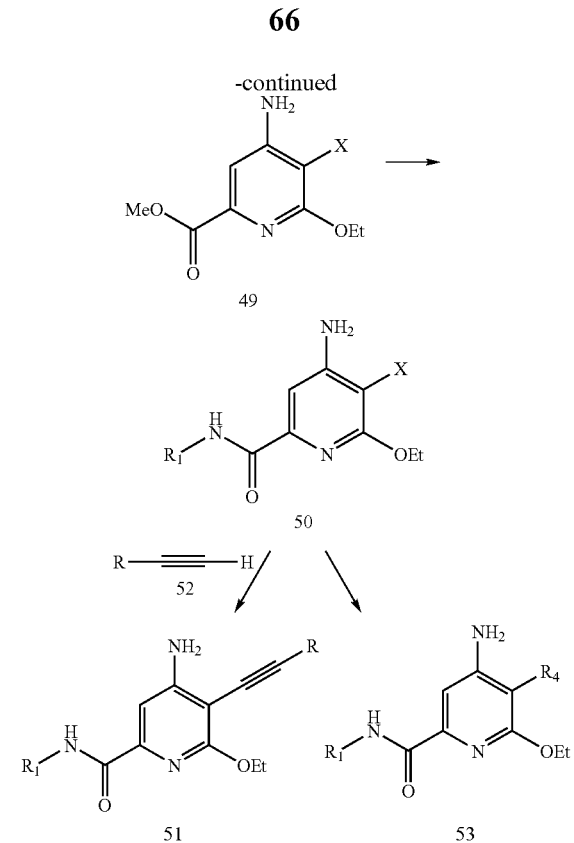

Compounds of formula 46 can be converted to compounds of formula 47 using reaction conditions for the conversion of compounds of formula 31 to 32 as outlined in Scheme 6. Compounds of formula 47, when treated with an 4 atmosphere of carbon monoxide in the presence of [1,1'-bis(diphenylphosphino)ferrocene]dichloropalladium(II), provide compounds of formula 48. The reaction can be effected in a solvent such as, but not limited to, methanol, and at a temperature from about 60° C. to about 100° C. Compounds of formula 48 can be converted to halides of formula 49 wherein X is Cl, Br, I or F by reaction with N-chlorosuccinimide, N-bromosuccinimide, N-iodosuccinimide, and Selectfluor™ fluorinating reagent respectively. Conversion of compounds of formula 49 to amides of formula 50 can be achieved using reaction conditions for the conversion of compounds of formula 6 to 8 as described in Scheme 2.

Compounds of formula 51 wherein R is alkyl or alkenyl can be derived from the reaction of compounds of formula 50 and alkynes of formula 52, in the presence of a palladium reagent such as, but not limited to, bis(triphenylphosphine) palladium(II) dichloride, a base such as, but not limited to, triethylamine, and copper(I) iodide. The conversion can be effected in an organic solvent such as, but not limited to, N,N-dimethyl formamide, and at an elevated temperature from about 50° C. to about 90° C.

Compounds of formula 53 wherein $R_4$ is heteroaryl or aryl can be obtained from compounds of formula 50 utilizing reaction conditions employed for the conversion of compounds of formula 40 to 43 as described in Scheme 9.

The compounds and processes of the present invention will be better understood by reference to the following examples, which are intended as an illustration of and not a limitation upon the scope of the invention. Further, all citations herein are incorporated by reference.

Examples 1-157 were named using ACD/ChemSketch version 5.01 and examples 158-298 were named using ACD/ChemSketch version 5.01 (developed by Advanced Chemistry Development, Inc., Toronto, ON, Canada) or were given names which appeared to be consistent with ACD nomenclature.

EXAMPLE 1

N-(4-Amino-5-cyano-6-ethoxy-pyridin-2-yl)-acetamide

Example 1A 4,6-Diamino-2-ethoxy-nicotinonitrile

To a 5 mL sealable heavy walled glass tube suitable for microwave heating containing 5 mL of absolute ethanol was added 150 mg (6.5 mmol) of sodium metal. The mixture was stirred until all of the sodium had reacted, then 1.00 g (4.71 mmol) of 2-bromo-4,6-diaminonicotinonitrile (E. I. du Pont de Nemours and Company U.S. Pat. No. 2,790,806, 1957) was added. The tube was sealed, and the reaction was heated with a microwave apparatus at 150° C. for 10 minutes then cooled and diluted with 15 mL of water. The orange precipitate which formed was washed with water until pH=7, then dried under reduced pressure at 105° C. to provide 0.545 g (65%) of a light orange solid. $^1$H NMR (300 MHz, $d_6$-DMSO) δ 6.19 (s, 2H), 6.14 (s, 2H), 5.32 (s, 1H), 4.23 (q, 2H, J=7.1 Hz), 1.25 (t, 3H, J=7.1 Hz), MS (ES) m/e=151 (M−Et+H)$^+$, 179 (M+H)$^+$.

Example 1B

N-(4-Amino-5-cyano-6-ethoxy-pyridin-2-yl)-acetamide

To 50 mg (0.28 mmol) of 4,6-diamino-2-ethoxy-nicotinonitrile dissolved in 1 mL of pyridine was added 60 µL (0.84 mmol) of acetyl chloride. The mixture was stirred at ambient temperature for 2 hours then diluted with 7 mL of water. The precipitate was filtered and washed with 5 mL of water. The supernatant was extracted with ethyl acetate (3×5 mL), then the combined ethyl acetate layers were back extracted with brine (1×5 mL), dried over MgSO$_4$, filtered, and concentrated under reduced pressure to a solid. This was combined with the precipitated product, dissolved in methanol/ethyl acetate, and concentrated. Most of the remaining pyridine was removed by coevaporation with toluene under reduced pressure. The product was purified via silica gel chromatography, eluting with 50% ethyl acetate/hexanes to provide 31 mg (50%) of a white solid. $^1$H NMR (300 MHz, $d_6$-DMSO) δ 10.73 (s, 1H), 7.17 (s, 1H), 6.88 (s, 2H), 4.32 (q, 2H, J=7.1 Hz), 2.07 (s, 3H), 1.29 (t, 3H, J=7.1 Hz); MS (ESI) m/e=221 (M+H)$^+$, m/e=219 (M−H)$^-$.

EXAMPLE 2

N-(4-amino-5-cyano-6-ethoxypyridin-2-yl)cyclopentanecarboxamide

To 50 mg (0.28 mmol) of 4,6-diamino-2-ethoxy-nicotinonitrile (Example 1A) dissolved in 1 mL of pyridine was added 4 drops of cyclopentane carbonylchloride. The mixture was stirred at ambient temperature for 18 hours then diluted with 7 mL of water. The precipitate was centrifuged, the supernatant was decanted and the precipitate was resuspended in 7 mL of water, centrifuged, and decanted two additional times, then it was taken up in 3 mL of methanol and concentrated under reduced pressure. The crude product was recrystallized from methanol to provide 20 mg (26%) of the desired amide as a white solid. TLC (30% ethyl acetate/hexanes). $^1$H NMR (300 MHz, $d_6$-DMSO) δ 10.01 (s, 1H), 7.20 (s, 1H), 6.86 (s, 2H), 4.33 (q, 2H, J=7.1 Hz), 2.91 (m, 1H), 1.80 (m, 2H), 1.65 (m, 4H), 1.52 (m, 2H), 1.29 (t, 3H, J=7.1 Hz); MS (ESI) m/e=275 (M+H)$^+$.

EXAMPLE 3

N-(4-amino-5-cyano-6-ethoxypyridin-2-yl)pentanamide

The titled compound was prepared according to the procedure described in Example 2, substituting penatnoyl chloride for cyclopentanecarbonyl chloride. The crude product was purified by reverse phase HPLC, eluting with a 0-70% CH$_3$CN in 0.1% aq. TFA gradient to provide 20 mg (27%) of a white solid. TLC (30% ethyl acetate/hexanes). $^1$H NMR (300 MHz, $d_6$-DMSO) δ 10.03 (s, 1H), 7.20 (s, 1H), 6.87 (s, 2H), 4.33 (q, 2H, J=7.1 Hz), 2.36 (m, 2H), 1.53 (m, 2H), 1.29 (m, 5H), 0.88 (t, 3H, J=7.3 Hz); MS (ESI) m/e=263 (M+H)$^+$.

EXAMPLE 4

N-(4-amino-5-cyano-6-ethoxypyridin-2-yl)benzamide

The titled compound was prepared according to the procedure described in Example 2, substituting benzoyl chloride for cyclopentanecarbonyl chloride. The crude product was recrystallized from methanol to provide 30 mg (38%) of a white solid. TLC (30% ethyl acetate/hexanes). $^1$H NMR (300 MHz, $d_6$-DMSO) δ 10.27 (s, 1H), 7.94 (m, 2H), 7.60 (m, 1H), 7.51 (m, 2H), 7.33 (s, 1H), 6.97 (s, 2H), 4.38 (q, 2H, J=7.1 Hz); 1.31 (t, 3H, J=7.1 Hz); MS (ESI) m/e=283 (M+H)$^+$, 305 (M+Na)$^+$.

EXAMPLE 5

N-(4-amino-5-cyano-6-ethoxypyridin-2-yl)cyclobutanecarboxamide

The titled compound was prepared according to the procedure described in Example 2, substituting cyclobutanecarbonyl chloride for cyclopentanecarbonyl chloride. The crude product was recrystallized from 10 mL of abs. ethanol to provide 28 mg (36%) of a white solid. TLC (30% ethyl acetate/hexanes). $^1$H NMR (300 MHz, $d_6$-DMSO) δ 9.89 (s, 1H), 7.22 (s, 1H), 6.88 (s, 1H), 4.32 (q, 2H, J=7.1 Hz), 3.37 (m, 1H), 2.12 (m, 4H), 1.85 (m, 2H), 1.29 (t, 3H, J=7.1 Hz); MS (ESI) m/e=261 (M+H)$^+$, 283 (M+Na)$^+$.

EXAMPLE 6

N-(4-amino-5-cyano-6-ethoxypyridin-2-yl)butanamide

The titled compound was prepared according to the procedure described in Example 2, substituting butyryl chloride for cyclopentanecarbonyl chloride. The crude product was recrystallized from methanol to provide 29 mg (42%) of a white solid. TLC (30% ethyl acetate/hexanes). $^1$H NMR (300 MHz, $d_6$-DMSO) δ 10.02 (s, 1H), 7.20 (s, 1H), 6.87 (s, 2H), 4.33 (q, 2H, J=7.1 Hz), 2.34 (q, 2H, J=7.5 Hz), 1.56 (m, 2H), 1.29 (t, 3H, J=7.1 Hz), 0.89 (t, 3H, J=7.5 Hz); MS (ESI) m/e=249 (M+H)$^+$, 247 (M−H)$^-$.

EXAMPLE 7

N-(4-amino-5-cyano-6-ethoxypyridin-2-yl)-3-methylbutanamide

The titled compound was prepared according to the procedure described in Example 2, substituting 3-methylbutyryl chloride for cyclopentanecarbonyl chloride. The crude product was purified by reverse phase HPLC, eluting with a gradient of 5-100% $CH_3CN$ in 0.1% aq. TFA to provide 12 mg (16%) of a white solid. TLC (30% ethyl acetate/hexanes). $^1H$ NMR (300 MHz, $d_6$-DMSO) δ 10.01 (s, 1H), 7.22 (s, 1H0, 6.87 (s, 2H), 4.33 (q, 2H, J=7.1 Hz), 2.25 (d, 2H, J=7.1 Hz), 2.03 (m, 1H), 1.29 (t, 3H, J=7.1 Hz), 0.90 (d, 6H, J=6.4 Hz); MS (ESI) m/e=263 $(M+H)^+$, 261 $(M-H)^-$.

EXAMPLE 8

N-(4-amino-5-cyano-6-ethoxypyridin-2-yl)hexanamide

The titled compound was prepared according to the procedure described in Example 2, substituting pentanoyl chloride for cyclopentanecarbonyl chloride. The crude product was recrystallized from methanol to provide 47 mg (60%) of a white solid. TLC (30% ethyl acetate/hexanes). $^1H$ NMR (300 MHz, $d_6$-DMSO) δ 10.02 (s, 1H), 7.20 (s, 1H), 6.87 (s, 2H), 4.32 (q, 2H, J=7.1 Hz), 2.35 (t, 2H, J=7.5 Hz), 1.54 (m, 2H), 1.26 (m, 7H), 0.86 (t, 3H, J=6.8 Hz); MS (ESI) m/e=277 $(M+H)^+$, 275 $(M-H)^-$.

EXAMPLE 9

N-(4-amino-6-butoxy-5-cyanopyridin-2-yl)acetamide

Example 9A

4,6-Diamino-2-butoxy-nicotinonitrile

A heavy walled, sealable tube suitable for microwave heating was charged with 3 mL of n-butanol and 40 mg (1.7 mmol) of sodium. The mixture was stirred until all of the sodium had reacted, then 212 mg (1.00 mmol) of 2-bromo-4,6-diaminonicotinonitrile was added. The tube was sealed, and the mixture was heated with a microwave apparatus at 150° C. for 10 minutes then cooled and poured into 10 mL of toluene. The solvents were removed under reduced pressure, then the residue was partitioned between 2 mL of saturated $NaHCO_{3(aq.)}$ solution and 10 mL of toluene. This was concentrated again under reduced pressure, and the residue was taken up in 5 mL of water, then extracted with ethyl acetate (1×10 mL, then 2×5 mL). The combined ethyl acetate layers were back extracted with brine (1×5 mL), dried over $MgSO_4$, filtered, and concentrated to a yellow solid. This was purified via silica gel chromatography, eluting with 50% ethyl acetate/hexanes to provide a white solid. $^1H$ NMR (300 MHz, $d_6$-DMSO) δ 6.19 (s, 2H), 6.14 (s, 2H), 5.31 (s, 1H), 4.18 (t, 2H, J=6.6 Hz), 2.50 (m, 1H), 1.62 (m, 2H), 1.38 (m, 2H), 0.92 (m, 3H, J=7.1 Hz); MS (ESI) m/e=151 $(M-Bu+H)^+$, 207 $(M+H)^+$, 205 $(M-H)^-$.

Example 9B

N-(4-amino-6-butoxy-5-cyanopyridin-2-yl)acetamide

To 50 mg (0.24 mmol) of 4,6-diamino-2-butoxy-nicotinonitrile in 1 mL of pyridine was added 3 drops of acetyl chloride. The mixture was stirred at ambient temperature for 4 hours then diluted with 10 mL of water and stirred. After 30 minutes the precipitate was collected, washed with water (3×5 mL), and allowed to dry on the filter. The product was recrystallized from 1 mL of methanol to provide 16 mg (27%) of a white solid. $^1H$ NMR (300 MHz, $d_6$-DMSO) δ 10.07 (s, 1H), 7.17 (s, 1H), 6.89 (s, 2H), 4.27 (t, 2H, J=6.6 Hz), 2.06 (s, 3H), 1.67 (m, 2H), 1.40 (m, 2H), 0.93 (t, 3H, J=7.5 Hz); MS (ESI) m/e=193 $(M-Bu+H)^+$, 249 $(M+H)^+$, 247 $(M-H)^-$.

EXAMPLE 10

N-(4-amino-5-cyano-6-methoxypyridin-2-yl)acetamide

Example 10A

4,6-Diamino-2-methoxy-nicotinonitrile

A heavy walled, sealable tube suitable for microwave heating was charged with 3 mL of methanol and 40 mg (1.7 mmol) of sodium. The mixture was stirred until all of the sodium had reacted, then 212 mg (1.00 mmol) of 2-bromo-4,6-diaminonicotinonitrile was added. The tube was sealed, and the mixture was heated with a microwave apparatus at 150° C. for 10 minutes then cooled and concentrated under reduced pressure. The residue was suspended in 10 mL of water, and extracted with ethyl acetate (1×20 mL, then 2×10 mL). The combined ethyl acetate layers were back extracted with brine (1×10 mL), dried over $MgSO_4$, filtered, and concentrated to a solid. This was purified via silica gel chromatography, eluting with 60:40 hexanes:ethyl acetate to provide 114 mg (70%) of a white solid.

Example 10B

N-(4-amino-5-cyano-6-methoxypyridin-2-yl)acetamide

To a solution of 50 mg (0.30 mmol) of 4,6-diamino-2-methoxy-nicotinonitrile in 1 mL of pyridine was added 3 drops of acetyl chloride. The mixture was stirred at ambient temperature for 2 hours then diluted with 10 mL of water. The aqueous suspension was stirred for 15 minutes then the precipitate was collected and washed with water. Recrystallization from 1 mL of methanol gave 17 mg (27%) of a white solid. $^1H$ NMR (300 MHz, $d_6$-DMSO) δ 10.13 (s, 1H), 7.19 (s, 1H), 6.92 (s, 2H), 3.85 (s, 3H), 2.07 (s, 3H); MS (ESI) m/e=207 $(M+H)^+$, 205 $(M-H)^-$.

EXAMPLE 11

N-(4-amino-5-cyano-6-ethoxypyridin-2-yl)-2-phenylacetamide

The titled compound was prepared according to the procedure described in Example 2, substituting phenylacetyl chloride for cyclopentanecarbonyl chloride. The crude product was recrystallized from methanol to provide 8 mg (11%) of a white solid. TLC (30% ethyl acetate/hexanes). $^1H$ NMR (300 MHz, $d_6$-DMSO) δ 10.31 (s, 1H), 7.26 (m, 5H), 7.16 (s, 1H), 6.89 (s, 2H), 4.34 (q, 2H, J=7.1 Hz), 3.70 (s, 2H), 1.30 (t, 1H, J=7.1 Hz); MS (ESI) m/e=269 $(M-Et+H)^+$, 297 $(M+H)^+$, 295 $(M-H)^-$.

EXAMPLE 12

N-(4-amino-5-cyano-6-ethoxypyridin-2-yl)-3-phenylpropanamide

The titled compound was prepared according to the procedure described in Example 2, substituting hydrocinnamoyl chloride for cyclopentanecarbonyl chloride. The crude product was recrystallized from methanol to provide 29 mg (41%) of a white solid. TLC (30% ethyl acetate/hexanes). $^1H$ NMR (300 MHz, $d_6$-DMSO) δ 10.09 (s, 1H), 7.22 (m, 6H), 6.89 (s, 2H), 4.31 (q, 2H, J=7.1 Hz), 2.87 (t, 2H, J=7.5 Hz), 2.69 (t, 2H, J=7.5 Hz), 1.29 (t, 2H, J=7.1 Hz); MS (ESI) m/e=283 (M−Et+H)$^+$, 311 (M+H)$^+$, 309 (M−H)$^−$.

EXAMPLE 13

N-(4-amino-5-cyano-6-ethoxypyridin-2-yl)propanamide

The titled compound was prepared according to the procedure described in Example 2, substituting propionyl chloride for cyclopentanecarbonyl chloride. The crude product was recrystallized from methanol to provide 12 mg (22%) of a white solid. TLC (30% ethyl acetate/hexanes). $^1$H NMR (300 MHz, $d_6$-DMSO) δ 10.02 (s, 1H), 7.19 (s, 1H), 6.87 (s, 2H), 4.32 (q, 2H, J=7.1 Hz), 2.37 (q, 2H, J=7.5 Hz), 1.29 (t, 3H, J=7.1 Hz), 1.04 (t, 3H, J=7.5 Hz); MS (ESI) m/e=207 (M−Et+H)$^+$, 235 (M+H)$^+$, 233 (M−H)$^−$.

EXAMPLE 14

N-(4-amino-5-cyano-6-ethoxypyridin-2-yl)-2-methylpropanamide

The titled compound was prepared according to the procedure described in Example 2, substituting isobutyryl chloride for cyclopentanecarbonyl chloride. The crude product was recrystallized from methanol to provide 40 mg (69%) of a white solid. TLC (30% ethyl acetate/hexanes). $^1$H NMR (300 MHz, $d_6$-DMSO) δ 10.01 (s, 1H), 7.20 (s, 1H), 6.87 (s, 2H), 4.33 (q, 2H, J=7.1 Hz), 2.75 (m, 1H, J=6.8 Hz), 1.29 (t, 3H, J=7.1 Hz), 1.05 (d, 6H, J=7.1 Hz); MS (ESI) m/e=221 (M−Et+H)$^+$, 249 (M+H)$^+$, 247 (M−H)$^−$.

EXAMPLE 15

N-(4-amino-5-cyano-6-ethoxypyridin-2-yl)-2,2-dimethylpropanamide

The titled compound was prepared according to the procedure described in Example 2, substituting 2,2-dimethylpropionyl chloride for cyclopentanecarbonyl chloride. The crude product was recrystallized from methanol to provide 17 mg (27%) of a white solid. TLC (30% ethyl acetate/hexanes). $^1$H NMR (300 MHz, $d_6$-DMSO) δ 9.11 (s, 1H), 7.18 (s, 1H), 6.88 (s, 2H), 4.36 (q, 2H, J=7.1 Hz), 1.29 (t, 3H, J=7.1 Hz), 1.21 (s, 9H); MS (ESI) m/e=235 (M−Et+H)$^+$, 263 (M+H)$^+$, 261 (M−H)$^−$.

EXAMPLE 16

N-(4-amino-5-cyano-6-phenoxypyridin-2-yl)acetamide

Example 16A 4,6-Diamino-2-phenoxy-nicotinonitrile

A heavy walled, sealable tube suitable for microwave heating was charged with 60 mg (1.5 mmol) of NaH (60% dispersion in mineral oil) and 3 mL of dioxane. To the suspension was added 150 mg (1.59 mmol) of phenol, then the mixture was stirred for 15 min. Next, 212 mg (1.00 mmol) of 2-bromo-4,6-diaminonicotinonitrile was added. The tube was sealed, and the mixture was heated with a microwave apparatus at 190° C. for 25 minutes then cooled and concentrated under reduced pressure. The residue was diluted with 10 mL of toluene and concentrated again under reduced pressure. The remaining material was taken up in 20 mL of ethyl acetate and extracted with 2M NaOH$_{(aq.)}$ (3×5 mL), and brine (1×5 mL), draining some red precipitate with the aqueous layers. The organic layer was dried over MgSO$_4$, filtered, and concentrated to 178 mg (79%) of an orange solid. The product could be further purified via silica gel chromatography, eluting with 50:50 ethyl acetate:hexanes to provide a white solid. $^1$H NMR (300 MHz, $d_6$-DMSO) δ 7.38 (m, 2H), 7.17 (m, 1H), 7.10 (m, 2H), 6.37 (s, 2H), 6.25 (s, 2H), 5.41 (s, 1H); MS (ESI) m/e=227 (M+H)$^+$, 225 (M−H)$^−$.

Example 16B

N-(4-amino-5-cyano-6-phenoxypyridin-2-yl)acetamide

To a solution of 100 mg (0.442 mmol) of 4,6-diamino-2-phenoxy-nicotinonitrile in 2 mL of pyridine was added 4 drops of acetyl chloride. The mixture was stirred at ambient temperature for 10 minutes then sonicated briefly to break up any remaining clumps that formed on addition of the acetyl chloride. The mixture was diluted with 20 mL of water and filtered to recover a light yellow precipitate. The residue was taken up in 5 mL of ethyl acetate, dried over MgSO$_4$, filtered, and concentrated to a solid. The solid was suspended in 10 mL of toluene and concentrated under reduced pressure to remove some remaining pyridine, recrystallized from 2 mL of ethyl acetate to provide 25 mg of a pale yellow solid. The supernatant was concentrated, and the residue was purified via silica gel chromatography, eluting with 50:50 ethyl acetate:hexanes to provide 33 mg of a white solid. The total yield was 58 mg (49%). $^1$H NMR (300 MHz, $d_6$-DMSO) δ 9.99 (s, 1H), 7.41 (m, 2H), 7.32 (s, 1H), 7.22 (m, 1H), 7.16 (m, 4H), 1.99 (s, 3H); MS (ESI) m/e=269 (M+H)$^+$, 267 (M−H)$^−$.

EXAMPLE 17

N-(4-amino-5-cyano-6-isopropoxypyridin-2-yl)acetamide

A heavy walled, sealable tube suitable for microwave heating was charged with 2 mL of 2-propanol and 15 mg (0.65 mmol) of sodium. The mixture was stirred and heated at 95° C. for 15 minutes until all of the sodium had reacted, then 100 mg (0.469 mmol) of 2-bromo-4,6-diaminonicotinonitrile was added. The tube was sealed, and the mixture was heated with a microwave apparatus at 150° C. for 10 minutes then cooled and concentrated under reduced pressure. The residue was taken up in 10 mL of ethyl acetate, and extracted with water (2×5 mL), then brine (1×5 mL), dried over MgSO$_4$, filtered, and concentrated under reduced pressure to an oil.

The oil was dissolved in 2 mL of pyridine, and cooled to 0 C. To this solution was added 4 drops of acetyl chloride, and the mixture was stirred at 0° C. for 15 min. Next, 0.5 mL of water was added, and the mixture was concentrated under reduced pressure. The residue was suspended in 5 mL of water, and extracted with ethyl acetate (2×5 mL). The combined ethyl acetate layers were back extracted with brine, dried over MgSO$_4$, filtered, and concentrated under reduced pressure to a solid. This was recrystallized from methanol to provide 12 mg (11%) of a white solid. $^1$H NMR (300 MHz, $d_6$-DMSO) δ 10.05 (s, 1H), 7.15 (s, 1H), 6.84 (s, 2H), 5.27 (m, 1H), 2.06 (s, 3H), 1.28 (d, 6H, J=6.4 Hz); MS (ESI) m/e=193 (M−Pr+H)+, 235 (M+H)+, 233 (M−H)−.

EXAMPLE 18

N-(4-amino-5-cyano-6-ethoxypyridin-2-yl)-2-methoxyacetamide

To a solution of 50 mg (0.23 mmol) of 4,6-diamino-2-ethoxy-nicotinonitrile in 1 mL of THF was added 100 mL (0.574 mmol) of N,N-diisopropylethylamine, follwed by 8 drops of methoxyacetyl chloride. The mixture was stirred for 5 minutes after which the mixture was diluted with 7 mL of water. The precipitate was collected and washed with water, recrystallized from 20 mL of methanol to provide 14 mg (24%) of a colorless solid. $^1$H NMR (300 MHz, $d_6$-DMSO) δ 9.55 (s, 1H), 7.17 (s, 1H), 6.97 (s, 2H), 4.31 (q, 2H, J=7.1 Hz), 4.04 (s, 2H), 3.35 (s, 3H), 1.29 (t, 3H, J=7.1 Hz); MS (ESI) m/e=223 (M−Et+H)+, 251 (M+H)+, 249 (M−H)−.

EXAMPLE 19

N-(4-amino-5-cyano-6-ethoxypyridin-2-yl)-2-(3-methoxyphenyl)acetamide

To a solution of 28 mg (0.17 mmol) of (3-methoxyphenyl) acetic acid in 0.5 mL of $CH_2Cl_2$ (or the minimum amount necessary for dissolution) was added 20 µL (0.22 mmol) of oxalyl chloride. The solution was swirled, allowed to stand for 5 minutes at ambient temperature, then added to a solution of 30 mg (0.14 mmol) of 4,6-diamino-2-ethoxy-nicotinonitrile in 0.5 mL of pyridine. The mixture was shaken for 15 minutes, diluted with 1 mL of water and concentrated under reduced pressure. The residue was taken up in 3 mL of ethyl acetate, and extracted with water (2×1 mL), 1M $HCl_{(aq.)}$ (1×1 mL), saturated $NaHCO_{3(aq.)}$ (2×1 mL), and brine (1×1 mL), dried over $MgSO_4$, filtered, and concentrated to a solid. This was recrystallized from 1 mL of methanol to provide 9 mg (16%) of a colorless solid. $^1$H NMR (300 MHz, $d_6$-DMSO) δ10.28 (s, 1H), 7.22 (m, 1H), 7.16 (m, 1H), 6.89 (m, 4H), 6.81 (m, 1H), 4.34 (q, 2H, J=7.1 Hz), 3.74 (s, 3H), 3.67 (s, 2H), 1.31 (t, 3H, J=7.1 Hz); MS (ESI) m/e=299 (M−Et+H)+, 327 (M+H)+, 349 (M+Na)+.

EXAMPLE 20

N-(4-amino-5-cyano-6-ethoxypyridin-2-yl)-2-(4-methoxyphenyl)acetamide

The titled material was prepared according to the same procedure outlined in Example 19, substituting (4-methoxyphenyl)acetic acid for (3-methoxyphenyl)acetic acid to provide 9 mg (16%). $^1$H NMR (300 MHz, $d_6$-DMSO) δ 10.24 (s, 1H), 7.23 (d, 2H, J=8.8 Hz), 7.15 (s, 1H), 6.87 (d, 4H, J=8.8 Hz), 4.34 (q, 2H, J=7.1 Hz), 3.72 (s, 3H), 3.62 (s, 2H), 1.30 (t, 3H, J=7.1 Hz); MS (ESI) m/e=299 (M−Et+H)+, 327 (M+H)+, 349 (M+Na)+.

EXAMPLE 21

N-(4-amino-5-cyano-6-ethoxypyridin-2-yl)-2-(2-fluorophenyl)acetamide

The titled material was prepared according to the same procedure outlined in Example 19, substituting (2-fluorophenyl)acetic acid for (3-methoxyphenyl)acetic acid to provide 10 mg (19%). $^1$H NMR (300 MHz, $d_6$-DMSO) δ10.35 (s, 1H), 7.32 (m, 2H), 7.16 (m, 3H), 6.89 (s, 2H), 4.35 (q, 2H, J=7.1 Hz), 3.80 (s, 2H), 1.31 (t, 3H, J=7.1 Hz). MS (ESI) m/e=287 (M−Et+H)+, 315 (M+H)+, 313 (M+−H)−.

EXAMPLE 22

N-(4-amino-5-cyano-6-ethoxypyridin-2-yl)-2-(4-fluorophenyl)acetamide

The titled material was prepared according to the same procedure outlined in Example 19, substituting (4-fluorophenyl)acetic acid for (3-methoxyphenyl)acetic acid to provide 7 mg (13%). $^1$H NMR (300 MHz, $d_6$-DMSO) δ 10.32 (s, 1H), 7.34 (m, 2H), 7.14 (m, 3H), 6.90 (s, 2H), 4.34 (q, J=7.1 Hz, 2H), 3.70 (s, 2H), 1.30 (t, J=7.1 Hz, 3H); MS (ESI) m/e=287 (M−Et+H)+, 315 (M+H)+, 313 (M+−H)−.

EXAMPLE 23

N-(4-amino-5-cyano-6-ethoxypyridin-2-yl)-2-(2-chlorophenyl)acetamide

The titled material was prepared according to the same procedure outlined in Example 19, substituting (2-chlorophenyl)acetic acid for (3-methoxyphenyl)acetic acid to provide 10 mg (18%). $^1$H NMR (300 MHz, $d_6$-DMSO) δ 10.38 (s, 1H), 7.41 (m, 2H), 7.31 (m, 2H), 7.13 (s, 1H), 6.89 (s, 2H), 4.35 (q, 2H, J=7.1 Hz), 3.90 (s, 2H), 1.31 (t, 3H, J=7.1 Hz); MS (ESI) m/e=303 (M−Et+H)+, 331 (M+H)+, 329 (M+−H)−.

EXAMPLE 24

N-(4-amino-5-cyano-6-ethoxypyridin-2-yl)-2-(4-chlorophenyl)acetamide

The titled material was prepared according to the same procedure outlined in Example 19, substituting (4-chlorophenyl)acetic acid for (3-methoxyphenyl)acetic acid to provide 8 mg (14%) $^1$H NMR (300 MHz, $d_6$-DMSO) δ 10.33 (s, 1H), 7.35 (m, 4H), 7.15 (s, 1H), 6.90 (s, 2H), 4.34 (q, 2H, J=7.1 Hz), 3.71 (s, 2H), 1.30 (t, 3H, J=7.1 Hz); MS (ESI) m/e=303 (M−Et+H)+, 331 (M+H)+, 329 (M−H)−.

EXAMPLE 25

N-(4-amino-5-cyano-6-ethoxypyridin-2-yl)-2-(2-bromophenyl)acetamide

The titled material was prepared according to the same procedure outlined in Example 19, substituting (2-bromophenyl)acetic acid for (3-methoxyphenyl)acetic acid to provide 7 mg (11%) $^1$H NMR (300 MHz, $d_6$-DMSO) δ 10.38 (s, 1H), 7.61 (d, 1H, J=7.8 Hz), 7.36 (m, 2H), 7.21 (m, 1H), 7.13 (s, 1H), 6.89 (s, 2H), 4.35 (q, 2H, J=7.1 Hz), 3.91 (s, 2H), 1.31 (t, 3H, J=7.1 Hz); MS (ESI) m/e=347 (M−Et+H)+, 349 (M−Et+H)+, 375 (M+H)+, 377 (M+H)+, 373 (M−H)−, 375 (M−H)−.

EXAMPLE 26

N-(4-amino-5-cyano-6-ethoxypyridin-2-yl)-2-(3-bromophenyl)acetamide

The titled material was prepared according to the same procedure outlined in Example 19, substituting (3-bromophenyl)acetic acid for (3-methoxyphenyl)acetic acid to provide 2 mg (3%). $^1$H NMR (300 MHz, $d_6$-DMSO) δ 10.35 (s, 1H), 7.53 (m, 1H), 7.45 (m, 1H), 7.30 (m, 2H), 7.15 (s, 1H), 6.90

(s, 2H), 4.34 (q, 2H, J=7.1 Hz), 3.72 (s, 2H), 1.31 (t, 3H, J=7.1 Hz); MS (ESI) m/e=347 (M−Et+H)⁺, 349 (M−Et+H)⁺, 375 (M+H)⁺, 377 (M+H)⁺, 373 (M−H)⁻, 375 (M−H)⁻.

EXAMPLE 27

N-(4-amino-5-cyano-6-ethoxypyridin-2-yl)-2-(4-bromophenyl)acetamide

The titled material was prepared according to the same procedure outlined in Example 19, substituting (4-bromophenyl)acetic acid for (3-methoxyphenyl)acetic acid to provide 4 mg (6%). ¹H NMR (300 MHz, d₆-DMSO) δ 10.34 (s, 1H), 7.51 (m, 2H), 7.27 (m, 2H), 7.15 (s, 1H), 6.90 (s, 2H), 4.34 (q, 2H, J=7.1 Hz), 3.70 (s, 2H), 1.30 (t, 3H, J=7.1 Hz); MS (ESI) m/e=347 (M−Et+H)⁺, 349 (M−Et+H)⁺, 375 (M+H)⁺, 377 (M+H)⁺, 373 (M−H)⁻, 375 (M−H)⁻.

EXAMPLE 28

N-(4-amino-5-cyano-6-ethoxypyridin-2-yl)-2-(2-methylphenyl)acetamide

The titled material was prepared according to the same procedure outlined in Example 19, substituting (2-methylphenyl)acetic acid for (3-methoxyphenyl)acetic acid to provide 10 mg (10%). ¹H NMR (300 MHz, d₆-DMSO) δ 10.28 (s, 1H), 7.19 (t, 1H, J=7.5 Hz), 7.16 (s, 1H), 7.07 (m, 3H), 6.89 (s, 2H), 4.34 (q, 2H, J=7.1 Hz), 3.65 (s, 2H), 2.28 (s, 3H), 1.30 (t, 3H, J=7.1 Hz); MS (ESI) m/e=283 (M−Et+H)⁺, 311 (M+H)⁺, 309 (M−H)⁻.

EXAMPLE 29

N-(4-amino-5-cyano-6-ethoxypyridin-2-yl)-2-(3-methylphenyl)acetamide

The titled material was prepared according to the same procedure outlined in Example 19, substituting (3-methylphenyl)acetic acid for (3-methoxyphenyl)acetic acid. Yield 10 mg (10%). ¹H NMR (500 MHz, d₆-DMSO) δ 10.31-10.28 (s, 1H), 7.20 (t, 1H, J=7.6 Hz), 7.16 (s, 1H), 7.13-7.08 (m, 2H), 7.05 (d, 1H, J=7.3 Hz), 6.89 (s, 2H), 4.34 (q, 2H, J=7.0 Hz), 3.65 (s, 2H), 2.28 (s, 3H), 1.30 (t, 3H, J=7.0 Hz); MS (ESI) m/e=283 (M−Et+H)⁺, 311 (M+H)⁺, 309 (M−H)⁻.

EXAMPLE 30

N-(4-amino-5-cyano-6-ethoxypyridin-2-yl)-2-(4-methylphenyl)acetamide

The titled material was prepared according to the same procedure outlined in Example 19, substituting (4-methylphenyl)acetic acid for (3-methoxyphenyl)acetic acid to provide 20 mg (19%). ¹H NMR (300 MHz, d₆-DMSO) δ 10.26 (s, 1H), 7.15 (m, 5H), 6.88 (s, 2H), 4.34 (q, 2H, J=7.1 Hz), 3.64 (s, 2H), 2.27 (s, 3H), 1.30 (t, 3H, J=7.1 Hz); MS (ESI) m/e=283 (M−Et+H)⁺, 311 (M+H)⁺, 309 (M−H)⁻.

EXAMPLE 31

N-(4-amino-5-cyano-6-ethoxypyridin-2-yl)-2-(2-methoxyphenyl)acetamide

The titled material was prepared according to the same procedure outlined in Example 19, substituting (2-methoxyphenyl)acetic acid for (3-methoxyphenyl)acetic acid to provide 10 mg (9%). ¹H NMR (300 MHz, d₆-DMSO) δ 10.10 (s, 1H), 7.24 (m, 1H), 7.17 (dd, 1H, J=7.5, 1.7 Hz), 7.13 (s, 1H), 6.97 (d, 1H, J=7.1 Hz), 6.89 (m, 3H), 4.34 (q, 2H, J=7.1 Hz), 3.76 (s, 3H), 3.68 (s, 2H), 1.31 (t, 3H, J=7.1 Hz); MS (ESI) m/e=299 (M−Et+H)⁺, 327 (M+H)⁺, 325 (M−H)⁻.

EXAMPLE 32

N-(4-amino-5-cyano-6-ethoxypyridin-2-yl)-2-(2,5-difluorophenyl)acetamide

The titled material was prepared according to the same procedure outlined in Example 19, substituting (2,5-difluorophenyl)acetic acid for (3-methoxyphenyl)acetic acid to provide 20 mg (18%). ¹H NMR (500 MHz, d₆-DMSO) δ 10.39 (s, 1H), 7.30 (m, 2H), 7.22 (m, 2H), 6.91 (s, 2H), 4.35 (q, 2H, J=7.0 Hz), 3.81 (s, 2H), 1.31 (t, 3H, J=7.0 Hz); MS (ESI) m/e=299 (M−Et+H)⁺, 327 (M+H)⁺, 325 (M−H)⁻; MS (ESI) m/e=305 (M−Et+H)⁺, 333 (M+H)⁺, 331 (M−H)⁻.

EXAMPLE 33

N-(4-amino-5-cyano-6-ethoxypyridin-2-yl)-2-(3-fluorophenyl)acetamide

The titled material was prepared according to the same procedure outlined in Example 19, substituting (3-fluorophenyl)acetic acid for (3-methoxyphenyl)acetic acid. The product was purified via reverse phase HPLC, eluting with a 0-70% CH₃CN gradient in 0.1% aq. TFA to provide 4 mg (7%). ¹H NMR (300 MHz, d₆-DMSO) δ 10.35 (s, 1H), 7.36 (m, 1H), 7.09 (m, 4H), 6.90 (s, 2H), 4.34 (q, 2H, J=7.1 Hz), 3.74 (s, 2H), 1.31 (t, 3H, J=7.1 Hz); MS (ESI) m/e=287 (M−Et+H)⁺, 315 (M+H)⁺.

EXAMPLE 34

N-(4-amino-5-cyano-6-ethoxypyridin-2-yl)-2-(3-chlorophenyl)acetamide

The titled material was prepared according to the same procedure outlined in Example 19, substituting (3-chlorophenyl)acetic acid for (3-methoxyphenyl)acetic acid. The product was purified via reverse phase HPLC, eluting with a 0-70% CH₃CN gradient in 0.1% aq. TFA to provide 8 mg (14%). ¹H NMR (300 MHz, d₆-DMSO) δ 10.35 (s, 1H), 7.38 (m, 1H, J=1.7 Hz), 7.31 (m, 3H), 7.15 (s, 1H), 6.90 (s, 2H), 4.34 (q, 2H, J=7.0 Hz), 3.73 (s, 2H), 1.31 (t, 3H, J=7.1 Hz); MS (ESI) m/e=303 (M−Et+H)⁺, 331 (M+H)⁺, 329 (M−H)⁻.

EXAMPLE 35

N-(4-amino-5-cyano-6-ethoxypyridin-2-yl)-2-(2-nitrophenyl)acetamide

The titled material was prepared according to the same procedure outlined in Example 19, substituting (2-nitrophenyl)acetic acid for (3-methoxyphenyl)acetic acid to provide 10 mg (9%). ¹H NMR (500 MHz, d₆-DMSO) δ 10.41 (s, 1H), 8.06 (dd, 1H, J=8.2, 1.2 Hz), 7.20 (m, 3H), 7.12 (s, 1H), 6.91 (s, 2H), 4.36 (q, 2H, J=7.0 Hz), 4.19 (s, 2H), 1.32 (t, 3H, J=7.0 Hz); MS (ESI) m/e=314 (M−Et+H)⁺, 342 (M+H)⁺, 340 (M−H)⁻.

EXAMPLE 36

N-(4-amino-5-cyano-6-ethoxypridin-2-yl)-2-(2,4-dichlorophenyl)acetamide

The titled material was prepared according to the same procedure outlined in Example 19, substituting (2,4-dichlorophenyl)acetic acid for (3-methoxyphenyl)acetic acid to provide 10 mg (9%) $^1$H NMR (300 MHz, d$_6$-DMSO) δ 10.41 (s, 1H), 7.60 (m, 1H), 7.41 (m, 2H), 7.12 (s, 1H), 6.90 (s, 2H), 4.35 (q, 2H, J=7.1 Hz), 3.91 (s, 2H), 1.31 (t, 3H, J=7.1 Hz); MS (ESI) m/e=343 (M−Et+H)$^+$, 365 (M+H)$^+$.

EXAMPLE 37

N-(4-amino-5-cyano-6-ethoxypyridin-2-yl)-2-(3-nitrophenyl)acetamide

The titled material was prepared according to the same procedure outlined in Example 19, substituting (3-nitrophenyl)acetic acid for (3-methoxyphenyl)acetic acid to provide 4 mg (7%). $^1$H NMR (300 MHz, d$_6$-DMSO) δ 10.44 (s, 1H), 8.23 (m, 1H), 8.13 (m, 1H), 7.77 (m, 1H), 7.63 (t, 1H, J=8.0 Hz), 7.16 (s, 1H), 6.91 (s, 2H), 4.35 (q, 2H, J=7.1 Hz), 3.90 (s, 2H), 1.31 (t, 3H, J=7.1 Hz); MS (ESI) m/e=314 (M−Et+H)$^+$, 342 (M+H)$^+$, 340 (M−H)$^−$.

EXAMPLE 38

N-(4-amino-5-cyano-6-ethoxypyridin-2-yl)-2-(4-nitrophenyl)acetamide

The titled material was prepared according to the same procedure outlined in Example 19, substituting (4-nitrophenyl)acetic acid for (3-methoxyphenyl)acetic acid to provide 15 mg (26%). $^1$H NMR (300 MHz d$_6$-DMSO) δ 10.44 (s, 1H), 8.19 (m, 2H), 7.59 (m, 2H), 7.15 (s, 1H), 6.91 (s, 2H), 4.34 (q, 2H, J=7.1 Hz), 3.90 (s, 2H), 1.31 (t, 3H, J=7.1 Hz); MS (ESI) m/e=314 (M−Et+H)$^+$, 342 (M+H)$^+$.

EXAMPLE 39

N-(4-amino-5-cyano-6-ethoxypridin-2-yl)-2-[3-(trifluoromethyl)phenyl]acetamide

The titled material was prepared according to the same procedure outlined in Example 19, substituting (3-trifluoromethylphenyl)acetic acid for (3-methoxyphenyl)acetic acid to provide 4 mg (7%). $^1$H NMR (300 MHz, d$_6$-DMSO) δ 10.40 (s, 1H), 7.69 (s, 1H), 7.60 (m, 3H), 7.16 (s, 1H), 6.90 (s, 2H), 4.35 (q, 2H, J=7.1 Hz), 3.84 (s, 2H), 1.31 (t, 3H, J=7.1 Hz); MS (ESI) m/e 337 (M−Et+H)$^+$, 365 (M+H)$^+$, 363 (M−H)$^−$.

EXAMPLE 40

N-(4-amino-5-cyano-6-ethoxypyridin-2-yl)-2-[4-(benzyloxy)phenyl]acetamide

The titled material was prepared according to the same procedure outlined in Example 19, substituting (4-benzyloxyphenyl)acetic acid for (3-methoxyphenyl)acetic acid to provide 15 mg (22%). $^1$H NMR (300 MHz, d$_6$-DMSO) δ 10.24 (s, 1H), 7.38 (m, 5H), 7.22 (m, 2H), 7.15 (s, 1H), 6.95 (m, 2H), 6.88 (s, 2H), 5.08 (s, 2H), 4.34 (q, 2H, J=7.1 Hz), 3.62 (s, 2H), 1.30 (t, 3H, J=7.1 Hz); MS (ESI) m/e=375 (M−Et+H)$^+$, 403 (M+H)$^+$, 401 (M−H)$^−$.

EXAMPLE 41

N-(4-amino-5-cyano-6-ethoxypyridin-2-yl)-2-(1-naphthyl)acetamide

The titled material was prepared according to the same procedure outlined in Example 19, substituting 1-naphthylacetic acid for (3-methoxyphenyl)acetic acid to provide 6 mg (10%). $^1$H NMR (300 MHz, d$_6$-DMSO) δ 10.46 (s, 1H), 8.09 (m, 1H), 7.93 (m, 1H), 7.84 (dd, 1H, J=6.4, 3.1 Hz), 7.52 (m, 4H), 7.12 (s, 1H), 6.87 (s, 2H), 4.37 (q, 2H, J=7.1 Hz), 4.22 (s, 2H), 1.32 (t, 3H, J=7.1 Hz); MS (ESI) m/e=319 (M−Et+H)$^+$, 347 (M+H)$^+$, 345 (M−H)$^−$.

EXAMPLE 42

N-(4-amino-5-cyano-6-ethoxypyridin-2-yl)-2-(2-naphthyl)acetamide

The titled material was prepared according to the same procedure outlined in Example 19, substituting 2-naphthylacetic acid for (3-methoxyphenyl)acetic acid to provide 11 mg (19%). $^1$H NMR (300 MHz, d$_6$-DMSO) δ 10.40 (s, 1H), 7.88 (m, 3H), 7.81 (s, 1H), 7.49 (m, 3H), 7.18 (s, 1H), 6.89 (s, 2H), 4.35 (q, 2H, J=7.1 Hz), 3.89 (s, 2H), 1.31 (t, 3H, J=7.1 Hz); MS (ESI) m/e=319 (M−Et+H)$^+$, 347 (M+H)$^+$, 345 (M−H)$^−$.

EXAMPLE 43

N-(4-amino-5-cyano-6-ethoxypyridin-2-yl)-2-(2,5-dimethylphenyl)acetamide

The titled material was prepared according to the same procedure outlined in Example 19, substituting 2-naphthylacetic acid for (3-methoxyphenyl)acetic acid to provide 9 mg (16%). $^1$H NMR (300 MHz, d$_6$-DMSO) δ 10.26 (s, 1H), 7.15 (s, 1H), 7.04 (m, 2H), 6.93 (m, 3H), 4.35 (q, 2H, J=7.1 Hz), 3.70 (s, 2H), 2.23 (s, 3H), 2.21 (s, 3H), 1.31 (t, 3H, J=7.1 Hz); MS (ESI) m/e=297 (M−Et+H)$^+$, 325 (M+H)$^+$, 323 (M−H)$^−$.

EXAMPLE 44

N-(4-amino-5-cyano-6-ethoxypyridin-2-yl)-2-(3,5-dimethylphenyl)acetamide

The titled material was prepared according to the same procedure outlined in Example 3019, substituting (3,5-dimethylphenyl)acetic acid for (3-methoxyphenyl)acetic acid to provide 8 mg (14%). $^1$H NMR (300 MHz, d$_6$-DMSO) δ 10.26 (s, 1H), 7.16 (s, 1H), 6.88 (m, 5H), 4.34 (q, 2H, J=7.1 Hz), 3.61 (s, 2H), 2.24 (s, 6H), 1.30 (t, 3H, J=7.1 Hz); MS (ESI) m/e=297 (M−Et+H)$^+$, 325 (M+H)$^+$, 323 (M−H)$^−$.

EXAMPLE 45

N-(4-amino-5-cyano-6-ethoxypyridin-2-yl)-2-(2,4-dimethoxyphenyl)acetamide

The titled material was prepared according to the same procedure outlined in Example 19, substituting (2,4-dimethoxyphenyl)acetic acid for (3-methoxyphenyl)acetic acid to provide 24 mg (40%). $^1$H NMR (300 MHz, d$_6$-DMSO) δ 10.01 (s, 1H), 7.12 (s, 1H), 7.07 (d, 1H, J=8.5 Hz), 6.87 (s, 2H), 6.54 (d, 1H, J=2.4 Hz), 6.47 (dd, 1H, J=8.5, 2.4 Hz), 4.33 (q, 2H, J=7.1 Hz), 3.74 (s, 6H), 3.59 (s, 2H), 1.30 (t, 3H, J=7.1 Hz); MS (ESI) m/e=329 (M−Et+H)$^+$, 357 (M+H)$^+$, 355 (M−H)$^−$.

EXAMPLE 46

N-(4-amino-5-cyano-6-ethoxypyridin-2-yl)-2-(2,5-dimethoxyphenyl)acetamide

The titled material was prepared according to the same procedure outlined in Example 19, substituting (2,5-dimethoxyphenyl)acetic acid for (3-methoxyphenyl)acetic acid to provide 11 mg (18%). $^1$H NMR (300 MHz, d$_6$-DMSO) δ 10.10 (s, 1H), 7.12 (s, 1H), 6.90 (m, 3H), 6.79 (m, 2H), 4.34 (q, 2H, J=7.1 Hz), 3.70 (s, 3H), 3.69 (s, 3H), 3.66 (s, 2H), 1.31 (t, 3H, J=7.1 Hz); MS (ESI) m/e=329 (M−Et+H)$^+$, 357 (M+H)$^+$, 355 (M−H)$^−$.

EXAMPLE 47

N-(4-amino-5-cyano-6-ethoxypyridin-2-yl)-2-(3,4-dimethoxyphenyl)acetamide

The titled material was prepared according to the same procedure outlined in Example 19, substituting (3,4-dimethoxyphenyl)acetic acid for (3-methoxyphenyl)acetic acid to provide 8 mg (12%). $^1$H NMR (300 MHz, d$_6$-DMSO) δ 10.22 (s, 1H), 7.16 (s, 11H), 6.90 (m, 4H), 6.82 (m, 1H), 4.34 (q, 2H, J=7.1 Hz), 3.73 (s, 3H), 3.72 (s, 3H), 3.61 (s, 2H), 1.30 (t, 3H, J=7.1 Hz); MS (ESI) m/e=329 (M−Et+H)$^+$, 357 (M+H)$^+$, 355 (M−H)$^−$.

EXAMPLE 48

N-(4-amino-5-cyano-6-ethoxypyridin-2-yl)-2-(3,5-dimethoxyphenyl)acetamide

The titled material was prepared according to the same procedure outlined in Example 19, substituting (3,5-dimethoxyphenyl)acetic acid for (3-methoxyphenyl)acetic acid to provide 20 mg (12%). $^1$H NMR (300 MHz, d$_6$-DMSO) δ 10.26 (s, 1H), 7.16 (s, 1H), 6.90 (s, 2H), 6.48 (d, J=2.4 Hz, 2H), 6.38 (t, 1H, J=2.4 Hz), 4.34 (q, 2H, J=7.1 Hz), 3.72 (s, 2H), 3.31 (s, 6H), 1.30 (t, 3H, J=7.1 Hz); MS (ESI m/e=329 (M−Et+H)$^+$, 357 (M+H)$^+$, 355 (M−H)$^−$.

EXAMPLE 49

N-(4-amino-5-cyano-6-ethoxypyridin-2-yl)-2-(1,3-benzodioxol-5-yl)acetamide

The titled material was prepared according to the same procedure outlined in Example 19, substituting (3,5-dimethoxyphenyl)acetic acid for (3-methoxyphenyl)acetic acid to provide 17 mg (30%). $^1$H NMR (300 MHz, d$_6$-DMSO) δ 10.24 (s, 1H), 7.14 (s, 1H), 6.88 (s, 2H), 6.88 (d, 1H, J=1.7 Hz), 6.85 (d, 1H, J=7.8 Hz), 6.76 (dd, 1H, J=7.8, 1.7 Hz), 5.97 (s, 2H), 4.34 (q, 2H, J=7.1 Hz), 3.60 (s, 2H), 1.30 (t, 3H, J=7.1 Hz); MS (ESI) m/e=313 (M−Et+H)$^+$, 341 (M+H)$^+$, 339 (M−H)$^−$.

EXAMPLE 50

N-(4-amino-5-cyano-6-ethoxypyridin-2-yl)-2-(2,3-difluorophenyl)acetamide

The titled material was prepared according to the same procedure outlined in Example 19, substituting (2,3-difluorophenyl)acetic acid for (3-methoxyphenyl)acetic acid to provide 13 mg (24%). $^1$H NMR (300 MHz, d$_6$-DMSO) δ 10.41 (s, 1H), 7.33 (m, 1H), 7.18 (m, 2H), 7.13 (s, 1H), 6.90 (s, 2H), 4.35 (q, 2H, J=7.1 Hz), 3.87 (s, 2H), 1.31 (t, 3H, J=7.1 Hz); MS (ESI) m/e=305 (M−Et+H)$^+$, 333 (M+H)$^+$, 331 (M−H)$^−$.

EXAMPLE 51

N-(4-amino-5-cyano-6-ethoxypyridin-2-yl)-2-(1,1'-biphenyl-4-yl)acetamide

The titled material was prepared according to the same procedure outlined in Example 19, substituting (4-phenyl) phenylacetic acid for (3-methoxyphenyl)acetic acid. The product was purified via reverse phase HPLC, eluting with a 5-75% CH$_3$CN gradient in 0.01M NH$_4$OAc$_{(aq.)}$ to provide 9 mg (14%). $^1$H NMR (300 MHz, d$_6$-DMSO) δ 10.36 (s, 1H), 7.63 (m, 4H), 7.40 (m, 5H), 7.17 (s, 1H), 6.90 (s, 2H), 4.35 (q, 2H, J=7.1 Hz), 3.75 (s, 2H), 1.31 (t, 3H, J=7.1 Hz); MS (ESI) m/e=345 (M−Et+H)$^+$, 373 (M+H)$^+$, 371 (M−H)$^−$.

EXAMPLE 52

N-(4-amino-5-cyano-6-ethoxypyridin-2-yl)-2-[4-(dimethylamino)phenyl]acetamide

The titled material was prepared according to the same procedure outlined in Example 19, substituting (4-dimethylaminophenyl)acetic acid for (3-methoxyphenyl)acetic acid. The product was purified via reverse phase HPLC, eluting with a 5-75% CH$_3$CN gradient in 0.01M NH$_4$OAc$_{(aq.)}$ to provide 1 mg (2%). $^1$H NMR (300 MHz, d$_6$-DMSO) δ 10.16 (s, 1H), 7.15 (s, 1H), 7.12 (d, J=8.5 Hz, 2H), 6.87 (s, 2H), 6.67 (d, J=8.5 Hz, 2H), 4.33 (q, J=7.1 Hz, 2H), 3.54 (s, 2H), 2.85 (s, 6H), 1.30 (t, J=7.1 Hz, 3H); MS (ESI) m/e=312 (M−Et+H)$^+$, 340 (M+H)$^+$, 338 (M−H)$^−$.

EXAMPLE 53

N-(4-amino-5-cyano-6-ethoxypyridin-2-yl)-2-[4-(trifluoromethyl)phenyl]acetamide

The titled material was prepared according to the same procedure outlined in Example 19, substituting (4-trifluoromethyl)phenylacetic acid for (3-methoxyphenyl)acetic acid. The product was purified via reverse phase HPLC, eluting with a 5-75% CH$_3$CN gradient in 0.01M NH$_4$OAc$_{(aq.)}$ to provide 7 mg (11%). $^1$H NMR (300 MHz, d$_6$-DMSO) δ 10.41 (s, 1H), 7.69 (d, 2H, J=8.1 Hz), 7.53 (d, 2H, J=8.1 Hz), 7.15 (s, 1H), 6.91 (s, 2H), 4.35 (q, 2H, J=7.1 Hz), 3.84 (s, 2H), 1.31 (t, 3H, J=7.1 Hz); MS (ESI) m/e=337 (M−Et+H)$^+$, 365 (M+H)$^+$, 363 (M−H)$^−$.

EXAMPLE 54

N-(4-amino-5-cyano-6-ethoxypyridin-2-yl)-2-[4-(trifluoromethoxy)phenyl]acetamide The titled material was prepared according to the same procedure outlined in Example 19, substituting (4-trifluoromethyl)phenylacetic acid for (3-methoxyphenyl)acetic acid. The product was purified via reverse phase HPLC, eluting with a 5-75% CH$_3$CN gradient in 0.01M NH$_4$OAc$_{(aq.)}$ to provide 7 mg (12%). $^1$H NMR (300 MHz, d$_6$-DMSO) δ 10.37 (s, 1H), 7.46 (t, 1H, J=8.1 Hz), 7.34 (m, 2H), 7.25 (d, 1H, J=9.2 Hz), 7.16 (s, 1H), 6.91 (s, 2H), 4.35 (q, 2H, J=7.1 Hz), 3.79 (s, 2H), 1.31 (t, 3H, J=7.1 Hz); MS (ESI) m/e=353 (M−Et+H)$^+$, 381 (M+H)$^+$, 379 (M−H)$^−$.

EXAMPLE 55

N-(4-amino-5-cyano-6-ethoxypyridin-2-yl)-2-(4-phenoxyphenyl)acetamide

The titled material was prepared according to the same procedure outlined in Example 19, substituting (4-phenoxy) phenylacetic acid for (3-methoxyphenyl)acetic acid. The product was purified via reverse phase HPLC, eluting with a 5-75% CH$_3$CN gradient in 0.01M NH$_4$OAc$_{(aq.)}$ to provide 8 mg (13%). $^1$H NMR (300 MHz, d$_6$-DMSO) δ 10.32 (s, 1H), 7.36 (m, 4H), 7.17 (s, 1H), 7.13 (d, 1H, J=7.5 Hz), 6.97 (m, 4H), 6.90 (s, 2H), 4.34 (q, 2H, J=7.1 Hz), 3.69 (s, 2H), 1.30 (t, 3H, J=7.1 Hz); MS (ESI) m/e=361 (M−Et+H)$^+$, 389 (M+H)$^+$, 387 (M−H)$^-$.

EXAMPLE 56

N-(4-amino-5-cyano-6-ethoxypyridin-2-yl)-2-(3,4,5-trimethoxyphenyl)acetamide

The titled material was prepared according to the same procedure outlined in Example 19, substituting (3,4,5-trimethoxyphenyl)acetic acid for (3-methoxyphenyl)acetic acid. The product was purified via reverse phase HPLC, eluting with a 5-75% CH$_3$CN gradient in 0.01M NH$_4$OAc$_{(aq.)}$ to provide 4 mg (7%) $^1$H NMR (300 MHz, d$_6$-DMSO) δ 10.25 (s, 1H), 7.17 (s, 1H), 6.89 (s, 2H), 6.63 (s, 2H), 4.34 (q, 2H, J=7.1 Hz), 3.76 (m, 6H), 3.63 (s, 5H), 1.30 (t, 3H, J=7.1 Hz); MS (ESI) m/e=359 (M−Et+H)$^+$, 387 (M+H)$^+$, 385 (M−H)$^-$.

EXAMPLE 57

N-(4-amino-5-cyano-6-ethoxypyridin-2-yl)-3,3-dimethylbutanamide

To 30 mg (0.17 mmol) of 4,6-diamino-2-ethoxy-nicotinonitrile in 0.5 mL of pyridine was added 4 drops of 3,3-dimethylbutyryl chloride. The mixture was stirred at ambient temperature for 5 minutes then diluted with 5 mL of water. The precipitate was filtered, washed with water, and recrystallized from methanol to provide 5 mg (11%) of white crystals. $^1$H NMR (300 MHz, d$_6$-DMSO) δ 9.94 (s, 1H), 7.24 (s, 1H), 6.86 (s, 2H), 4.33 (q, 2H, J=7.1 Hz), 2.27 (s, 2H), 1.29 (t, 3H, J=7.1 Hz), 0.99 (s, 9H); MS (ESI) m/e=249 (M−Et+H)$^+$, 277 (M+H)$^+$, 275 (M−H)$^-$.

EXAMPLE 58

N-(4-amino-5-cyano-6-ethoxypyridin-2-yl)-2-(2,3-dimethoxyphenyl)acetamide

To 67 mg (0.34 mmol) of (2,3-dimethoxyphenyl)acetic acid in 1 mL of CH$_2$Cl$_2$ was added 32 μL (0.37 mmol) of oxalyl chloride. The solution was stirred at ambient temperature for 20 minutes then added to a solution of 60 mg (0.28 mmol) of 4,6-diamino-2-ethoxy-nicotinonitrile in 0.5 mL of pyridine. The mixture was complete within 5 minutes though some diaminopyridine remained. The solvent was removed under reduced pressure, then the residue was taken up in 10 mL of ethyl acetate and extracted with water (2×5 mL), saturated NaHCO$_{3(aq.)}$ (1×5 mL), and brine (1×5 mL), dried over MgSO$_4$, filtered, and concentrated to an oil. This was recrystallized from 8 mL of methanol to provide 35 mg (35%) of white crystals. $^1$H NMR (300 MHz, d$_6$-DMSO) δ 10.22 (s, 1H), 7.15 (s, 1H), 6.97 (m, 2H), 6.88 (s, 2H), 6.81 (dd, 1H, J=7.1, 2.0 Hz), 4.35 (q, 2H, J=7.1 Hz), 3.79 (s, 3H), 3.71 (s, 2H), 3.68 (s, 3H), 1.31 (t, 3H, J=7.1 Hz); MS (ESI) m/e=327 (M−Et+H)$^+$, 357 (M+H)$^+$.

EXAMPLE 59

N-(4-amino-5-cyano-6-ethoxypyridin-2-yl)-2-thien-2-ylacetamide

To 50 mg (0.28 mmol) of 4,6-diamino-2-ethoxy-nicotinonitrile in 1 mL of pyridine was added 150 μL (1.21 mmol) of 2-thiopheneacetyl chloride, dropwise. The mixture was stirred for 5 min at ambient temperature, then 1 mL of water was added. The mixture was stirred for an additional 30 minutes then concentrated under reduced pressure. The residue was taken up in 10 mL of ethyl acetate, extracted with water (2×5 mL), 1M HCl$_{(aq.)}$ (1×5 mL), saturated NaHCO$_3$ $_{(aq.)}$ (2×5 mL), and brine (1×5 mL), dried over MgSO$_4$, filtered, and concentrated to an oil. This was partially purified via silica gel chromatography, eluting with 30% ethyl acetate: hexanes to provide a sticky, yellow solid. This was triturated with methanol to provide 8 mg (9%) of a white solid. $^1$H NMR (300 MHz, d$_6$-DMSO) δ 10.33 (s, 1H), 7.38 (m, 1H), 7.18 (s, 1H), 6.97 (m, 2H), 6.92 (s, 2H), 4.34 (q, 2H, J=7.1 Hz), 3.94 (s, 2H), 1.30 (t, 3H, J=7.1 Hz); MS (ESI) m/e=275 (M−Et+H)$^+$, 303 (M+H)$^+$, 301 (M−H)$^-$.

EXAMPLE 60

N-(4-amino-5-cyano-6-isopropoxypyridin-2-yl)-2-(2,5-dimethoxyphenyl)acetamide

Example 60A 4,6-Diamino-2-isopropoxy-nicotinonitrile

A heavy walled, sealable tube suitable for microwave heating was charged with 6 mL of 2-propanol and 150 mg (6.5 mmol) of sodium. The mixture was stirred at 95° C. until all of the sodium had reacted (15 minutes), then 650 mg (3.05 mmol) of 2-bromo-4,6-diaminonicotinonitrile was added. The tube was sealed, and the mixture was heated with a microwave apparatus at 150° C. for 10 minutes then cooled and diluted with 30 mL of water. The precipitate was collected, washed with water until pH=7, then dried under reduced pressure at 95° C. to provide 312 mg (53%) of pale yellow crystals.

Example 60B

N-(4-amino-5-cyano-6-isopropoxypyridin-2-yl)-2-(2,5-dimethoxyphenyl)acetamide

To a solution of 100 mg (0.520 mmol) of 4,6-diamino-2-isopropoxy-nicotinonitrile in 1 mL of pyridine was added 3 mL of CH$_2$Cl$_2$ followed by a solution of 150 mg (0.699 mmol) of 2,5-dimethoxyphenylacetyl chloride (prepared from (2,5-dimethoxyphenyl)acetic acid and oxalyl chloride in CH$_2$Cl$_2$) in 1 mL of CH$_2$Cl$_2$. The mixture was stirred at ambient temperature for 10 minutes then 1 mL of water was added, and the mixture was concentrated under reduced pressure. The residue was taken up in 20 mL of warm ethyl acetate and extracted with water (1×5 mL), 1M HCl$_{(aq.)}$ (2×5 mL), saturated NaHCO$_{3(aq.)}$ (2×5 mL), and brine (1×5 mL), dried over MgSO$_4$, filtered, and concentrated to a solid. Recrystallization from methanol or 2-propanol provided 90 mg (47%) of a white solid. $^1$H NMR (300 MHz, d$_6$-DMSO) δ 10.06 (s, 1H), 7.10 (s, 1H), 6.90 (m, 1H), 6.84 (s, 2H), 6.79 (m, 2H), 5.28 (septet, 1H, J=6.1 Hz), 3.70 (s, 3H), 3.69 (s, 3H), 3.66 (s, 2H), 1.29 (d, 6H, J=6.1 Hz); MS (ESI) m/e=329 (M−Pr+H)$^+$, 371 (M+H)$^+$, 369 (M−H)$^-$.

EXAMPLE 61

N-[4-amino-5-cyano-6-(2-methoxyethoxy)pyridin-2-yl]-2-(2,5-dimethoxyphenyl)acetamide

Example 61A

4,6-Diamino-2-(2-methoxy-ethoxy)-nicotinonitrile

A heavy walled, sealable tube suitable for microwave heating was charged with 3 mL of 2-propanol and 35 mg (1.5 mmol) of sodium. The mixture was stirred at ambient temperature until all of the sodium had reacted, then 213 mg (1.00 mmol) of 2-bromo-4,6-diaminonicotinonitrile was added. The tube was sealed, the mixture was heated with a microwave apparatus at 150° C. for 10 minutes after which it was cooled and concentrated under reduced pressure. The residue was taken up in 10 mL of water, and extracted with ethyl acetate (3×5 mL). The combined ethyl acetate layers were back extracted with water (1×5 mL), using a small amount of saturated $NaHCO_{3(aq.)}$ solution to aid separation if necessary, and brine (1×5 mL), dried over $MgSO_4$, filtered, and concentrated to 154 mg of a yellow solid. $^1$H NMR (300 MHz, $d_6$-DMSO) δ 6.22 (s, 2H), 6.18 (s, 2H), 5.33 (s, 1H), 4.31 (m, 2H), 3.59 (m, 2H), 3.30 (s, 3H); MS (ESI) m/e=151 $(M-CH_2CH_2OCH_3+H)^+$, 209 $(M+H)^+$, 207 $(M-H)^-$.

Example 61B

N-[4-amino-5-cyano-6-(2-methoxyethoxy)pyridin-2-yl]-2-(2,5-dimethoxyphenyl)acetamide To a solution of 42 mg (0.20 mmol) of 4,6-diamino-2-(2-methoxy-ethoxy)-nicotinonitrile in 0.2 mL of pyridine and 1 mL of $CH_2Cl_2$ was added 75 mg (0.35 mmol) of 2,5-dimethoxyphenylacetyl chloride (Example 60B). The mixture was stirred at ambient temperature for 10 minutes then diluted with 1 mL of water and concentrated under reduced pressure. The residue was dissolved in 1 mL of ethyl acetate, then extracted with water (1×10 mL), 1M $HCl_{(aq.)}$ (2×5 mL), saturated $NaHCO_{3(aq.)}$ (2×5 mL), and brine (1×5 mL), dried over $MgSO_4$, filtered, and concentrated to a yellow solid. The residue was recrystallized from 3 mL of ethyl acetate to provide 30 mg (38%) of a white solid. $^1$H NMR (300 MHz, $d_6$-DMSO) δ 10.11 (s, 1H), 7.14 (s, 1H), 6.90 (m, 3H), 6.79 (m, 2H), 4.42 (m, 2H), 3.70 (s, 3H), 3.69 (s, 3H), 3.64 (m, 4H), 3.31 (s, 3H); MS (ESI) m/e=329 $(M-CH_2CH_2OCH_3+H)^+$, 387 $(M+H)^+$, 385 $(M-H)^-$.

EXAMPLE 62

N-[4-amino-5-cyano-6-(2-hydroxyethoxy)pyridin-2-yl]-2-(2,5-dimethoxyphenyl)acetamide

Example 62A

4,6-Diamino-2-(2-hydroxy-ethoxy)-nicotinonitrile

A heavy walled, sealable tube suitable for microwave heating was charged with 3 mL of ethylene glycol and 50 mg (2.2 mmol) of sodium. The mixture was stirred at 95° C. until all of the sodium had reacted, then 213 mg (1.00 mmol) of 2-bromo-4,6-diaminonicotinonitrile was added. The tube was sealed, and the mixture was heated with a microwave apparatus at 150° C. for 10 minutes then cooled. The mixture was diluted with 15 mL of water, and extracted with ethyl acetate (3×5 mL). The combined ethyl acetate layers were back extracted with water (1×5 mL), and brine (1×5 mL), dried over $MgSO_4$, filtered, and concentrated to provide 85 mg (44%) of a solid. $^1$H NMR (300 MHz, $d_6$-DMSO) δ 6.20 (s, 2H), 6.16 (s, 2H), 5.32 (s, 1H), 4.76 (t, 1H, J=5.3 Hz), 4.21 (m, 2H), 3.64 (q, 2H, J=5.4 Hz); MS (ESI) m/e=151 $(M-EtOH+H)^+$, 195 $(M+H)^+$.

Example 62B

N-[4-amino-5-cyano-6-(2-hydroxyethoxy)pyridin-2-yl]-2-(2,5-dimethoxyphenyl)acetamide To a solution of 39 mg (0.20 mmol) of 4,6-diamino-2-(2-hydroxy-ethoxy)-nicotinonitrile in 0.2 mL of pyridine and 1 mL of $CH_2Cl_2$ was added 75 mg (0.39 mmol) of 2,5-dimethoxyphenylacetyl chloride (Example 60B). The mixture was stirred at ambient temperature for 1 hours then 1 mL of water was added, and the solvents were removed under reduced pressure. The residue was taken up in 10 mL of ethyl acetate, then extracted with 1M $HCl_{(aq.)}$ (2×5 mL), saturated $NaHCO_{3(aq.)}$ (2×5 mL), and brine (1×5 mL), dried over $MgSO_4$, filtered, and concentrated to an oil. This was dissolved in 1:1 DMSO:methanol and purified by reversed phase HPLC, eluting with a 5-100% $CH_3CN$ gradient in 0.01M $NH_4OAc_{(aq.)}$ to provide a white solid. This was dissolved in 1 mL of THF, and 1 mL of 2M $NaOH_{(aq.)}$ was added. The solution was stirred at ambient temperature for 18 hours then concentrated under reduced pressure. The residue was taken up in 10 mL of ethyl acetate, then extracted with water (1×3 mL), 2M $NaOH_{(aq.)}$ (1×3 mL), and brine (1×3 mL), dried over $MgSO_4$, filtered, and concentrated under reduced pressure to a white solid. This was recrystallized from 1 mL of methanol to provide 4 mg (5%) of a white solid. $^1$H NMR (300 MHz, $d_6$-DMSO) δ 10.10 (s, 1H), 7.13 (s, 1H), 6.90 (m, 3H), 6.79 (m, 2H), 4.81 (t, 1H, J=5.4 Hz), 4.31 (m, 2H), 3.69 (m, 8H), 3.66 (s, 2H); MS (ESI) m/e=329 $(M-EtOH+H)^+$, 373 $(M+H)^+$, 371 $(M-H)^-$.

EXAMPLE 63

N-(4-amino-5-cyano-6-ethoxypyridin-2-yl)-2-cyclohexylacetamide

The titled material was prepared according to the same procedure outlined in Example 59, substituting cyclohexanecarbonyl chloride for 2-thiopheneacetyl chloride, and increasing the scale twofold. The product was recrystallized from methanol to provide 37 mg (22%) of a white solid. $^1$H NMR (300 MHz, $d_6$-DMSO) δ 10.01 (s, 1H), 7.21 (s, 1H), 6.86 (s, 2H), 4.32 (q, 2H, J=7.1 Hz), 2.24 (d, 2H, J=6.8 Hz), 1.71 (m, 6H), 1.29 (t, 3H, J=7.1 Hz), 1.16 (m, 3H), 0.94 (m, 2H); MS (ESI) m/e=275 $(M-Et+H)^+$, 303 $(M+H)^+$, 301 $(M-H)^-$.

EXAMPLE 64

N-(4-amino-5-cyano-6-ethoxypyridin-2-yl)-2-cyclopentylacetamide

The titled material was prepared according to the same procedure outlined in Example 59, substituting cyclopentanecarbonyl chloride for 2-thiopheneacetyl chloride, and increasing the scale twofold. The product was recrystallized from methanol to provide 27 mg (17%) of a white solid. $^1$H NMR (300 MHz, $d_6$-DMSO) δ 10.01 (s, 1H), 7.21 (s, 1H), 6.87 (s, 2H), 4.32 (q, 2H, J=7.1 Hz), 2.50 (quintet, 2H, J=1.7 Hz), 2.37 (d, 2H, J=7.1 Hz), 2.18 (m, 1H), 1.72 (m, 2H), 1.54

(m, 4H), 1.29 (t, 3H, J=7.1 Hz); MS (ESI) m/e=261 (M−Et+H)$^+$, 289 (M+H)$^+$, 287 (M−H)$^−$

EXAMPLE 65

N-(4-amino-5-cyano-6-phenylpyridin-2-yl)acetamide

Example 65A

N-(4-Amino-6-bromo-5-cyano-pyridin-2-yl)-acetamide 4,6-Diamino-2-bromo-nicotinonitrile (100 mg, 0.47 mmol) was dissolved in 1.0 mL of anhydrous pyridine. AcCl (225 µL, 2.35 mmol) was dropped in slowly. The resulting mixture was shaken overnight at ambient temperature. Water (5 mL) was added to the mixture mixture. The resulting brown solid was collected through filtration, washed with cold water, and dried in a vacuum oven to provide the title compound (100 mg, 83%).

Example 65B

N-(4-amino-5-cyano-6-phenylpyridin-2-yl)acetamide

A mixture of bromide from Example 65A (45 mg, 0.18 mmol), Na$_2$CO$_3$ (38 mg, 0.35 mmol), and Pd(PPh$_3$)$_4$ (10 mg, 0.009 mmol) was stirred in DMF/THF/H$_2$O (1:1:0.5) under nitrogen in a microwave reactor vial. Phenyl boric acid (26 mg, 0.21 mmol) was added. The resulting mixture was capped and heated at 130° C. for 20 min in a microwave reactor. The crude mixture was partitioned between EtOAc and water. The organic layer washed with water and brine, dried over Na$_2$SO$_4$, and evaporated under reduced pressure. The crude residue was purified by a Gilson reverse phase HPLC to provide the titled compound (33 mg, 72% yield). $^1$H NMR (300 MHz, d$_6$-DMSO) δ 10.44 (s, 1H), 7.74-7.68 (m, 2H), 7.55 (s, 1H), 7.52-7.46 (m, 3H), 6.98 (s, 2H), 2.08 (s, 3H). MS (ESI) m/e 253 (M+H)$^+$; m/e 251 (M−H)$^−$.

EXAMPLE 66

N-(4-amino-5-cyano-6-propylpyridin-2-yl)acetamide

To 2.1 g (32 mmol) of freshly activated zinc dust was added 5.4 mL of DMF, then 930 mg of n-propyl iodide. The mixture was stirred under a nitrogen atmosphere at 85° C. for 20 minutes then cooled, and the excess zinc was allowed to settle.

To 128 mg of N-(4-amino-6-bromo-5-cyano-pyridin-2-yl)-acetamide (Example 65A), 6 mg (0.027 mmol) of palladium(II)acetate, and 30 mg (0.098 mmol) of tri(o-tolyl)phosphine was added 0.5 mL of DMF. The mixture was put under N$_2$ and stirred, then 2.0 mL of the n-propylzinc iodide solution was added via syringe. The mixture was heated at 90° C. for 10 minutes then poured into a stirred mixture of 10 mL water and 10 mL ethyl acetate. The metal salts were filtered away through diatomaceous earth, then the layers were separated. The organic layer was extracted with water (2×10 mL), and brine (1×10 mL), dried over MgSO$_4$, filtered, and concentrated to a solid. This was purified via silica gel chromatography, eluting with 50:50 hexanes:ethyl acetate and loading as a solution in hot ethyl acetate to provide 34 mg (31%) of a white solid. $^1$H NMR (300 MHz, d$_6$-DMSO) δ 10.29 (s, 1H), 7.39 (s, 1H), 6.82 (s, 2H), 2.63 (m, 2H), 2.07 (m, 3H), 1.67 (m, 2H), 0.92 (t, 3H, J=7.5 Hz); MS (ESI) m/e 219 (M+H)$^+$; m/e 217 (M−H)$^−$.

EXAMPLE 67

N-(4-amino-5-cyano-6-isobutylpyridin-2-yl)-2-(3-methoxyphenyl)acetamide

Example 67A 4,6-Diamino-2-isobutyl-nicotinonitrile

To a solution of 2.1 g (32 mmol) of Zn dust was added 5.4 mL of DMF. The flask was purged with N$_2$, then 1.00 g (5.43 mmol) of isobutyl iodide was added. The mixture was stirred at 100° C. for 5 minutes then cooled and allowed to settle.

To 6 mg (0.027 mmol) of palladium(II)acetate, 106 mg (0.50 mmol) of 2-bromo-4,6-diaminonicotinonitrile, and 30 mg (0.10 mmol) of tri(o-tolyl)phosphine was added 0.5 mL of DMF. The mixture was put under N$_2$ and stirred, then 1.5 mL of the isobutylzinc iodide solution was added via syringe. The solution was stirred at 100° C. for 10 minutes then cooled and allowed to stand at ambient temperature for 18 h. The mixture was poured into a stirred mixture of 10 mL ethyl acetate and 10 mL water, then filtered through diatomaceous earth to remove the metal salts. The filter cake was washed with ethyl acetate (5 mL), then the layers were separated. The organic layer was extracted with water (2×10 mL), and brine (1×10 mL), dried over MgSO$_4$, filtered, and concentrated to an oil. This was purified via silica gel chromatography, eluting with 75% ethyl acetate:hexanes to provide 22 mg (23%) of a white solid. $^1$H NMR (300 MHz, d$_6$-DMSO) δ 6.17 (s, 2H), 6.08 (s, 2H), 5.52 (s, 1H), 2.40 (d, J=7.5 Hz, 2H), 2.03 (m, 1H), 0.88 (d, J=6.8 Hz, 6H); MS (ESI) m/e 191 (M+H)$^+$, 189 (M−H)$^−$.

Example 67B

N-(4-amino-5-cyano-6-isobutylpyridin-2-yl)-2-(3-methoxyphenyl)acetamide

To a solution of 20 mg (0.11 mmol) of 4,6-diamino-2-isobutyl-nicotinonitrile in 1 mL of CH$_2$Cl$_2$ was added 40 µL (0.49 mmol) of pyridine, then 30 µL (0.19 mmol) of (3-methoxyphenyl)acetyl chloride. The solution was stirred at ambient temperature for 10 minutes then 0.5 mL of water was added. The mixture was concentrated under reduced pressure, then the residue was taken up in 5 mL of ethyl acetate and extracted with water (2×2 mL), saturated NaHCO$_{3(aq.)}$, and brine (1×2 mL), dried over MgSO$_4$, filtered, and concentrated to an oil. The product was partially purified via silica gel chromatography, eluting with 30% ethyl acetate:hexanes to provide a solid. This was recrystallized from methanol to provide 8 mg (23%) of a white solid. $^1$H NMR (300 MHz, d$_6$-DMSO) δ 10.48 (s, 1H), 7.37 (s, 1H), 7.22 (t, 1H, J=7.8 Hz), 6.84 (m, 5H), 3.73 (s, 3H), 3.66 (s, 2H), 2.54 (d, 2H, J=7.1 Hz), 2.09 (m, 1H), 0.92 (d, 6H, J=6.1 Hz); MS (ESI) m/e 339 (M+H)$^+$, 337 (M−H)$^−$.

EXAMPLE 68

N-(4-amino-5-cyano-6-propylpyridin-2-yl)-2-(2,5-dimethoxyphenyl)acetamide

Example 68A (2,5-dimethoxylphenyl)acetyl chloride

To a solution of 196 mg (1.00 mmol) of (2,5-dimethoxyphenyl)acetic acid in 3 mL of CH$_2$Cl$_2$ was added 100 µL of oxalyl chloride. The mixture was stirred at ambient temperature for 1 hour then concentrated under reduced pressure to a thick liquid.

Example 68B

4,6-Diamino-2-propyl-nicotinonitrile

To a solution of 2.1 g (32 mmol) of freshly activated Zn dust was added 5.4 mL of DMF, followed by 930 mg (5.5 mmol) of n-propyl iodide. The mixture was stirred under $N_2$ at 90° C. for 20 minutes. The suspension was cooled to ambient temperature, and allowed to settle.

To 5 mg (0.023 mmol) of palladium(II)acetate, 213 mg (1.00 mmol) of 2-bromo-4,6-diaminonicotinonitrile, and 60 mg (0.20 mmol) of tri(o-tolyl)phosphine was added 0.5 mL of DMF. The flask was purged with $N_2$ while stirring, then 5.0 mL of the n-propylzinc iodide solution was via syringe. The mixture was heated at 85° C. for 2.5 hours then cooled. The mixture was poured into a stirred mixture of 20 mL ethyl acetate and 20 mL water, filtered through diatomaceous earth. The filter cake was washed with ethyl acetate (2×5 mL), and the layers were separated. The organic layer was extracted with water (2×20 mL), and brine (1×20 mL), dried over $MgSO_4$, filtered, and concentrated under reduced pressure to an oil. The oil was purified via silica gel chromatography, eluting with 75% ethyl acetate:hexanes to provide 23 mg (13%) of a white solid. $^1$H NMR (300 MHz, $d_6$-DMSO) δ 6.17 (s, 2H), 6.09 (s, 2H), 5.52 (s, 1H), 2.50 (t, 2H, J=7.6 Hz), 1.62 (m, 2H), 0.90 (t, J=7.3 Hz, 3H); MS (ESI) m/e 177 $(M+H)^+$, 175 $(M-H)^-$.

Example 68C

N-(4-amino-5-cyano-6-propylpyridin-2-yl)-2-(2,5-dimethoxyphenyl)acetamide

To a solution of 23 mg (0.13 mmol) of 4,6-diamino-2-propyl-nicotinonitrile (Example 68B) and 50 mg (0.63 mmol) of pyridine in 1 mL of $CH_2Cl_2$ was added 35 mg (0.16 mmol) of (2,5-dimethoxyphenyl)acetyl chloride (Example 68A). The mixture was stirred at ambient temperature for 10 minutes then diluted with 3 mL of water. The mixture was extracted with ethyl acetate (3×3 mL), then the combined ethyl acetate layers were back extracted with saturated $NaHCO_{3(aq.)}$ (1×3 mL), and brine (1×3 mL), dried over $MgSO_4$, filtered, and concentrated to an oil. This was suspended in 5 mL of toluene, then concentrated under reduced pressure to remove some pyridine. The product was purified via silica gel chromatography, eluting with 60:40 ethyl acetate:hexanes to provide 21 mg (46%) of a white solid. $^1$H NMR (300 MHz, $d_6$-DMSO) δ 10.27 (s, 1H), 7.34 (s, 1H), 6.83 (m, 5H), 3.70 (m, 6H), 3.65 (s, 2H), 2.64 (m, 2H), 1.68 (m, 2H), 0.93 (t, 3H, J=7.3 Hz); MS (ESI) m/e 355 $(M+H)^+$, 353 $(M-H)^-$.

EXAMPLE 69

N-(4-amino-5-cyano-6-phenylpyridin-2-yl)-2-(2,5-dimethoxyphenyl)acetamide

Example 69A

4,6-Diamino-2-phenyl-nicotinonitrile

A 5 mL sealable heavy walled glass tube suitable for microwave heating was charged with 213 mg (1.00 mmol) of 4,6-diamino-2-bromo-nicotinonitrile, 183 mg (1.5 mmol) of phenylboronic acid, 11 mg (0.050 mmol) of palladium(II) acetate, 60 mg (0.020 mmol) of tri(o-tolyl)phosphine, and 220 mg (2.05 mmol) of sodium carbonate. To this mixture was added 2 mL of DMF, 2 mL of THF, and 1 mL of water. The tube was sealed, then heated with a microwave apparatus at 130° C. for 20 min. The mixture was poured into 20 mL of water, extracted with ethyl acetate (3×10 mL). The combined ethyl acetate layers were back extracted with 1M $NaOH_{(aq.)}$ (2×10 mL) and brine (1×10 mL), dried over $MgSO_4$, filtered, and concentrated under reduced pressure. The product was partially purified via silica gel chromatography, eluting with 60:40 ethyl acetate:hexanes to provide an off-white solid. This was taken up in ethyl acetate, then hexane was added (until about 50:50 hexanes:ethyl acetate) to precipitate 63 mg (30%) of white crystals. $^1$H NMR (300 MHz, $d_6$-DMSO) δ 7.66 (m, 2H), 7.45 (m, 3H), 6.35 (s, 2H), 6.25 (s, 2H), 5.69 (s, 1H); MS (ESI) m/e 211 $(M+H)^+$, 209 $(M-H)^-$.

Example 69B

N-(4-amino-5-cyano-6-phenylpyridin-2-yl)-2-(2,5-dimethoxyphenyl)acetamide

To a solution of 50 mg (0.24 mmol) of 4,6-diamino-2-phenyl-nicotinonitrile in 2 mL of $CH_2Cl_2$ was added 150 mg (0.70 mmol) of (2,5-dimethoxyphenyl)acetyl chloride (Example 68A), then 100 μL (1.23 mmol) of pyridine. The mixture was stirred at ambient temperature for 10 minutes then the solvent was removed under reduced pressure. The residue was taken up in 10 mL of ethyl acetate, then extracted with 1 M $HCl_{(aq.)}$ (2×5 mL), saturated $NaHCO_{3(aq)}$ (2×5 mL), and brine (1×5 mL), dried over $MgSO_4$, filtered, and concentrated to an oil. This was purified via silica gel chromatography, eluting with 40% ethyl acetate:hexanes to provide 11 mg (12%) of a white solid. $^1$H NMR (300 MHz, $d_6$-DMSO) δ 10.43 (m, 1H), 7.75 (m, 2H), 7.51 (m, 4H), 6.99 (m, 2H), 6.91 (m, 1H), 6.81 (m, 2H), 3.69 (m, 8H); MS (ESI) m/e 389 $(M+H)^+$, 387 $(M-H)^-$.

General Procedure for Examples 70-77

A 5.0 mL microwave reaction vessel which contained a micro-flea teflon-coated magnetic stir bar was charged with 150-200 mg of 40% w/w $KF/Al_2O_3$. To the solid was then added an acetonitrile solution or suspension (2.00 mL) which contained 0.600 mmol of a phenol, followed by a solution of 16.0 mg (0.06 mmol) of 18-Crown-6 dissolved in 1.00 mL of acetonitrile. Finally 50 mg (0.23 mmol) of 2-bromo-4,6-diaminonicotinonitrile was added to the mixture in one portion as a dry solid. The microwave reaction vessel was capped and placed in a Personal Chemistry Optimizer Microwave Reactor, then heated to 175° C. for 20 minutes with stirring. After cooling to ambient temperature, the reaction vessel was removed from the microwave reactor and uncapped. The suspension was filtered through a fiberglass wool plug, and the filtrate was diluted with 10 mL of distilled water. The aqueous suspension was extracted with $CH_2Cl_2$ (5-7 mL); and the aqueous layer was discarded. The organic layer was extracted with 1M $NaOH_{(aq.)}$ (4×5 mL); saturated aqueous NaCl (1×5 mL); dried over $Na_2SO_4$, filtered, and an aliquot of the filtrate was removed for subsequent LC/MS analysis. If the desired MW product was detected by LC/MS analysis the crude dried organic phase was evaporated under reduced pressure, redissolved in 1.5 ml of 1:1 DMSO/MeOH (v/v); and purified by reverse-phase HPLC on a $C_{18}$ column using an acetonitrile/water/0.1% trifluoroacetic acid gradient system. Column fractions which contained the desired product as determined by LC/MS analysis were combined and evaporated under reduced pressure.

The purified phenoxydiaminopyridine was redissolved in acetonitrile and the resulting solution was transferred to a 20 mL scintillation vial. The solution was evaporated under reduced pressure and the residue was redissolved in 1.0 mL of pyridine. To the pyridine solution was added 4 drops of neat acetyl chloride. The vial was capped and shaken for 10 minutes at ambient temperature. The vial was then uncapped, and the mixture was quenched by addition of 1.0 mL of water. The resulting aqueous suspension was evaporated under reduced pressure. The residue was then subjected to LC/MS analysis, redissolved in 1.5 mL of DMSO/Methanol (1:1), and purified by reverse-phase $C_{18}$ HPLC using an acetonitrile/water/0.1% trifluoroacetic acid gradient. Column fractions which contained the desired product as determined by LC/MS analysis were combined and evaporated under reduced pressure to provide the title compounds for Examples 70-77.

EXAMPLE 70

N-[4-amino-5-cyano-6-(4-methylphenoxy)pyridin-2-yl]acetamide

Prepared according to the general procedure for examples 70-77. $^1$H NMR (500 MHz, $d_6$-DMSO/$D_2$O) δ 7.28 (s, 1H), 7.24-7.20 (m, 2H), 7.05-7.01 (m, 2H), 2.31 (s, 3H), 2.00 (s, 3H); MS (ESI+) m/e=283 (M+H)$^+$, (ESI−) m/e 281 (M−H)$^-$.

EXAMPLE 71

N-[4-amino-5-cyano-6-(4-phenoxyphenoxy)pyridin-2-yl]acetamide

Prepared according to the general procedure for examples 70-77. $^1$H NMR (500 MHz, $d_6$-DMSO/$D_2$O) δ 7.45-7.40 (m, 2H), 7.29 (s, 1H), 7.22-7.15 (m, 3H), 7.08-7.02 (m, 4H), 2.02 (s, 3H); MS (ESI+) m/e=361 (M+H)$^+$, 383 (M+Na); (ESI−) m/e=359 (M−H).

EXAMPLE 72

N-{4-amino-5-cyano-6-[4-(1H-pyrrol-1-yl)phenoxy]pyridin-2-yl}-acetamide

Prepared according to the general procedure for examples 70-77. $^1$H NMR (500 MHz, $d_6$-DMSO/$D_2$O) δ 7.61-7.57 (m, 2H), 7.32 (t, 2H, J=2.18 Hz), 7.30 (s, 1H), 7.27-7.23 (m, 2H), 6.29 (t, 2H, J=2.18 Hz), 2.00 (s, 3H); MS (ESI+) m/e=334 (M+H); (ESI−) m/e=332 (M−H).

EXAMPLE 73

N-[4-amino-6-(4-benzylphenoxy)-5-cyanopyridin-2-yl]acetamide

Prepared according to the general procedure for examples 70-77. $^1$H NMR (500 MHz, $d_6$-DMSO/$D_2$O) δ 7.34-7.26 (m, 7H), 7.23-7.19 (m, 1H), 7.09-7.05 (m, 2H), 3.94 (s, 2H), 1.98 (s, 3H); MS (ESI+) m/e=359 (M+H); 381 (M+Na); ESI(−) m/e=357 (M−H).

EXAMPLE 74

N-[4-amino-6-(4-tert-butylphenoxy)-5-cyanopyridin-2-yl]acetamide

Prepared according to the general procedure for examples 70-77. $^1$H NMR (500 MHz, $d_6$-DMSO/$D_2$O) δ 7.44-7.40 (m, 2H), 7.29 (s, 1H), 7.09-7.05 (m, 2H), 2.00 (s, 3H), 1.29 (s, 9H); MS (ESI+) m/e=325 (M+H); (ESI−) m/e=323 (M−H).

EXAMPLE 75

N-(4-{[6-(acetylamino)-4-amino-3-cyanopyridin-2-yl]oxy}phenyl)acetamide

Prepared according to the general procedure for examples 70-77. $^1$H NMR (500 MHz, $d_6$-DMSO/$D_2$O) δ 7.59-7.55 (m, 2H), 7.27 (s, 1H), 7.12-7.08 (m, 2H), 2.05 (s, 3H), 1.99 (s, 3H); MS (ESI+) m/e=326 (M+H); 348 (M+Na); (ESI−) m/e=324 (M−H).

EXAMPLE 76

N-[4-amino-5-cyano-6-(4-propoxyphenoxy)pyridin-2-yl]acetamide

Prepared according to the general procedure for examples 70-77. $^1$H NMR (500 MHz, $d_6$-DMSO/$D_2$O) δ 7.26 (s, 1H), 7.04-7.09 (m, 2H), 6.92-6.97 (m, 2H), 3.92 (t, 2H, J=6.55 Hz), 2.00 (s, 3H), 1.73 (qt, 2H, J=7.33, 6.55 Hz), 0.99 (t, 3H, J=7.33 Hz); MS (ESI+) m/e=327 (M+H); (ESI−) m/e=325 (M−H).

EXAMPLE 77

N-[4-amino-5-cyano-6-(4-ethoxyphenoxy)pyridin-2-yl]acetamide

Prepared according to the general procedure for examples 70-77. $^1$H NMR (500 MHz, $d_6$-DMSO/$D_2$O) δ 7.26 (s, 1H), 7.09-7.04 (m, 2H), 6.96-6.92 (m, 2H), 4.02 (q, 2H, J=6.97 Hz), 2.00 (s, 3H), 1.33 (t, 3H, J=7.02 Hz); MS (ESI+) m/e=313 (M+H); (ESI−) m/e=311 (M−H).

General Procedure for Examples 78-100

A Smith Process vial (0.5-2 ml) was charged with a stir bar. To the vessel was added 25 mg (0.1 mmol) of N-(4-Amino-6-bromo-5-cyano-pyridin-2-yl)-acetamide (Example 65A) then the phenylboronic acid (0.13 mmol) in 1.5 ml EtOH/DME (1:1). Next, 3.5 mg (0.005 mmol) of PdCl$_2$(PPh$_3$)$_2$ was added to the solution followed by 0.13 ml of 1M K$_2$CO$_{3(aq.)}$. The reaction vessel was sealed and heated in a microwave apparatus at 110° C. for 600 s. After cooling, the reaction vessel was uncapped and filtered through a column packed with Si-carbonate (2 g, from Silicycle), the column was washed with MeOH. The filtrate was collected and dried under reduced pressure. The products were purified via reversed phase HPLC over a CiS column using an acetonitrile/water/0.1% trifluoroacetic acid gradient system. Following concentration of the product containing fractions, the title compounds were isolated as TFA salts.

EXAMPLE 78

N-[4-amino-5-cyano-6-(3-methylphenyl)pyridin-2-yl]acetamide

Prepared according to the general procedure for examples 78-100. $^1$H NMR (500 MHz, $d_6$-DMSO) δ 10.41 (s, 1H), 7.52 (m, 3H), 6.93 (br, 2H), 7.37 (m, 1H), 7.31 (m, 1H), 2.37 (s, 3H), 2.08 (s, 3H); MS (ESI+) m/e=267 (M+H).

EXAMPLE 79 methyl 4-[6-(acetylamino)-4-amino-3-cyanopyridin-2-yl]benzoate

Prepared according to the general procedure for examples 78-100. $^1$H NMR (500 MHz, $d_6$-DMSO) δ 10.48 (s, 1H), 8.07 (d, 2H, J=10 Hz), 7.04 (br, 2H), 7.84 (d, 2H, J=10 Hz), 7.59 (s, 1H), 3.89 (s, 3H), 2.09 (s, 3H); MS (ESI+) m/e=311 (M+H).

EXAMPLE 80

N-[4-amino-5-cyano-6-(3-methoxyphenyl)pyridin-2-yl]acetamide

Prepared according to the general procedure for examples 78-100. $^1$H NMR (500 MHz, $d_6$-DMSO) δ 10.41 (s, 1H), 7.55 (s, 1H), 7.40 (m, 1H), 7.28 (m, 2H), 7.06 (dd, 1H, J=8.4 Hz, 1.9 Hz), 6.95 (br, 2H), 3.81 (s, 3H), 2.09 (s, 3H); MS (ESI+) m/e=283 (M+H).

EXAMPLE 81

N-[4-amino-5-cyano-6-(4-methoxyphenyl)pyridin-2-yl]acetamide

Prepared according to the general procedure for examples 78-100. $^1$H NMR (500 MHz, $d_6$-DMSO) δ 10.38 (s, 1H), 7.71 (d, 2H, J=8.7 Hz), 7.50 (s, 1H), 7.04 (d, 2H, J=8.7 Hz), 6.90 (br, 2H), 3.82 (s, 3H), 2.08 (s, 3H); MS (ESI+) m/e=283 (M+H).

EXAMPLE 82

N-[4-amino-6-(3-chlorophenyl)-5-cyanopyridin-2-yl]acetamide

Prepared according to the general procedure for examples 78-100. $^1$H NMR (500 MHz, $d_6$-DMSO) δ 10.45 (s, 1H), 7.71 (d, 1H, J=7.5 Hz), 7.52 (m, 4H), 7.03 (br, 2H), 2.09 (s, 3H); MS (ESI−) m/e=285 (M−H).

EXAMPLE 83

N-[4-amino-6-(4-chlorophenyl)-5-cyanopyridin-2-yl]acetamide

Prepared according to the general procedure for examples 78-100. $^1$H NMR (500 MHz, $d_6$-DMSO) δ 10.45 (s, 1H), 7.74 (d, 2H, J=8.8 Hz), 7.57 (d, 2H, J=8.8 Hz), 7.56 (s, 1H), 7.00 (br, 2H), 2.08 (s, 3H); MS (ESI+) m/e=287 (M+H).

EXAMPLE 84

N-[4-amino-5-cyano-6-(3-cyanophenyl)pyridin-2-yl]acetamide

Prepared according to the general procedure for examples 78-100. $^1$H NMR (500 MHz, $d_6$-DMSO) δ 10.46 (s, 1H), 8.16 (s, 1H), 8.08 (m, 1H), 7.97 (m, 1H), 7.73 (m, 1H), 7.59 (s, 1H), 7.08 (br, 2H), 2.09 (s, 3H); MS (ESI+) m/e=278 (M+H).

EXAMPLE 85

N-[4-amino-5-cyano-6-(4-cyanophenyl)pyridin-2-yl]acetamide

Prepared according to the general procedure for examples 78-100. $^1$H NMR (500 MHz, $d_6$-DMSO) δ 10.49 (s, 1H), 7.98 (d, 2H, J=8.5 Hz), 7.90 (d, 2H, J=8.5 Hz), 7.59 (s, 1H), 7.08 (br, 2H), 2.08 (s, 3H); MS (ESI−) m/e=275.7 (M−H).

EXAMPLE 86

N-[6-(3-acetylphenyl)-4-amino-5-cyanopyridin-2-yl]acetamide

Prepared according to the general procedure for examples 78-100. $^1$H NMR (500 MHz, $d_6$-DMSO) δ 10.47 (s, 1H), 8.29 (s, 1H), 8.08 (d, 1H, J=7.8 Hz), 7.99 (d, 1H, J=7.8 Hz), 7.67 (t, 1H, J=7.8 Hz), 7.59 (s, 1H), 7.02 (br, 2H), 2.63 (s, 3H), 2.09 (s, 3H); MS (ESI+) m/e=295 (M+H).

EXAMPLE 87

N-[4-amino-5-cyano-6-(4-phenoxyphenyl)pyridin-2-yl]acetamide

Prepared according to the general procedure for examples 78-100. $^1$H NMR (500 MHz, $d_6$-DMSO) δ 10.47 (s, 1H) 7.76 (d, 2H, J=9.1 Hz), 7.53 (s, 1H), 7.44 (m, 2H), 7.20 (m, 1H), 7.10 (m, 4H), 6.96 (br, 2H), 2.09 (s, 3H); MS (ESI+) m/e=345 (M+H).

EXAMPLE 88

N-[6-(4-acetylphenyl)-4-amino-5-cyanopyridin-2-yl]acetamide

Prepared according to the general procedure for examples 78-100. $^1$H NMR (500 MHz, $d_6$-DMSO) δ 10.47 (s, 1H), 8.07 (d, 2H, J=8.7 Hz), 7.85 (d, 2H, J=8.7 Hz), 7.59 (s, 1H), 7.03 (br, 2H), 2.64 (s, 3H), 2.09 (s, 3H); MS (ESI+) m/e=295 (M+H).

EXAMPLE 89

N-{4-amino-5-cyano-6-[4-(trifluoromethoxy)phenyl]pyridin-2-yl}acetamide

Prepared according to the general procedure for examples 78-100. $^1$H NMR (500 MHz, $d_6$-DMSO) δ 10.44 (s, 1H), 7.85 (d, 2H, J=9.1 Hz), 7.57 (s, 1H), 7.50 (d, 2H, J=9.1 Hz), 7.03 (br, 2H), 2.09 (s, 3H); MS (ESI+) m/e=337 (M+H).

EXAMPLE 90

N-[4-amino-5-cyano-6-(3,4-dimethylphenyl)pyridin-2-yl]acetamide

Prepared according to the general procedure for examples 78-100. $^1$H NMR (500 MHz, $d_6$-DMSO) δ 10.38 (s, 1H), 7.50 (m, 3H), 7.24 (d, 1H, J=7.8 Hz) 6.90 (br, 2H), 2.50 (s, 3H), 2.28 (s, 3H), 2.08 (s, 3H); MS (ESI+) m/e=281 (M+H).

EXAMPLE 91

N-[4-amino-5-cyano-6-(3,5-dimethylphenyl)pyridin-2-yl]acetamide

Prepared according to the general procedure for examples 78-100. $^1$H NMR (500 MHz, $d_6$-DMSO) δ 10.38 (s, 1H), 7.53 (s, 1H), 7.32 (s, 1H), 7.12 (s, 1H), 6.93 (br, 2H), 2.33 (s, 6H), 2.08 (s, 3H); MS (ESI+) m/e=281 (M+H).

EXAMPLE 92

N-[4-amino-5-cyano-6-(2,4-dimethoxyphenyl)pyridin-2-yl]acetamide

Prepared according to the general procedure for examples 78-100. $^1$H NMR (500 MHz, $d_6$-DMSO) δ 10.44 (s, 1H) 7.46 (s, 1H), 7.21 (d, 1H, J=8.1 Hz), 6.93 (br, 2H), 6.67 (d, 1H, J=2.2 Hz), 6.61 (dd, 1H, J=8.1, 22 Hz), 3.82 (s, 3H), 3.77 (s, 3H), 2.06 (s, 3H); MS (ESI+) m/e=313 (M+H).

EXAMPLE 93

N-(4-amino-5-cyano-6-thien-2-ylpyridin-2-yl)acetamide

Prepared according to the general procedure for examples 78-100. $^1$H NMR (500 MHz, $d_6$-DMSO) δ 10.25 (s, 1H), 7.99 (m, 1H), 7.75 (m, 1H), 7.48 (s, 1H), 7.20 (m, 1H), 6.98 (br, 2H), 2.11 (s, 3H); MS (ESI+) m/e=259 (M+H).

EXAMPLE 94

N-(4-amino-5-cyano-6-thien-3-ylpyridin-2-yl)acetamide

Prepared according to the general procedure for examples 78-100. $^1$H NMR (500 MHz, $d_6$-DMSO) δ 10.33 (s, 1H), 8.09 (m, 1H), 7.64 (m, 1H), 7.60 (m, 1H), 7.50 (s, 1H), 6.92 (br, 2H), 2.09 (s, 3H); MS (ESI+) m/e=259 (M+H).

EXAMPLE 95

N-[4-amino-6-(1-benzofuran-2-yl)-5-cyanopyridin-2-yl]acetamide

Prepared according to the general procedure for examples 78-100. $^1$H NMR (500 MHz, $d_6$-DMSO) δ 10.53 (s, 1H), 7.81 (d, 1H, J=7.2 Hz), 7.66 (s, 1H), 7.60 (s, 1H), 7.44 (m, 1H), 7.34 (m, 1H), 7.07 (br, 2H), 2.12 (s, 3H); MS (ESI−) m/e=291 (M−H).

EXAMPLE 96

N-[6-(5-acetylthien-2-yl)-4-amino-5-cyanopyridin-2-yl]acetamide

Prepared according to the general procedure for examples 78-100. $^1$H NMR (500 MHz, $d_6$-DMSO) δ 10.35 (s, 1H) 8.00 (d, 1H, J=4.1 Hz), 7.95 (d, 1H, J=4.1 Hz), 7.55 (s, 1H), 7.10 (br, 2H), 2.56 (s, 3H), 2.11 (s, 3H); MS (ESI+) m/e=301 (M+H).

EXAMPLE 97

N-[4-amino-5-cyano-6-(2-naphthyl)pyridin-2-yl]acetamide

Prepared according to the general procedure for examples 78-100. $^1$H NMR (500 MHz, $d_6$-DMSO) δ 10.48 (s, 1H), 8.29 (s, 1H), 8.02 (m, 3H), 7.84 (m, 1H), 7.59 (m, 3H), 7.00 (br, 2H), 2.11 (s, 3H); MS (ESI−) m/e=301 (M−H).

EXAMPLE 98

N-(4-amino-3-cyano-2,3'-bipyridin-6-yl)acetamide

Prepared according to the general procedure for examples 78-100. $^1$H NMR (500 MHz, $d_6$-DMSO) δ 10.35 (s, 1H), 8.92 (m, 1H), 8.70 (m, 1H), 8.19 (m, 1H), 7.59 (m, 2H), 7.08 (br, 2H), 2.09 (s, 3H); MS (ESI+) m/e=254 (M+H).

EXAMPLE 99

N-[4-amino-5-cyano-6-(3,4-dihydro-2H-1,5-benzodioxepin-7-yl)pyridin-2-yl]acetamide Prepared according to the general procedure for examples 78-100. $^1$H NMR (500 MHz, $d_6$-DMSO) δ 10.35 (s, 1H), 7.51 (s, 1H), 7.38 (m, 2H), 7.06 (m, 1H), 6.93 (br, 2H), 4.40 (m, 4H), 2.15 (m, 2H), 2.08 (s, 3H); MS (ESI+) m/e=325 (M+H).

EXAMPLE 100

N-{4-amino-5-cyano-6-[4-(methylsulfonyl)phenyl]pyridin-2-yl}acetamide

Prepared according to the general procedure for examples 78-100. $^1$H NMR (500 MHz, $d_6$-DMSO) δ 10.48 (s, 1H), 8.05 (d, 2H, J=8.4 Hz), 7.97 (d, 2H, J=8.4 Hz), 7.60 (s, 1H), 7.08 (br, 2H), 3.29 (s, 3H), 2.09 (s, 3H); MS (ESI+) m/e=331 (M+H).

EXAMPLE 101

N-(4-amino-5-cyano-6-ethylpyridin-2-yl)acetamide

Example 101A 4,6-Diamino-2-ethyl-nicotinonitrile

A mixture of 4,6-diamino-2-bromo-nicotinonitrile from Example 65A (250 mg, 1.2 mmol), Pd(dppf)Cl$_2$ (96 mg, 0.12 mmol), Cs$_2$CO$_3$ (576 mg, 1.8 mmol) in anhydrous DMF was flushed with nitrogen for 5 min before BEt$_3$ (1.0 M solution in hexane, 1.42 mL, 1.4 mmol) was added. The sealed tube was heated@ 120° C. in a microwave reactor for 20 min. The reaction mixture was then partitioned between EtOAc and water, the organic layer was washed with water and brine, dried over Na$_2$SO$_4$, and concentrated in vacuo. The crude residue was purified by silica gel sep-pak, eluting with 30-50% EtOAc in hexane. The product was further purified by recrystalization from EtOAc/hexane to provide the titled compound as a light brown solid (77 mg, 40% yield). $^1$H NMR (300 MHz, DMSO-$d_6$) δ 6.18 (s, 2H), 6.10 (s, 2H), 5.52 (s, 1H), 2.54 (q, J=7.6 Hz, 2H), 1.14 (t, J=7.6 Hz, 3H); MS (ESI) m/e 163 (M+H)$^+$.

Example 101B

N-(4-amino-5-cyano-6-ethylpyridin-2-yl)acetamide

The 4,6-diamino nicotinonitrile from Example 101A (35 mg, 0.22 mmol) was dissolved in 0.5 mL of anhydrous pyridine. AcCl was then dropped in until the TLC shows the starting material was completely consumed (appr. 150 μL of AcCl used). Water was then added, the light-yellow precipitate was collected through filtration and dried in vacuum oven to provide the titled compound (30 mg, 68% yield). $^1$H NMR (300 MHz, DMSO-$d_6$) δ 10.28 (s, 1H), 7.39 (s, 1H), 6.82 (s, 2H), 2.66 (q, J=7.5 Hz, 2H), 2.06 (s, 3H), 1.19 (t, J=7.5 Hz, 3H). MS (ESI) m/e 205 (M+H)$^+$.

EXAMPLE 102

4-azido-5-cyano-N-(2,5-dimethoxybenzyl)-6-isopropoxypyridine-2-carboxamide

Example 102A

6-Dimethoxymethyl-2-isopropoxy-4-methylsulfanyl-nicotinonitrile

6-Dimethoxymethyl-2-hydroxy-4-methylsulfanyl-nicotinonitrile sodium salt synthesized as described by Mahata, P. K. et al. Tetrahedron 59, 2003, 2631-2639 (3.5 g, 13.3 mmol) in 40 mL of anhydrous DMF was heated at 120° C. while 2-iodopropane (1.6 mL, 16.0 mmol) was added dropwise. The resulting mixture was heated at 120° C. for another 30 min before it was cooled to ambient temperature and partitioned between water and EtOAc. The organic layer was washed with water and brine, dried over $Na_2SO_4$, evaporated in vacuo. Purification on an Analogix MPLC system (SiO2 column) eluting with 10% EtOAc in hexanes yielded the titled compound as a light yellow solid upon standing (3.0 g, 80% yield).

Example 102B

4-Azido-5-cyano-6-isopropoxy-pyridine-2-carboxylic acid

6-Dimethoxymethyl-2-isopropoxy-4-methylsulfanyl-nicotinonitrile from Example 102A (72 mg, 0.26 mmol) in 2 mL of $CH_2Cl_2$ at r.t. was stirred with mCPBA (110 mg, 0.64 mmol) for over night. Volatile solvent was then removed in vacuo and the residue was taken up in 2 mL of $CH_3CN$. N,N-diisopropylethylamine and tetrabutylammonium azide were added and the resulting mixture heated at 70° C. for 90 min. The crude product was then purified on an AllTech $SiO_2$ sep-pak eluting with 10% EtOAc to provide 4-azido-6-dimethoxymethyl-2-isopropoxy-nicotinonitrile (58 mg, 0.21 mmol, 82% yield over two steps). A mixture of this dimethylacetal in 1.5 mL of THF and 0.36 mL of 1N aq. HCl was heated at 65° C. for 2 h. The cooled reaction mixture was partitioned between EtOAc and sat. $NaHCO_3$. The organic layer was washed with brine, dried over $Na_2SO_4$, and evaporated in vacuo. The residue was taken up in EtOH. $AgNO_3$ (66 mg, 0.39 mmol) in 0.3 mL of water was added, followed the addtion of 29 mg of KOH in 0.3 mL of water. After stirred for 1 hour at ambient temperature, the mixture was filtered through celite and washed with hot EtOH and water. The combined filtrate was evaporated in vacuo to minimal volume. The pH of the solution was adjusted to cat. 4 with 3N HCl, and was pumped to dryness in vacuo. The crude titled acid was used without any further purification.

Example 102C

4-azido-5-cyano-N-(2,5-dimethoxybenzyl)-6-isopropoxypyridine-2-carboxamide The titled compound was prepared according to the procedure described in Example 104B, substituting 4-azido-5-cyano-6-isopropoxy-pyridine-2-carboxylic acid for 4-amino-5-cyano-6-ethoxy-pyridine-2-carboxylic acid used in Example 104B. $^1$H NMR (300 HZ, DMSO-$d_6$) δ 9.12 (t, J=6.4 Hz, 1H), 7.57 (s, 1H), 6.94 (d, J=8.8 Hz, 1H), 6.80 (dd, J=8.8, 5.8 Hz, 1H), 6.72 (d, J=3.1 Hz, 1H), 5.71 (quintet, J=6.4 Hz, 1H), 4.47 (d, J=6.4 Hz, 2H), 3.79 (s, 3H), 3.65 (s, 3H), 1.36 (d, J=6.4 Hz, 6H). MS (m/e) 397 (M+H)$^+$.

EXAMPLE 103

4-amino-5-cyano-N-(2,5-dimethoxybenzyl)-6-isopropoxypyridine-2-carboxamide

The azide from Example 102C (10 mg, 0.025 mmol) was hydrogenated in MeOH under a hydrogen balloon with cat. 10% Pd/C for 1 hour. The reaction mixture was filtered through a celite plug and washed with MeOH. The combined filtrate was evaporated and pumped in vacuo to provide the titled compound as a white solid (9.3 mg, 100% yield). $^1$H NMR (300 HZ, DMSO-$d_6$) δ 8.81 (t, J=6.3 Hz, 1H), 7.30 (broad s, 2H), 7.04 (s, 1H), 6.93 (d, J=8.8 Hz, 1H), 6.79 (dd, J=8.8, 3.1 Hz, 1H), 6.71 (d, J=3.1 Hz, 1H), 5.53 (quintet, J=6.4 Hz, 1H), 4.41 (d, J=6.4 Hz, 2H), 3.79 (s, 3H), 3.65 (s, 3H), 1.31 (d, J=6.4 Hz, 6H). MS (m/e) 371 (M+H)$^+$, 393 (M+Na)$^+$.

EXAMPLE 104

4-amino-5-cyano-N-(2,5-dimethoxybenzyl)-6-ethoxypyridine-2-carboxamide

Example 104A

4-amino-5-cyano-6-ethoxy-pyridine-2-carboxylic acid

To 3-amino-3-ethoxy-acrylic acid ethyl ester HCl salt (19.6 g, 100 mmol) in $CHCl_3$ (100 mL) was added malonitrile (6.6 g, 100 mmol) and $Et_3N$ (12 g, 120 mmol). The mixture was heated at 80° C. overnight. The mixture was washed with water (2×50 mL), dried over $MgSO_4$, and concentrated to provide a gummy solid (20 g). 1 g of this crude material was dissolved in anhydrous EtOH (3 mL) and EtONa (2.5 M, 2 mL, 5 mmol) was added. The mixture was heated at 170° C. under microwave irradiation for 40 min. EtOAc was added followed by addition of 1 N aqueous HCl until pH of 1 was achieved. The mixture was extracted with EtOAc (3×50 mL). The EtOAc extract was dried over $MgSO_4$ and concentrated to crude 4-amino-2-ethoxy-6-hydroxy-nicotinonitrile (1.1 g). This material was dissolved in $CH_2Cl_2$ (10 mL) followed by $Et_3N$ (1.4 g, 14 mmol) and PhNTf$_2$ (2.8 g, 7 mmol). The mixture was stirred at ambient temperature for 4 hours and washed with water, dried over $MgSO_4$, concentrated, and purified by column chromatography to provide trifluoromethanesulfonic acid 4-amino-5-cyano-6-ethoxy-pyridin-2-yl ester (900 mg, 60% over 3 steps). This material was dissolved in MeOH (20 mL). PdCl$_2$CH$_2$Cl$_2$dppf (100 mg, 0.12 mmol) and Et$_3$N (0.6 g, 6 mmol) were added. The mixture was heated at 50° C. under CO (400 psi) for 16 hours. The crude material was concentrated and purified by column chromatography to provide 4-amino-5-cyano-6-ethoxy-pyridine-2-carboxylic acid methyl ester (350 mg, 50%). To a portion of this material (97 mg, 0.44 mmol) was added EtOH/$H_2O$ (5:3, 1.5 mL) followed by addition of LiOH (160 mg, 4 mmol). The mixture was stirred for 30 min and 2N aqueous HCl was added to adjust the acidity to pH1. The mixture was extracted with EtOAc. The organic extract was dried and concentrated to provide 4-amino-5-cyano-6-ethoxy-pyridine-2-carboxylic acid (69 mg, 76%).

Example 104B

4-amino-5-cyano-N-(2,5-dimethoxybenzyl)-6-ethoxypyridine-2-carboxamide

To 4-amino-5-cyano-6-ethoxy-pyridine-2-carboxylic acid (0.1 mmol) in DMF (0.1 mL) was added 2,5-dimethoxybenzylamine (0.2 mmol), Et$_3$N (0.2 mmol), and TBTU (0.1 mmol) sequentially. The reaction mixture was stirred at ambient temperature for 16 hours and water was added. The precipitates were collected and purified by column chromatography to provide the titled compound. $^1$H NMR (400 MHZ, DMSO-d$_6$) δ 8.81 (t, J=6.4 Hz, 1H), 7.31 (broad s, 2H), 7.07 (s, 1H), 6.92 (d, J=8.8 Hz, 1H), 6.79 (dd, J=2.8, 8.8 Hz, 1H), 6.72 (d, J=3.2 Hz, 1H), 4.49 (q, J=7.2 Hz, 2H), 4.42 (d, J=6.4 Hz, 2H), 3.79 (s, 3H), 3.65 (s, 3H), and 1.33 (t, J=7.2, 3H). MS (m/e) positive mode: 357 (M+H)$^+$, 379 (M+Na)$^+$; negative mode: 355 (M–H)$^-$.

EXAMPLE 105

4-amino-5-cyano-6-ethoxy-N-(1-phenylethyl)pyridine-2-carboxamide

The titled compound was prepared according to the procedure described in Example 104B, substituting α-methyl benzylamine for 2,5-dimethoxybenzylamine used in Example 104B. $^1$H NMR (500 HZ, DMSO-d$_6$) δ 8.54 (d, J=8.5 Hz, 1H), 7.38 (d, J=7.0 Hz, 2H), 7.33 (t, J=7.5 Hz, 4H, overlapped with NH$_2$), 7.24 (t, J=7.0 Hz, 1H), 7.03 (s, 1H), 5.12 (quintet, J=8.0 Hz, 1H), 4.50 (m, 2H), 1.50 (d, J=7.0 Hz, 3H), and 1.33 (t, J=7.0, 3H). MS (m/e) positive mode: 311 (M+H)$^+$.

EXAMPLE 106

4-amino-5-cyano-6-ethoxy-N-(pyridin-4-ylmethyl)pyridine-2-carboxamide

The titled compound was prepared according to the procedure described in Example 104B, substituting aminomethyl 4-pyridine for 2,5-dimethoxybenzylamine used in Example 104B. $^1$H NMR (500 HZ, DMSO-d$_6$) δ 9.16 (t, J=6.5 Hz, 1H), 8.49 (d, J=6.5 Hz, 2H), 7.33 (broad s, 2H), 7.26 (d, J=6.5 Hz, 2H), 7.07 (s, 1H), 4.52 (q, J=7.0 Hz, 2H), 4.48 (d, J=6.5 Hz, 2H), and 1.32 (t, J=7.0, 3H). MS (m/e) positive mode: 298 (M+H)$^+$; negative mode: 296 (M–H)$^-$

EXAMPLE 107

4-amino-5-cyano-6-ethoxy-N-(pyridin-3-ylmethyl)pyridine-2-carboxamide

The titled compound was prepared according to the procedure described in Example 104B, substituting aminomethyl 3-pyridine for 2,5-dimethoxybenzylamine used in Example 104B. $^1$H NMR (500 HZ, DMSO-d$_6$) δ 9.13 (t, J=6.5 Hz, 1H), 8.52 (d, J=1.5 Hz, 1H), 8.45 (dd, J=1.5, 4.5 Hz, 1H), 7.68 (d, J=3.0 Hz, 1H), 7.34 (dd, J=5.0, 8.0 Hz, 1H), 7.32 (broad s, 2H), 7.07 (s, 1H), 4.50 (q, J=7.0 Hz, 2H), 4.48 (d, J=6.5 Hz, 2H), and 1.31 (t, J=7.0 Hz, 3H). MS (m/e) positive mode: 298 (M+H)$^+$.

EXAMPLE 108

4-amino-5-cyano-6-ethoxy-N-(pyridin-2-ylmethyl)pyridine-2-carboxamide

The titled compound was prepared according to the procedure described in Example 104B, substituting aminomethyl 2-pyridine for 2,5-dimethoxybenzylamine used in Example 104B. $^1$H NMR (500 HZ, DMSO-d$_6$) δ 9.17 (t, J=6.0 Hz, 1H), 8.51 (d, J=4.5 Hz, 2H), 7.76 (dt, 2.0, 8.0 Hz, 1H), 7.34 (broad s, 2H), 7.27 (t, J=7.0 Hz, 1H), 7.27 (d, J=5.5 Hz, 1H), 7.08 (s, 1H), 4.57 (d, J=6.0 Hz, 2H), 4.51 (q, J=7.0 Hz, 2H), and 1.34 (t, J=7.0, 3H). MS (m/e) positive mode: 298 (M+H)$^+$; negative mode: 296 (M–H)$^-$.

EXAMPLE 109

4-amino-N-benzyl-5-cyano-6-ethoxypyridine-2-carboxamide

In a 20 mL scintillation vial, 4-amino-5-cyano-6-ethoxy-pyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of benzylamine (11 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.31 (t, 3H) 4.43-4.54 (m, 4H) 7.06-7.11 (m, 1H) 7.21-7.36 (m, 5H) 9.07-9.14 (m, 1H).

EXAMPLE 110

4-amino-5-cyano-6-ethoxy-N-(2-methylbenzyl)pyridine-2-carboxamide

In a 20 mL scintillation vial, 4-amino-5-cyano-6-ethoxy-pyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 2-methylbenzylamine (12 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.31 (t, 3H) 2.28-2.34 (m, 3H) 4.38-4.55 (m, 4H) 7.05-7.10 (m, 1H) 7.11-7.21 (m, 4H) 8.92-8.99 (m, 1H). MS (ESI) positive ion 311 (M+H)$^+$; negative ion 309 (M–H)$^-$.

EXAMPLE 111

4-amino-5-cyano-6-ethoxy-N-(3-methylbenzyl)pyridine-2-carboxamide

In a 20 mL scintillation vial, 4-amino-5-cyano-6-ethoxy-pyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3-methylbenzylamine (12 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.28-1.35 (m, 3H) 2.23-2.31 (m, 3H) 4.40-4.54 (m, 4H) 7.03-7.12 (m, 3H) 7.17-7.24 (m, 1H) 9.02-9.12 (m, 1H). MS (ESI) positive ion 311 (M+H)$^+$; negative ion 309 (M–H)$^-$.

EXAMPLE 112

4-amino-5-cyano-6-ethoxy-N-(4-methylbenzyl)pyridine-2-carboxamide

In a 20 mL scintillation vial, 4-amino-5-cyano-6-ethoxy-pyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 4-methylbenzylamine (12 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) 1.23-1.36 (m, 3H) 2.20-2.34 (m, 3H) 4.37-4.55 (m, 4H) 7.04-7.22 (m, 4H) 8.97-9.10 (m, 1H). MS (ESI) positive ion 311 (M+H)$^+$; negative ion 309 (M−H)$^−$.

EXAMPLE 113

4-amino-N-(2-aminobenzyl)-5-cyano-6-ethoxypyridine-2-carboxamide

In a 20 mL scintillation vial, 4-amino-5-cyano-6-ethoxy-pyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 2-aminobenzylamine (12 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.27 (t, 3H) 4.21-4.37 (m, 2H) 4.45 (q, 2H) 6.33-7.25 (m, 5H). MS (ESI) negative ion 310 (M−H)$^−$.

EXAMPLE 114

4-amino-N-(3-aminobenzyl)-5-cyano-6-ethoxypyridine-2-carboxamide

In a 20 mL scintillation vial, 4-amino-5-cyano-6-ethoxy-pyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3-aminobenzylamine (12 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.27-1.39 (m, 3H) 4.18-4.75 (m, 4H) 6.31-7.50 (m, 5H). MS (ESI) positive ion 312 (M+H)+

EXAMPLE 115

4-amino-N-(4-aminobenzyl)-5-cyano-6-ethoxypyridine-2-carboxamide

In a 20 mL scintillation vial, 4-amino-5-cyano-6-ethoxy-pyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 4-aminobenzylamine (12 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.24-1.35 (m, 3H) 4.03-4.84 (m, 4H) 6.43-7.65 (m, 5H). MS (ESI) positive ion 310 (+H)$^+$; negative ion 312 (M−H)$^−$.

EXAMPLE 116

4-amino-5-cyano-6-ethoxy-N-{4-[(trifluoromethyl)thio]benzyl}pyridine-2-carboxamide In a 20 mL scintillation vial, 4-amino-5-cyano-6-ethoxy-pyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 4-(trifluoromethylthio)benzylamine (21 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.23-1.39 (m, 3H) 4.45-4.60 (m, 4H) 7.00-7.14 (m, 1H) 7.34-7.50 (m, 2H) 7.61-7.73 (m, 2H). MS (ESI) negative ion 395 (M−H)$^−$.

EXAMPLE 117

4-amino-5-cyano-6-ethoxy-N-[3-fluoro-5-(trifluoromethyl)benzyl]pyridine-2-carboxamide In a 20 mL scintillation vial, 4-amino-5-cyano-6-ethoxy-pyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3-fluoro-5-trifluoromethylbenzylamine (19 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.29-1.36 (m, 3H) 4.46-4.59 (m, 4H) 7.05-7.08 (m, 1H) 7.42-7.57 (m, 3H). MS (ESI) negative ion 381 (M−H)$^−$.

EXAMPLE 118 methyl 4-({[(4-amino-5-cyano-6-ethoxypyridin-2-yl)carbonyl]amino}methyl)benzoate In a 20 mL scintillation vial, 4-amino-5-cyano-6-ethoxy-pyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of methyl-4-(aminomethyl)benzoate (20 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.32 (t, 3H) 3.79-3.91 (m, 3H) 4.44-4.60 (m, 4H) 7.04-7.12 (m, 1H) 7.43 (d, 2H) 7.90 (d, 2H) 9.11-9.25 (m, 1H). MS (ESI) negative ion 353 (M−H)$^−$.

EXAMPLE 119

4-amino-5-cyano-6-ethoxy-N-(2-methoxybenzyl)pyridine-2-carboxamide

In a 20 mL scintillation vial, 4-amino-5-cyano-6-ethoxy-pyrindine-2-carboxylic acid (19 mg, 0.09 mmol) was dissolved in DMA (0.7 mL). Then TBTU (30 mg, 0.09 mmol)

dissolved in DMA (0.7 mL) was added, followed by the addition of 2-methoxybenzylamine (14 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.33 (t, 3H) 3.81-3.86 (m, 3H) 4.40-4.53 (m, 4H) 6.91 (t, 1H) 7.01 (d, 1H) 7.05-7.09 (m, 1H) 7.13 (d, 1H) 7.27 (t, 1H) 8.89 (t, 1H). MS (ESI) positive ion 327 (M+H)$^+$; negative ion 325 (M−H)$^−$.

EXAMPLE 120

4-amino-5-cyano-6-ethoxy-N-(3-methoxybenzyl)pyridine-2-carboxamide

In a 20 mL scintillation vial, 4-amino-5-cyano-6-ethoxypyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3-methoxybenzylamine (14 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.31 (t, 3H) 3.72-3.74 (m, 3H) 4.40-4.54 (m, 4H) 6.80-6.90 (m, 3H) 7.06-7.09 (m, 1H) 7.25 (t, 1H) 9.08 (t, 1H). MS (ESI) positive ion 327 (M+H)$^+$; negative ion 325 (M−H)$^−$.

EXAMPLE 121

4-amino-5-cyano-6-ethoxy-N-(4-methoxybenzyl)pyridine-2-carboxamide

In a 20 mL scintillation vial, 4-amino-5-cyano-6-ethoxypyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 4-methoxybenzylamine (14 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.31 (t, 3H) 3.72-3.73 (m, 3H) 4.37-4.52 (m, 4H) 6.88 (d, 2H) 7.06-7.09 (m, 1H) 7.25 (d, 2H) 9.03 (t, 1H). MS (ESI) positive ion 327 (M+H)$^+$; negative ion 325 (M−H)$^−$.

EXAMPLE 122

4-amino-5-cyano-6-ethoxy-N-(2-fluorobenzyl)pyridine-2-carboxamide

In a 20 mL scintillation vial, 4-amino-5-cyano-6-ethoxypyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 2-fluorobenzylamine (13 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.31 (t, 3H) 3.78 (d, 1H) 4.31-4.59 (m, 4H) 7.03-7.10 (m, 1H) 7.11-7.65 (m, 4H) 9.05 (t, 1H). MS (ESI) positive ion 315 (M+H)$^+$; negative ion 313 (M−H)$^−$.

EXAMPLE 123

4-amino-5-cyano-6-ethoxy-N-(3-fluorobenzyl)pyridine-2-carboxamide

In a 20 mL scintillation vial, 4-amino-5-cyano-6-ethoxypyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3-fluorobenzylamine (13 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.32 (t, 3H) 4.39-4.56 (m, 4H) 6.98-7.46 (m, 5H) 9.18 (t, 1H). MS (ESI) positive ion 315 (+H)$^+$; negative ion 313 (M−H)$^−$.

EXAMPLE 124

4-amino-5-cyano-6-ethoxy-N-(4-fluorobenzyl)pyridine-2-carboxamide

In a 20 mL scintillation vial, 4-amino-5-cyano-6-ethoxypyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 4-fluorobenzylamine (13 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.31 (t, 3H) 4.31-4.75 (m, 4H) 6.92-7.46 (m, 5H) 9.14 (t, 1H). MS (ESI) negative ion 313 (M−H)$^−$.

EXAMPLE 125

4-amino-N-(2-chlorobenzyl)-5-cyano-6-ethoxypyridine-2-carboxamide

In a 20 mL scintillation vial, 4-amino-5-cyano-6-ethoxypyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 2-chlorobenzylamine (14 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.33 (t, 3H) 4.35-4.64 (m, 4H) 7.02-7.13 (m, 1H) 7.21-7.54 (m, 4H) 9.10 (t, 1H). MS (ESI) negative ion 329 (M−H)$^−$.

EXAMPLE 126

4-amino-N-(3-chlorobenzyl)-5-cyano-6-ethoxypyridine-2-carboxamide

In a 20 mL scintillation vial, 4-amino-5-cyano-6-ethoxypyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3-chlorobenzylamine (14 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). ¹H NMR (500 MHz, DMSO-D₆/D₂O) δ ppm 1.28-1.37 (m, 3H) 4.41-4.56 (m, 4H) 7.06-7.10 (m, 1H) 7.19-7.41 (m, 4H) 9.18 (t, 1H). MS (ESI) negative ion 329 (M–H)⁻.

EXAMPLE 127

4-amino-N-(4-chlorobenzyl)-5-cyano-6-ethoxypyridine-2-carboxamide

In a 20 mL scintillation vial, 4-amino-5-cyano-6-ethoxypyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 4-chlorobenzylamine (14 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). ¹H NMR (500 MHz, DMSO-D₆/D₂O) δ ppm 1.25-1.37 (m, 3H) 4.38-4.55 (m, 4H) 7.05-7.11 (m, 1H) 7.26-7.43 (m, 4H) 9.15 (t, 1H). MS (ESI) negative ion 329 (M–H)⁻.

EXAMPLE 128

4-amino-N-(2-bromobenzyl)-5-cyano-6-ethoxypyridine-2-carboxamide

In a 20 mL scintillation vial, 4-amino-5-cyano-6-ethoxypyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 2-bromobenzylamine (19 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). ¹H NMR (500 MHz, DMSO-D₆/D₂O) δ ppm 1.33 (t, 3H) 4.46-4.54 (m, 4H) 7.06-7.09 (m, 1H) 7.19-7.27 (m, 2H) 7.37 (t, 1H) 7.64 (d, 1H). MS (ESI) positive ion 375 (M+H)⁺; negative ion 373 (M–H)⁻.

EXAMPLE 129

4-amino-N-(3-bromobenzyl)-5-cyano-6-ethoxypyridine-2-carboxamide

In a 20 mL scintillation vial, 4-amino-5-cyano-6-ethoxypyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3-bromobenzylamine hydrochloride (22 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). ¹H NMR (500 MHz, DMSO-D₆/D₂O) δ ppm 1.33 (t, 3H) 4.42-4.56 (m, 4H) 7.05-7.10 (m, 1H) 7.22-7.54 (m, 4H) 9.18 (t, 1H). MS (ESI) negative ion 374 (M–H)⁻.

EXAMPLE 130

4-Amino-5-cyano-6-ethoxy-pyridine-2-carboxylic acid 3-nitro-benzylamide

In a 20 mL scintillation vial, 4-amino-5-cyano-6-ethoxypyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3-nitrobenzylamine hydrochloride (19 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). ¹H NMR (500 MHz, DMSO-D₆/D₂O) δ ppm 1.32 (t, 3H) 4.24-4.66 (m, 4H) 6.90-8.29 (m, 5H) 9.26 (t, 1H). MS (ESI) negative ion 340 (M–H)⁻.

EXAMPLE 131

4-Amino-5-cyano-6-ethoxy-pyridine-2-carboxylic acid 4-nitro-benzylamide

In a 20 mL scintillation vial, 4-amino-5-cyano-6-ethoxypyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 4-nitrobenzylamine hydrochloride (19 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). ¹H NMR (500 MHz, DMSO-D₆/D₂O) δ ppm 1.34 (t, 3H) 4.27-4.71 (m, 4H) 6.80-8.25 (m, 5H). MS (ESI) negative ion 340 (M–H)⁻.

EXAMPLE 132

4-amino-5-cyano-6-ethoxy-N-[4-(trifluoromethoxy)benzyl]pyridine-2-carboxamide

In a 20 mL scintillation vial, 4-amino-5-cyano-6-ethoxypyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 4-trifluoromethoxybenzylamine (19 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). ¹H NMR (500 MHz, DMSO-D₆/D₂O) δ ppm 1.32 (t, 3H) 4.39-4.58 (m, 4H) 7.05-7.11 (m, 1H) 7.23-7.48 (m, 4H) 9.18 (t, 1H). MS (ESI) negative ion 379 (M–H)⁻.

EXAMPLE 133

4-amino-5-cyano-N-[4-(dimethylamino)benzyl]-6-ethoxypyridine-2-carboxamide

In a 20 mL scintillation vial, 4-amino-5-cyano-6-ethoxypyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 4-dimethylaminobenzylamine digydrochloride (22 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). ¹H NMR (500 MHz, DMSO-D₆/D₂O) δ ppm 1.32 (t, 3H) 2.88-3.04 (m, 6H) 4.25-4.59 (m, 4H) 6.86-7.34 (m, 5H). MS (ESI) positive ion 340 (M+H)⁺.

EXAMPLE 134

4-amino-5-cyano-6-ethoxy-N-[3-(trifluoromethyl)benzyl]pyridine-2-carboxamide

In a 20 mL scintillation vial, 4-amino-5-cyano-6-ethoxypyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3-(trifluoromethyl)benzylamine (18 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.28 (t, 3H) 4.26-4.65 (m, 4H) 6.59-7.96 (m, 5H) 9.21 (t, 1H). MS (ESI) negative ion 363 (M−H)$^-$.

EXAMPLE 135

4-amino-5-cyano-6-ethoxy-N-[4-(trifluoromethyl)benzyl]pyridine-2-carboxamide

In a 20 mL scintillation vial, 4-amino-5-cyano-6-ethoxy-pyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 4-(trifluoromethyl)benzylamine (18 mg, 0.11 mmol, 1.2 eq.) in DMA (0.6 mL). Then TEA (9.37 mg, 0.09 mmol) dissolved in DMA (0.7 mL) was added. The reaction mixture was shaken at room temperature for 24 hours. The crude mixture was purified using reverse phase HPLC (TFA). $^1$H NMR (500 MHz, DMSO-D$_6$/D$_2$O) δ ppm 1.33 (t, 3H) 4.23-4.88 (m, 4H) 7.00-7.18 (m, 1H) 7.25-7.87 (m, 4H) 9.19 (t, 1H). MS (ESI) negative ion 363 (M−H)$^-$.

EXAMPLE 136

4-amino-5-cyano-6-ethoxy-N-[3-(trifluoromethoxy)benzyl]pyridine-2-carboxamide

In a 20 mL scintillation vial, 4-amino-5-cyano-6-ethoxy-pyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3-(trifluoromethoxy)benzylamine (19 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.30 (t, 3H) 4.34-4.63 (m, 4H) 6.95-7.16 (m, 1H) 7.14-7.71 (m, 4H) 9.20 (t, 1H). MS (ES) positive ion 381 (M+H)$^+$; negative ion 379 (M−H)$^-$.

EXAMPLE 137

4-amino-5-cyano-6-ethoxy-N-(1-naphthylmethyl)pyridine-2-carboxamide

In a 20 mL scintillation vial, 4-amino-5-cyano-6-ethoxy-pyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 1-napthylenemethylamine (16 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.31 (t, 3H) 4.33-5.07 (m, 4H) 7.04-7.13 (m, 1H) 7.35-7.67 (m, 4H) 7.76-8.26 (m, 3H). MS (ESI) positive ion 347 (M+H)$^+$; negative ion 345 (M−H)$^-$.

EXAMPLE 138

4-amino-N-(4-tert-butylbenzyl)-5-cyano-6-ethoxypyridine-2-carboxamide

In a 20 mL scintillation vial, 4-amino-5-cyano-6-ethoxy-pyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 4-t-butylbenzylamine (16 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.18-1.29 (m, 9H) 1.32 (t, 3H) 4.33-4.60 (m, 4H) 7.02-7.12 (m, 1H) 7.18-7.40 (m, 4H) 9.07 (t, 1H). MS (ESI) positive ion 353 (M+H)$^+$; negative ion 351 (M−H)$^-$.

EXAMPLE 139

4-amino-5-cyano-N-(2,3-dimethylbenzyl)-6-ethoxy-pyridine-2-carboxamide

In a 20 mL scintillation vial, 4-amino-5-cyano-6-ethoxy-pyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 2,3-Dimethylbenzylamine (14 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.31 (t, 3H) 2.17-2.22 (m, 3H) 2.24-2.28 (m, 3H) 4.30-4.57 (m, 4H) 6.82-7.22 (m, 4H) 8.86 (t, 1H). MS (ESI) positive ion 325 (M+H)$^+$; negative ion 323 (M−H)$^-$.

EXAMPLE 140

4-amino-5-cyano-N-(2,4-dimethylbenzyl)-6-ethoxy-pyridine-2-carboxamide

In a 20 mL scintillation vial, 4-amino-5-cyano-6-ethoxy-pyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 2,4-dimethylbenzylamine (14 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O)$_6$ ppm 1.31 (t, 3H) 2.18-2.45 (m, 6H) 4.27-4.56 (m, 4H) 6.77-7.24 (m, 4H) 8.87 (t, 1H). MS (ESI) positive ion 325 (M+H)$^+$; negative ion 323 (M−H)$^-$.

EXAMPLE 141

4-amino-5-cyano-N-(2,5-dimethylbenzyl)-6-ethoxy-pyridine-2-carboxamide

In a 20 mL scintillation vial, 4-amino-5-cyano-6-ethoxy-pyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 2,5-dimethylbenzylamine (14 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.31 (t, 3H) 2.16-2.33 (m, 6H) 4.33-4.54 (m, 4H) 6.87-7.12 (m, 4H) 8.88 (t, 1H). MS (ESI) positive ion 325 (M+H)$^+$; negative ion 323 (M–H)$^-$.

EXAMPLE 142

4-amino-5-cyano-N-(3,4-dimethylbenzyl)-6-ethoxypyrindine-2-carboxamide

In a 20 mL scintillation vial, 4-amino-5-cyano-6-ethoxypyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3,4-dimethylbenzylamine (14 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.31 (t, 3H) 2.11-2.26 (m, 6H) 4.31-4.54 (m, 4H) 6.77-7.21 (m, 4H) 8.93-9.07 (m, 1H). MS (ESI) positive ion 325 (M+H)$^+$; negative ion 323 (M–H)$^-$.

EXAMPLE 143

4-amino-5-cyano-N-(3,5-dimethylbenzyl)-6-ethoxypyridine-2-carboxamide

In a 20 mL scintillation vial, 4-amino-5-cyano-6-ethoxypyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3,5-dimethylbenzylamine (14 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.32 (t, 3H) 2.08-2.33 (m, 6H) 4.11-4.60 (m, 4H) 6.65-6.95 (m, 3H) 7.04-7.14 (m, 1H). MS (ESI) positive ion 325 (M+H)$^+$; negative ion 323 (M–H)$^-$.

EXAMPLE 144

4-amino-5-cyano-N-(2,3-dimethoxybenzyl)-6-ethoxypyridine-2-carboxamide

In a 20 mL scintillation vial, 4-amino-5-cyano-6-ethoxypyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 2,3-dimethoxylbenzylamine (17 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.28 (t, 3H) 3.80 (d, 6H) 4.26-4.66 (m, 4H) 6.67-7.19 (m, 4H) 8.87 (t, 1H). MS (ESI) positive ion 357 (M+H)$^+$; negative ion 355 (M–H)$^-$.

EXAMPLE 145

4-amino-5-cyano-N-(2,4-dimethoxybenzyl)-6-ethoxypyridine-2-carboxamide

In a 20 mL scintillation vial, 4-amino-5-cyano-6-ethoxypyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 2,4-dimethoxylbenzylamine (17 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm. 1.30 (t, 3H) 3.73-3.76 (m, 3H) 3.79-3.87 (m, 3H) 4.31-4.62 (m, 4H) 6.34-7.13 (m, 4H) 8.74 (t, 1H). MS (ESI) positive ion 357 (M+H)$^+$; negative ion 355 (M–H)$^-$.

EXAMPLE 146

4-amino-5-cyano-N-(3,4-dimethoxybenzyl)-6-ethoxypyridine-2-carboxamide

In a 20 mL scintillation vial, 4-amino-5-cyano-6-ethoxypyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3,4-dimethoxylbenzylamine (17 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.31 (t, 3H) 3.73 (d, 6H) 4.18-4.66 (m, 4H) 6.63-7.24 (m, 4H) 8.97 (t, 1H). MS (ESI) positive ion 357 (M+H)$^+$; negative ion 355 (M–H)$^-$.

EXAMPLE 147

4-amino-5-cyano-N-(3,5-dimethoxybenzyl)-6-ethoxypyridine-2-carboxamide

In a 20 mL scintillation vial, 4-amino-5-cyano-6-ethoxypyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3,5-dimethoxylbenzylamine (17 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.32 (t, 3H) 3.81 (d, 6H) 4.17-4.74 (m, 4H) 5.84-7.19 (m, 4H) 9.04 (t, 1H). MS (ESI) positive ion 357 (M+H)$^+$; negative ion 355 (M–H)$^-$.

EXAMPLE 148

4-amino-N-(1,3-benzodioxol-5-ylmethyl)-5-cyano-6-ethoxypyridine-2-carboxamide

In a 20 mL scintillation vial, 4-amino-5-cyano-6-ethoxypyrindine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3,4,-methylenedioxybenzylamine (15 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.27 (t, 3H) 4.25-

4.56 (m, 4H) 5.73-6.12 (m, 2H) 6.52-7.23 (m, 4H). MS (ESI) positive ion 341 (M+H)$^+$; negative ion 339 (M−H)$^−$.

EXAMPLE 149

4-amino-5-cyano-6-ethoxy-N-(3,4,5-trimethoxybenzyl)pyridine-2-carboxamide

In a 20 mL scintillation vial, 4-amino-5-cyano-6-ethoxy-pyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3,4,5-trimethoxybenzylamine (20 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.31 (t, 3H) 3.61-3.64 (m, 3H) 3.73-3.78 (m, 6H) 4.11-4.65 (m, 4H) 6.41-6.76 (m, 2H) 6.96-7.17 (m, 1H) 8.99 (t, 1H). MS (ESI) positive ion 387 (M+H)$^+$; negative ion 385 (M−H)$^−$.

EXAMPLE 150

4-amino-5-cyano-N-(2,3-dichlorobenzyl)-6-ethoxy-pyridine-2-carboxamide

In a 20 mL scintillation vial, 4-amino-5-cyano-6-ethoxy-pyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 2,3-dichlorobenzylamine (18 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.30 (t, 3H) 4.29-4.73 (m, 4H) 6.83-7.67 (m, 4H). MS (ESI) negative ion 364 (M−H)$^−$.

EXAMPLE 151

4-amino-5-cyano-N-(2,4-dichlorobenzyl)-6-ethoxy-pyridine-2-carboxamide

In a 20 mL scintillation vial, 4-amino-5-cyano-6-ethoxy-pyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 2,4-dichlorobenzylamine (18 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.28 (t, 3H) 4.02-4.91 (m, 4H) 6.41-7.99 (m, 4H). MS (ESI) negative ion 364 (M−H)$^−$.

EXAMPLE 152

4-amino-5-cyano-N-(2,5-dichlorobenzyl)-6-ethoxy-pyridine-2-carboxamide

In a 20 mL scintillation vial, 4-amino-5-cyano-6-ethoxy-pyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 2,5-dichlorobenzylamine (18 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.24 (t, 3H) 4.03-4.86 (m, 4H) 5.88-7.87 (m, 4H). MS (ESI) positive ion 365 (M+H)$^+$; negative ion 363 (M−H)$^−$.

EXAMPLE 153

4-amino-5-cyano-N-(3,5-dichlorobenzyl)-6-ethoxy-pyridine-2-carboxamide

In a 20 mL scintillation vial, 4-amino-5-cyano-6-ethoxy-pyridine-2-carboxylic acid (19 mg, 0.09 mmol) was dissolved in DMA (0.7 mL). Then TBTU (30 mg, 0.09 mmol) dissolved in DMA (0.7 mL) was added, followed by the addition of 3,5-dichlorobenzylamine (18 mg, 0.11 mmol, 1.2 eq.) in DMA (0.6 mL). Then TEA (9.37 mg, 0.09 mmol) dissolved in DMA (0.7 mL) was added. The mixture was shaken at room temperature for 24 hours. The crude mixture was purified using reverse phase HPLC (TFA). $^1$H NMR (500 MHz, DMSO-D$_6$/D$_2$O) δ ppm 1.28 (t, 3H) 4.19-4.81 (m, 4H) 6.33-7.81 (m, 4H). MS (ESI) negative ion 363 (M−H)$^−$.

EXAMPLE 154

5-cyano-N-(2,5-dimethoxybenzyl)-6-ethoxypyridine-2-carboxamide

Example 154A 5-cyano-6-ethoxy-pyridine-2-carboxylic acid

To dimethyl uracil (10.5 g, 75 mmol) in EtOH (75 mL) was added malonitrile (9.9 g, 150 mmol) and EtONa (2.5 M, 60 mL, 150 mmol). The mixture was refluxed for 2 h and the precipitates were collected and washed with EtOH. The solid was treated with 2N aqueous HCl and extracted with EtOAc to provide 2-ethoxy-6-hydroxy-nicotinonitrile (8.7 g, 71%). A portion of this material (8.2 g, 50 mmol) was dissolved in CH$_2$Cl$_2$ (75 mL) followed by addition of PhNTf$_2$ (19.6 g, 55 mmol) and Et$_3$N (6.06 g, 60 mmol). The mixture was allowed to stir at ambient temperature overnight and washed with water and purified by column chromatography to provide trifluoro-methanesulfonic acid 5-cyano-6-ethoxy-pyridin-2-yl ester (15.9 g, coeluted with PhNHTf). A portion of this material (9.5 g, impure) was dissolved in MeOH (40 mL) followed by addition of PdCl$_2$CH$_2$Cl$_2$dppf (1.4 g, 1.7 mmol) and Et$_3$N (6.5 g, 65 mmol). The mixture was heated at 50° C. under CO (100 psi) for 6 h. The mixture was purified by column chromatography to provide 5-cyano-6-ethoxy-pyridine-2-carboxylic acid methyl ester (2 g, 32% over 2 steps). A portion of this material (1.5 g, 7.3 mmol) was dissolved in EtOH/H$_2$O (5:3, 15 mL) followed by addition of LiOH (640 mg, 15 mmol). The mixture was stirred for 30 min and 2N aqueous HCl was added to adjust the acidity to pH of 1. Precipitates were collected and washed to provide 5-cyano-6-ethoxy-pyridine-2-carboxylic acid (1.0 g, 71%).

Example 154B 5-cyano-N-(2,5-dimethoxybenzyl)-6-ethoxypyridine-2-carboxamide The titled compound was prepared according to the procedure described in Example 104B, substituting 5-cyano-6-ethoxy-pyridine-2-carboxylic acid for 4-amino-5-cyano-6- ethoxy-pyridine-2-carboxylic acid used in Example 104B. $^1$H NMR (300 HZ, DMSO-d$_6$) δ 9.10 (t, J=6.6 Hz, 1H), 8.43 (d, J=7.8 Hz, 1H), 7.71 (d, J=7.5 Hz, 1H), 6.81 (d, J=8.7 Hz, 1H), 6.79 (dd, J=3.0, 9.0 Hz, 1H), 6.73 (d, J=3.0 Hz, 1H), 4.64 (q, J=7.2 Hz, 2H), 4.47 (d, J=6.3 Hz, 2H), 3.79 (s, 3H), 3.65 (s, 3H), and 1.39 (t, J=7.2 Hz, 3H). MS (m/e) positive mode: 342 (M+H)$^+$; negative mode: 340 (M−H)$^-$.

EXAMPLE 155

5-cyano-N-(2,5-dimethoxybenzyl)-6-isopropoxypyridine-2-carboxamide

Example 155A

2-Isopropoxy-6-methyl-nicotinonitrile

To a stirred solution of 2-hydroxy-6-methyl-nicotinonitrile (10.1 g, 75.3 mmol) in 150 mL of absolute EtOH as added KOH (4.97 g, 75.3 mmol). The resulting mixture was heated at 80° C. for 2 h before it was cooled to ambient temperature. The solvent was removed in vacuo and the resulting residue was dried in a vacuum oven for over night. A suspension of the hydroxy pyridine potassium salt in 75 mL of anhydrous DMF was heated at 120° C. while 2-iodopropane (6.0 mL, 90.3 mmol) was added in portions. After 90 min at 120° C., TLC indicated the complete consumption of the starting material. Cooled and 100 mL of water was added to the mixture. The yellow solid was collected through filtration, washed with cold water and dried in vacuum oven to provide the titled compound as a light yellow solid (10.2 g, 77%).

Example 155B

5-Cyano-6-isopropoxy-pyridine-2-carboxylic acid

A suspension of 2-isopropoxy-6-methyl-nicotinonitrile (1.0 g, 5.7 mmol) in 25 mL of water was heated at 80° C. while KMnO$_4$ (2.3 g, 13.1 mmol) was added poritionwise. The resulting mixture was heated at 80° C. for 3 hour before it was filtered through celite hot. The brown solid was washed with hot water. The combined filtrate was concentrated in vacuo to minimal volume and acidified to pH ~2 with 3N HCl. The white precipitate was collected through filtration to provide the titled compound (35 mg, 3% yield).

Example 155C 5-cyano-N-(2,5-dimethoxybenzyl)-6-isopropoxypyridine-2-carboxamide

The titled compound was prepared according to the procedure described in Example 104B, substituting 5-cyano-6-isopropoxy-pyridine-2-carboxylic acid for 4-amino-5-cyano-6-ethoxy-pyridine-2-carboxylic acid used in Example 104B. $^1$H NMR (300 HZ, DMSO-d$_6$) δ 9.08 (t, J=6.4 Hz, 1H), 8.41 (d, J=7.8 Hz, 1H), 7.69 (d, J=7.8 Hz, 1H), 6.94 (d, J=8.8 Hz, 1H), 6.80 (dd, J=8.8, 3.1 Hz, 1H), 6.73 (d, J=3.1 Hz, 1H), 5.72 (quintet, J=6.1 Hz, 1H), 4.47 (d, J=6.1 Hz, 2H), 3.79 (s, 3H), 3.65 (s, 3H), 1.37 (d, J=6.1 Hz, 6H). MS (ESI(+)) m/e 356 (M+H)$^+$, 378 (M+Na)$^+$.

EXAMPLE 156

N-(2,5-dimethoxybenzyl)-6-ethoxypyridine-2-carboxamide

Example 156A

6-Bromo-pyridine-2-carboxylic acid 2,5-dimethoxy-benzylamide

To a mixture of 6-bromopicolinic acid (1.01 g, 5.0 mmol) and 2,5-dimethoxybenzylamine (753 μL, 5.0 mmol) in DMF (10 mL) was added TBTU (1.77 g, 5.5 mmol), followed by N,N-diisopropylethylamine (871 μL, 5.0 mmol). The mixture was stirred at room temperature for 2 hours. After addition of saturated NaHCO$_3$, the mixture was extracted with ethyl acetate. The organic phase was washed with brine (×3), dried (MgSO$_4$), filtered and concentrated. It was triturated with CH$_3$CN to provide the titled compound as white solid (1.05 g, 57%).

Example 156B

N-(2,5-dimethoxybenzyl)-6-ethoxypyridine-2-carboxamide

A mixture of bromide from Example 156A (35 mg, 0.1 mmol) and NaOEt (21% w/w ethanol soulution, 56 μL, 0.15 mmol) in ethanol (500 μL) was heated in a microwave oven at 150° C. for 10 minutes. It was partitioned between ethyl acetate and water. The organic phase was dried (MgSO$_4$), filtered and concentrated. The residue was purified by flash chromatography on silica gel column using ethyl acetate: hexane (1:1) to provide the titled compound (22 mg, 70%). MS (ESI(+)) m/e 317 (M+H)$^+$; $^1$H NMR (300 MHz, DMSO-d$_6$) δ 8.89 (t, J=6.4 Hz, 1H), 7.89-7.84 (m, 1H), 7.63-7.60 (m, 1H), 7.02-6.74 (m, 4H), 4.46 (d, J=6.4 Hz, 2H), 4.45 (q, J=7.1 Hz, 2H), 3.80 (s, 3H), 3.65 (s, 3H), 1.35 (t, J=7.1 Hz, 3H).

EXAMPLE 157

6-ethoxy-N-(pyridin-3-ylmethyl)pyridine-2-carboxamide

The titled compound was prepared according to the procedure described in Example 156, substituting 3-(aminomethyl)pyridine for 2,5-dimethoxybenzylamine used in Example 156A. MS (ESI(+)) m/e 258 (M+H); $^1$H NMR (300 MHz, DMSO-d$_6$) δ 9.19 (t, J=6.4 Hz, 1H), 8.56-8.55 (m, 1H), 8.46-8.44 (m, 1H), 7.89-7.83 (m, 1H), 7.75-7.70 (m, 1H), 7.63-7.60 (m, 1H), 7.38-7.33 (m, 1H), 7.01-6.98 (m, 1H), 4.53 (d, J=6.4 Hz, 2H), 4.46 (q, J=7.1 Hz, 2H), 1.34 (t, J=7.1 Hz, 3H).

EXAMPLE 158

4-amino-N-[2-(aminosulfonyl)benzyl]-5-cyano-6-ethoxypyridine-2-carboxamide

The title compound was prepared according to the procedure described in Example 104B, substituting 2-aminomethyl-benzenesulfonamide (Cignarella, G and Teotino, U., *JACS*, 1960, 82, 1594-1596) for 2,5-dimethoxybenzylamine. $^1$H NMR (300 MHz, DMSO-d$_6$) δ 9.10 (t, J=6.61 Hz, 1H), 7.89 (dd, J=7.80, 1.36 Hz, 1H), 7.64 (s, 2H), 7.56 (td, J=7.54, 1.53 Hz, 1H), 7.40-7.49 (m, 2H), 7.34 (s, 2H), 7.08 (s, 1H), 4.89 (d, J=6.44 Hz, 2H), 4.48 (q, J=7.12 Hz, 2H), and 1.31 (t, J=7.12 Hz, 3H); MS (ESI) m/e positive ion 398 [M+Na]+, 376 [M+H]+; negative ion 374 [M–H]−.

EXAMPLE 159

4-amino-5-cyano-N-{2-[(dimethylamino)sulfonyl] benzyl}-6-ethoxypyridine-2-carboxamide To a solution of Example 158 (50 mg, 0.13 mmol) and $K_2CO_3$ (200 mg, 1.4 mmol) in methanol (1.5 mL) was added methyl iodide (300 µL, 4.8 mmol). The reaction was stirred at room temperature for 12 h., concentrated in vacuo, and purified by reverse phase HPLC (0-70% $CH_3CN$ in 10 mM aq. ammonium acetate). The title compound was obtained as a white solid (3.0 mg, 5.7%). $^1$H NMR (300 MHz, DMSO-$d_6$) δ 9.08 (t, J=6.44 Hz, 1H), 7.80 (dd, J=7:80, 1.02 Hz, 1H), 7.65 (td, J=7.54, 1.19 Hz, 1H), 7.42-7.55 (m, 2H), 7.30-7.40 (m, 2H), 7.07 (s, 1H), 4.81 (d, J=6.44 Hz, 2H), 4.50 (q, J=6.89 Hz, 2H), 2.79 (s, 6H), and 1.32 (t, J=7.12 Hz, 3H); MS (ESI) m/e positive ion 426 [M+Na]+, 404 [M+H]+; negative ion 402 [M–H]−.

EXAMPLE 160 methyl 3-[5-({[(4-amino-5-cyano-6-ethoxypyridin-2-yl)carbonyl]amino}methyl)pyridin-2-yl]benzoate To a mixture of Example 185 (40 mg, 0.12 mmol), 3-methoxycarbonylphenylboronic acid (33 mg, 0.18 mmol), tetrakis(triphenylphosphine)palladium(0) (14 mg, 0.012 mmol), and $K_3PO_4$ (77 mg, 0.36 mmol) was added 1:1 tetrahydrofuran/$H_2O$ (1.5 mL). The solution was purged with $N_2$, capped, and heated to 100° C. for 4 hours. The mixture was extracted in ethyl acetate, concentrated in vacuo, and separated by reverse phase-HPLC (0-70% $CH_3CN$ in aq. ammonium acetate) providing the title compound as a white solid (6.2 mg, 14%). $^1$H NMR (300 MHz, DMSO-$d_6$) δ 9.18 (t, J=6.61 Hz, 1H), 8.61-8.70 (m, 2H), 8.32 (ddd, J=7.97, 1.86, 1.36 Hz, 1H), 7.97-8.06 (m, 2H), 7.82 (dd, 1H), 7.65 (t, J=7.63 Hz, 1H), 7.33 (s, 2H), 7.08 (s, 1H), 4.43-4.63 (m, 4H), 3.90 (s, 3H), and 1.32 (t, J=6.95 Hz, 3H); MS (ESI) m/e positive ion 432 [M+H]+; negative ion 430 [M–H]−.

EXAMPLE 161

4-amino-5-cyano-6-ethoxy-N-[4-(phenylsulfinyl) benzyl]pyridine-2-carboxamide

Example 161A

4-Phenylsulfanyl-benzylamine

To a stirred solution of 4-fluorobenzonitrile (0.3 g, 2.5 mmol) in 2.5 mL of anhydrous N,N-dimethylformamide was added sodium thiophenoxide (0.6 g, 4 mmol). The resulting mixture was stirred at room temperature overnight. The solvent was removed under reduced pressure to afford an oil, which was purified via silica gel chromatography, eluting with 25% ethyl acetate/hexanes to provide a white solid (0.3 g). This and Raney Ni (100 mg, prewashed with methanol) was mixed in 30 mL of ammonia (20% solution in methanol). The heavy walled reaction vessel was charged with $H_2$ (60 psi) and the reaction was shaken at room temperature for 15 h. The mixture was filtered to remove the catalyst, and the filtrate was concentrated to give 0.2 g of the titled compound as an oil, which was used without further purification in the next step.

Example 161B

4-Amino-5-cyano-6-ethoxy-pyridine-2-carboxylic acid 4-phenylsulfanyl-benzylamide To a mixture of Example 161A (85 mg, 0.39 mmol) and Example 104A (52 mg, 0.25 mmol), was added O-benzotriazol-1-yl-N,N,N',N'-tetramethyluronium tetrafluoroborate (94 mg, 0.3 mmol), followed by N,N-diisopropylamine (52 µL, 0.3 mmol). The mixture was stirred at room temperature for 20 h. The crude product was purified via reverse phase HPLC (0-70% $CH_3CN$ in 10 mM aq. ammonium acetate) to provide 70 mg (70%) of a white solid. $^1$H NMR (300 MHz, DMSO-$d_6$) δ ppm 1.31 (t, J=7.1 Hz, 3H), 4.43-4.56 (m, 4H), 7.07 (s, 1H), 7.22-7.40 (m, 11H), 9.09 (t, J=6.4 Hz, 1H). MS (ESI+) m/e=405 (M+H)+.

Example 161C

4-Amino-5-cyano-6-ethoxy-pyridine-2-carboxylic acid 4-benzenesulfinyl-benzylamide A mixture of Example 161B (61 mg, 0.15 mmol), 2 mL of acetic acid, 0.15 mL of hydrogen peroxide (30% solution in water) in 0.5 mL of N,N-dimethylformamide was stirred at room temperature for 2 h. Water was added, the resulting precipitate was then filtered. The solid was triturated with methanol to provide the titled compound as a beige solid (44 mg, 70%). $^1$H NMR (400 MHz, DMSO-$d_6$) δ ppm 1.30 (t, J=7.1 Hz, 3H), 4.43-4.53 (m, 4H), 7.05 (s, 1H), 7.29 (bs, 2H), 7.43 (d, J=8.6 Hz, 2H), 7.46-7.55 (m, 3H), 7.63-7.72 (m, 4H), 9.08 (t, J=6.4 Hz, 1H). MS (ESI+) m/e=421 (M+H)+.

EXAMPLE 162

4-amino-5-cyano-6-ethoxy-N-[(6-{4-[(methylamino) carbonyl]phenyl}pyridin-3-yl)methyl]pyridine-2-carboxamide To a solution of Example 164 (47 mg, 0.1 mmol, example 160) in 1:2:2 methanol/tetrahydrofuran/$H_2O$ (1 mL) was added LiOH monohydrate (84 mg, 2 mmol). The reaction mixture was stirred for 3 h., acidified to pH 3, and filtered. To a homogeneous, stirred solution of the solid obtained (24 mg, 0.058 mmol), and O-benzotriazol-1-yl-N,N,N',N'-tetramethyluronium tetrafluoroborate (24 mg, 0.075 mmol) in N,N-dimethylformamide (1 mL) was added methylamine hydrochloride (5.0 mg, 0.075 mmol) and triethylamine (0.2 mL). The reaction mixture was stirred for 3 hours and extracted in ethyl acetate (5 mL), and washed with $H_2O$ (10 mL). The ethyl acetate layer was concentrated in vacuo and purified by reverse phase HPLC (0-70% $CH_3CN$ in aq. ammonium acetate). The titled compound was obtained as a white solid (4.3 mg, 17%). $^1$H NMR (300 MHz, DMSO-$d_6$) δ 9.16 (t, J=6.27 Hz, 1H), 8.64 (d, J=1.70 Hz, 1H), 8.49 (q, J=4.41 Hz, 1H), 8.14 (dt, J=8.73, 1.74 Hz, 2H), 8.00 (dd, J=8.14, 0.68 Hz, 1H), 7.93 (d, J=8.48 Hz, 2H), 7.81 (dd, J=8.31, 2.20 Hz, 1H), 7.32 (s, 2H), 7.24 (s, 1H), 4.54 (d, J=6.89 Hz, 2H), 4.51 (q, J=6.89 Hz, 2H), 2.80 (d, J=4.41 Hz, 3H), and 1.32 (t, J=7.12 Hz, 3H); MS (ESI) m/e positive ion 453 [M+Na]+, 431 [M+H]+; negative ion 429 [M–H]−.

EXAMPLE 163

4-amino-5-cyano-6-isopropoxy-N-[4-(methylsulfonyl)benzyl]pyridine-2-carboxamide

The titled compound was prepared according to the procedure described in Example 102 and Example 103, substituting 4-methanesulfonyl-benzylamine hydrochloride for 2,5-dimethoxybenzylamine used in Example 102C. $^1$H NMR (300 MHz, DMSO-$d_6$) δ 9.16 (t, J=6.4 Hz, 1H), 7.88 (d, J=8.5 Hz, 2H), 7.54 (d, J=8.5 Hz, 2H), 7.29 (s, 2H), 7.05 (s, 1H), 5.62 (septet, J=6.1 Hz, 1H), 4.57 (d, J=6.4 Hz, 2H), 3.18 (s, 3H), 1.30 (d, J=6.1 Hz, 6H). MS (m/e) positive mode: 389 (M+H)$^+$; negative mode: 387 (M−H)$^−$.

EXAMPLE 164 methyl 4-[5-({[(4-amino-5-cyano-6-ethoxypyridin-2-yl)carbonyl]amino}methyl)pyridin-2-yl]benzoate The title compound was prepared according to the procedure described in Example 160, substituting 4-methoxycarbonylphenylboronic acid for 3-methoxycarbonylphenylboronic acid.

$^1$H NMR (300 MHz, DMSO-$d_6$) δ 9.18 (t, J=6.27 Hz, 1H), 8.66 (d, J=2.03 Hz, 1H), 8.22 (d, J=8.48 Hz, 2H), 8.06 (d, J=8.48 Hz, 2H), 8.01-8.07 (m, 1H), 7.83 (dd, J=8.14, 2.37 Hz, 1H), 7.33 (s, 2H), 7.08 (s, 1H), 4.55 (d, J=6.10 Hz, 2H), 4.51 (q, J=7.12 Hz, 2H), 3.88 (s, 3H), and 1.32 (t, J=6.95 Hz, 3H); MS (ESI) m/e positive ion 432 [M+H]$^+$; negative ion 430 [M−H]$^−$.

EXAMPLE 165

4-amino-N-[2-(aminosulfonyl)benzyl]-5-chloro-6-ethoxypyridine-2-carboxamide

Example 165A

2-Chloro-6-ethoxy-pyridin-4-ylamine

To 2,6-dichloro-pyridin-4-ylamine (1.08 g, 6.6 mmol) in ethanol (1.5 mL) was added sodium ethoxide (2.5 M, 2.7 mL, 6.6 mmol) and the mixture was heated in a sealed tube at 150° C. for 6 h. Water was added, and the mixture was extracted with ethyl acetate. The extracts were concentrated and purified by silica gel flash column eluting with 30% ethyl acetate in hexanes to give the titled compound (1.0 g, 88%).

Example 165B

4-Amino-6-ethoxy-pyridine-2-carboxylic acid methyl ester

Example 165A (3 g, 17 mmol) was dissolved in methanol (20 mL). (diphenylphospino)ferrocenyl palladium chloride dichloromethane (360 mg, 0.44 mmol) and triethylamine (4.9 mL, 35 mmol) were added. The mixture was heated at 100° C. under carbon monoxide (100 psi) for 6 h. The crude material was concentrated and purified by silica gel flash column eluting with 50% ethyl acetate in hexanes to give the titled compound (2.4 g, 72%).

Example 165C 4-amino-5-chloro-6-ethoxy-pyridine-2-carboxylic acid

Step A

To Example 165B (400 mg, 2.0 mmol) in N,N-dimethylformamide (4 mL) was added N-chlorosuccinimide (267 mg, 2.0 mmol). The mixture was stirred at r.t for 3 days before water was added. The precipitates were collected and purified by silica gel flash column eluting with 50% ethyl acetate in hexanes to give 4-amino-5-chloro-6-ethoxy-pyridine-2-carboxylic acid methyl ester (220 mg, 48%).

Step B

This material from step A was treated with LiOH in ethanol/water (5:3, 1 M, 2 mL) at ambient temperature for 2 h. HCl(aq) was added after 30 min to adjust pH value to 1. The precipitates were collected to afford the titled compound (130 mg, 70%).

Example 165D 4-amino-N-[2-(aminosulfonyl)benzyl]-5-chloro-6-ethoxypyridine-2-carboxamide The titled compound was prepared according to the procedure described in Example 104B, substituting 2-aminomethyl-benzenesulfonamide for 2,5-dimethoxybenzylamine and substituting the acid from Example 165C for the acid from Example 104. $^1$H NMR (500 MHz, DMSO-$d_6$) δ 9.01 (t, J=6.0 Hz, 1H), 7.89 (dd, J=2.0, 9.5 Hz, 1H), 7.63 (broad s, 2H), 7.56 (dt, J=1.5, 8.0 Hz, 1H), 7.45 (m, 2H), 7.13 (s, 1H), 6.54 (broad s, 2H), 4.88 (d, J=6.5 Hz, 2H), 4.43 (q, J=7.0 Hz, 2H), and 1.31 (t, J=7.0, 3H). MS (m/e) positive mode: 385, 387 (3:1, M+H)$^+$; negative mode: 383, 385 (3:1, M−H)$^−$.

EXAMPLE 166

4-amino-5-cyano-6-ethoxy-N-[4-(1,2,3-thiadiazol-5-yl)benzyl]pyridine-2-carboxamide The titled compound was prepared according to the procedure described in Example 104B, substituting 4[1,2,3]thiadiazo-5-yl-benzylamine for 2,5-dimethoxy-benzylamine. $^1$H NMR (300 MHZ, DMSO-$d_6$) δ 9.58 (s, 1H), 9.14 (t, J=6.4 Hz, 1H), 8.10 (d, J=8.1 Hz, 2H), 7.47 (d, J=8.1 Hz, 2H), 7.33 (bs, 2H), 7.09 (s, 1H), 4.57-4.50 (m, 4H), 1.32 (t, J=7.1 Hz, 3H). MS (m/e) 381 (M+H)$^+$.

EXAMPLE 167

4-amino-5-cyano-N-(4-cyanobenzyl)-6-ethoxypyridine-2-carboxamide

The titled compound was prepared according to the procedure described in Example 161B, substituting 4-cyanobenzyamine for 4-phenylsulfanyl-benzylamine used in Example 161B. $^1$H NMR (300 MHz, DMSO-$d_6$) δ ppm 1.32 (t, J=7.1 Hz, 3H), 4.45-4.58 (m, 4H), 7.06 (s, 1H), 7.31 (bs, 2H), 7.47 (d, J=8.5 Hz, 2H), 7.79 (d, J=8.5 Hz, 2H), 9.18 (t, J=6.4 Hz, 1H). MS (ESI+) m/e=322 (M+H)$^+$.

EXAMPLE 168

N-(4-amino-5-cyano-6-ethoxypyridin-2-yl)-2-(4-amino-2,5-dimethoxyphenyl)acetamide

Example 168A (2,5-Dimethoxy-4-nitro-phenyl)-acetic acid

A solution of of 2,5-dimethoxyphenylacetic acid (1.00 g, 5.10 mmol) in 10 mL of acetic acid was added 6.5 mL of 1.0M $HNO_3$ in acetic acid. The reaction was stirred at ambient temperature for 10 min, and diluted with 75 mL of water. The yellow precipitate was collected and washed with water (3×10 mL), then dried on the filter. Recrystallization from 20 mL of 2-propanol gave 846 mg (69%) of the titled compound as fine yellow crystals.

Example 168B (2,5-Dimethoxy-4-nitrophenyl)acetyl chloride

To of Example 168A (241 mg, 1.00 mmol) was added 2 mL of thionyl chloride. The reaction mixture was stirred at reflux for 1 h, during which time the starting acid dissolved completely, then the excess thionyl chloride was concentrated in vacuo to give a yellow solid. This was taken up in 3 mL of dichloromethane and concentrated in vacuo to give the acid chloride.

Example 168C

N-(4-Amino-5-cyano-6-ethoxy-pyridin-2-yl)-2-(2,5-dimethoxy-4-nitro-phenyl)-acetamide To a solution of 356 mg (2.00 mmol) of Example 1A in 6 mL of pyridine and 6 mL of dichloromethane at −78° C. was added a solution of 1.0 g (3.9 mmol) of Example 168B. The reaction was stirred at −78° C. for 20 min, then 5 mL of water was added. The mixture was warmed until the ice had melted, then the solvents were removed in vacuo. The residue was taken up in 75 mL of ethyl acetate and extracted with 1 M HCl (3×10 mL). Next, 30 mL of hexanes was added, and the organic phase was extracted with saturated $NaHCO_{3(aq.)}$ (3×10 mL), then brine (1×10 mL), dried over $MgSO_4$, filtered, and concentrated in vacuo to a yellow solid. This was partially recrystallized from 10 mL of methanol to give 479 mg (60%) of the titled compound as fine yellow crystals.

Example 168D

N-(4-amino-5-cyano-6-ethoxypyridin-2-yl)-2-(4-amino-2,5-dimethoxyphenyl)acetamide To a suspension of 250 mg (0.623 mmol) of Example 168C in 10 mL of glacial acetic acid and 2 mL of water at 90° C. was added 500 mg (7.65 mmol) of Zn dust. The reaction was heated at 90° C. for 30 min, then the amber solution was decanted from the excess Zn and the solvents were removed in vacuo. The residue was suspended in water, filtered, and the precipitate was washed with additional water. The product was purified by dissolution in 10 mL of methanol and 0.5 mL of 1M $HCl_{(aq.)}$, then addition of 0.3 mL of 2M NaOH to give a yellow precipitate. This was filtered, washed with methanol, and dried in vacuo to give 100 mg (43%) of the title compound. $^1H$ NMR (300 MHz, DMSO-$d_6$) δ ppm 9.78 (s, 1H), 7.12 (s, 1H), 6.88 (s, 2H), 6.67 (s, 1H), 6.35 (s, 1H), 4.69 (s, 2H), 4.32 (q, J=6.9 Hz, 2H), 3.68 (s, 3H), 3.64 (s, 3H), 3.51 (s, 2H), 1.30 (t, J=7.1 Hz, 3H); MS (ESI) m/z=372 $[M+H]^+$.

EXAMPLE 169

4-amino-5-cyano-6-ethoxy-N-[(6-methoxypyridin-3-yl)methyl]pyridine-2-carboxamide The titled compound was prepared according to the procedure described in Example 104B, substituting C-(6-Methoxy-pyridin-3-yl)-methylamine for 2,5-dimethoxy-benzylamine. $^1H$ NMR (300 MHz, DMSO-$d_6$) δ 9.03 (t, J=6.4 Hz, 1H), 8.11 (dd, J=2.7, 0.7 Hz, 1H), 7.64 (dd, J=2.7, 8.5 Hz, 1H), 7.33 (bs, 2H), 7.06 (s, 1H), 6.78 (dd, J=8.5, 0.7 Hz, 1H), 4.49 (q, J=7.1 Hz, 2H), 4.39 (d, J=6.4 Hz, 2H), 3.82 (s, 3H), 1.32 (t, J=7.1 Hz, 3H). MS (m/e) 328 $(M+H)^+$.

EXAMPLE 170

N-(4-amino-5-cyano-6-ethoxypyridin-2-yl)-2-[2-methoxy-5-(methylthio)phenyl]acetamide

Example 170A (5-Bromo-2-methoxy-benzyloxy)-tert-butyl-dimethyl-silane

To a solution of 2.17 g (10.0 mmol) of 5-bromo-2-methoxybenzyl alcohol in 10 mL of N,N-dimethylformamide was added 1.36 g (20.0 mmol) of imidazole, then 2.26 g (15.0 mmol) of tert-butyldimethylsilyl chloride. The reaction was stirred at ambient temperature for 30 min, and poured into 100 mL of water. The aqueous suspension was extracted with diethyl ether (3×15 mL), then the combined ether layers were back extracted with 1 M HCl (2×15 mL), saturated $NaHCO_3$ $_{(aq.)}$ (2×15 mL), and brine (1×15 mL), dried over $MgSO_4$, filtered, and concentrated to an oil. This was purified via silica gel chromatography, eluting with 95:5 hexanes:ethyl acetate to give 2.91 g (88%) of the titled compound as a colorless oil.

Example 170B (2-Methoxy-5-methylsulfanyl-phenyl)-methanol

To a solution of Example 170A (2.91 g, 8.75 mmol) in 20 mL of tetrahydrofuran at −78° C. was added 1.6 M n-butyllithium in hexanes (7.1 mL, 11.4 mmol). The reaction was stirred at −78° C. for 10 min, then 1.5 mL of dimethyldisulfide was added. The reaction was warmed to ambient temperature and stirred for 2 h, then concentrated in vacuo. The residue was taken up in 50 mL of diethyl ether, then extracted with water (2×15 mL), 2 M $NaOH_{(aq.)}$ (1×15 mL), and brine (1×15 mL), dried over $MgSO_4$, filtered, and concentrated in vacuo to an oil. This was taken up in 15 mL of tetrahydrofuran and treated with 2.0 g (ca. 7 mmol) of tetrabutylammonium fluoride hydrate. The reaction was stirred at ambient temperature for 1 h, then concentrated in vacuo. The residue was taken up in 30 mL of diethyl ether, then extracted with water (2×10 mL), 2M $NaOH_{(aq.)}$ (1×10 mL), and brine (1×10 mL), dried over $MgSO_4$, filtered, and concentrated in vacuo to an oil. The product was purified via silica gel chromatography, eluting with a 20-40% ethyl acetate in hexanes gradient to give 1.23 g (76%) of the alcohol. The product was about 90% pure by $^1$H NMR analysis.

Example 170C

2-Chloromethyl-1-methoxy-4-methylsulfanyl-benzene

To a solution of Example 170B (1.23 g, 6.69 mmol) in 15 mL of N,N-dimethylformamide was added LiCl (567 mg, 13.4 mmol), then 2 mL (27 mmol) of thionyl chloride. The solution warmed spontaneously on addition of the thionyl chloride. After 15 min, 50 mL of water was added, then the aqueous suspension was extracted with diethyl ether (3×15 mL). The combined organic layers were back extracted with water (1×15 mL), saturated NaHCO$_{3(aq.)}$ (2×15 mL), and brine (1×15 mL), dried over MgSO$_4$, filtered, and concentrated in vacuo to 1.24 g (92%) of an oil. This was used in the next step on the same day and without further purification.

Example 170D (2-Methoxy-5-methylsulfanyl-phenyl)-acetonitrile

To a solution of 1.24 g (6.12 mmol) of Example 170C in 10 mL of CH$_3$CN was added 162 mg (0.61 mmol) of 18-Crown-6, then 797 mg (12.2 mmol) of potassium cyanide. The reaction was stirred at reflux under N$_2$ for 18 h, then concentrated in vacuo. The residue was taken up in 30 mL of water and extracted with diethyl ether (3×15 mL). The combined ether layers were back extracted with brine (1×5 mL), dried over MgSO$_4$, filtered, and concentrated to an oil. This was purified via silica gel chromatography, eluting with a 10-40% ethyl acetate in hexanes gradient to give 910 mg (77%) of a white solid.

Example 170E (2-Methoxy-5-methylsulfanyl-phenyl)-acetic acid

To 910 mg (4.71 mmol) of Example 170D was added 5 mL of 12M HCl$_{(aq.)}$. The reaction was heated at reflux for 20 h, then cooled to ambient temperature. Next, 50 mL of diethyl ether was added, and the organic phase was washed with water (2×10 mL), then saturated NaHCO$_{3(aq.)}$. The combined NaHCO$_{3(aq.)}$ layers were acidified with 3 mL of 12 M HCl, then the suspension was extracted with diethyl ether (2×15 mL). The last set of ether layers was back extracted with brine (1×10 mL), dried over MgSO$_4$, filtered, and concentrated to 906 mg (91%) of a white solid.

Example 170F

N-(4-amino-5-cyano-6-ethoxypyridin-2-yl)-2-[2-methoxy-5-(methylthio)phenyl]acetamide To 212 mg of Example 170E was added 3 mL of thionyl chloride. The mixture was stirred at reflux for 20 min, and concentrated in vacuo. The residue was taken up in 4 mL of dichloromethane and added to a solution of 212 mg (1.2 mmol) of 4,6-diamino-3-cyano-2-ethoxypyridine in 4 mL of pyridine and 4 mL of dichloromethane at −78° C. The reaction was stirred at −78° C. for 45 min, then 3 mL of water was added, and the mixture was warmed until the ice had melted. The solvents were removed in vacuo, then the residue was partitioned between 10 mL of ethyl acetate and 5 mL of 1 M HCl. Next, 10 mL of hexanes was added, and the layers were shaken and separated. The organic layer was extracted with 1 M HCl$_{(aq.)}$ (2×10 mL), saturated NaHCO$_{3(aq.)}$ (2×10 mL), and brine (1×10 mL), dried over MgSO$_4$, filtered, and concentrated in vacuo to a white solid. This was recrystallized from 2 mL of methanol in a sealed vial to give 52 mg (14%) of the titled compound as a white solid. $^1$H NMR (300 MHz, DMSO-d$_6$) δ ppm 10.13 (s, 1H), 7.19 (m, 2H), 7.12 (s, 1H), 6.95 (d, J=8.5 Hz, 1H), 6.87 (s, 2H), 4.34 (q, J=7.1 Hz, 2H), 3.73 (s, 3H), 3.68 (s, 2H), 2.42 (s, 3H), 1.31 (t, J=7.1 Hz, 3H); MS (ESI+) m/z=373 [M+H]$^+$. Anal. Calc'd for C$_{18}$H$_{20}$N$_4$O$_3$S: C, 58.05; H, 5.41; N, 15.04.
Found: C, 57.84; H, 5.25; N, 14.82.

EXAMPLE 171

4-amino-5-cyano-6-ethoxy-N-{4-[(2-hydroxyethyl)sulfonyl]benzyl}pyridine-2-carboxamide The titled compound was prepared according to the procedure described in Example 104B, substituting 2-(4-aminomethyl-benzenesulfonyl)-ethanol for 2,5-dimethoxybenzylamine used in Example 104B. $^1$H NMR (300 MHz, DMSO-d$_6$) δ ppm 1.32 (t, J=7.1 Hz, 3H), 3.41 (t, J=6.4 Hz, 2H), 3.66 (t, J=6.4 Hz, 2H), 4.46-4.60 (m, 4H), 7.08 (s, 1H), 7.32 (bs, 2H), 7.52 (d, J=8.5 Hz, 2H), 7.84 (d, J=8.5 Hz, 2H), 9.18 (t, J=6.4 Hz, 1H). MS (ESI+) m/e=405 (M+H)$^+$.

EXAMPLE 172

4-amino-N-[2-(aminosulfonyl)benzyl]-5-chloro-6-isopropoxypyridine-2-carboxamide

Example 172A 4-amino-5-chloro-6-isopropoxy-pyridine-2-carboxylic acid

To Example 165C (120 mg, 0.56 mmol) was added 6 N HCl(aq) (1 ML) and the mixture was heated to 145° C. for 40 min under microwave irradiation. The precipitate (87 mg, 84%) was collected. This hydroxy acid (75 mg, 0.4 mmol) was added to toluene (1 mL). 2-iodopropane (140 mg, 0.81 mmol) and Ag$_2$CO$_3$ (110 mg, 0.4 mmol) were added and the mixture was heated to 100° C. for 24 h. The insoluble material was filtered off and the filtrate was purified by silica gel flash column eluting with 50% ethyl acetate in hexanes to give 4-amino-5-chloro-6-isopropoxy-pyridine-2-carboxylic acid isopropyl ester (40 mg, 37%). This material was treated with aq. LiOH at room temperature in ethanol/water (5:3, 1 M, 1 mL). HCl(aq) was added after 30 min to adjust pH value to 1. The precipitates were collected to afford the title compound (37 mg, 110%).

Example 172B 4-amino-N-[2-(aminosulfonyl)benzyl]-5-chloro-6-isopropoxypyridine-2-carboxamide The titled compound was prepared according to the procedure described in Example 104B, substituting 2-aminomethyl-benzenesulfonamide for 2,5-dimethoxybenzylamine, and substituting Example 172A for Example 104A. $^1$H NMR (500 MHz, DMSO-d$_6$) δ 8.98 (t, J=7.0 Hz, 1H), 7.89 (dd, J=1.5, 9.5 Hz, 1H), 7.63 (broad s, 2H), 7.56 (dt, J=1.5, 8.0 Hz, 1H), 7.44 (m, 2H), 7.11 (s, 1H), 6.51 (broad s, 2H), 5.46 (septet, J=6.0 Hz, 1H), 4.88 (d, J=6.5 Hz, 2H), and 1.28 (d, J=6.0, 6H). MS (m/e) positive mode: 399, 401 (3:1, M+H)$^+$; negative mode: 397, 399 (3:1, M−H)$^−$.

EXAMPLE 173

4-amino-5-cyano-6-ethoxy-N-[4-(phenylsulfonyl)benzyl]pyridine-2-carboxamide

A mixture of Example 161B (61 mg, 0.15 mmol), 2 mL of acetic acid, 0.15 mL of hydrogen peroxide (30% solution in water) in 0.5 mL of N,N-dimethylformamide was stirred at room temperature for 24 h. Water was added, the resulting precipitate was then filtered. This solid was purified via reverse phase HPLC (0-70% CH$_3$CN in 10 mM aq. ammonium acetate) to afford the titled compound as white solid (40 mg, 61%). $^1$H NMR (300 MHz, DMSO-d$_6$) δ ppm 1.30 (t, J=7.1 Hz, 3H), 4.43-4.56 (m, 4H), 7.05 (s, 1H), 7.32 (bs, 2H), 7.50 (d, J=6.0 Hz, 2H), 7.56-7.73 (m, 3H), 7.88-7.97 (m, 4H), 9.14 (t, J=6.4 Hz, 1H). MS (ESI+) m/e=437 (M+H)$^+$.

EXAMPLE 174

4-amino-5-cyano-6-ethoxy-N-[(6-piperidin-1-ylpyridin-3-yl)methyl]pyridine-2-carboxamide The titled compound was prepared according to the procedure described in Example 196, substituting piperidine for piperidine-4-carboxylic acid methyl ester. $^1$H NMR (500 MHz, DMSO-d$_6$) δ 8.92 (t, J=6.4 Hz, 1H), 8.04 (d, J=2.4 Hz, 1H), 7.45 (dd, J=2.4, 8.8 Hz, 1H), 7.31 (bs, 2H), 7.06 (s, 1H), 6.76 (d, J=8.8, 1H), 4.48 (q, J=7.0 Hz, 2H), 4.31 (d, J=6.4 Hz, 2H), 3.48-3.42 (m, 4H), 1.62-1.48 (m, 6H), 1.31 (t, J=7.0 Hz, 3H). MS (m/e) 381 (M+H)$^+$.

EXAMPLE 175

4-amino-5-cyano-6-ethoxy-N-[4-(isopropylsulfonyl)benzyl]pyridine-2-carboxamide

Example 175A

4-Isopropylsulfanyl-benzylamine

To a stirred solution of 4-isopropylsulfanyl-benzonitrile (0.24 g, 2.0 mmol) in 2.0 mL of anhydrous N,N-dimethylformamide was added sodium 2-propanethiolate (0.25 g, 2.5 mmol). The resulting mixture was stirred at room temperature overnight. The solvent was removed under reduced pressure to afford an oil (0.1 g), which was mixed with Raney Ni (50 mg, prewashed with methanol) in 30 mL of ammonia (20% solution in methanol). The heavy walled reaction vessel was charged with H$_2$ (60 psi) and the reaction was shaken at room temperature for 15 h. The mixture was filtered to remove the catalyst, and the filtrate was concentrated to yield 60 mg of the titled compound as a light brown solid, which was used without further purification in the next step.

Example 175B

4-Amino-5-cyano-6-ethoxy-pyridine-2-carboxylic acid 4-isopropylsulfanyl-benzylamide The titled compound was prepared according to the procedure described in Example 161B, substituting 4-isopropylsulfanyl-benzylamine for 4-phenylsulfanyl-benzylamine used in Example 161B. $^1$H NMR (300 MHz, DMSO-d$_6$) δ ppm 1.21 (d, J=6.8 Hz, 6H), 1.31 (t, J=7.0 Hz, 3H), 3.42 (quintet, J=6.8 Hz, 1H), 4.40-4.56 (m, 4H), 7.07 (s, 1H), 7.20-7.40 (m, 6H), 9.06 (t, J=6.4 Hz, 1H). MS (ESI+) m/e=371 (M+H)$^+$.

Example 175C

4-amino-5-cyano-6-ethoxy-N-[4-(isopropylsulfonyl)benzyl]pyridine-2-carboxamide A mixture of Example 175B (37 mg, 0.1 mmol), 1.5 mL of acetic acid, 0.12 mL of hydrogen peroxide (30% solution in water) in 0.5 mL of N,N-dimethylformamide was stirred at room temperature for 20 h. Water was added, the resulting precipitate was then filtered. The solid was purified via reverse phase HPLC (0-70% CH$_3$CN in 10 mM aq. ammonium acetate) to give a white solid (24 mg, 60%). $^1$H NMR (400 MHz, DMSO-d$_6$) δ ppm 1.14 (d, J=6.8 Hz, 6H), 1.32 (t, J=7.1 Hz, 3H), 3.37 (quintet, J=6.8 Hz, 1H), 4.51 (q, J=7.1 Hz, 2H), 4.58 (d, J=6.4 Hz, 2H), 7.08 (s, 1H), 7.31 (bs, 2H), 7.55 (d, J=8.6 Hz, 2H), 7.81 (d, J=8.6 Hz, 2H), 9.18 (t, J=6.4 Hz, 1H). MS (ESI+) m/e=403 (M+H)$^+$.

EXAMPLE 176

4-amino-5-cyano-6-ethoxy-N-[4-(methylsulfonyl)benzyl]pyridine-2-carboxamide

The title compound was prepared according to the procedure described in Example 104B, substituting 4-methylsulfonylbenzylamine for 2,5-dimethoxybenzylamine. $^1$H NMR (300 MHz, DMSO-d$_6$) δ 9.19 (t, J=6.44 Hz, 1H), 7.88 (d, J=8.48 Hz, 2H), 7.54 (d, J=8.48 Hz, 2H), 7.33 (s, 2H), 7.07 (s, 1H), 4.56 (d, J=7.12 Hz, 2H), 4.51 (q, 2H), 3.18 (s, 3H), and 1.32 (t, J=7.12 Hz, 3H); MS (ESI) m/e positive ion 397 [M+Na]$^+$, 375 [M+H]$^+$; negative ion 373 [M−H]$^−$.

EXAMPLE 177

2-[4-(acetylamino)-2,5-dimethoxyphenyl]-N-(4-amino-5-cyano-6-ethoxypyridin-2-yl)acetamide To a solution of 20 mg (0.054 mmol) of Example 168 D in 0.5 mL of dioxane, warmed to aid dissolution, was added 0.3 mL of saturated NaHCO$_{3(aq.)}$, then 2 drops of acetic anhydride. The reaction was stirred for 10 minutes, and concentrated in vacuo. The residue was taken up in methanol/water, and purified via reversed-phase HPLC (0-70% CH$_3$CN in 10 mM aq. ammonium acetate) to give 5 mg (22%) of the title compound as a white solid. $^1$H NMR (300 MHz, DMSO-d$_6$) δ ppm 10.04 (s, 1H), 9.11 (s, 1H), 7.72 (s, 1H), 7.12 (s, 1H), 6.92 (s, 1H), 6.87 (s, 2H), 4.34 (q, J=7.1 Hz, 2H), 3.76 (s, 3H), 3.66 (s, 3H), 3.65 (s, 2H), 2.08 (s, 3H), 1.31 (t, J=7.1 Hz, 3H); MS (ESI+) m/z=414 [M+H]$^+$.

EXAMPLE 178

4-amino-5-cyano-N-{4-[(dimethylamino)sulfonyl]benzyl}-6-ethoxypyridine-2-carboxamide The title compound was prepared according to the procedure described in Example 104B, substituting 4-aminomethyl-N,N-dimethyl-benzenesulfonamide (Eliel, E. L.; Nelson, K. W. JOC, 1955, 20, 1657-1665) for 2,5-dimethoxybenzylamine. $^1$H NMR (300 MHz, DMSO-d$_6$) δ 9.20 (t, J=6.10 Hz, 1H), 7.71 (d, J=8.48 Hz, 2H), 7.53 (d, J=8.48 Hz, 2H), 7.34 (s, 2H), 7.08 (s, 1H), 4.57 (d, J=6.44 Hz, 2H), 4.51 (q, J=7.12 Hz, 2H), 2.59 (s, 6H), and 1.32 (t, J=7.12

Hz, 3H); MS (ESI) m/e positive ion 426 [M+Na]⁺, 404 [M+H]⁺; negative ion 402 [M–H]⁻.

EXAMPLE 179

4-amino-5-cyano-N-{[6-(3,5-dimethoxyphenyl)pyridin-3-yl]methyl}-6-ethoxypyridine-2-carboxamide The title compound was prepared according to the procedure described in Example 160, substituting 3,5-dimethoxyphenylboronic acid (Dol, G. C.; Kamer, P. C. J.; van Leeuwen, P. W. N. M. Eur. *J. Org. Chem.* 1998, 359-364) for 3-methoxycarbonylphenylboronic acid. ¹H NMR (300 MHz, DMSO-d₆) δ 9.14 (t, J=6.44 Hz, 1H), 8.60 (d, J=1.70 Hz, 1H), 7.92 (dd, J=8.14, 0.68 Hz, 1H), 7.76 (dd, J=8.31, 2.20 Hz, 1H), 7.32 (s, 2H), 7.20 (d, J=2.37 Hz, 2H), 7.08 (s, 1H), 6.56 (t, J=2.20 Hz, 1H), 4.51 (q, J=7.12 Hz, 2H), 4.52 (d, J=6.10 Hz, 2H), 3.81 (s, 6H), and 1.32 (t, J=6.95 Hz, 3H); MS (ESI) m/e 434 [M+H]⁺.

EXAMPLE 180

4-amino-5-cyano-6-ethoxy-N-[4-(methylsulfonyl)-3-(trifluoromethyl)benzyl]pyridine-2-carboxamide Example 180A 4-Methanesulfonyl-3-trifluoromethyl-benzylamine A mixture of 4-fluoro-3-trifluoromethylbenzonitrile (75 mg, 0.40 mmol), sodium sulfinate (44.5 mg, 0.44 mmol) in N,N-dimethylformamide (1.5 mL) was heated at 100° C. for 2 h. The reaction mixture was cooled to room temperature, quenched with water. The resulting white solid was collected via filtration, washed with cold water, dried in a vacuum oven to give 4-methanesulfonyl-3-trifluoromethyl-benzonitrile (90 mg, 90% yield). This benzonitrile was hydrogenated in 2N NH₃ in methanol with 35 mg of Raney Ni under a hydrogen balloon for 2 h. The reaction mixture was filtered through a celite plug, washed with methanol, evaporated in vacuo to give the titled compound.

Example 180B 4-amino-5-cyano-6-ethoxy-N-[4-(methylsulfonyl)-3-(trifluoromethyl)benzyl]pyridine-2-carboxamide The titled compound was prepared according to the procedure described in Example 104B, substituting Example 180A for 2,5-dimethoxybenzylamine. ¹H NMR (300 MHz, DMSO-d₆) δ 9.26 (t, J=6.3 Hz, 1H), 8.20 (d, J=8.1 Hz, 2H), 7.97 (s, 2H), 7.84 (d, J=8.5 Hz, 2H), 7.34 (s, 2H), 7.06 (s, 1H), 4.63 (d, J=6.4 Hz, 2H), 4.52 (q, J=7.1 Hz, 2H), 3.28 (s, 3H), 1.33 (t, J=7.1 Hz, 3H). MS (m/e) positive mode: 443 (M+H)⁺; negative mode: 441 (M–H)⁻.

EXAMPLE 181

4-amino-5-cyano-6-(cyclopenylmethoxy-N-[4-(methylsulfonyl)benzyl]pyridine-2-carboxamide Example 181A 3-Amino-4,4-dicyano-3-enoic acid ethyl ester To a stirred mixture of ethyl 3-amino-3-ethoxyacrylate hydrochloride (25 g, 128 mmol) in chloroform (120 ml) was added malononitrile (9.3 g, 14 mmol) and triethylamine (14.1 g, 140 mmol). The mixture was refluxed for 3 hours, and then washed with water (2×50 ml), and then concentrated. The residue was purified on silica gel cartridge by AnaLogix to yield the titled compound (17.5 g, 88.7%) as light yellow solid. ¹H NMR (300 MHz, DMSO-d₆) δ 8.77 (s, 1H), 8.68 (s, 1H), 4.15 (q, J=6.0 Hz, 2H), 3.53 (s, 2H), 1.20 (t, J=6.0 Hz, 3H).

Example 181B

4-Amino-2-chloro-6-hydroxynicotononitrile

The compound from Example 181A was dissolved in 100 ml concentrated HCl and stirred at r.t for 4 hours. The white solid precipitated was collected, washed with water and dried to yield the title compound (14.3 g, 90%). ¹H NMR (300 MHz, DMSO-d₆) δ 11.58 (s, 1H), 7.01 (s, 2H), 5.81 (s, 1H).

Example 181C

Trifluoro-methanesulfonic acid 4-amino-6-chloro-5-cyano-pyridin-2-yl ester

Example 181B (8.0 g, 47 mmol) was reacted with triflic anhydride (16 g, 57 mmol) in a mixed solvent of pyridine and dichloromethane (1:1, 60 ml). The mixture was stirred at room temperature for 6 hours, and then solvents were removed in vacuo. The residue was dispersed in ethyl estate and water. The organic layer washed with brine and dried over MgSO₄, and then concentrated to yield the titled compound (9.8 g, 69%) as a white solid. ¹H NMR (300 MHz, DMSO-d₆) δ 8.06 (s, 2H), 6.6 (s, 1H).

Example 181D

4-Amino-5-cyano-6-ethoxy-pyridine-2-carboxylic acid methyl ester

Example 181C (9.1 g, 30 mmol) was carbonylated with carbon monoxide (60 psi) and catalyzed by [1,1'-bis(diphenylphosphino)ferrocene]dichloropalladium(II) (1.19 g, 5 mol %) and triethylamine (8.4 ml, 60 mmol) in methanol (250 ml) for 16 hours at room temperature. After reaction finished checked by LC/MS, reaction mixture was filtered and the solid was collected to yield the title compound.

Example 181E

4-Amino-6-chloro-5-cyano-pyridine-2-carboxylic acid

The Example 181D was dissolved in methanol (100 ml) and 3N NaOH aqua (10 ml) and stirred at r.t for 2 hours. Solvents were removed in vacuo and the residue was dissolved in 2N NaOH aqueous solution. After filtered, the filtrate was adjusted to pH 2 with 6N HCl. The white solid precipitated was collected, washed with water and dried to provide the titled compound (4.9 g, 82%). ¹H NMR (300 MHz, DMSO-d₆) δ 13.53 (s, 1H), 7.76 (s, 2H), 7.37 (s, 1H).

Example 181F

4-Amino-6-chloro-5-cyano-pyridine-2-carboxylic acid 4-methanesulfonyl-benzylamide Example 181E (2.3 g, 11.5 mmol) was dissolved with 4-sulfonylbenzylamine hydrochloride (2.8 g, 12.6 mmol) in N,N-dimethylformamide, O-benzotriazol-1-yl-N,N,N',N'-tetramethyluronium tetrafluoroborate (4.4 g, 13.8 mmol) was added, followed by triethylamine to adjust pH 5~6. The reaction mixture was stirred at r.t for 1 hour, and then filtered. The white solid was washed with methanol (10 ml×2) and dried to afford the titled compound (3.7 g, 88% yield). $^1$H NMR (300 MHz, DMSO-$d_6$) δ 9.30 (t, J=6.44 Hz, 1H), 7.87 (d, J=8.48 Hz, 2H), 7.79 (s, 2H), 7.54 (d, J=8.14 Hz, 2H), 7.38 (s, 1H), 4.53 (d, J=6.44 Hz, 2H), 3.17 (s, 3H); MS (APCI) m/z 365 [M+H]$^+$, 363 [M−H]$^−$.

Example 181G 4-amino-5-cyano-6-(cyclopentylmethoxy)-N-[4-(methylsulfonyl)benzyl]pyridine-2-carboxamide Example 181F (36.5 mg, 0.1 mmol), CuI (1.9 mg, 0.01 mmol), 1,10-phenanthroline (3.6 mg, 0.02 mmol), $Cs_2CO_3$ (65 mg, 0.2 mmol) and cyclopentylmethanol (1 ml) were stirred in a sealed tube. The reaction mixture was running for 24 hours in 110° C. oil-bath, and then filtered and purified on HPLC (ammonium acetate, 0-70% $CH_3CN$—$H_2O$) to give the titled compound (26.6 mg, 62%). $^1$H NMR (300 MHz, DMSO-$d_6$) δ 9.17 (t, J=6.0 Hz, 1H), 7.88 (d, J=9.0 Hz, 2H), 7.54 (d, J=9.0 Hz, 2H), 7.33 (s, 2H), and 7.07 (s, 1H), 4.57 (d, J=6.0 Hz, 2H), 4.35 (d, J=9.0 Hz, 2H), 3.18 (s, 3H), 2.29 (m, 1H), 1.75 (s, 2H), 1.65-1.51 (m, 4H), 1.35 (m, 2H); MS (APCI) m/z 429 [M+H]$^+$, 427 [M−H]$^−$.

EXAMPLE 182

4-amino-5-cyano-6-(isopropylamino)-N-[4-(methylsulfonyl)benzyl]pyridine-2-carboxamide A mixture of Example 181F (36 mg, 0.1 mmol), isopropylamine (85 μL, 1.0 mmol) in N,N-dimethylacetamide (500 μL) was heated at 190° C. for 80 minutes in a microwave reactor. The crude mixture was diluted with 1 mL acetonitrile and purified by reverse phase HPLC (0-70% $CH_3CN$ in 10 mM aq. ammonium acetate), followed by second purification via silica gel chromatography, eluting with hexane/ethyl acetate (1:1 to 100% ethyl acetate) to provide the titled compound (8 mg, 21% yield). $^1$H NMR (300 MHz, DMSO-$d_6$) δ 9.02 (t, J=6.4 Hz, 1H), 7.88 (d, J=8.5 Hz, 2H), 7.53 (d, J=8.5 Hz, 2H), 6.89 (bs, 2H), 6.69 (s, 1H), 6.15 (d, J=8.1, 1H), 4.58-4.46 (m, 3H), 3.17 (s, 3H), 1.16 (t, J=6.8 Hz, 6H). MS (m/e) 388 (M+H)$^+$.

EXAMPLE 183

4-amino-5-cyano-6-ethoxy-N-[4-(ethylsulfonyl)benzyl]pyridine-2-carboxamide

The titled compound was prepared according to the procedure described in Example 161B, substituting 4-ethanesulfonyl-benzylamine for 4-phenylsulfanyl-benzylamine used in Example 161B. $^1$H NMR (300 MHz, DMSO-$d_6$) δ ppm 1.08 (t, J=7.3 Hz, 3H), 1.32 (t, J=7.0 Hz, 3H), 3.25 (q, J=7.5 Hz, 2H), 4.45-4.62 (m, 4H), 7.07 (s, 1H), 7.34 (bs, 2H), 7.54 (d, J=8.5 Hz, 2H), 7.84 (d, J=8.5 Hz, 2H), 9.20 (t, J=6.4 Hz, 1H). MS (ESI+) m/e=389 (M+H)$^+$.

EXAMPLE 184

4-amino-5-chloro-6-ethoxy-N-[4-(methylsulfonyl)benzyl]pyridine-2-carboxamide

The titled compound was prepared according to the procedure described in Example 104B, substituting 4-methanesulfonyl-benzylamine for 2,5-dimethoxybenzylamine, and substituting Example 165C for Example 104A. $^1$H NMR (300 MHz, DMSO-$d_6$) δ 9.07 (t, J=6.0 Hz, 1H), 7.89 (d, J=8.4 Hz, 2H), 7.54 (d, J=8.1 Hz, 2H), 7.13 (s, 1H), 6.52 (broad s, 2H), 4.56 (d, J=6.6 Hz, 2H), 4.46 (q, J=7.2 Hz, 2H), 3.17 (s, 3H), and 1.32 (d, J=6.9, 3H). MS (m/e) positive mode: 384, 386 (3:1, M+H)$^+$. Anal. Calcd for $C_{16}H_{18}ClN_3O_4S$: C, 50.06; H, 4.73; N, 10.95. Found: C, 49.89; H, 4.73; N, 10.82.

EXAMPLE 185

4-amino-N-[(6-chloropyridin-3-yl)methyl]-5-cyano-6-ethoxypyridine-2-carboxamide

The title compound was prepared according to the procedure described in Example 104B, substituting 5-aminomethyl-2-chloropyridine for 2,5-dimethoxybenzylamine. $^1$H NMR (300 MHz, DMSO-$d_6$) δ 9.14 (t, J=6.27 Hz, 1H), 8.36 (d, J=2.37 Hz, 1H), 7.76 (dd, J=8.48, 2.37 Hz, 1H), 7.48 (d, J=8.48 Hz, 1H), 7.33 (s, 2H), 7.06 (s, 1H), 4.50 (q, J=7.12 Hz, 2H), 4.48 (d, J=7.12 Hz, 2H), and 1.32 (t, J=7.12 Hz, 3H); MS (ESI) m/e positive ion 332 [M+H]$^+$; negative ion 330 [M−H]$^−$.

EXAMPLE 186

4-amino-5-cyano-6-(cyclopropylmethoxy-N-[4-(methylsulfonyl)benzyl]pyridine-2-carboxamide The titled compound was prepared according to the procedure described in Example 181G, substituting cyclopropylmethanol for cyclopentylmethanol. Yield is 70%. $^1$H NMR (300 MHz, DMSO-$d_6$) δ 9.17 (t, J=6.0 Hz, 1H), 7.88 (d, J=9.0 Hz, 2H), 7.54 (d, J=9.0 Hz, 2H), 7.32 (s, 2H), and 7.07 (s, 1H), 4.56 (d, J=6.0 Hz, 2H), 4.33 (d, J=9.0 Hz, 2H), 3.18 (s, 3H), 1.25 (m, 1H), 0.57 (m, 2H), 0.35 (m, 4H); MS (APCI) m/z 401 [M+H]$^+$, 399 [M−H]$^−$.

EXAMPLE 187

4-amino-5-chloro-6-isopropoxy-N-[4-(methylsulfonyl)benzyl]pyridine-2-carboxamide The titled compound was prepared according to the procedure described in Example 104B, substituting 4-methanesulfonyl-benzylamine for 2,5-dimethoxybenzylamine, and substituting Example 172A for Example 104A. $^1$H NMR (500 MHz, DMSO-$d_6$) δ 9.06 (t, J=6.5 Hz, 1H), 7.87 (d, J=8.0 Hz, 2H), 7.54 (d, J=8.5 Hz, 2H), 7.10 (s, 1H), 6.50 (broad s, 2H), 5.56 (septet, J=6.0 Hz, 1H), 4.56 (d, J=7.0 Hz, 2H), 3.18 (s, 3H), and 1.28 (d, J=6.5, 6H). MS (m/e) positive mode: 398, 400 (3:1, M+H)$^+$. Anal. Calcd for $C_{17}H_{20}ClN_3O_4S \cdot 0.45H_2O$: C, 50.29; H, 5.19; N, 10.35. Found: C, 50.38; H, 5.29; N, 10.18.

EXAMPLE 188

4-amino-5-cyano-6-ethoxy-N-{4-[2-(methylamino)-2-oxoethoxy]benzyl}pyridine-2-carboxamide

Example 188A

Ethyl [4-({[(4-amino-5-cyano-6-ethoxypyridin-2-yl)carbonyl]amino}methyl)phenoxy]acetate To a stirred mixture of Example 209 (107 mg, 0.34 mmol) and $Cs_2CO_3$ (111 mg, 0.34 mmol) in N,N-dimethylformamide (3.4 mL) was added ethyl bromoacetate (38 μL, 0.34 mmol). The reaction mixture was stirred at ambient temperature for 1.5 hr, and then partitioned between ethyl acetate and water. The organic layer was washed with brine, dried over $MgSO_4$, and concentrated in vacuo. The crude residue was triturated with acetonitrile to provide the titled compound as white solid (105 mg, 78%).

Example 188B

[4-({[(4-amino-5-cyano-6-ethoxypyridin-2-yl)carbonyl]amino}methyl)phenoxy]acetic acid To a solution of Example 188A (102 mg, 0.26 mmol) in a mixed solvent of methanol (2 mL) and tetrahydrofuran (2 mL) was added 2N NaOH (300 μL, 0.6 mmol). The reaction mixture was stirred at ambient temperature for 2 hr, and then acidified with 600 μL 1N HCl. It was partitioned between ethyl acetate and water. The organic layer was washed with brine, dried over $MgSO_4$, and concentrated in vacuo to provide the titled compound as white solid (95 mg, 100%).

Example 188C 4-amino-5-cyano-6-ethoxy-N-{4-[2-(methylamino)-2-oxoethoxy]benzyl}pyridine-2-carboxamide To a mixture of Example 188B (19 mg, 0.05 mmol), methylamine HCl salt (7 mg, 0.1 mmol) in N,N-dimethylformamide (500 μL) was added O-benzotriazol-1-yl-N,N,N',N'-tetramethyluronium tetrafluoroborate (18 mg, 0.055 mmol), followed by N,N-diisopropylethylamine (44 μL). The reaction mixture was stirred at ambient temperature for 1 hr. It was diluted with 1 mL acetonitrile and purified by reverse phase HPLC (0-70% $CH_3CN$ in 10 mM aq. ammonium acetate) to provide the titled compound as white solid. $^1$H NMR (300 MHz, DMSO-$d_6$) δ 8.95 (t, J=6.4 Hz, 1H), 8.00-7.94 (m, 1H), 7.29 (bs, 2H), 7.23 (d, J=8.9 Hz, 2H), 7.07 (s, 1H), 6.91 (d, J=8.9 Hz, 2H), 4.49 (q, J=7.1 Hz, 2H), 4.42 (s, 2H), 4.40 (d, J=6.4 Hz, 2H), 2.65 (d, J=4.6 Hz, 3H), 1.31 (t, J=7.1 Hz, 3H). MS (m/e) 384 (M+H)$^+$.

EXAMPLE 189

4-amino-5-cyano-6-(cyclopentylamino)-N-[4-(methylsulfonyl)benzyl]pyridine-2-carboxamide A mixture of Example 181F (36.5 mg, 0.1 mmol) and cyclopentylamine (25.5 mg, 0.3 mmol) in N,N-dimethylacetamide (1.5 ml) was stirred in a sealed tube. This reaction mixture was heated in a microwave reactor at 160° C. for 20 min. and purified on HPLC (10 mM ammonium acetate, 5% acetonitirle in $H_2O/CH_3CN$) to give titled compound (33.5 mg, 81%). $^1$H NMR (300 MHz, DMSO-$d_6$) δ 8.97 (t, J=6.0 Hz, 1H), 7.88 (d, J=9.0 Hz, 2H), 7.53 (d, J=9.0 Hz, 2H), 6.89 (s, 2H), and 6.70 (s, 1H), 6.27 (d, J=6.0 Hz, 2H), 4.57 (d, J=6.0 Hz, 2H), 4.57 (m, 1H), 3.18 (s, 3H), 1.95 (m, 1H), 1.67 (m, 2H), 1.50 (m, 4H); MS (APCI) m/z 414 [M+H]$^+$, 412 [M−H]$^−$.

EXAMPLE 190

4-amino-N-(1H-benzimidazol-2-ylmethyl)-5-cyano-6-ethoxypyridine-2-carboxamide

The titled compound was prepared according to the procedure described in Example 104B, substituting C-(1H-benzoimidazol-2-yl)-methylamine dihydrochloride for 2,5-dimethoxybenzylamine. $^1$H NMR (300 MHz, DMSO-$d_6$) δ 9.28 (t, J=5.8 Hz, 1H), 7.71 (dd, J=6.1, 3.4 Hz, 2H), 7.44 (dd, J=6.1, 3.1 Hz, 2H), 7.39 (s, 2H), 7.11 (s, 1H), 4.90 (d, J=5.8 Hz, 2H), 4.53 (q, J=7.1 Hz, 2H), 1.34 (t, J=7.1 Hz, 3H). MS (m/e) positive mode: 337 (M+H)$^+$.

EXAMPLE 191

4-amino-5-cyano-6-ethoxy-N-(4-morpholin-4-ylbenzyl)pyridine-2-carboxamide

The title compound was prepared according to the procedure described in Example 104B, substituting 4-morpholinobenzylamine for 2,5-dimethoxybenzylamine. $^1$H NMR (400 MHz, DMSO-$d_6$) δ 7.19 (d, J=8.5 Hz, 2H), 7.07 (s, 1H), 6.89 (d, J=8.5 Hz, 2H), 4.47 (q, J=7.1 Hz, 2H), 4.37 (s, 2H), 3.76-3.71 (m, 4H), 3.05 (m, 4H), 1.31 (t, J=7.1 Hz, 3H). MS (ESI) m/z 382[M+H]$^+$, 380 [M−H]$^−$.

EXAMPLE 192

4-amino-5-cyano-N-[4-(methylsulfonyl)benzyl]-6-thien-3-ylpyridine-2-carboxamide

Example 181F (36.5 mg, 0.1 mmol), 3-thienylboronic acid, $PdCl_2(PPh_3)_2$ (7 mg, 0.01 mmol), $Na_2CO_3$ (21 mg, 0.2 mmol) were taken up in a mixed solvent of dimethyl ether, ethanol and $H_2O$ (7:2:3, 2 ml). The reaction mixture was stirred in a microwave reactor at 160° C. for 10 min. The mixture was filtered and purified on HPLC (10 mM ammonium acetate and 5% $CH_3CN$ in $H_2O/CH_3CN$) to yield titled compound (31 mg, 75%). $^1$H NMR (300 MHz, DMSO-$d_6$) δ 9.44 (t, J=6.0 Hz, 1H), 8.43 (dd, J=3.0 Hz, 1H), 7.94 (dd, J=3.0 Hz, 1H), 7.87 (d, J=9.0 Hz, 2H), 7.70 (dd, J=3.0 Hz, 2H), 7.56 (d, J=9.0 Hz, 2H), 7.39 (s, 2H), 7.36 (s, 1H), 4.60 (d, J=6.0 Hz, 2H), 3.18 (s, 3H); MS (APCI) m/z 413 [M+H]$^+$, 411 [M−H]$^−$.

EXAMPLE 193

4-amino-5-cyano-6-(cyclobutylamino)-N-[4-(methylsulfonyl)benzyl]pyridine-2-carboxamide The titled compound was prepared according to the procedure described in Example 189, substituting cyclobutylamine for cyclopentylamine. Yield is 80%. $^1$H NMR (300 MHz, DMSO-$d_6$) δ 8.98 (t, J=6.0 Hz, 1H), 7.88 (d, J=9.0 Hz, 2H), 7.54 (d, J=9.0 Hz, 2H), 6.89 (s, 2H), 6.73 (d, J=9.0 Hz, 1H), 6.71 (s, 2H), 4.76 (q, J=9.0 Hz, 1H), 4.58 (d, J=6.0 Hz, 2H), 3.17 (s, 3H), 2.25 (m, 2H), 2.06 (m, 2H), 1.62 (m, 2H); MS (APCI) m/z 400 [M+H]$^+$, 398 [M−H]$^−$.

EXAMPLE 194 methyl 4-{[4-({[(4-amino-5-cyano-6-ethoxypyridin-2-yl)carbonyl]amino}methyl)piperidin-1-yl]carbonyl}benzoate

Example 194A

4-Amino-5-cyano-6-ethoxy-pyridine-2-carboxylic acid (piperidin-4-ylmethyl)-amide To Example 104A (104 mg, 0.5 mmol) in N,N-dimethylformamide (1.2 mL) was added 4-aminomethyl-piperidine-1-carboxylic acid tert-butyl ester (107 mg, 0.5 mmol) followed by triethylamine (50 mg, 0.5 mmol) and O-benzotriazol-1-yl-N,N,N',N'-tetramethyluronium tetrafluoroborate (160 mg, 0.5 mmol). The mixture was stirred for 24 h and partitioned between water and ethyl acetate. The ethyl acetate layer was washed with water (3×15 mL). The crude was dissolved in dichloromethane (3 mL) and trifluoroacetic acid (3 mL). The volatiles were removed after 3 h. The residue was dissolved in ethyl acetate and washed with NaOH(aq). The organic extracts were dried over MgSO4 and concentrated to give the titled compound (110 mg, 73%).

Example 194B methyl 4-{[4-({[(4-amino-5-cyano-6-ethoxypyridin-2-yl)carbonyl]amino}methyl)piperidin-1-yl]carbonyl}benzoate To Example 194A (39 mg, 0.13 mmol) in N,N-dimethylformamide (0.25 mL) was added terephthalic acid monomethyl ester (23 mg, 0.13 mmol) followed by triethylamine (30 mg, 0.3 mmol) and O-benzotriazol-1-yl-N,N,N',N'-tetramethyluronium tetrafluoroborate (41 mg, 0.13 mmol). The mixture was stirred for 1 h and purified by silica gel flash column eluting with 100% ethyl acetate to give the title compound (23 mg, 39%). $^1$H NMR (300 MHz, DMSO-$d_6$) δ 8.52 (t, J=6.0 Hz, 1H), 8.01 (d, J=8.1 Hz, 2H), 7.50 (d, J=8.4 Hz, 1H), 7.30 (broad s, 2H), 7.04 (s, 1H), 4.47 (q, J=7.2 Hz, 2H), 3.87 (s, 3H), 3.19 (t, J=6.3 Hz, 2H), 3.00 (m, 1H), 2.78 (m, 1H), 1.85 (m, 1H), 1.71 (m, 1H), 1.59 (m, 1H), 1.31 (d, J=7.2 Hz, 3H), and 1.15 (m, 2H). (two equatorial protons of the methylenes next to the nitrogen on the piperidine ring were buried under the water peak). MS (m/e) positive mode: 466 (M+H)$^+$; negative mode: 464 (M−H)$^−$.

EXAMPLE 195

4-amino-5-cyano-6-ethoxy-N-{[6-(trifluoromethyl)pyridin-3-yl]methyl}pyridine-2-carboxamide The title compound was prepared according to the procedure described in Example 104B, substituting 3-aminomethyl-6-(trifluoromethyl)pyridine for 2,5-dimethoxybenzylamine. $^1$H NMR (300 MHz, DMSO-$d_6$) δ 9.21 (t, J=6.27 Hz, 1H), 8.72 (s, 1H), 7.96 (dd, J=8.14, 1.69, 1H), 7.87 (d, J=8.14, 1H), 7.33 (s, 2H), 7.06 (s, 1H), 4.59 (d, J=6.10 Hz, 2H), 4.51 (q, J=7.12 Hz, 2H), and 1.32 (t, J=7.12 Hz, 3H); MS (ESI) m/e positive ion 366 [M+H]$^+$; negative ion 364 [M−H]$^−$.

EXAMPLE 196 methyl 1-[5-({[(4-amino-5-cyano-6-ethoxypyridin-2-yl)carbonyl]amino}methyl)pyridin-2-yl]piperidine-4-carboxylate A mixture of Example 185 (50 mg, 0.15 mmol) and piperidine-4-carboxylic acid methyl ester (0.75 mL) were heated to 140° C. for 20 min. in a microwave reactor. The reaction mixture was extracted with ethyl acetate (5 mL) and washed with 1M HCl (2×10 mL). The organic layer was concentrated in vacuo and purified by silica gel chromatography (50-100% ethyl acetate in hexanes) providing the title compound as an off white solid (34 mg, 52%). $^1$H NMR (300 MHz, DMSO-$d_6$) δ 8.92 (t, J=6.44 Hz, 1H), 8.05 (d, J=2.03 Hz, 1H), 7.47 (dd, J=8.82, 2.37 Hz, 1H), 7.30 (s, 2H), 7.06 (s, 1H), 6.80 (d, J=8.48 Hz, 1H), 4.48 (q, J=7.12 Hz, 2H), 4.31 (d, J=6.10 Hz, 2H), 4.14 (d, J=13.22 Hz, 2H), 3.60 (s, 3H), 2.82-2.98 (m, 2H), 2.56-2.67 (m, 1H), 1.85 (dd, J=13.56, 3.39 Hz, 2H), 1.43-1.62 (m, 2H), and 1.30 (t, J=7.12 Hz, 3H); MS (ESI) m/e positive ion 461 [M+Na]$^+$, 439 [M+H]$^+$; negative ion 437 [M−H]$^−$.

EXAMPLE 197

N-(4-amino-5-cyano-6-isopropoxypyridin-2-yl)-2-[2,5-dimethoxy-4-(methylsulfonyl)phenyl]acetamide

Example 197A 2-(2,5-Dimethoxy)phenylethanol

To a solution of 3.84 g (19.6 mmol) of (2,5-dimethoxy)phenylacetic acid in 20 mL of tetrahydrofuran at 0° C. and under $N_2$ was added 24 mL of 1.0 M $BH_3$.tetrahydrofuran, adding slowly to control foaming. The reaction was stirred at ambient temperature for 2 h, and cooled with an ice bath. The excess $BH_3$ was destroyed by dropwise addition of 5 mL $H_2O$, and the solvents were removed in vacuo. The residue was taken up in 25 mL of water and extracted with diethyl ether (2×25 mL). The combined ether layers were extracted with water (1×25 mL), 1 M NaOH$_{(aq.)}$ (1×10 mL), and brine (1×25 mL), dried over MgSO$_4$, filtered, and concentrated in vacuo to 2.60 g (73%) of the titled compound as a colorless oil.

Example 197B 2-(4-Bromo-2,5-dimethoxy)phenylethanol

To a solution of 2.60 g (14.3 mmol) of Example 197A in 8 mL of acetic acid was added 14.5 mL of 1.0 M $Br_2$ in acetic acid, then 2.0 g (14.7 mmol) of sodium acetate trihydrate. The reaction was stirred at ambient temperature for 30 min, and poured into 100 mL of water. The aqueous suspension was extracted with 2:1 ethyl acetate:hexanes (3×25 mL), then the combined organic layers were back extracted with saturated NaHCO$_{3(aq.)}$ (1×25 mL), and brine (1×25 mL), dried over MgSO$_4$, filtered, and concentrated in vacuo to an oil. This was taken up in 18 mL of methanol, and to the solution was added 2.0 g (14.5 mmol) of $K_2CO_3$ in 5 mL of water. This mixture was stirred at ambient temperature for 18 h, and the solvents were removed in vacuo. The residue was taken up in 25 mL of water, and extracted with ethyl acetate (2×25 mL). The combined ethyl acetate layers were back extracted with brine (1×25 mL), dried over MgSO$_4$, filtered, and concentrated in vacuo to an oil. This was purified via silica gel chromatography, eluting with a 30-40% ethyl acetate:hexanes gradient to give 3.16 g (85%) of the titled compound as a white solid.

Example 197C

[2-(4-Bromo-2,5-dimethoxy-phenyl)-ethoxy]-tert-butyl-dimethyl-silane

To a solution of 3.16 g (12.1 mmol) of Example 197B in 15 mL of N,N-dimethylformamide was added 1.65 g (24.2 mmol) of imidazole, then 2.19 g (14.5 mmol) of tert-butyldimethylsilyl chloride. The reaction was stirred at ambient temperature for 1.5 h, and it was poured into 100 mL of water. The aqueous suspension was extracted with hexanes (3×20 mL), then the combined hexanes layers were back extracted with water (1×20 mL), 5% (w/w) $NH_4OH$ (2×20 mL), 1 M $HCl_{(aq.)}$ (2×20 mL), and brine (1×20 mL), dried over $MgSO_4$, filtered, and concentrated in vacuo to an oil. This was heated at 110° C. at ca. 1 mm Hg for 1 h to remove any volatile impurities, giving 4.38 g (96%) of the titled compound as a colorless oil.

Example 197D 2-(2,5-Dimethoxy-4-methylsulfanyl-phenyl)-ethanol

To a solution of 4.37 g (11.6 mmol) of Example 197C in 25 mL of tetrahydrofuran at −78° C. and under $N_2$ was added 6 mL (15 mmol) of 2.5 M n-butyllithium in hexanes. The reaction was stirred at −78° C. for 10 min, and 2.3 mL (25.5 mmol) of dimethyldisulfide was added. The reaction was warmed to ambient temperature over 30 min, then 3 mL of water was added, and the solution was concentrated in vacuo. The residue was taken up in 50 mL of hexanes, and extracted with water (3×20 mL), then brine (1×20 mL), dried over $MgSO_4$, filtered, and concentrated in vacuo to a white solid. This was taken up in 30 mL of tetrahydrofuran, and to the solution was added 4.5 g (ca. 15.7 mmol) of tetrabutylammonium fluoride hydrate. After 2.5 h, the solution was concentrated in vacuo to a solid. This was washed with water (3×20 mL), then hexanes (2×20 mL). The solid was dissolved in ethyl acetate, dried over $MgSO_4$, and filtered. The ethyl acetate was removed in vacuo, and the residue was purified via silica gel chromatography, eluting with a 20-40% ethyl acetate:hexanes gradient to give 1.70 g (64%) of the titled compound as a white solid.

Example 197E 2-(4-Methanesulfonyl-2,5-dimethoxy-phenyl)-ethanol

To a solution of 1.70 g (7.44 mmol) of Example 197D in 12 mL of trifluoroacetic acid was added 1.82 mL (17.8 mmol) of 9.8 M $H_2O_{2(aq.)}$. The reaction was stirred at ambient temperature for 4 h, then $NaHSO_{3(aq.)}$ was added to destroy any excess $H_2O_2$, until starch-KI paper showed no excess oxidant. The reaction was concentrated in vacuo, and the residue was taken up in 50 mL of methanol. To the solution was added 6 g (43.4 mmol) of $K_2CO_3$ and 10 mL of water, then the mixture was stirred at ambient temperature for 10 min. The solvents were removed in vacuo, and the residue was taken up in 50 mL of ethyl acetate. This was filtered to remove the inorganic salts, then the salts were washed with ethyl acetate (2×5 mL). The combined filtrate and washings were extracted with brine (2×20 mL), water (2×20 mL), saturated $NaHCO_{3(aq.)}$ (1×20 mL), and again with brine (1×20 mL), dried over $MgSO_4$, filtered, and concentrated to 1.33 g (69%) of the titled compound as a solid.

Example 197F (4-Methanesulfonyl-2,5-dimethoxy-phenyl)-acetic acid

To a solution of 1.33 g (5.11 mmol) of Example 197E in 25 mL of acetone was added 6.5 mL (13.0 mmol) of 2.0M $H_2CrO_{4(aq.)}$. After 1 h, an additional 2 mL (4.0 mmol) of 2.0 M $H_2CrO_{4(aq.)}$ was added, then the reaction was stirred for another 2 h. The excess chromic acid was quenched by addition of 10 mL of water, followed by $NaHSO_{3(aq.)}$ to discharge the yellow-orange color. The solvents were removed in vacuo, and the residue was taken up in 25 mL of water, then extracted with ethyl acetate (3×35 mL). The combined ethyl acetate layers were back extracted with water (2×10 mL), and brine (1×10 mL), dried over $MgSO_4$, filtered, and concentrated to a solid. This was recrystallized from 30 mL of ethyl acetate to give 453 mg (32%) of the titled compound as a white solid.

Example 197G (4-Methanesulfonyl-2,5-dimethoxy-phenyl)-acetyl chloride

To 300 mg (1.09 mmol) of Example 197F was added 4 mL of thionyl chloride. The mixture was heated at reflux for 20 min, then concentrated in vacuo. The residue was taken up in dichloromethane and concentrated in vacuo two times to remove traces of thionyl chloride. The acid chloride was then taken up in 6 mL of dichloromethane to make a 0.17 M solution for use in subsequent acylations.

Example 197H

N-(4-amino-5-cyano-6-isopropoxypyridin-2-yl)-2-[2,5-dimethoxy-4-(methylsulfonyl)phenyl]acetamide To 55 mg (0.29 mmol) Example 17 (Step A) in 3 mL of pyridine and 3 mL of dichloromethane at −78° C. was added 3 mL (0.51 mmol) of 0.17 M Example 197G in dichloromethane. The reaction was stirred at −78° C. for 20 min, then 2 mL of water was added, and the reaction was allowed to warm until the ice melted. The solvents were removed in vacuo, then the residue was taken up in 15 mL of ethyl acetate and 10 mL of hexanes and extracted with water (1×3 mL), 1 M HCl (3×3 mL), saturated $NaHCO_{3(aq.)}$ (3×3 mL), and brine (1×3 mL), dried over $MgSO_4$, filtered, and concentrated in vacuo to a solid. This was recrystallized from 2 mL of methanol in a capped 4 mL vial to give 49 mg (38%) of the titled compound as a colorless solid. $^1H$ NMR (300 MHz, DMSO-$d_6$) δ ppm 10.25 (s, 1H), 7.30 (s, 1H), 7.26 (s, 1H), 7.08 (s, 1H), 6.86 (s, 2H), 5.30 (m, 1H), 3.89 (s, 3H), 3.82 (s, 2H), 3.76 (s, 3H), 3.24 (s, 3H), 1.30 (d, J=6.4 Hz, 6H); MS (ESI+) m/z=449 [M+H]$^+$. Anal. Calc'd for $C_{20}H_{24}N_4O_6S \cdot 0.33$ $CH_3OH$: C, 53.19; H, 5.56; N, 12.20. Found: C, 53.08; H, 5.27; N, 12.18.

EXAMPLE 198

4-amino-5-cyano-6-ethoxy-N-(4-fluoro-3-methoxy-benzyl)pyridine-2-carboxamide

The titled compound was prepared according to the procedure described in Example 104B, substituting 4-fluoro-3-methoxy-benzylamine for 2,5-dimethoxybenzylamine. $^1H$ NMR (300 MHz, DMSO-$d_6$) δ 9.02 (t, J=6.4 Hz, 1H), 7.31 (s, 2H), 7.15-7.09 (m, 2H), 7.07 (s, 1H), 6.83 (m, 1H), 4.5 (q, J=7.0 Hz, 2H), 4.43 (d, J=6.4 Hz, 2H), 3.81 (s, 3H), 3.30 (s, 3H), 1.31 (t, J=6.95 Hz, 3H). MS (m/e) positive mode: 345 (M+H)$^+$;

EXAMPLE 199

4-amino-5-cyano-6-ethoxy-N-[4-({[4-(methylsulfonyl)phenyl]amino}methyl)benzyl]pyridine-2-carboxamide

Example 199A (4-Aminomethyl-benzyl)-(4-methanesulfonyl-phenyl)-amine

A solution of tert-butyl N-(4-formylbenzyl)carbamate (45 mg, 0.2 mmol) and 4-methanesulfonylaniline hydrochloride (41 mg, 0.2 mmol) in 1 mL of methanol was stirred at room temperature for 30 min, then 0.15 mL of acetic acid was added, followed by 16 mg (0.24 mmol) of sodium cyanoborohydride. The reaction was complete in 5 h. The mixture was treated with saturated sodium bicarbonate solution until pH=8, then extracted with ethyl acetate twice. The combined organics were dried over MgSO$_4$, filtered, and concentrated. The solid was dissolved in 1 mL of methylene chloride, followed by the addition of 0.1 mL of trifluoroacetic acid. The mixture was stirred at room temperature overnight, then concentrated to afford the titled compound as an oil.

Example 199B 4-amino-5-cyano-6-ethoxy-N-[4-({[4-(methylsulfonyl)phenyl]amino}methyl)benzyl]pyridine-2-carboxamide The titled compound was prepared according to the procedure described in Example 161B, substituting Example 199A for Example 161A. $^1$H NMR (300 MHz, DMSO-d$_6$) δ ppm 1.31 (t, J=7.1 Hz, 3H), 3.26 (s, 3H), 4.37 (s, 2H), 4.43-4.56 (m, 4H), 7.07 (s, 1H), 7.22-7.30 (m, 8H), 7.31 (bs, 2H), 9.04 (t, J=6.3 Hz, 1H). MS (ESI+) m/e=480 (M+H)$^+$.

EXAMPLE 200

N-[4-({[(4-amino-5-cyano-6-ethoxypyridin-2-yl)carbonyl]amino}methyl)phenyl]glycinamide A solution of example 296 (10 mg, 0.03 mmol), 1-(3-dimethylaminopropyl)-3-ethylcarbodiimide hydrochloride (6 mg, 0.04 mmol, and 1-hydroxybenzotriazole hydrate (8 mg, 0.04 mmol) was stirred room temperature for 1 h, then 0.1 mL of ammonium hydroxide solution was added (28% ammonia in water). The reaction was complete after 24 h. The solvent was removed under reduced pressure to give an oil, which was purified via reverse phase HPLC (0-70% CH$_3$CN in 10 mM aq. TFA) to yield 4 mg (40%) of the tilted compound as the trifluoroacetic acid salt. $^1$H NMR (400 MHz, DMSO-d$_6$) δ ppm 1.30 (t, J=7.1 Hz, 3H), 3.57 (s, 2H), 4.32 (d, J=6.4 Hz, 2H), 4.47 (q, J=7.1 Hz, 2H), 6.53 (d, J=8.0 Hz, 2H), 7.02-7.09 (m, 3H), 7.28 (bs, 2H), 8.80 (t, J=6.3 Hz, 1H). MS (ESI+) m/e=370 (M+H)$^+$.

EXAMPLE 201

4-amino-5-cyano-6-isobutoxy-N-[4-(methylsulfonyl)benzyl]pyridine-2-carboxamide

The titled compound was prepared according to the procedure described in Example 181F, substituting 2-isobutanol for cyclopentylmethanol. Yield is 68%. $^1$H NMR (300 MHz, DMSO-d$_6$) δ 9.13 (t, J=6.0 Hz, 1H), 7.87 (d, J=9.0 Hz, 2H), 7.53 (d, J=9.0 Hz, 2H), 7.31 (s, 2H), and 7.06 (s, 1H), 4.56 (d, J=6.0 Hz, 2H), 4.23 (d, J=9.0 Hz, 2H), 3.16 (s, 3H), 2.0 (m, 1H), 0.98 (d, J=6.0 Hz, 6H); MS (APCI) m/z 403 [M+H]$^+$, 401 [M−H]$^-$.

EXAMPLE 202

N-[4-(acetylamino)benzyl]4-amino-5-cyano-6-ethoxypyridine-2-carboxamide

The titled compound was prepared according to the procedure described in Example 104B, substituting N-(4-aminomethyl-phenyl)-acetamide for 2,5-dimethoxy-benzylamine. $^1$H NMR (300 MHz, DMSO-d$_6$) δ 9.89 (s, 1H), 8.98 (t, J=6.4 Hz, 1H), 7.50 (d, J=8.5, 2H), 7.31 (bs, 2H), 7.21 (d, J=8.5 Hz, 2H), 7.07 (s, 1H), 4.49 (q, J=7.1 Hz, 2H), 4.40 (d, J=6.4 Hz, 2H), 2.01 (s, 3H), 1.31 (t, J=7.1 Hz, 3H). MS (m/e) 354 (M+H)$^+$.

EXAMPLE 203

4-amino-5-cyano-6-ethoxy-N-[2-methoxy-4-(methylsulfonyl)benzyl]pyridine-2-carboxamide The titled compound was prepared according to the procedure described in Example 180, substituting 2-methoxy-4-fluorobenzonitrile for 4-fluoro-3-trifluoromethylbenzonitrile used in Example 180A. $^1$H NMR (300 MHz, DMSO-d$_6$) δ 9.00 (t, J=6.3 Hz, 1H), 7.48 (1H, J=7.8, 1.7 Hz, 1H), 7.46 (broad s, 1H), 7.33 (d, J=7.8 Hz, 1H), 7.33 (broad s, 2H), 7.07 (s, 1H), 4.52 (q, J=6.8 Hz, 2H), 4.49 (d, J=5.1 Hz, 2H), 3.96 (s, 3H), 3.20 (s, 3H), 1.33 (t, J=7.1 Hz, 3H). MS (m/e) positive mode: 405 (M+H)$^+$; negative mode: 403 (M−H)$^-$.

EXAMPLE 204

4-amino-N-[4-(aminosulfonyl)benzyl]-5-cyano-6-ethoxypyridine-2-carboxamide

The title compound was prepared according to the procedure described in Example 104B, substituting 4-aminomethyl-benzenesulfonamide for 2,5-dimethoxybenzylamine. $^1$H NMR (300 MHz, DMSO-d$_6$) δ 9.15 (t, J=6.44 Hz, 1H), 7.74-7.82 (m, 2H), 7.45 (d, J=8.48 Hz, 2H), 7.33 (s, 2H), 7.29 (s, 2H), 7.07 (s, 1H), 4.53 (d, J=6.10 Hz, 2H), 4.51 (q, J=7.01 Hz, 2H), and 1.32 (t, J=6.95 Hz, 3H); MS (ESI) m/e positive ion 398 [M+Na]$^+$, 376 [M+H]$^+$; negative ion 374 [M−H]$^-$.

EXAMPLE 205

4-amino-5-cyano-6-ethoxy-N-{2-[(5-nitropyridin-2-yl)amino]ethyl}pyridine-2-carboxamide The title compound was prepared according to the procedure described in Example 104B, substituting 2-(2-aminoethylamino)-5-nitropyridine for 2,5-dimethoxybenzylamine. $^1$H NMR (300 MHz, DMSO-d$_6$) δ 8.90 (d, J=2.71 Hz, 1H), 8.60 (m, 1H), 8.25 (m, 1H), 8.05-8.16 (m, 1H), 7.31 (s, 2H), 7.05 (s, 1H), 6.56 (d, J=8.48 Hz, 1H), 4.44 (q, J=6.89 Hz, 2H), 3.52-3.67 (m, 2H), 3.41-3.52 (m, 2H), and 1.30 (t, J=7.12 Hz, 3H); MS (ESI) m/e positive ion 394 [M+Na]$^+$, 372 [M+H]$^+$; negative ion 370 [M−H]$^−$.

EXAMPLE 206

4-amino-5-cyano-6-ethoxy-N-({6-[3-(methylsulfonyl)phenyl]pyridin-3-yl}methyl)pyridine-2-carboxamide The title compound was prepared according to the procedure described in Example 160, substituting 3-methylsulfonylphenylboronic acid for 3-methoxycarbonylphenylboronic acid. $^1$H NMR (300 MHz, DMSO-d$_6$) δ 9.18 (t, J=6.44 Hz, 1H), 8.68 (d, J=1.70 Hz, 1H), 8.59 (t, J=1.87 Hz, 1H), 8.35-8.43 (m, 1H), 8.07 (d, J=8.14 Hz, 1H), 7.98 (ddd, J=7.80, 1.86, 1.19 Hz, 1H), 7.85 (dd, J=8.31, 2.20 Hz, 1H), 7.77 (t, J=7.80 Hz, 1H), 7.32 (s, 2H), 7.08 (s, 1H), 4.56 (d, J=6.44 Hz, 2H), 4.52 (q, J=7.01 Hz, 2H), 3.28 (s, 3H), and 1.33 (t, J=6.95 Hz, 3H); MS (ESI) m/e positive ion 474 [M+Na]$^+$, 452 [M+H]$^+$; negative ion 450 [M−H]$^−$.

EXAMPLE 207

4-amino-5-cyano-6-ethoxy-N-[2-(methylthio)benzyl]pyridine-2-carboxamide

The title compound was prepared according to the procedure described in Example 104B, substituting 2-(methylthio)benzylamine for 2,5-dimethoxybenzylamine. $^1$H NMR (300 MHz, DMSO-d$_6$) δ 8.99 (t, J=6.27 Hz, 1H), 7.22-7.43 (m, 4H), 7.14 (d, J=3.05 Hz, 2H), 7.07 (s, 1H), 4.46 (d, J=6.44 Hz, 2H), 4.50 (q, J=7.12 Hz, 2H), 2.49 (s, 3H), and 1.32 (t, J=7.12 Hz, 3H); MS (ESI) m/e positive ion 365 [M+Na]$^+$, 343 [M+H]$^+$; negative ion 341 [M−H]$^−$.

EXAMPLE 208 methyl N-{[4-({[(4-amino-5-cyano-6-ethoxypyridin-2-yl)carbonyl]amino}methyl)phenyl]sulfonyl}glycinate

Example 208A methyl N-{[4-(aminomethyl)phenyl]sulfonyl}glycinate

To 4-cyano-benzenesulfonyl chloride in dichloromethane (10 mL) was added amino-acetic acid methyl ester hydrochloride (250 mg, 2 mmol) and triethylamine (1.01 g, 10 mmol). The mixture was stirred for 20 min at r.t and was washed with water. The crude was triturated in methanol to give (4-cyano-benzenesulfonylamino)-acetic acid methyl ester (240 mg, 47%). This material was dissolved in NH$_3$ in methanol (30 mL) followed by addition of Raney Ni (3 g). The mixture was hydrogenated under H$_2$ (60 psi, 1 h, r.t) to provide the title compound (1:5, 230 mg).

Example 208B methyl N-{[4-({[(4-amino-5-cyano-6-ethoxypyridin-2-yl)carbonyl]amino}methyl)phenyl]sulfonyl}glycinate The titled compound (20 mg, 8.2%) was prepared using the procedure as described in Example 104B, substituting Example 208A for 2,5-dimethoxybenzylaminez, DMSO-d$_6$) δ 9.17 (t, J=7.0 Hz, 1H), 7.95 (broad s, 1H), 7.73 (d, J=8.5 Hz, 2H), 7.46 (d, J=8.5 Hz, 1H), 7.33 (broad s, 2H), 7.07 (s, 1H), 4.53 (d, J=6.5 Hz, 2H), 4.51 (q, J=7.0 Hz, 2H), 3.67 (s, 2H), 3.50 (s, 3H), and 1.32 (d, J=7.5 Hz, 3H). MS (m/e) positive mode: 448 (M+H)$^+$; negative mode: 446 (M−H)$^−$.

EXAMPLE 209

4-amino-5-cyano-6-ethoxy-N-(4-hydroxybenzyl)pyridine-2-carboxamide

The titled compound was prepared according to the procedure described in Example 104B, substituting 4-aminomethyl-phenol for 2,5-dimethoxy-benzylamine. $^1$H NMR (300 MHz, DMSO-d$_6$) δ 9.25 (s, 1H), 8.88 (t, J=6.4 Hz, 1H), 7.30 (bs, 2H), 7.10 (d, J=8.5, 2H), 7.07 (s, 1H), 6.70 (d, J=8.5 Hz, 2H), 4.48 (q, J=6.8 Hz, 2H), 4.35 (d, J=6.1 Hz, 2H), 1.30 (t, J=6.8 Hz, 3H). MS (m/e) 313 (M+H)$^+$.

EXAMPLE 210

4-amino-5-cyano-6-ethoxy-N-[(1-pyrimidin-2-ylpiperidin-4-yl)methyl]pyridine-2-carboxamide The titled compound was prepared according to the procedure described in Example 104B, substituting C-(1-pyrimidin-2-yl-piperidin-4-yl)-methylamine (prepared according to literature procedure: *J. Med. Chem.* 1999, 42, 17, 3342-3355) for 2,5-dimethoxy-benzylamine. $^1$H NMR (300 MHz, DMSO-d$_6$) δ 8.50 (t, J=6.4 Hz, 1H), 8.32 (d, J=4.8 Hz, 2H), 7.30 (bs, 2H), 7.04 (s, 1H), 6.56 (t, J=4.8 Hz, 1H), 4.68-4.58 (m, 2H), 4.48 (q, J=7.1 Hz, 2H), 3.21-3.16 (m, 2H), 2.90-2.87 (m, 2H), 1.92-1.78 (m, 1H), 1.73-1.62 (m, 2H), 1.31 (t, J=7.1 Hz, 3H), 1.18-1.01 (m, 2H). MS (m/e) 382 (M+H)$^+$.

EXAMPLE 211

4-amino-5-cyano-6-ethoxy-N-{[6-(methylsulfonyl)pyridin-3-yl]methyl}pyridine-2-carboxamide The title compound was prepared according to the procedure described in Example 104B, substituting 5-aminomethyl-2-methylsulfonylpyridine for 2,5-dimethoxybenzylamine. $^1$H NMR (300 MHz, DMSO-d$_6$) δ 9.20-9.27 (m, 1H), 8.72 (s, 1H), 8.02 (d, J=1.36 Hz, 2H), 7.34 (s, 2H), 7.06 (s, 1H), 4.60 (d, J=6.78 Hz, 2H), 4.51 (q, J=7.12 Hz, 2H), 3.26 (s, 3H), and 1.33 (t, J=7.12 Hz, 3H); MS (ESI) m/e positive ion 398 [M+Na]$^+$, 376 [M+H]$^+$.

EXAMPLE 212

4-amino-5-cyano-6-ethoxy-N-{[6-(methylthio)pyridin-3-yl]methyl}pyridine-2-carboxamide A solution of Example 185 (70 mg, 0.21 mmol) and sodium methylthiolate (32 mg, 0.46 mmol) in dimethyl sulfoxide (0.8 mL) was heated to 90° C. for 12 h., extracted with ethyl acetate (5 mL), and washed with H$_2$O (2×5 mL). The organic layer was concentrated in vacuo and purified by silica gel chromatography (50-100% ethyl acetate in hexanes) providing the title compound as an off white solid (42 mg, 58%). $^1$H NMR (300 MHz, DMSO-d$_6$) δ 8.98-9.15 (m, 1H), 8.32-8.44 (m, 1H), 7.57 (dd, J=8.31, 2.20 Hz, 1H), 7.32 (s, 2H), 7.25 (dd, J=8.31, 0.85 Hz, 1H), 7.06 (s, 1H), 4.49 (q, J=7.12 Hz, 2H), 4.41 (d, J=6.44 Hz, 2H), 2.48 (s, 3H), and 1.31 (t, J=7.12 Hz, 3H); MS (ESI) m/e positive ion 344 [M+H]$^+$; negative ion 342 [M−H]$^−$.

EXAMPLE 213

4-amino-5-cyano-6-ethoxy-N-[4-(isopropylsulfinyl)benzyl]pyridine-2-carboxamide

A mixture of 37 mg of Example 175B (0.1 mmol), 1.5 mL of acetic acid, 0.12 mL of hydrogen peroxide (30% solution in water) in 0.5 mL of N,N-dimethylformamide was stirred at room temperature for 2 h. Water was added, the resulting precipitate was then filtered. The solid was purified via reverse phase HPLC (0-70% $CH_3CN$ in 10 mM aq. TFA) to give 20 mg of the titled compound (52%). $^1$H NMR (400 MHz, DMSO-$d_6$) δ ppm 0.93 (d, J=6.8 Hz, 3H), 1.15 (d, J=6.8 Hz, 3H), 1.32 (t, J=7.1 Hz, 3H), 2.90 (quintet, J=7.0 Hz, 1H), 4.46-4.58 (m, 4H), 7.08 (s, 1H), 7.31 (bs, 2H), 7.47 (d, J=8.0 Hz, 2H), 7.56 (d, J=8.0 Hz, 2H), 9.12 (t, J=8.0 Hz, 1H). MS (ESI+) m/e=3=87 $(M+H)^+$.

EXAMPLE 214

4-amino-5-cyano-N-[4-(methylsulfonyl)benzyl]-6-[(1E)-prop-1-enyl]pyridine-2-carboxamide

Example 214A 4-amino-6-bromo-5-cyano-pyridine-2-carboxylic acid methyl ester To Example 104A (1.2 g, 5.4 mmol) in 1,4-dioxane (9 mL) was added $POBr_3$ (3.4 g, 12 mmol) pyridinium hydrobromide (12 mg, 0.08 mmol), and $H_3PO_4$ (12 uL). The mixture was stirred vigorously and then heated at 120° C. for 25 min. The mixture was quenched with ice chips and extracted with ethyl acetate. The crude material was purified by silica gel flash column eluting with 50% ethyl acetate in hexanes to give the titled compound (370 mg, 27%).

Example 214B 4-amino-6-bromo-5-cyano-pyridine-2-carboxylic acid 4-methanesulfonyl-benzylamide Step A
Example 214A (500 mg, 1.95 mmol) was hydrolyzed in LiOH (1N, ethanol:water 5:3) at room temperature for 1 h. The reaction mixture was then acidified with 3N HCl to pH~4. The resulting precipitates were collected through filtration, washed with cold water, and dried in vacuum oven for overnight to give the title compound.

Step B
The titled compound was prepared using the procedure as described in Example 104B, substituting the intermediate obtained from step A (480 mg, 1.98 mmol) for 2,5-dimethoxy benzylamine (370 mg, 46% for 2 steps).

Example 214C 4-amino-5-cyano-N-[4-(methylsulfonyl)benzyl]-6-[(1E)-prop-1-enyl]pyridine-2-carboxamide Example 214B (41 mg, 0.1 mmol) was dissolved in toluene (0.3 mL) and ethanol (0.1 mL) followed by addition of trans-ptopene-1-boronic acid (17 mg, 0.2 mmol), tetrakis(triphenylphosphine)palladium(0) (12 mg, 0.01 mmol), and $Na_2CO_3$(aq) (3M, 0.2 mL, 0.6 mmol). The mixture was heated to 110° C. under microwave irradiation for 30 min. The precipitates were collected and recrystallized in methanol to give the title compound (25 mg, 61%). $^1$H NMR (400 MHz, DMSO-$d_6$) δ 9.41 (t, J=6.4 Hz, 1H), 7.88 (d, J=8.4 Hz, 2H), 7.55 (d, J=8.4 Hz, 2H), 7.39 (dq, J=14.0, 7.2 Hz, 1H), 7.25 (s, 1H), 7.23 (broad s, 2H), 6.65 (dq, J=14.8, 1.6 Hz, 1H), 4.57 (d, J=6.8 Hz, 2H), 3.17 (s, 3H), and 1.96 (dd, J=2.0, 6.4 Hz, 3H). MS (m/e) 471 $(M+H)^+$; 469 $(M-H)^-$.

EXAMPLE 215 tert-butyl N-{[4-({[(4-amino-5-cyano-6-ethoxypyridin-2-yl)carbonyl]amino}methyl)phenyl]sulfonyl}-β-alaninate The titled compound was synthesized according to the procedure as described in Example 208, substituting 3-amino-propionic acid tert-butyl ester for the glycine methyl ester used in Example 208A. $^1$H NMR (300 MHz, DMSO-$d_6$) δ 9.16 (t, J=6.3 Hz, 1H), 7.74 (d, J=8.4 Hz, 2H), 7.64 (t, J=5.4 Hz, 1H), 7.48 (d, J=8.4 Hz, 1H), 7.33 (broad s, 2H), 7.07 (s, 1H), 4.54 (d, J=6.3 Hz, 2H), 4.51 (q, J=6.9 Hz, 2H), 2.89 (q, J=6.9 Hz, 2H), 2.32 (t, J=6.9 Hz, 2H), 1.36 (s, 9H), and 1.32 (d, J=6.9 Hz, 3H). MS (m/e) positive mode: 504 $(M+H)^+$; 526 $(M+Na)^+$.

EXAMPLE 216

4-amino-5-cyano-6-ethoxy-N-[(6-methylpyridin-3-yl methyl]pyridine-2-carboxamide

6-Methyl-nicotinonitrile (80 mg, 0.7 mmol) and Raney Ni (60 mg, prewashed with methanol) was mixed in 30 mL of ammonia (20% solution in methanol). The heavy walled reaction vessel was charged with $H_2$ (60 psi) and the reaction was shaken at room temperature for 3 h. The mixture was filtered to remove the catalyst, and the filtrate was concentrated to afford an oil (50 mg). This oil was dissolved in 2 mL of anhydrous N,N-dimethylformamide, followed by the addition of 4-amino-5-cyano-6-ethoxy-pyridine-2-carboxylic acid (52 mg, 0.25 mmol), O-benzotriazol-1-yl-N,N,N',N'-tetramethyluronium tetrafluoroborate (94 mg, 0.3 mmol), and N,N-diisopropylamine (52 μL, 0.3 mmol). The mixture was stirred at room temperature for 20 h. The crude product was purified via reverse phase HPLC (0-70% $CH_3CN$ in 10 mM aq. TFA) to provide 35 mg (45%) of the titled compound as the TFA salt. $^1$H NMR (300 MHz, DMSO-$d_6$) δ ppm 1.33 (t, J=7.1 Hz, 3H), 2.63 (s, 3H), 4.45-4.60 (m, 4H), 7.05 (s, 1H), 7.34 (bs, 2H), 7.71 (d, J=8.1 Hz, 1H), 8.18 (d, J=8.1 Hz, 1H), 8.64 (s, 1H), 9.18 (t, J=6.3 Hz, 1H). MS (ESI+) m/e=312 $(M+H)^+$.

EXAMPLE 217

4-amino-N-{2-[(tert-butylamino)sulfonyl]benzyl}-5-cyano-6-ethoxypyridine-2-carboxamide Step A
To a solution of N-tert-butyl-2-cyano-benzenesulfonamide (200 mg, 0.84 mmol, prepared as described in Balode, D. E.; et. al. *Chem. Heterocycl. Compd.* 1978, 14, 1632-1635) in tetrahydrofuran (1 mL) at 0° C. was added lithium aluminum hydride (150 mg, 3.9 mmol). The reaction mixture was allowed to warm to room temperature and stirred for 2 hours. The mixture was cooled to 0° C., 1M HCl was added until $H_2$ evolution ceased, and the reaction mixture was filtered through a 0.45 μm filter. The filtered reaction mixture was concentrated in vacuo and was used without further purification.

Step B

The title compound was prepared according to the procedure described in Example 104B, substituting the intermediate obtained from step A for 2,5-dimethoxybenzylamine. $^1$H NMR (300 MHz, DMSO-d$_6$) δ 9.07 (t, J=6.44 Hz, 1H), 7.92 (dd, J=7.80, 1.36 Hz, 1H), 7.72 (s, 1H), 7.57 (td, J=7.46, 1.36 Hz, 1H), 7.42 (d, J=7.46 Hz, 1H), 7.44 (t, J=7.63 Hz, 1H), 7.34 (s, 2H), 7.08 (s, 1H), 4.90 (d, J=6.44 Hz, 2H), 4.49 (q, J=7.12 Hz, 2H), 1.32 (t, J=6.95 Hz, 3H), and 1.15 (s, 9H); MS (ESI) m/e positive ion 454 [M+Na]$^+$, 432 [M+H]$^+$; negative ion 430 [M−H]$^−$.

EXAMPLE 218

N-(4-amino-5-cyano-6-ethoxypyridin-2-yl)-2-{2,5-dimethoxy-4-[(methylsulfonyl)amino]phenyl}acetamide To a solution of 20 mg (0.054 mmol) of Example 168D in 0.5 mL of pyridine and 0.5 mL of dichloromethane was added 4 drops of methanesulfonyl chloride. The reaction was stirred at ambient temperature for 30 min, then 1 mL of water was added, and the solvents were removed in vacuo. The residue was taken up in methanol, and the product was purified via reversed-phase HPLC (0-70% CH$_3$CN in 10 mM aq. ammonium acetate) to give 3 mg (12%) of the titled compound as a foam. $^1$H NMR (300 MHz, DMSO-d$_6$) δ ppm 10.12 (s, 1H), 8.89 (s, 1H), 7.12 (s, 1H), 6.99 (s, 1H), 6.88 (s, 3H), 4.34 (q, J=6.9 Hz, 2H), 3.76 (s, 3H), 3.69 (s, 3H), 3.68 (m, 2H), 2.95 (s, 3H), 1.31 (m, 3H); MS (ESI+) m/z=450 [M+H]$^+$.

EXAMPLE 219

4-amino-5-cyano-6-ethoxy-N-[2-(methylsulfonyl)benzyl]pyridine-2-carboxamide

The title compound was prepared according to the procedure described in Example 104B, substituting 2-methylsufonylbenzylamine for 2,5-dimethoxybenzylamine. $^1$H NMR (300 MHz, DMSO-d$_6$) δ 9.15 (t, J=6.44 Hz, 1H), 7.94 (d, J=7.80 Hz, 1H), 7.70 (td, J=7.54, 1.19 Hz, 1H), 7.55 (t, J=7.63 Hz, 2H), 7.35 (s, 2H), 7.06 (s, 1H), 4.85 (d, J=6.78 Hz, 2H), 4.50 (q, J=7.12 Hz, 2H), 3.37 (s, 3H), and 1.33 (t, J=7.12 Hz, 3H); MS (ESI) m/e positive ion 397 [M+Na]$^+$, 375 [M+H]$^+$; negative ion 373 [M−H]$^−$.

EXAMPLE 220

4-amino-5-cyano-6-ethoxy-N-(4-propionylbenzyl)pyridine-2-carboxamide

The titled compound was prepared according to the procedure described in Example 104B, substituting 1-(4-aminomethyl-phenyl)-propan-1-one trifluoroacetic acid salt for 2,5-dimethoxybenzylamine used in Example 104B. $^1$H NMR (300 MHz, DMSO-d$_6$) δ 9.14 (t, J=6.4 Hz, 1H), 7.92 (d, J=8.5 Hz, 2H), 7.41 (d, J=8.1 Hz, 2H), 7.32 (s, 2H), 7.01 (s, 1H), 4.53 (d, J=6.9 Hz, 2H), 4.51 (q, J=7.1 Hz, 2H), 3.01 (q, J=7.4 Hz, 2H), 1.32 (t, J=7.1 Hz, 3H), 1.07 (t, J=7.3 Hz, 3H). MS (m/e) positive mode: 353 (M+H)$^+$.

EXAMPLE 221

4-amino-5-cyano-6-ethoxy-N-[(5-methylpyridin-3-yl)methyl]pyridine-2-carboxamide

The titled compound was prepared according to the procedure described in Example 104B, substituting (5-methyl-pyridin-3-yl)-methylamine for 2,5-dimethoxybenzylamine used in Example 104B. $^1$H NMR (500 MHz, DMSO-d$_6$) δ 9.09 (t, J=7.0 Hz, 1H), 8.32 (s, 1H), 8.29 (s, 1H), 7.49 (s, 1H), 7.32 (broad s, 2H), 7.07 (s, 1H), 4.50 (q, J=7.0 Hz, 2H), 4.45 (d, J=6.5 Hz, 2H), 2.27 (s, 3H), and 1.32 (d, J=7.0, 3H). MS (m/e) positive mode: 312 (M+H)$^+$, negative mode: 310 (M−H)$^−$.

EXAMPLE 222

4-amino-5-cyano-N-{4-[2-(dimethylamino)-2-oxoethoxy]benzyl}-6-ethoxypyridine-2-carboxamide The titled compound was prepared according to the procedure described in Example 188C, substituting dimethylamine for methylamine. $^1$H NMR (300 MHz, DMSO-d$_6$) δ 8.96 (t, J=6.4 Hz, 1H), 7.32 (bs, 2H), 7.20 (d, J=8.8 Hz, 2H), 7.06 (s, 1H), 6.85 (d, J=8.8 Hz, 2H), 4.75 (s, 2H), 4.48 (q, J=7.1 Hz, 2H), 4.39 (d, J=6.4 Hz, 2H), 2.98, 2.82 (s, s, 6H), 1.31 (t, J=7.1 Hz, 3H). MS (m/e) 398 (M+H)$^+$.

EXAMPLE 223

4-amino-5-cyano-N-[4-(phenylsulfonyl)benzyl]-6-thien-3-ylpyridine-2-carboxamide

Example 223A

4-Amino-6-chloro-5-cyano-pyridine-2-carboxylic acid 4-benzenesulfonyl-benzylamide 4-Benzenesulfonyl-benzonitrile (100 mg, 0.41 mmol) and Raney Ni (70 mg, prewashed with methanol) was mixed in 30 mL of ammonia (20% solution in methanol). The heavy walled reaction vessel was charged with H$_2$ (60 psi) and the reaction was shaken at room temperature for 10 h. The mixture was filtered to remove the catalyst, then the filtrate was concentrated to afford an oil (80 mg). To this oil, was added 4-amino-6-chloro-5-cyano-pyridine-2-carboxylic acid from Example 181D (50 mg, 0.25 mmol) in 1 mL of anhydrous N,N-dimethylformamide, followed by O-benzotriazol-1-yl-N,N,N',N'-tetramethyluronium tetrafluoroborate (94 mg, 0.3 mmol), and N,N-diisopropylamine (52 µL, 0.3 mmol). The mixture was stirred at room temperature for 20 h. The crude product was purified via reverse phase HPLC (0-70% CH$_3$CN in 10 mM aq. ammonium acetate) to provide 45 mg (42%) of titled compound as a white solid. $^1$H NMR (300 MHz, DMSO-d$_6$) δ ppm 4.48 (d, J=6.4 Hz, 2H), 7.35 (s, 1H), 7.50 (d, J=8.5 Hz, 2H), 7.56-7.71 (m, 3H), 7.79 (s, 2H), 7.86-7.97 (m, 4H), 9.26 (t, J=6.3 Hz, 1H). MS (ESI+) m/e=427 (M+H)$^+$.

Example 223B 4-amino-5-cyano-N-[4-(phenylsulfonyl)benzyl]-6-thien-3-ylpyridine-2-carboxamide A 2.5 mL microwave reaction vessel was charged with 17 mg of Example 223A (0.05 mmol), 12 mg of thiophene-3-boronic acid (0.1 mmol), 3 mg of tetrakis(triphenylphosphine)palladium(0) (0.0025 mmol), and 14 mg of potassium carbonate (0.1 mmol). To this mixture was added 1 mL of N,N-dimethylformamide, 1 mL of dioxane, and 0.2 mL of water. The tube was sealed, then heated with a microwave apparatus at 150° C. for 20 min. The mixture was filtered through celite to remove the catalyst, the filtrate was then purified via reverse phase HPLC (0-70% $CH_3CN$ in 10 mM aq. ammonium acetate) yielding 15 mg (32%) of the titled compound. $^1$H NMR (300 MHz, DMSO-$d_6$) δ ppm 4.55 (d, J=6.4 Hz, 2H), 7.34 (s, 1H), 7.36 (bs, 2H), 7.52 (d, J=8.5 Hz, 2H), 7.56-7.72 (m, 4H), 7.87-7.97 (m, 5H), 8.40 (dd, J=3.1, 1.4 Hz, 1H), 9.38 (t, J=6.3 Hz, 1H). MS (ESI+) m/e=475 $(M+H)^+$.

EXAMPLE 224

4-amino-5-bromo-6-ethoxy-N-[4-(methylsulfonyl)benzyl]pyridine-2-carboxamide

Example 224A 4-amino-5-bromo-6-ethoxy-pyridine-2-carboxylic acid

The titled compound was prepared according to the procedure described in Example 165C, substituting N-bromosuccinimide for N-chlorosuccinimide used in Example 165C.

Example 224B 4-amino-5-bromo-6-ethoxy-N-[4-(methylsulfonyl)benzyl]pyridine-2-carboxamide The titled compound was prepared according to the procedure described in Example 104B, substituting 4-methanesulfonyl-benzylamine for 2,5-dimethoxybenzylamine, and substituting Example 224A for Example 104A. $^1$H NMR (300 MHz, DMSO-$d_6$) δ 9.08 (t, J=6.3 Hz, 1H), 7.88 (d, J=8.4 Hz, 2H), 7.54 (d, J=8.4 Hz, 2H), 7.09 (s, 1H), 6.48 (broad s, 2H), 4.56 (d, J=6.6 Hz, 2H), 4.45 (q, J=7.2 Hz, 2H), 3.17 (s, 3H), and 1.32 (d, J=7.2, 3H). MS (m/e) positive mode: 428, 430 (1:1, M+H)$^+$; negative mode: 426, 428 (1:1, M–H)$^-$.

EXAMPLE 225

4-amino-5-cyano-6-ethoxy-N-(3-hydroxybenzyl)pyridine-2-carboxamide

The titled compound was prepared according to the procedure described in Example 161B, substituting 3-aminomethyl-phenol for Example 161A. $^1$H NMR (300 MHz, DMSO-$d_6$) δ ppm 1.31 (t, J=7.0 Hz, 3H), 4.39 (d, J=6.4 Hz, 2H), 4.50 (q, J=6.9 Hz, 2H), 6.61 (dd, J=7.3, 1.9 Hz, 1H), 6.70 (d, J=7.3 Hz, 2H), 7.04-7.13 (m, 2H), 7.32 (bs, 2H), 8.99 (t, J=6.4 Hz, 1H), 9.30 (s, 1H). MS (ESI+) m/e=313 (M+H)$^+$.

EXAMPLE 226

4-amino-N-[4-(2-amino-2-oxoethoxy)benzyl]-5-cyano-6-ethoxypyridine-2-carboxamide The titled compound was prepared according to the procedure described in Example 188C, substituting $NH_4Cl$ (in large excess) for methylamine. $^1$H NMR (300 MHz, DMSO-$d_6$) δ 8.96 (t, J=6.4 Hz, 1H), 7.46, 7.35 (br, bs, 2H), 7.30 (bs, 2H), 7.23 (d, J=8.8 Hz, 2H), 7.07 (s, 1H), 6.90 (d, J=8.8 Hz, 2H), 4.49 (q, J=7.1 Hz, 2H), 4.40 (d, J=6.4 Hz, 2H), 4.38 (s, 2H), 1.31 (t, J=7.1 Hz, 3H). MS (m/e) 370 (M+H)$^+$.

EXAMPLE 227

N-(4-amino-5-cyano-6-ethoxypyridin-2-yl)-2-[2-methoxy-5-(methylsulfonyl)phenyl]acetamide To a solution of 18 mg (0.048 mmol) of Example 170F in 1 mL of trifluoroacetic acid was added 1.5 mL (0.20 mmol) of 0.13 M $H_2O_2$ in trifluoroacetic acid (prepared from 30% $H_2O_{2(aq.)}$). The solution was stirred at ambient temperature for 1 h, then diluted with 10 mL of water. The aqueous suspension was extracted with diethyl ether (3×5 mL), then the ether layers were back extracted with saturated $NaHCO_3$ $_{(aq.)}$ (2×5 mL), and brine (1×5 mL), dried over $MgSO_4$, filtered, and concentrated to 13 mg (67%) of the titled compound as a white solid. $^1$H NMR (300 MHz, DMSO-$d_6$) δ ppm 10.27 (s, 1H), 7.83 (dd, J=8.6, 2.5 Hz, 1H), 7.78 (d, J=2.4 Hz, 1H), 7.21 (d, J=8.5 Hz, 1H), 7.12 (s, 1H), 6.87 (s, 2H), 4.35 (q, J=7.0 Hz, 2H), 3.86 (s, 3H), 3.81 (s, 2H), 3.15 (s, 3H), 1.31 (t, J=7.1 Hz, 3H); MS (ESI+) m/z=405 [M+H]$^+$.

EXAMPLE 228

4-amino-5-cyano-6-ethoxy-N-[3-(methylsulfonyl)benzyl]pyridine-2-carboxamide

The title compound was prepared according to the procedure described in Example 104B, substituting 3-methylsulfonylbenzylamine for 2,5-dimethoxybenzylamine. $^1$H NMR (300 MHz, DMSO-$d_6$) δ 9.18 (t, J=6.61 Hz, 1H), 7.86 (s, 1H), 7.81 (dt, J=6.87, 1.99 Hz, 1H), 7.55-7.68 (m, 2H), 7.32 (s, 2H), 7.07 (s, 1H), 4.57 (d, J=6.44 Hz, 2H), 4.51 (q, J=7.12 Hz, 2H), 3.19 (s, 3H), and 1.32 (t, J=7.12 Hz, 3H); MS (ESI) m/e positive ion 397 [M+Na]$^+$, 375 [M+H]$^+$; negative ion 373 [M–H]$^-$.

EXAMPLE 229 benzyl 4-({[(4-amino-5-cyano-6-ethoxypyridin-2-yl)carbonyl]amino}methyl)piperidine-1-carboxylate The titled compound was prepared according to the procedure described in Example 253, substituting benzyl chloroformate for isobutyl chloroformate used in Example 253. $^1$H NMR (500 MHz, DMSO-$d_6$) δ 8.50 (t, J=6.0 Hz, 1H), 7.35 (m, 7H), 7.04 (s, 1H), 5.06 (s, 2H), 4.47 (q, J=7.0 Hz, 2H), 3.99 (broad d, J=13.5 Hz, 2H), 3.16 (t, J=6.5 Hz, 2H), 2.78 (broad s, 2H), 1.74 (m, 1H), 1.62 (d, J=12.0 Hz, 2H), 1.31 (d, J=7.0 Hz, 3H), and 1.05 (dq, J=4.0, 12.5 Hz, 2H). MS (m/e) positive mode: 338 (M+H)$^+$; negative mode: 336 (M–H)$^-$.

EXAMPLE 230

4-amino-5-cyano-6-ethoxy-N-(4-ethoxybenzyl)pyridine-2-carboxamide

The titled compound was prepared according to the procedure described in Example 104B, substituting 4-ethoxy-benzylamine for 2,5-dimethoxy-benzylamine. $^1$H NMR (300 MHz, DMSO-$d_6$) δ 8.97 (t, J=6.4 Hz, 1H), 7.30 (bs, 2H), 7.21 (d, J=8.8 Hz, 2H), 7.07 (s, 1H), 6.86 (d, J=8.8 Hz, 2H), 4.48 (q, J=7.1 Hz, 2H), 4.39 (d, J=6.4 Hz, 2H), 3.98 (q, J=7.1 Hz, 2H), 1.31, 1.31 (t, t, J=7.1 Hz, 6H). MS (m/e) 341 (M+H)$^+$.

EXAMPLE 231

4-amino-5-cyano-6-ethoxy-N-{4-[(methylamino)carbonyl]benzyl}pyridine-2-carboxamide

Example 231A

4-{[(4-Amino-5-cyano-6-ethoxy-pyridine-2-carbonyl)-amino]-methyl}-benzoic acid

To a mixture of 4-aminomethyl-benzoic acid (60 mg, 0.36 mmol) and Example 104A (63 mg, 0.3 mmol), was added O-benzotriazol-1-yl-N,N,N',N'-tetramethyluronium tetrafluoroborate (120 mg, 0.36 mmol), followed by N,N-diisopropylamine (63 µL, 0.36 mmol). The mixture was stirred at room temperature for 20 h, then concentrated under reduced pressure to give an oil. This was stirred in 1 mL of NaOH (2M solution in water) and 2 mL of ethyl acetate for 30 min. The layers were separated, after which concentrated HCl was added to the aqueous layer until pH<2. The white solid was filtered and washed with water, then dried in vacuum oven to give 60 mg (61%) of the titled compound. $^1$H NMR (300 MHz, DMSO-$d_6$) δ ppm 1.31 (t, J=6.9 Hz, 3H), 4.45-4.58 (m, 4H), 7.08 (s, 1H), 7.34 (bs, 2H) 7.39 (d, J=8.1 Hz, 2H), 7.90 (d, J=8.1 Hz, 2H), 9.14 (t, J=6.6 Hz, 1H), 12.85 (bs, 1H). MS (ESI+) m/e=340 (M+H)$^+$.

Example 231B 4-amino-5-cyano-6-ethoxy-N-{4-[(methylamino)carbonyl]benzyl}pyridine-2-carboxamide To a mixture of Example 231A (17 mg, 0.05 mmol) and methylamine hydrochloride (4 mg, 0.06 mmol), was added O-benzotriazol-1-yl-N,N,N',N'-tetramethyluronium tetrafluoroborate (24 mg, 0.06 mmol), followed by N,N-diisopropylamine (21 µL, 0.12 mmol). The mixture was stirred at room temperature for 20 h. The crude product was purified via reverse phase HPLC (0-70% CH$_3$CN in 10 mM aq. ammonium acetate) yielding 8 mg (45%) of the titled compound. $^1$H NMR (500 MHz, DMSO-$d_6$) δ ppm 1.31 (t, J=7.0 Hz, 3H), 2.77 (d, J=4.3 Hz, 3H), 4.47-4.57 (m, 4H), 7.07 (s, 1H), 7.27-7.42 (m, 4H), 7.78 (d, J=8.2 Hz, 2H), 8.33-8.40 (m, 1H), 9.11 (q, J=6.1 Hz, 1H). MS (ESI+) m/e=354 (M+H)$^+$.

EXAMPLE 232

4-[5-({[(4-amino-5-cyano-6-ethoxypyridin-2-yl carbonyl]amino}methyl)pyridin-2-yl]benzoic acid To a solution of Example 160 (47 mg, 0.11 mmol) in 1:2:2 methanol/tetrahydrofuran/H$_2$O (1 mL) was added lithium hydroxide monohydrate (84 mg, 2 mmol). The reaction mixture was stirred for 3 h., acidified to pH 3, and filtered to provide the titled compound as a white solid (27 mg, 59%). $^1$H NMR (300 MHz, DMSO-$d_6$) δ 12.98 (brs, 1H), 9.18 (t, J=6.10 Hz, 1H), 8.66 (d, J=1.70 Hz, 1H), 8.18 (d, J=8.48 Hz, 2H), 8.04 (d, J=8.48 Hz, 2H), 8.02 (d, J=7.80 Hz, 1H), 7.82 (dd, J=8.14, 2.37 Hz, 1H), 7.33 (s, 2H), 7.08 (s, 1H), 4.55 (d, J=6.10 Hz, 2H), 4.51 (q, J=7.12 Hz, 2H), and 1.32 (t, J=7.12 Hz, 3H); MS (ESI) m/e positive ion 440 [M+Na]$^+$, 418 [M+H]$^+$; negative ion 416 [M–H]$^-$.

EXAMPLE 233

4-amino-5-cyano-6-ethoxy-N-[(6-{3-[(methylamino)carbonyl]phenyl}pyridin-3-yl)methyl]pyridine-2-carboxamide The title compound was prepared according to the procedure described in Example 162, substituting the methyl ester from Example 160 for the methyl ester from Example 164. $^1$H NMR (300 MHz, DMSO-$d_6$) δ 9.17 (t, J=6.44 Hz, 1H), 8.65 (d, J=2.03 Hz, 1H), 8.55 (q, J=4.75 Hz, 1H), 8.50 (t, J=1.53 Hz, 1H), 8.19 (d, J=7.80 Hz, 1H), 7.99 (d, J=8.14 Hz, 1H), 7.87 (dt, J=7.80, 1.36 Hz, 1H), 7.83 (dd, J=8.31, 2.20 Hz, 1H), 7.57 (t, J=7.63 Hz, 1H), 7.33 (s, 2H), 7.08 (s, 1H), 4.55 (d, J=5.76 Hz, 2H), 4.52 (q, J=7.01 Hz, 2H), 2.81 (d, J=4.41 Hz, 3H), and 1.33 (t, J=7.12 Hz, 3H); MS (ESI) m/e positive ion 453 [M+Na]$^+$, 431 [M+H]$^+$; negative ion 429 [M–H]$^-$.

EXAMPLE 234

4-amino-5-cyano-6-ethoxy-N-[(6-phenylpyridin-3-yl)methyl]pyridine-2-carboxamide

The title compound was prepared according to the procedure described in Example 160, substituting phenylboronic acid for 3-methoxycarbonylphenylboronic acid. $^1$H NMR (300 MHz, DMSO-$d_6$) δ 9.16 (t, J=6.27 Hz, 1H), 8.61 (d, J=2.03 Hz, 1H), 8.03-8.08 (m, 2H), 7.92 (d, J=8.14 Hz, 1H), 7.78 (dd, J=8.31, 2.20 Hz, 1H), 7.38-7.52 (m, 3H), 7.32 (s, 2H), 7.08 (s, 1H), 4.53 (d, J=6.10 Hz, 2H), 4.51 (q, J=6.89 Hz, 2H), and 1.32 (t, J=6.95 Hz, 3H); MS (ESI) m/e positive ion 374 [M+H]$^+$; negative ion 372 [M–H]$^-$.

EXAMPLE 235

4-amino-5-cyano-6-ethoxy-N-({6-[4-(methylsulfonyl)phenyl]pyridin-3-yl}methyl pyridine-2-carboxamide The title compound was prepared according to the procedure described in Example 160, substituting 4-methanesulfonylphenylboronic acid for 3-methoxycarbonylphenylboronic acid. $^1$H NMR (300 MHz, DMSO-$d_6$) δ 9.19 (t, J=6.44 Hz, 1H), 8.68 (d, J=1.70 Hz, 1H), 8.28-8.35 (m, 2H), 8.06 (d, J=8.14 Hz, 1H), 8.03 (d, J=8.81 Hz, 2H), 7.85 (dd, J=8.31, 2.20 Hz, 1H), 7.33 (s, 2H), 7.08 (s, 1H), 4.56 (d, J=6.10 Hz, 2H), 4.52 (q, J=7.01 Hz, 2H), 3.26 (s, 3H), and 1.33 (t, J=7.12 Hz, 3H); MS (ESI) m/e positive ion 474 [M+Na]$^+$, 452 [M+H]$^+$; negative ion 450 [M–H]$^-$.

EXAMPLE 236

4'-amino-2'-ethoxy-N-[4-(methylsulfonyl)benzyl]-2,3'-bipyridine-6'-carboxamide

To a mixture Example 240 (50 mg, 0.11 mmol), tris(dibenzylideneacetone)dipalladium(0) (6 mg, 0.0066 mmol), CsF (40 mg, 0.26 mmol) in N,N-dimethylformamide under N$_2$ were added 2-pyridine-tributyltin (46 mg, 0.12 mmol) and tri tert-butylphosphine (10% in hexane, 93 mL, 0.026 mmol). The resulting mixture was heated in an oil bath at 100° C. for over night. The resulting mixture was partitioned between ethyl acetate and sat. aq. KF solution. The organic layer was washed with brine, dried over Na$_2$SO$_4$, and evaporated in vacuo. Reverse phase HPLC ((0-70% CH$_3$CN in 10 mM aq. ammonium acetate) purification provided the titled compound (18 mg, 38% yield). $^1$H NMR (300 MHz, DMSO-$d_6$) δ

9.10 (t, J=6.1 Hz, 1H), 8.63 (m, 1H), 7.87 (d, J=8.5 Hz, 2H), 7.81-7.90 (m, 1H), 7.74 (d, J=8.1 Hz, 1H), 7.57 (d, J=8.1 Hz, 2H), 7.30 (m, 1H), 7.16 (s, 1H), 6.87 (s, 2H), 4.60 (2H, J=6.1 Hz, 2H), 4.46 (q, J=7.1 Hz, 2H), 3.18 (s, 3H), 1.26 (t, J=7.1 Hz, 3H). MS (m/e) positive mode: 427 (M+H)$^+$.

EXAMPLE 237 methyl 3-{[4-({[(4-amino-5-cyano-6-ethoxypyridin-2-yl)carbonyl]amino}methyl)piperidin-1-yl]carbonyl}benzoate The titled compound was prepared according to the procedure described in Example 194B, substituting isophthalic acid monomethyl ester for terephthalic acid monomethyl ester. $^1$H NMR (300 MHz, DMSO-d$_6$) δ 8.52 (t, J=6.6 Hz, 1H), 8.01 (dt, J=7.5, 1.8 Hz, 1H), 7.89 (t, J=1.8 Hz, 1H), 7.65 (dt, J=7.5, 1.5 Hz, 1H), 7.60 (t, J=7.8 Hz, 1H), 7.30 (broad s, 2H), 7.04 (s, 1H), 4.47 (q, J=7.2 Hz, 2H), 4.02 (m, 1H), 3.87 (s, 3H), 3.50 (m, 1H), 3.19 (t, J=6.3 Hz, 2H), 3.02 (m, 1H), 2.78 (m, 1H), 1.85 (m, 1H), 1.71 (m, 1H), 1.56 (m, 1H), 1.32 (d, J=7.2 Hz, 3H), and 1.12 (m, 2H). MS (m/e) positive mode: 466 (M+H)$^+$; negative mode: 464 (M−H)$^−$.

EXAMPLE 238

4-amino-N-[(5-chlorothien-2-yl)methyl]-5-cyano-6-ethoxypyridine-2-carboxamide

The titled compound was prepared according to the procedure described in Example 104B, substituting C-(5-Chlorothiophen-2-yl)-methylamine for 2,5-dimethoxy-benzylamine. $^1$H NMR (300 MHz, DMSO-d$_6$) δ 9.13 (t, J=6.4 Hz, 1H), 7.33 (bs, 2H), 7.07 (s, 1H), 6.95 (d, J=3.7 Hz, 1H), 6.87 (d, J=3.7 Hz, 1H), 4.51 (d, J=6.4 Hz, 2H), 4.49 (q, J=7.1 Hz, 2H), 1.31 (t, J=7.1 Hz, 3H). MS (m/e) 337 (M+H)$^+$.

EXAMPLE 239

4-amino-5-cyano-6-(cyclopropylamino)-N-[4-(methylsulfonyl)benzyl]pyridine-2-carboxamide The titled compound was prepared according to the procedure described in Example 189, substituting cyclopropylamine for cyclopentylamine used in Example 189. Yield is 85%. $^1$H NMR (300 MHz, DMSO-d$_6$) δ 8.97 (t, J=6.0 Hz, 1H), 7.89 (d, J=9.0 Hz, 2H), 7.55 (d, J=9.0 Hz, 2H), 6.91 (s, 2H), 6.79 (d, J=3.0 Hz, 1H), 6.75 (s, 1H), 3.18 (s, 3H), 3.08 (m, 1H), 0.66 (m, 2H), 0.57 (m, 2H); MS (APCI) m/z 386 [M+H]$^+$, 384 [M−H]$^−$.

EXAMPLE 240

4-amino-6-ethoxy-5-iodo-N-[4-(methylsulfonyl)benzyl]pyridine-2-carboxamide

Example 240A 4-amino-5-iodo-6-ethoxy-pyridine-2-carboxylic acid

The titled compound was prepared according to the procedure described in Example 165C, substituting N-iodosuccinimide for N-chlorosuccinimide.

Example 240B 4-amino-6-ethoxy-5-iodo-N-[4-(methylsulfonyl)benzyl]pyridine-2-carboxamide The titled compound was prepared according to the procedure described in Example 104B, substituting 4-methanesulfonyl-benzylamine for 2,5-dimethoxybenzylamine, and substituting Example 240A for Example 104A. $^1$H NMR (300 MHz, DMSO-d$_6$) δ 9.09 (t, J=6.6 Hz, 1H), 7.88 (d, J=8.7 Hz, 2H), 7.54 (d, J=8.4 Hz, 2H), 7.02 (s, 1H), 6.39 (broad s, 2H), 4.56 (d, J=6.3 Hz, 2H), 4.42 (q, J=7.2 Hz, 2H), 3.17 (s, 3H), and 1.32 (d, J=6.9, 3H). MS (m/e) positive mode: 476 (M+H)$^+$; negative mode: 474 (M−H)$^−$.

EXAMPLE 241 tert-butyl 3-{[4-amino-3-cyano-6-({[4-(methylsulfonyl)benzyl]amino}carbonyl)pyridin-2-yl]amino}pyrrolidine-1-carboxylate The titled compound (36%) was prepared according to the procedure described in Example 189, substituting 3-amino-pyrrolidine-1-carboxylic acid-tert-butyl ester for cyclopentylamine used in Example 189. $^1$H NMR (300 MHz, DMSO-d$_6$) δ 9.10 (t, J=6.0 Hz, 1H), 7.88 (d, J=9.0 Hz, 2H), 7.53 (d, J=9.0 Hz, 2H), 6.95 (s, 2H), 6.76 (s, 1H), 6.66 (d, J=9.0 Hz, 1H), 4.4 (m, 1H), 4.56 (d, J=4.5 Hz, 1H), 3.63 (m, 1H), 3.41 (m, 1H), 3.27 (m, 1H), 3.10 (m, 1H), 3.17 (s, 1H), 1.39 (m, 9H); MS (APCI) m/z 515 [M+H]$^+$, 513 [M−H]$^−$.

EXAMPLE 242

4-amino-5-cyano-6-ethoxy-N-(2-hydroxybenzyl)pyridine-2-carboxamide

The titled compound was prepared according to the procedure described in Example 104B, substituting 2-hydroxybenzylamine for 2,5-dimethoxy-benzylamine. $^1$H NMR (300 MHz, DMSO-d$_6$) δ 9.64 (s, 1H), 8.89 (t, J=6.1 Hz, 1H), 7.32 (bs, 2H), 7.08 (s, 1H), 7.11-7.04 (m, 2H), 6.85-6.71 (m, 2H), 4.47 (q, J=7.1 Hz, 2H), 4.42 (d, J=6.1 Hz, 2H), 1.32 (t, J=7.1 Hz, 3H). MS (m/e) 313 (M+H)$^+$.

EXAMPLE 243

4-amino-5-cyano-6-ethoxy-N-(4-pentanoylbenzyl)pyridine-2-carboxamide

The titled compound was prepared according to the procedure described in Example 104B, substituting 1-(4-aminomethyl-phenyl)-petan-1-one trifluoroacetic acid salt for 2,5-dimethoxybenzylamine used in Example 104B. $^1$H NMR (300 MHz, DMSO-d$_6$) δ 9.14 (t, J=6.3 Hz, 1H), 7.92 (d, J=8.5 Hz, 2H), 7.41 (d, J=8.1 Hz, 2H), 7.33 (s, 2H), 7.07 (s, 1H), 4.53 (d, J=7.1 Hz, 2H), 4.51 (q, J=6.9 Hz, 2H), 2.98 (m, J=7.1 Hz, 2H), 1.58 (m, 2H), 1.41-1.25 (m, 2H), 1.32 (t, J=7.0 Hz, 3H), 0.89 (t, J=7.3 Hz, 3H). MS (m/e) positive mode: 381 (M+H)$^+$.

EXAMPLE 244

4-amino-5-cyano-6-ethoxy-N-[3-methoxy-4-(methylsulfonyl)benzyl]pyridine-2-carboxamide The titled compound was prepared according to the procedure described in Example 180, substituting 3-methoxy-4- fluorobenzonitrile for 4-fluoro-3-trifluoromethylbenzonitrile used in Example 180A. $^1$H NMR (300 MHz, DMSO-d$_6$) δ 9.14 (t, J=6.4 Hz, 1H), 7.74 (d, J=8.1 Hz, 1H), 7.32 (s, 2H), 7.24 (s, 1H), 7.07 (s, 1H), 7.04 (d, J=8.1 Hz, 1H), 4.54 (d, J=7.0 Hz, 2H), 4.52 (q, J=7.0 Hz, 2H), 3.93 (s, 3H), 3.20 (s, 3H), 1.32 (t, J=7.0 Hz, 3H). MS (m/e) positive mode: 405 (M+H)$^+$; negative mode: 403 (M−H)$^−$.

EXAMPLE 245

4-amino-5-cyano-6-ethoxy-N-[(5-pyridin-2-ylthien-2-yl)methyl]pyridine-2-carboxamide In a 20 mL vial a solution of Example 104A (32.5 mg, 0.16 mmol) dissolved in N,N-dimethylacetamide (0.8 mL) was added, followed by the addition of O-benzotriazol-1-yl-N,N,N',N'-tetramethyluronium tetrafluoroborate (50.4 mg, 0.16 mmol) dissolved in N,N-dimethylacetamide (0.8 mL). Then, commercially available [5-(2-pyridinyl)-2-thienyl]methylamine (36.2 mg, 0.19 mmol) dissolved in N,N-dimethylacetamide (0.6 mL) was added followed by the addition of diisopropyl ethyl amine (57.9 uL, 0.31 mmol) dissolved in N,N-dimethylacetamide (0.8 mL). The mixture was shaken at room temperature overnight. The reaction was checked by LC/MS and concentrated to dryness. The residue was dissolved in 1:1 dimethyl sulfoxide/methanol and purified by reverse phase HPLC (0-70% CH$_3$CN in 10 mM aq. ammonium acetate) to give the titled compound. $^1$H NMR (500 MHz, DMSO-d$_6$) δ ppm 1.08-1.28 (m, 3H) 1.29-1.37 (m, 2H) 4.25-4.53 (m, 2H) 4.54-4.69 (m, 2H) 6.95-7.06 (m, 1H) 7.09-7.12 (m, 1H) 7.16-7.32 (m, 1H) 7.49-7.64 (m, 1H) 7.68-7.91 (m, 2H) 8.31-8.52 (m, 1H); MS (ESI) positive ion 380 (M+H).

EXAMPLE 246

4-amino-5-cyano-6-ethoxy-N-[(6-fluoropyridin-3-yl)methyl]pyridine-2-carboxamide

The titled compound was prepared according to the procedure described in Example 104B, substituting C-(6-Fluoropyridin-3-yl)-methylamine (J. C. S. 1970, page 1517) for 2,5-dimethoxy-benzylamine. $^1$H NMR (300 MHz, DMSO-d$_6$) δ 9.13 (t, J=5.8 Hz, 1H), 8.19-8.17 (m, 1H), 7.91 (dd, J=2.4, 8.5 Hz, 1H), 7.33 (bs, 2H), 7.14 (dd, J=2.7, 8.5 Hz, 1H), 7.06 (s, 1H), 4.50 (q, J=7.1 Hz, 2H), 4.48 (d, J=5.8 Hz, 2H), 1.32 (t, J=7.1 Hz, 3H). MS (m/e) 316 (M+H)$^+$.

EXAMPLE 247

4-amino-N-[(1-benzylpiperidin-4-yl)methyl]-5-cyano-6-ethoxypyridine-2-carboxamide The titled compound was prepared according to the procedure described in Example 104B, substituting commercially available C-(1-benzyl-piperidin-4-yl)-methylamine for 2,5-dimethoxybenzylamine used in Example 104B. $^1$H NMR (500 MHz, DMSO-d$_6$) δ 9.17 (broad s, 1H), 8.57 (t, J=6.5 Hz, 1H), 7.48 (m, 6H), 7.22 (broad s, 2H), 7.03 (s, 1H), 4.48 (q, J=7.0 Hz, 2H), 4.26 (d, J=5.0 Hz, 2H), 3.18 (t, J=6.5 Hz, 2H), 2.90 (q, J=12.5 Hz, 2H), 2.01 (m, 3H), 1.36 (q, J=13.5 Hz, 2H), and 1.32 (d, J=7.5 Hz, 3H). MS (m/e) positive mode: 394 (M+H)$^+$; negative mode: 392 (M−H)$^−$.

EXAMPLE 248

4-amino-N-[(2-chloropyridin-3-yl)methyl]-5-cyano-6-ethoxypyridine-2-carboxamide

The titled compound was prepared according to the procedure described in Example 104B, substituting C-(2-Chloropyridin-3-yl)-methylamine (J. Med. Chem. 46, 4, 2003, 453-456) for 2,5-dimethoxy-benzylamine. $^1$H NMR (300 MHz, DMSO-d$_6$) δ 9.15 (t, J=6.4 Hz, 1H), 8.32 (dd, J=2.4, 5.1 Hz, 1H), 7.63 (dd, J=2.4, 7.8 Hz, 1H), 7.42 (dd, J=5.1, 7.8 Hz, 1H), 7.36 (bs, 2H), 7.07 (s, 1H), 4.52 (d, J=6.4 Hz, 2H), 4.52 (q, J=7.1 Hz, 2H), 1.33 (t, J=7.1 Hz, 3H). MS (m/e) 332 (M+H)$^+$.

EXAMPLE 249

N-(4-amino-5-cyano-6-ethoxypyridin-2-yl)-2-[2,5-dimethoxy-4-(methylsulfonyl)phenyl]acetamide To a solution of 55 mg (0.31 mmol) of Example 1A in 3 mL of pyridine and 3 mL of dichloromethane at −78° C. was added 3 mL (0.55 mmol) of a solution of 0.18 M Example 197G in dichloromethane. The mixture was stirred at −78° C. for 20 min, then 3 mL of water was added. The reaction was allowed to warm until the ice had melted, then the solvents were removed in vacuo. The residue was taken up in 15 mL of ethyl acetate and 10 mL of hexanes, then extracted with water (1×3 mL), 1M HCl (3×3 mL), saturated NaHCO$_{3(aq)}$ (3×3 mL), and brine (1×3 mL), dried over MgSO$_4$, filtered, and concentrated in vacuo to a solid. This was recrystallized from 2 mL of methanol in a capped 4 mL vial to give 34 mg (25%) of the titled compound as a colorless solid. $^1$H NMR (300 MHz, DMSO-d$_6$) δ ppm 10.27 (s, 1H), 7.30 (s, 1H), 7.26 (s, 1H), 7.10 (s, 1H), 6.88 (s, 2H), 4.35 (q, J=7.0 Hz, 2H), 3.89 (s, 3H), 3.82 (s, 2H), 3.76 (s, 3H), 3.24 (s, 3H), 1.32 (t, J=7.1 Hz, 3H); MS (ESI+) m/z=435 [M+H]$^+$. Anal. Calc'd for C$_{19}$H$_{22}$N$_4$O$_6$S.0.25CH$_3$OH: C, 52.25; H, 5.24; N, 12.66. Found: C, 52.01; H, 4.85; N, 12.50.

EXAMPLE 250

4-amino-5-cyano-6-ethoxy-N-[4-(morpholin-4-ylcarbonyl)benzyl]pyridine-2-carboxamide The titled compound was prepared according to the procedure described in Example 231B, substituting morpholine for methylamine. $^1$H NMR 300 MHz, DMSO-d$_6$) δ ppm 1.32 (t, J=7.1 Hz, 3H), 3.57 (bs, 4H), 4.46-4.55 (m, 4H), 7.07 (s, 1H), 7.27-7.41 (m, 6H), 9.10 (t, J=6.4 Hz, 1H). MS (ESI+) m/e=410 (M+H)$^+$.

EXAMPLE 251 ethyl 2-[5-({[(4-amino-5-cyano-6-ethoxypyridin-2-yl)carbonyl]amino}methyl pyridin-2-yl]benzoate The title compound was prepared according to the procedure described in Example 160, substituting 2-ethoxycarbonylphenylboronic acid for 3-methoxycarbonylphenylboronic acid. $^1$H NMR (300 MHz, DMSO-d$_6$) δ 9.16 (t, J=6.27 Hz, 1H), 8.53 (d, J=1.70 Hz, 1H), 7.79 (dd, J=8.14, 2.37 Hz, 1H), 7.57-7.69 (m, 4H), 7.52 (ddd, J=7.54, 6.02, 2.71 Hz, 1H), 7.33 (s, 2H), 7.08 (s, 1H), 4.53 (d, J=6.10 Hz, 2H), 4.51 (q, J=7.12 Hz, 2H), 4.02 (q, J=7.12 Hz, 2H), 1.32 (t, J=7.12 Hz, 3H), and 0.93 (t, J=7.12 Hz, 3H); MS (ESI) m/e positive ion 468 [M+Na]$^+$, 446 [M+H]$^+$; negative ion 444 [M−H]$^−$.

EXAMPLE 252

Trans-4-amino-5-cyano-6-ethoxy-N-({4-[(methylsulfonyl)amino]cyclohexyl}methyl)pyridine-2-carboxamide The titled compound was prepared according to the procedure described in Example 288B, substituting Example 289 for Example 288A. $^1$H NMR (300 MHz, DMSO-$d_6$) δ 8.44 (t, J=6.1 Hz, 1H), 7.29 (s, 2H), 7.03 (s, 1H), 6.95 (d, J=7.5 Hz, 1H), 4.48 (q, J=7.1 Hz, 2H), 3.10 (t, J=6.4 Hz, 1H), 2.88 (s, 3H), 1.89 (d, J=8.5 Hz, 2H), 1.68 (d, J=11.5 Hz, 2H), 1.32 (t, J=7.1 Hz, 3H), 1.25-0.91 (m, 4H). MS (m/e) positive mode: 396 μM+H)$^+$.

EXAMPLE 253 isobutyl 4-({[(4-amino-5-cyano-6-ethoxypyridin-2-yl)carbonyl]amino}methyl)piperidine-1-carboxylate To Example 194 (20 mg, 0.07 mmol) in dichloromethane (0.2 mL) was added triethylamine (10 mg, 0.10 mmol) and isobutyl chloroformate (14 mg, 0.1 mmol) at −50° C. The mixture was stirred at r.t for 1 h and the crude mixture was purified by silica gel flash column eluting with 100% ethyl acetate to give the title compound (21 mg, 89%). $^1$H NMR (500 MHz, DMSO-$d_6$) δ 8.50 (t, J=6.5 Hz, 1H), 7.30 (broad s, 2H), 7.04 (s, 1H), 4.48 (q, J=7.0 Hz, 2H), 3.96 (broad d, J=13.5 Hz, 2H), 3.76 (d, J=6.0 Hz, 2H), 3.16 (t, J=7.0 Hz, 2H), 2.75 (broad s, 2H), 1.84 (septet, J=7.0 Hz, 1H), 1.74 (m, 1H), 1.61 (d, J=11.0 Hz, 2H), 1.32 (d, J=7.0 Hz, 2H), and 1.03 (dq, J=4.5, 13.0 Hz, 2H). MS (m/e) positive mode: 338 (M+H)$^+$; negative mode: 336 (M−H)$^-$.

EXAMPLE 254

2-(4-acetyl-4-phenylpiperidin-1-yl)-N-(4-amino-5-cyano-6-ethoxypyridin-2-yl)acetamide

Example 254A

N-(4-Amino-5-cyano-6-ethoxy-pyridin-2-yl)-2-bromoacetamide

To a solution of 770 mg (4.32 mmol) of Example 1A dissolved in 14 mL of 1:1 pyridine:dichloromethane at −78° C. was added 0.66 mL (7.8 mmol) of bromoacetyl bromide. The reaction mixture was poured into 140 mL of ice cold $H_2O$ and the resulting precipitate was filtered and rinsed with water. The solid was dried under vacuum to yield 1.0 g (3.32 mmol) of an orange solid (77% yield). $^1$H NMR (300 MHz, $d_6$-DMSO) δ 10.50 (s, 1H), 7.16 (s, 1H), 6.99 (s, 2H), 4.30-4.37 (q, J=7.12 Hz, 2H), 4.11 (s, 2H), 1.28-1.33 (t, J=7.12 Hz, 3H); MS (ESI) m/e=300 (M+H)$^+$, 298 (M−H)$^-$.

Example 254B 2-(4-acetyl-4-phenylpiperidin-1-yl)-N-(4-amino-5-cyano-6-ethoxypyridin-2-yl)acetamide To a solution of 30 mg (0.11 mmol) of Example 254A in 0.5 mL of N,N-dimethylformamide was added 41 mg (0.2 mmol) of 1-(4-phenyl-piperidine-4-yl)-ethanone and 0.05 mL (0.3 mmol) of N,N-diisopropylethylamine. The reaction stirred at room temperature for 1 h. It was concentrated under high vacuum with heating and the resulting solid was recrystallized from methanol to give 25 mg of a white solid (59% yield). $^1$H NMR (300 MHz, $d_6$-DMSO) δ 9.54 (s, 1H), 7.28-7.42 (m, 5H), 7.18 (s, 1H), 6.96 (s, 2H), 425-4.32 (q, J=7.12 Hz, 2H), 3.29 (s, 1H), 2.65-2.68 (m, 2H), 2.37-2.43 (m, 4H), 1.97-2.04 (m, 2H), 1.69 (s, 3H), 1.25-1.30 (t, J=7.12 Hz, 3H); MS (ESI) m/e=422 (M+H)$^+$, 420 (M−H)$^-$.

EXAMPLE 255

4-amino-5-cyano-6-ethoxy-N-[(1-pyridin-2-ylpiperidin-4-yl)methyl]pyridine-2-carboxamide The titled compound was prepared according to the procedure described in Example 104B, substituting C-(3,4,5,6-Tetrahydro-2H-[1,2']bipyridinyl-4-yl)-methylamine (*J. Med. Chem.* 1999, 42, 17, 3342-3355) for 2,5-dimethoxy-benzylamine. $^1$H NMR (300 HZ, DMSO-$d_6$) δ 8.50 (t, J=6.4 Hz, 1H), 8.10-8.05 (m, 1H), 7.52-7.45 (m, 1H), 7.30 (bs, 2H), 7.04 (s, 1H), 6.82-6.78 (m, 1H), 6.59-6.55 (m, 1H), 4.48 (q, J=7.1 Hz, 2H), 4.33-4.22 (m, 2H), 3.20-3.15 (m, 2H), 2.81-2.67 (m, 2H), 1.95-1.74 (m, 1H), 1.73-1.62 (m, 2H), 1.32 (t, J=7.1 Hz, 3H), 1.15-1.03 (m, 2H). MS (m/e) 381 (M+H)$^+$.

EXAMPLE 256

4-amino-5-cyano-6-ethoxy-N-{4-[(methylamino)sulfonyl]benzyl}pyridine-2-carboxamide The title compound was prepared according to the procedure described in Example 104B, substituting 4-aminomethyl-N-methyl-benzenesulfonamide (Ishidate; Momose *Chem. Abstr.* 1947, 214) for 2,5-dimethoxybenzylamine. $^1$H NMR (300 MHz, DMSO-$d_6$) δ 9.17 (t, J=6.27 Hz, 1H), 7.73 (d, J=8.14 Hz, 2H), 7.49 (d, J=8.48 Hz, 2H), 7.35-7.43 (m, 1H), 7.33 (s, 2H), 7.08 (s, 1H), 4.55 (d, J=5.76 Hz, 2H), 4.51 (q, J=7.35 Hz, 2H), 2.39 (d, J=5.09 Hz, 3H), and 1.32 (t, J=6.95 Hz, 3H); MS (ESI) m/e positive ion 412 [M+Na]$^+$, 390 [M+H]$^+$; negative ion 388 [M−H]$^-$.

EXAMPLE 257 methyl 1-{2-[(4-amino-5-cyano-6-ethoxypyridin-2-yl)amino]-2-oxoethyl}piperidine-4-carboxylate To a solution of 60 mg (0.2 mmol) of Example 254A in 1.0 mL of N,N-dimethylformamide was added 0.05 mL (0.4 mmol) of methyl isonipecotate and 0.1 mL (0.6 mmol) of N,N-diisopropylethylamine. The reaction stirred at room temperature for 2 h. It was concentrated under high vacuum with heating and the resulting solid was recrystallized from methanol to give 50 mg of a white solid (69% yield). $^1$H NMR (300 MHz, $d_6$-DMSO) δ 9.53 (s, 1H), 7.18 (s, 1H), 6.97 (s, 2H), 4.27-4.34 (q, J=7.12 Hz, 2H), 3.61 (s, 3H), 3.14 (s, 2H), 2.78-2.82 (m, 2H), 2.20-2.31 (m, 3H), 1.81-1.86 (m, 2H), 1.58-1.66 (m, 2H), 1.27-1.32 (t, J=7.12 Hz, 3H); MS (ESI) m/e=362 (M+H)$^+$, 360 (M−H)$^-$.

EXAMPLE 258

5-chloro-6-ethoxy-N-[4-(methylsulfonyl)benzyl]pyridine-2-carboxamide

Step A

To a suspension of Example 165 (231 mg, 1 mmol) in aqueous HCl (6 N, 1.5 mL) was added $NaNO_2$ (104 mg, 1.5 mmol) in water (1 mL) dropwise at 0° C. The mixture was stirred for 10 min and transferred to KI (2.5 g, 15 mmol) in water (3 mL) at 0° C. The mixture was stirred for 30 min and extracted with ethyl acetate. The crude was treated with LiOH (2N, ethanol:water 5:3) until pH>12. The mixture was then stirred at r.t for 2 h and acidified with HCl(aq). The precipitates were collected (280 mg) and dissolved in N,N-dimethylformamide (2 mL) followed by addition of 4-methanesulfonyl-benzylamine hydrochloride (189 mg, 0.86 mmol), triethylamine (300 mg, 3 mmol), and O-benzotriazol-1-yl-N,N,N',N'-tetramethyluronium tetrafluoroborate (276 mg, 0.86 mmol). The mixture was stirred overnight and partitioned between ethyl acetate and water. The organic layer was washed with brine, drived over $Na_2SO_4$, filtered, and evaporated in vacuo. The residue was purified by silica gel flash chromatography eluting with 100% ethyl acetate to give 5-chloro-6-ethoxy-4-iodo-pyridine-2-carboxylic acid 4-methanesulfonyl-benzylamide (160 mg, 32% 3 steps).

Step B

This material obtained from step A (50 mg, 0.1 mmol) was dissolved in N,N-dimethylformamide (0.1 mL) followed by addition of t-butyl acrylate (25 mg, 0.2 mmol), $(Tol)_3P$ (6 mg, 0.02 mmol), palladium(II) acetate (2 mg, 0.01 mmol), and triethylamine (20 mg, 0.2 mmol). The mixture was heated to 100° C. for 2 h, cooled to room temperature, and partitioned between ethyl acetate and water. The organic layer was washed with brine, drived over $Na_2SO_4$, filtered and evaporated in vacuo. The residue was purified by silica gel flash chromatography eluting with 100% ethyl acetate to provide the title compound (4 mg, 10%). $^1H$ NMR (500 MHz, DMSO-$d_6$) δ 9.29 (t, J=6.0 Hz, 1H), 8.05 (d, J=7.5 Hz, 1H), 7.88 (d, J=8.5 Hz, 2H), 7.61 (d, J=8.0 Hz, 1H), 7.57 (d, J=8.0 Hz, 2H), 4.60 (d, J=7.0 Hz, 2H), 4.59 (q, J=7.0 Hz, 2H), 3.18 (s, 3H), and 1.38 (d, J=7.0, 3H). MS (m/e) positive mode: 369, 71 (3:1, M+H)$^+$.

EXAMPLE 259

4-amino-5-cyano-6-ethoxy-N-(4-heptanoylbenzyl)pyridine-2-carboxamide

The titled compound was prepared according to the procedure described in Example 104B, substituting 1-(4-aminomethyl-phenyl)-heptan-1-one trifluoroacetic acid salt for 2,5-dimethoxybenzylamine used in Example 104B. $^1H$ NMR (300 MHz, DMSO-$d_6$) δ 9.14 (t, J=6.4 Hz, 1H), 7.91 (d, J=8.5 Hz, 2H), 7.41 (d, J=8.1 Hz, 2H), 7.33 (s, 2H), 7.07 (s, 1H), 4.53 (d, J=6.8 Hz, 2H), 4.51 (q, J=7.0 Hz, 2H), 2.97 (t, J=7.3 Hz, 2H), 1.59 (m, 2H), 1.32 (t, J=7.0 Hz, 3H), 1.26 (m, 6H), 0.86 (m, 3H). MS (m/e) positive mode: 409 (M+H)$^+$.

EXAMPLE 260

4-amino-5-cyano-6-ethoxy-N-[4-(pyridin-2-yloxy)benzyl]pyridine-2-carboxamide

The titled compound was prepared according to the procedure described in Example 104B, substituting 4-(pyridin-2-yloxy)-benzylamine (EP1348698 A1) for 2,5-dimethoxybenzylamine. $^1H$ NMR (300 MHz, DMSO-$d_6$) δ 9.07 (t, J=6.4 Hz, 1H), 8.15-8.12 (m, 1H), 7.87-7.79 (m, 1H), 7.37-7.32 (m, 4H), 7.12-6.98 (m, 5H), 4.51 (q, J=7.1 Hz, 2H), 4.48 (d, J=6.4 Hz, 2H), 1.32 (t, J=7.1 Hz, 3H). MS (m/e) 390 (M+H)$^+$.

EXAMPLE 261

4-amino-5-cyano-6-ethoxy-N-(1,3-thiazol-5-ylmethyl)pyridine-2-carboxamide

In a 20 mL vial a solution of Example 104A (32.5 mg, 0.16 mmol) dissolved in N,N-dimethylacetamide (0.8 mL) was added, followed by the addition of O-benzotriazol-1-yl-N,N,N',N'-tetramethyluronium tetrafluoroborate (50.4 mg, 0.16 mmol) dissolved in N,N-dimethylacetamide (0.8 mL). Then, 5-(aminomethyl)thiazole (21.7 mg, 0.19 mmol) dissolved in N,N-dimethylacetamide (0.6 mL) was added followed by the addition of diisopropyl ethyl amine (57.9 uL, 0.31 mmol) dissolved in N,N-dimethylacetamide (0.8 mL). The mixture was shaken at room temperature overnight. The reaction was checked by LC/MS and concentrated to dryness. The residue was dissolved in 1:1 dimethyl sulfoxide/methanol and purified by reverse phase HPLC (0-70% $CH_3CN$ in 10 mM aq. ammonium acetate) to give the titled compound. $^1H$ NMR (500 MHz, DMSO-$d_6$) δ ppm 1.25-1.39 (m, 3H) 4.43-4.54 (m, 2H) 4.58-4.68 (m, 2H) 7.04-7.14 (m, 1H) 7.37-7.45 (m, 1H) 8.83-9.19 (m, 1H); MS (ESI) positive ion 304 (M+H).

EXAMPLE 262

N-(4-amino-5-cyano-6-ethoxypyridin-2-yl)-2-[2-(methylthio)phenyl]acetamide

Example 262A

2-Methylsulfanyl-benzyl alcohol

To a solution of 1.00 g (6.57 mmol) of 2-methylsulfanyl-benzaldehyde in 10 mL of ethanol at 0° C. was added 250 mg of $NaBH_4$. The reaction was stirred at 0° C. for 10 min, then diluted with 50 mL of water. The aqueous suspension was extracted with diethyl ether (3×15 mL), then the combined ether layers were back extracted with brine (1×10 mL), dried over $MgSO_4$, filtered, and concentrated in vacuo to 1.01 g (100%) of the titled compound as an oil.

Example 262B

1-Chloromethyl-2-methylsulfanyl-benzene

To a solution of 1.01 g (6.57 mmol) of Example 262A and 550 mg (13.0 mmol) of lithium chloride in 20 mL of N,N-dimethylformamide was added 1.5 mL (20.6 mmol) of thionyl chloride. The reaction warmed spontaneously, then cooled to ambient temperature. After 45 min, 100 mL of water was added, then the aqueous suspension was extracted with diethyl ether (3×20 mL). The combined ether layers were back extracted with water (2×20 mL), and brine (1×20 mL), dried over $MgSO_4$, filtered, and concentrated to 978 mg (86%) of the titled compound as an oil.

Example 262C (2-Methylsulfanyl-phenyl)-acetonitrile

To a solution of 978 mg (5.66 mmol) of Example 262B in 10 mL of acetonitrile was added 737 mg (11.3 mmol) of potassium cyanide, then 150 mg (0.57 mmol) of 18-Crown-6. The reaction was stirred at reflux under $N_2$ for 24 h, then the solvents were removed in vacuo. The residue was taken up in 30 mL of diethyl ether and washed with water (3×10 mL), then brine (1×10 mL), dried over $MgSO_4$, filtered, and concentrated in vacuo to an oil. This was purified via silica gel chromatography, eluting with a 5-30% ethyl acetate in hexanes gradient to give 725 mg (78%) of the titled compound.

Example 262D (2-Methylsulfanyl-phenyl)-acetic acid

To 520 mg (3.19 mmol) of Example 262C was added 3 mL of 12 M HCl$_{(aq.)}$. The reaction was stirred at 80° C. for 24 h, then 15 mL of water was added, and the aqueous suspension was extracted with diethyl ether (3×10 mL). The combined ether layers were back extracted with 0.6M NaHCO$_{3(aq.)}$ (2×10 mL). The combined NaHCO$_3$ layers were then extracted with diethyl ether (1×10 mL) and all the ether layers were set aside. The NaHCO$_3$ solution was acidified with 3 mL of 6 M HCl$_{(aq.)}$, then the aqueous suspension was extracted with ether (2×10 mL). The last set of ether layers was extracted with brine (1×10 mL), dried over MgSO$_4$, filtered, and concentrated in vacuo to give the titled compound as a white solid.

Example 262E

N-(4-amino-5-cyano-6-ethoxypyridin-2-yl)-2-[2-(methylthio)phenyl]acetamide

To 200 mg (1.10 mmol) of Example 262D in 3 mL of dichloromethane was added 800 µL (9.17 mmol) of oxalyl chloride. The reaction was stirred at ambient temperature for 16 h, then the solvents were removed in vacuo. The residue was taken up in 3 mL of dichloromethane and this solution was added to a solution of 100 mg (0.562 mmol) of Example 1A in 1 mL of pyridine and 1 mL of dichloromethane at −78° C. This was stirred at −78° C. for 20 min, then 1 mL of water was added, and the solution was warmed until the ice had melted. The solvents were removed in vacuo, then the residue was taken up in 10 mL of ethyl acetate and 2 mL of hexanes. This was extracted with 1 M HCl$_{(aq.)}$ (3×5 mL), saturated NaHCO$_{3(aq.)}$ (2×5 mL), water (1×5 mL), and brine (1×5 mL), dried over MgSO$_4$, filtered, and concentrated in vacuo to a solid. The solid was recrystallized from ethyl acetate to give 65 mg (34%) of colorless crystals. $^1$H NMR (300 MHz, DMSO-d$_6$) δ ppm 10.30 (s, 1H), 7.29 (m, 2H), 7.23 (m, 1H), 7.13 (m, 2H), 6.88 (s, 2H), 4.35 (q, J=7.1 Hz, 2H), 3.83 (s, 2H), 2.43 (s, 3H), 1.31 (t, J=7.0 Hz, 3H); MS (ESI+) m/z=343 [M+H]$^+$. Anal. Calc'd for C$_{17}$H$_{18}$N$_4$O$_2$S: C, 59.63; H, 5.30; N, 16.36. Found: C, 59.47; H, 4.96; N, 15.97.

EXAMPLE 263

4-amino-5-cyano-6-(3-methoxyphenyl)-N-[4-(methylsulfonyl)benzyl]pyridine-2-carboxamide The titled compound was prepared according to the procedure described in Example 192, substituting 3-methoxyphenylboronic acid for 3-thienylboronic acid used in Example 192. Yield is 70%. $^1$H NMR (300 MHz, DMSO-d$_6$) δ 9.34 (t, J=6.0 Hz, 1H), 7.87 (d, J=9.0 Hz, 2H), 7.55 (d, J=9.0 Hz, 2H), 7.45-7.41 (m, 2H), 7.42 (s, 1H), 7.39 (s, 2H), 7.10 (m, 1H), 4.58 (d, J=6.0 Hz, 2H), 3.83 (s, 3H), 3.16 (s, 3H); MS (APCI) m/z 437 [M+H]$^+$, 435 [M−H]$^−$.

EXAMPLE 264 methyl trans-N-{[4-({[(4-amino-5-cyano-6-ethoxy-pyridin-2-yl)carbonyl]amino}methyl)cyclohexyl]carbonyl}-L-norleucinate Example 264A methyl trans-N-[(4-{[(tert-butoxycarbonyl)amino]methyl}cyclohexyl)carbonyl]-L-norleucinate The titled compound was prepared according to the procedure described in Example 104B, substituting 4-(tert-butoxycarbonylamino-methyl)-cyclohexanecarboxylic acid for Example 104A, and substituting norlucine methyl ester hydrochloride for 2,5-dimethoxybenzylamine.

Example 264B methyl trans-N-{[4-(aminomethyl)cyclohexyl]carbonyl}-L-norleucinate Example 264A was treated with trifluoroacetic acid/dichloromethane for 2 h at room temperature. Evaporation of volatile organic matters in vacuo provided the titled compound as the trifluoroacetic acid salt.

Example 264C methyl trans-N-{[4-({[(4-amino-5-cyano-6-ethoxy-pyridin-2-yl)carbonyl]amino}methyl)cyclohexyl]carbonyl}-L-norleucinate The titled compound was prepared according to the procedure described in Example 104B, substituting the amine from Example 264B for 2,5-dimethoxybenzylamine. $^1$H NMR (300 MHz, DMSO-d$_6$) δ 8.42 (t, J=6.3 Hz, 1H), 8.03 (d, J=7.5 Hz, 1H), 7.29 (s, 2H), 7.04 (s, 1H), 4.48 (q, J=7.1 Hz, 2H), 4.18 (m, 1H), 3.60 (s, 3H), 3.12 (t, J=6.6 Hz, 2H), 2.14 (t, J=11.7 Hz, 1H), 1.72 (d, J=11.2 Hz, 4H), 1.70-1.41 (m, 4H), 1.32 (t, J=7.1 Hz, 3H), 1.40-1.17 (m, 4H), 1.02-0.89 (m, 2H), 0.85 (m, 3H). MS (m/e) positive mode: 474 (M+H)$^+$.

EXAMPLE 265

4-amino-5-cyano-6-ethoxy-N-[(4-methyl-1H-imidazol-2-yl)methyl]pyridine-2-carboxamide In a 20 mL vial a solution of Example 104A (32.5 mg, 0.16 mmol) dissolved in N,N-dimethylacetamide (0.8 mL) was added, followed by the addition of O-benzotriazol-1-yl-N,N,N',N'-tetramethyluronium tetrafluoroborate (50.4 mg, 0.16 mmol) dissolved in N,N-dimethylacetamide (0.8 mL). Then, c-(4-Methyl-1H-imidazol-2-yl)-methylamine hydrochloride (21.1 mg, 0.19 mmol) dissolved in N,N-dimethylacetamide (0.6 mL) was added followed by the addition of diisopropyl ethyl amine (57.9 uL, 0.31 mmol) dissolved in N,N-dimethylacetamide (0.8 mL). The mixture was shaken at room temperature overnight. The reaction was checked by LC/MS and concentrated to dryness. The residue was dissolved in 1:1 dimethyl sulfoxide/methanol and purified by reverse phase (0-70% CH$_3$CN in 10 mM aq. ammonium acetate) to give the titled compound. $^1$H NMR (500 MHz, DMSO-d$_6$) δ ppm 1.08-1.48 (m, 3H) 1.88-2.28 (m, 2H) 4.28-4.46 (m, 2H) 4.47-4.58 (m, 2H) 6.32-6.82 (m, 1H) 6.90-7.21 (m, 1H); MS (ESI) positive ion 301 (M+H).

EXAMPLE 266

4-amino-5-cyano-N-(pyridin-3-ylmethyl)-6-thien-3-ylpyridine-2-carboxamide

Example 266A 4-amino-5-cyano-6-thien-3-ylpyridine-2-carboxylic acid

A suspension of Example 181D (212 mg, 1.0 mmol), 3-thiopheneboronic acid (134 mg, 1.05 mmol), dichlorobis (triphenylphosphine)-palladium(II) $(Ph_3P)_2PdCl_2$ (7 mg, 0.01 mmol), and $Na_2CO_3$ (212 mg, 2.0 mmol) in dimethyl ether: water: ethanol (7:3:2, 4 mL) was heated at 150° C. for 10 minutes in a microwave reactor. The crude mixture was acidified with 2N HCl (2 mL) and partitioned between ethyl acetate and water. The organic phase was washed with brine, dried over $MgSO_4$, filtered and concentrated. It was triturated with acetonitrile to provide the titled compound (51 mg, 21% yield).

Example 266B 4-amino-5-cyano-N-(pyridin-3-ylmethyl)-6-thien-3-ylpyridine-2-carboxamide To a mixture of Example 266A (12 mg, 0.05 mmol), C-pyridin-3-yl-methylamine (6 μL, 0.1 mmol) in N,N-dimethylformamide (400 μL) was added O-benzotriazol-1-yl-N,N,N',N'-tetramethyluronium tetrafluoroborate (17 mg, 0.053 mmol), followed by N,N-diisopropylethylamine (17 μL). The reaction mixture was stirred at ambient temperature for 3 hr. It was diluted with 1 mL acetonitrile and purified by reverse phase HPLC (0-70% $CH_3CN$ in 10 mM aq. ammonium acetate) to provide the titled compound as white solid (98 mg, 48%). $^1$H NMR (300 MHz, DMSO-$d_6$) δ 9.35 (t, J=6.4 Hz, 1H), 8.56-8.38 (m, 3H), 7.93-7.90 (m, 1H), 7.74-7.66 (m, 2H), 7.40-7.32 (m, 3H), 7.36 (s, 1H), 4.52 (d, J=6.4 Hz, 2H). MS (m/e) 336 (M+H)$^+$.

EXAMPLE 267 methyl 4-({[(4-amino-5-cyano-6-ethoxypyridin-2-yl)carbonyl]amino}methyl)piperidine-1-carboxylate The titled compound was prepared according to the procedure described in Example 253, substituting methyl chloroformate for isobutyl chloroformate. $^1$H NMR (500 MHz, DMSO-$d_6$) δ 8.50 (t, J=6.5 Hz, 1H), 7.30 (broad s, 2H), 7.04 (s, 1H), 4.48 (q, J=7.0 Hz, 2H), 3.93 (broad s, 2H), 3.56 (s, 3H), 3.16 (t, J=6.5 Hz, 2H), 2.73 (broad s, 2H), 1.74 (m, 1H), 1.61 (d, J=12.5 Hz, 2H), 1.32 (d, J=7.0 Hz, 3H), and 1.03 (dq, J=3.6, 12.5 Hz, 2H). MS (m/e) positive mode: 362 (M+H)$^+$.

EXAMPLE 268

4-amino-5-bromo-N-(2,5-dimethoxybenzyl)-6-ethoxypyridine-2-carboxamide

The titled compound was prepared according to the procedure described in Example 104B, substituting Example 224A for Example 104A. $^1$H NMR (400 MHz, DMSO-$d_6$) δ 8.72 (t, J=6.8 Hz, 1H), 7.09 (s, 1H), 6.93 (d, J=9.2 Hz, 1H), 6.79 (dd, J=2.8, 9.2 Hz, 1H), 6.73 (d, J=3.2 Hz, 1H), 6.48 (broad s, 2H), 4.42 (q, J=7.2 Hz, 2H), 4.41 (d, J=6.0 Hz, 2H), 3.39 (s, 3H), 3.65 (s, 3H), and 1.32 (d, J=7.2, 3H). MS (m/e) positive mode: 410, 412 (1:1, M+H)$^+$; negative mode: 408, 410 (1:1, M−H)$^-$.

EXAMPLE 269

4-amino-5-cyano-6-ethoxy-N-[(2-fluoropyridin-3-yl)methyl]pyridine-2-carboxamide

The titled compound was prepared according to the procedure described in Example 104B, substituting C-(2-fluoropyridin-3-yl)-methylamine for 2,5-dimethoxy-benzylamine. $^1$H NMR (300 HZ, DMSO-$d_6$) δ 9.09 (t, J=6.1 Hz, 1H), 8.16-8.11 (m, 1H), 7.84-7.76 (m, 1H), 7.38-7.31 (m, 3H), 7.07 (s, 1H), 4.51 (q, J=7.1 Hz, 2H), 4.50 (d, J=6.1 Hz, 2H), 1.32 (t, J=7.1 Hz, 3H). MS (m/e) 314 (M−H)$^-$.

EXAMPLE 270

4-amino-6-ethoxy-5-fluoro-N-[4-(methylsulfonyl)benzyl]pyridine-2-carboxamide

Example 270A 4-amino-6-ethoxy-5-fluoropyridine-2-carboxylic acid

To a solution of Example 165B (98 mg, 0.5 mmol) in acetonitrile (5 mL) was added solid selectfluor (195 mg, 0.55 mmol). The reaction mixture was stirred at ambient temperature for 1 hr. It was then partitioned between ethyl acetate and water. The organic layer was washed with brine, dried over $MgSO_4$, and concentrated in vacuo. The crude mixture was purified by flash chromatography on silica gel using hexane/ethyl acetate (20% to 50% ethyl acetate) to get 18 mg ester as pale yellow solid. The ester was dissolved in methanol/tetrahydrofuran (1 mL/1 mL), and treated with 300 μL 1N NaOH at ambient temperature for 3 hr. It was then acidified by adding 310 μL 1N HCl, and extracted with EtOAC. The organic phase was washed with water, dried over $MgSO_4$, filtered and concentrated to provide the titled compound as white solid (12 mg, 12%).

Example 270B 4-amino-6-ethoxy-5-fluoro-N-[4-(methylsulfonyl)benzyl]pyridine-2-carboxamide To a mixture of acid from Example 270A (10 mg, 0.05 mmol), 4-methylsulfonyl-benzylamineHCl (13 mg, 0.06 mmol) in N,N-dimethylformamide (400 μL) was added O-benzotriazol-1-yl-N,N,N',N'-tetramethyluronium tetrafluoroborate (18 mg, 0.055 mmol), followed by N,N-diisopropylethylamine (35L, 0.4 mmol). The reaction mixture was stirred at ambient temperature for 2 hr. It was diluted with 1 mL acetonitrile and purified by reverse phase HPLC (0-70% $CH_3CN$ in 10 mM aq. ammonium acetate) to provide the titled compound as white solid (14 mg, 78%). $^1$H NMR (300 MHz, DMSO-$d_6$) δ 9.03 (t, J=6.4 Hz, 1H), 7.88 (d, J=8.1 Hz, 2H), 7.54 (d, J=8.1 Hz, 2H), 7.14 (d, J=6.1 Hz, 1H), 6.32 (bs, 2H), 4.55 (d, J=6.4, 2H), 4.46 (q, J=7.1 Hz, 2H), 3.17 (s, 3H), 1.32 (t, J=7.1 Hz, 3H). MS (m/e) 368 (M+H)$^+$.

EXAMPLE 271

N-(4-amino-5-cyano-6-ethoxypyridin-2-yl)-2-[4-(methylsulfonyl)phenyl]acetamide

Example 271A

N-(4-amino-5-cyano-6-ethoxypyridin-2-yl)-2-[4-(methylthio)phenyl]acetamide

N-(4-Amino-5-cyano-6-ethoxy-pyridin-2-yl)-2-(4-methylsulfanyl-phenyl)-acetamide

To a solution of 200 mg (1.10) mmol of (4-methylsulfanyl)phenylacetic acid in 3 mL of dichloromethane was added 800 µL (9.17 mmol) of oxalyl chloride. The solution was stirred at ambient temperature for 1 h, then concentrated in vacuo to an oil. This was taken up in 2 mL of dichloromethane and added to a solution of 100 mg (0.562 mmol) of Example 1A in 2 mL of pyridine and 2 mL of dichloromethane at −78° C. The reaction was stirred at −78° C. for 50 min, then 3 mL of water was added, and the reaction was warmed until the ice had melted. The solvents were removed in vacuo, then the residue was taken up in 20 mL of ethyl acetate and extracted with 1 M $HCl_{(aq.)}$ (2×5 mL), saturated $NaHCO_{3(aq.)}$ (2×5 mL), and brine (1×5 mL), dried over $MgSO_4$, filtered, and concentrated to a solid. This was recrystallized from methanol to give 25 mg (13%) of colorless crystals.

Example 271B

N-(4-amino-5-cyano-6-ethoxypyridin-2-yl)-2-[4-(methylsulfonyl)phenyl]acetamide

To a solution of 25 mg (0.073 mmol) of Example 271A in 1 mL of trifluoroacetic acid was added 17 µl (0.17 mmol) of 30% $H_2O_{2(aq)}$. The solution was stirred at ambient temperature for 30 min, then 10 mL of water was added. The aqueous mixture was extracted with ethyl acetate (1×5 mL), then the organic layer was back extracted with saturated $NaHCO_{3(aq.)}$ (2×5 mL), and brine (1×5 mL), dried over $MgSO_4$, filtered, and concentrated in vacuo to a solid. This was purified via silica gel chromatography, eluting with a 60-100% ethyl acetate:hexanes gradient to give 9 mg (33%) of the titled compound as a white solid. $^1$H NMR (300 MHz, DMSO-$d_6$) δ ppm 10.43 (s, 1H), 7.88 (d, J=8.1 Hz, 2H), 7.58 (d, J=8.1 Hz, 2H), 7.14 (s, 1H), 6.91 (s, 2H), 4.35 (q, J=7.1 Hz, 2H), 3.86 (s, 2H), 3.19 (s, 3H), 1.31 (t, J=7.1 Hz, 3H); MS (ESI$^+$) m/z=375 [M+H]$^+$.

EXAMPLE 272

4-amino-5-cyano-6-ethoxy-N-[2-(methylsulfonyl)ethyl]pyridine-2-carboxamide

In a 20 mL vial a solution of Example 104A (32.5 mg, 0.16 mmol) dissolved in N,N-dimethylacetamide (0.8 mL) was added, followed by the addition of O-benzotriazol-1-yl-N,N,N′,N′-tetramethyluronium tetrafluoroborate (50.4 mg, 0.16 mmol) dissolved in N,N-dimethylacetamide (0.8 mL). Then, 2-aminoethylsulfone hydrochloride (30.3 mg, 0.19 mmol) dissolved in N,N-dimethylacetamide (0.6 mL) was added followed by the addition of diisopropyl ethyl amine (57.9 uL, 0.31 mmol) dissolved in N,N-dimethylacetamide (0.8 mL). The mixture was shaken at room temperature overnight. The reaction was checked by LC/MS and concentrated to dryness. The residue was dissolved in 1:1 dimethyl sulfoxide/methanol and purified by reverse phase (0-70% $CH_3CN$ in 10 mM aq. ammonium acetate) to give the titled compound. $^1$H NMR (500 MHz, DMSO-$d_6$) δ ppm 1.26-1.38 (m, 3H) 2.93-3.08 (m, 3H) 3.29-3.47 (m, 2H) 3.72-3.80 (m, 2H) 4.30-4.61 (m, 2H) 7.05-7.09 (m, 1H); MS (ESI) positive ion 313 (M+H).

EXAMPLE 273

4-amino-5-cyano-N-[4-(methylsulfonyl)benzyl]-6-{[3-(methylthio)propyl]amino}pyridine-2-carboxamide The titled compound was prepared according to the procedure described in Example 182, substituting 3-methylsulfanyl-propylamine for isopropylamine used in Example 182. $^1$H NMR (300 MHz, DMSO-$d_6$) δ 8.98 (t, J=6.4 Hz, 1H), 7.87 (d, J=8.5 Hz, 2H), 7.53 (d, J=8.5 Hz, 2H), 6.92 (s, 2H), 6.76 (t, J=5.8 Hz, 1H), 6.70 (s, 1H), 4.57 (d, J=6.8 Hz, 2H), 3.52 (q, J=6.7 Hz, 2H), 3.18 (s, 3H), 2.50 (m, 2H), 1.99 (s, 3H), 1.78 (m, 2H). MS (m/e) positive mode: 434 (M+H)$^+$; negative mode: 432 (M−H)$^-$.

EXAMPLE 274

4-amino-5-[(1E)-but-1-en-3-ynyl]-6-ethoxy-N-[4-(methylsulfonyl)benzyl]pyridine-2-carboxamide

Example 274A

4-Amino-5-(1,4-bis-trimethylsilanyl-but-1-en-3-ynyl)-6-ethoxy-pyridine-2-carboxylic acid 4-methanesulfonyl-benzylamide A mixture of Example 240B (95 mg, 0.2 mmol), ethynyl-trimethylsilane (59 mg, 0.6 mmol), $PdCl_2(Ph_3P)_2$ (7 mg, 0.01 mmol), CuI (4 mg, 0.02 mmol) and triethylamine (40 mg, 0.4 mmol) in N,N-dimethylformamide (2 ml) was sealed in a tube and heated at 110° C. for 6 hours, checked with LC/MS until starting material disappeared. The mixture was filtered and the filtrate was partitioned between ethyl acetate and water (30 ml, 1:1). The organic layer was washed with brine, dried over $MgSO_4$, filtered, and evaporated in vacuo. The crude product was purified on silica gel cartridge by Anal.ogix eluting with 100% ethyl acetate to give the titled compound (32 mg, 30%). $^1$H NMR (300 MHz, DMSO-$d_6$) δ ppm 9.03 (t, J=6.44 Hz, 1H), 7.87 (d, J=8.48 Hz, 2H), 7.55 (d, J=8.14 Hz, 2H), 7.06 (s, 1H), 6.75 (s, 1H), 6.05 (s, 2H) 4.57 (d, J=6.44 Hz, 2H), 4.36 (q, J=6.95 Hz, 2H), 3.17 (s, 3H), 1.29 (t, J=6.95 Hz, 3H), 0.21 (s, 9H), 0.11 (s, 9H); MS (APCI) m/z 544 [M+H]$^+$, 542 [M−H]$^-$.

Example 274B 4-amino-5-[(1E)-but-1-en-3-ynyl]-6-ethoxy-N-[4-(methylsulfonyl)benzyl]pyridine-2-carboxamide To a solution of compound from Example 274A (28 mg, 0.05 mmol) in tetrahydrofuran (5 ml) was added tetrabutyl ammonium fluoride (52 mg, 0.2 mmol). The mixture was stirred at room temperature for overnight, and then water and ethyl acetate (20 ml, 1:1) were added. The organic layer was washed with brine and dried over MgSO4. The crude product was purified by reverse phase HPLC (10 mM ammonium acetate, 5% acetonitrile in $H_2O/CH_3CN$) to give the titled compound (18.5 mg, 90%). $^1$H NMR (300 MHz, DMSO-$d_6$) δ ppm 9.02 (t, 1H), 7.87 (d, J=8.14 Hz, 2H), 7.54 (d, J=8.48 Hz, 2H), 7.08 (d, J=16.28 Hz, 1H), 7.04 (s, 1H), 6.57 (s, 2H), 6.48 (dd, $J_1$=16.28, 2.37 Hz, 1H), 4.56 (d, J=6.44 Hz, 2H), 4.46 (q, J=7.01 Hz, 2H), 4.09 (d, J=2.37 Hz, 1H), 3.17 (s, 3H), 1.34 (t, J=7.12 Hz, 3H); MS (APCI) m/z 400 [M+H]$^+$, 398 [M−H]$^−$.

EXAMPLE 275 methyl trans-4-({[(4-amino-5-cyano-6-ethoxypyridin-2-yl)carbonyl]amino}methyl)cyclohexanecarboxylate The titled compound was prepared according to the procedure described in Example 104B, substituting commercially available trans-aminomethyl cyclohexane carboxylic acid methyl ester hydrochloride for 2,5-dimethoxybenzylamine used in Example 104B. $^1$H NMR (300 MHz, DMSO-d$_6$) δ 8.44 (t, J=6.4 Hz, 1H), 7.63 (broad s, 1H), 7.29 (s, 2H), 4.48 (q, J=7.0 Hz, 2H), 3.57 (s, 3H), 3.12 (t, J=6.6 Hz, 2H), 2.86 (t, J=6.4 Hz, 1H), 2.24 (m, 1H), 1.95-1.40 (m, 6H), 1.32 (t, J=7.0 Hz, 3H), 0.95 (m, 2H). MS (m/e) positive mode: 361 (M+H)$^+$; negative mode: 359 (M−H)$^−$.

EXAMPLE 276

1-{2-[(4-amino-5-cyano-6-isopropoxypyridin-2-yl)amino]-2-oxoethyl}piperidine-4-carboxamide

Example 276A

N-(4-amino-5-cyano-6-isopropoxy-pyridin-2-yl)-2-bromo-acetamide

To a solution of 500 mg (2.60 mmol) of Example 254A at −78° C. in 5 mL of pyridine and 5 mL of dichloromethane was added a solution of 637 mg (3.16 mmol) of bromoacetyl bromide in 5 mL of dichloromethane. The reaction was stirred at −78° C. for 10 min, then 50 mL of water was added, and the mixture was warmed until all the ice had melted. The suspension was extracted with ethyl acetate (3×10 mL), then the combined ethyl acetate layers were back extracted with 1 M HCl (4×10 mL or until the pH=1 in the aqueous layer), then brine (1×10 mL), dried over MgSO$_4$, filtered, and concentrated in vacuo to 814 mg (100%) of the titled compound as a solid.

Example 276B

1-{2-[(4-amino-5-cyano-6-isopropoxypyridin-2-yl)amino]-2-oxoethyl}piperidine-4-carboxamide To a solution of 50 mg (0.16 mmol) of Example 276A and 25 mg (0.195 mmol) of isonipecotamide in 0.5 mL of N,N-dimethylformamide was added 50 μL (0.29 mmol) of N,N-diisopropyl-N-ethylamine. The reaction was stirred at ambient temperature for 30 min, then 10 mL of water was added. The solid was filtered and washed with water, then recrystallized from methanol to give 10 mg (17%) of the titled compound as a white solid. $^1$H NMR (300 MHz, DMSO-d$_6$) δ ppm 9.47 (s, 1H), 7.23 (s, 1H), 7.16 (s, 1H), 6.94 (s, 2H), 6.74 (s, 1H), 5.22 (m, 1H), 3.12 (s, 2H), 2.85 (m, J=11.5 Hz, 2H), 2.10 (m, 3H), 1.60 (m, 4H), 1.28 (d, J=6.1 Hz, 6H); MS (ESI+) m/z=361 [M+H]$^+$.

EXAMPLE 277

4-amino-5-cyano-6-ethoxy-N-{4-[(trifluoromethyl)sulfonyl]benzyl}pyridine-2-carboxamide The title compound was prepared according to the procedure described in Example 104B, substituting 4-trifluoromethanesulfonylbenzylamine for 2,5-dimethoxybenzylamine. $^1$H NMR (300 MHz, DMSO-d$_6$) δ 9.25 (t, J=6.44 Hz, 1H), 8.10 (d, J=8.48 Hz, 2H), 7.72 (d, J=8.48 Hz, 2H), 7.34 (s, 2H), 7.08 (s, 1H), 4.65 (d, J=6.44 Hz, 2H), 4.52 (q, J=7.12 Hz, 2H), and 1.32 (t, J=7.12 Hz, 3H); MS (ESI) m/e positive ion 429 [M+H]$^+$; negative ion 427 [M−H]$^−$.

EXAMPLE 278

4-amino-5-cyano-6-ethoxy-N-{3-[(4-methylphenyl)sulfonyl]propyl}pyridine-2-carboxamide

Example 278A

4-Amino-5-cyano-6-ethoxy-pyridine-2-carboxylic acid (3-bromopropyl)-amide

To a solution of 1.0 g (4.8 mmol) of Example 104A in 16 mL of N,N-dimethylformamide was added 2.3 g (7.2 mmol) O-benzotriazol-1-yl-N,N,N',N'-tetramethyluronium tetrafluoroborate. To the reaction mixture, 1.2 g (5.3 mmol) of 3-bromopropylamine hydrobromide and 1.8 mL (10.6 mmol) of N,N-diisopropylethylamine were added. The reaction stirred at room temperature for 1 h. It was diluted with 90 mL of H$_2$O and filtered. The solid was rinsed with H$_2$O and dried under vacuum to give 1.4 g of a white solid (89% yield). $^1$H NMR (300 MHz, d$_6$-DMSO) δ 8.57-8.61 (t, J=6.11 Hz, 1H), 7.30 (s, 2H), 7.05 (s, 1H), 4.46-4.53 (q, J=7.12 Hz, 2H), 3.52-3.56 (t, J=6.78 Hz, 2H), 3.84-3.41 (q, J=6.78 Hz, 2H), 2.02-2.11 (m, 2H), 1.29-1.34 (t, J=7.12 Hz, 3H); MS (ESI) m/e=326 (M+H)$^+$, 325 (M−H)$^−$.

Example 278B 4-amino-5-cyano-6-ethoxy-N-{3-[(4-methylphenyl)thio]propyl}pyridine-2-carboxamide To a suspension of 12 mg (0.29 mmol) NaH in 0.5 mL N,N-dimethylformamide was added 45 mg (0.344 mmol) 4-methylbenzenethiol. To the reaction mixture was added 75 mg (0.23 mmol) Example 278A in 0.5 mL of N,N-dimethylformamide. The reaction stirred at room temperature for 1 h. It was diluted with 5 mL H$_2$O and extracted with ethyl acetate (2×10 mL). The combined organic layers were washed with 2M NaOH (8 mL), H$_2$O (8 mL), and brine (8 ml), dried over MgSO$_4$ and concentrated. The resulting solid was triturated and filtered to give 40 mg of a white solid (47% yield). $^1$H NMR (300 MHz, d$_6$-DMSO) δ 8.53-8.57 (t, J=6.11 Hz, 1H), 7.28 (s, 2H), 7.22 (d, J=8.14 Hz, 2H), 7.12 (d, J=8.48 Hz, 2H), 7.04 (s, 1H), 4.44-4.57 (q, J=7.12 Hz, 2H), 3.31-3.38 (q, J=6.78 Hz, 2H), 2.69-2.94 (t, J=6.78 Hz, 2H), 2.26 (s, 3H), 1.73-1.82 (m, 2H), 1.28-1.33 (t, J=7.12 Hz, 3H); MS (ESI) m/e=371 (M+H)$^+$, 369 (M−H)$^−$.

Example 278C 4-amino-5-cyano-6-ethoxy-N-{3-[(4-methylphenyl)sulfonyl]propyl}pyridine-2-carboxamide To a solution of 30 mg (0.081 mmol) of Example 278B in 0.5 mL trifluoroacetic acid was added 0.4 mL (0.2 mmol) of 0.5 M H₂O₂ in trifluoroacetic acid. The excess peroxide was quenched with 5% aqueous NaHSO₃ solution and concentrated. It was taken up in saturated NaHCO₃ solution and extracted with ethyl acetate (2×10 mL). The combined organic layers were washed with brine (8 mL), dried over MgSO₄, filtered, and concentrated. The resulting oil was triturated with methanol and filtered to give 20 mg of a white solid (61% yield). ¹H NMR (300 MHz, d₆-DMSO) δ 8.56-8.60 (t, J=6.44 Hz, 1H), 7.75 (d, J=8.48 Hz, 2H), 7.44 (d, J=8.14 Hz, 2H), 7.28 (s, 2H), 7.01 (s, 1H), 4.43-4.50 (q, J=7.12 Hz, 2H), 3.26-3.31 (m, 4H), 2.40 (s, 3H), 1.73-1.78 (m, 2H), 1.28-1.33 (t, J=7.12 Hz, 3H); MS (ESI) m/e=403 (M+H)⁺, 401 (M−H)⁻.

EXAMPLE 279

(2E)-3-[4-amino-3-cyano-6-({[4-(methylsulfonyl)benzyl]amino}carbonyl)pyridin-2-yl]acrylic acid To Example 214B (82 mg, 0.2 mmol) in N,N-dimethylformamide (0.3 mL) was added t-butyl acrylate (38 mg, 0.3 mmol), (Tol)₃P (12 mg, 0.04 mmol), palladium(II) acetate (4.5 mg, 0.02 mmol), and triethylamine (30 mg, 0.3 mmol). The mixture was heated to 100° C. overnight and purified by silica gel flash column eluting with 5% MeOH in ethyl acetate to give 3-[4-amino-3-cyano-6-(4-methanesulfonyl-benzyl-carbamoyl)-pyridin-2-yl]-acrylic acid tert-butyl ester (20 mg, 22%). This material was dissolved in dichloromethane (0.3 mL) and trifluoroacetic acid (0.2 mL). The mixture was stirred overnight and volatiles were removed. Water was added to the residue and the precipitates were collected to give the title compound (10 mg, 57%). ¹H NMR (400 MHz, DMSO-d₆) δ 9.61 (t, J=6.0 Hz, 1H), 7.88 (d, J=8.4 Hz, 2H), 7.64 (d, J=15.2 Hz, 1H), 7.56 (d, J=8.4 Hz, 2H), 7.43 (d, J=15.2 Hz, 1H), 7.44 (broad s, 2H), 7.40 (s, 1H), 4.59 (d, J=6.4 Hz, 2H), and 3.17 (s, 3H). MS (m/e) positive mode: 401 (M+H)⁺; negative mode: 399 (M−H)⁻.

EXAMPLE 280

4-amino-5-cyano-6-{[(1R)-2-hydroxy-1-methyl-ethyl]amino}-N-[4-(methylsulfonyl)benzyl]pyridine-2-carboxamide The titled compound was prepared according to the procedure described in Example 189, substituting (R)-2-aminopropan-1-ol for cyclopentylamine used in Example 189. Yield 40%. ¹H NMR (300 MHz, DMSO-d₆) δ 9.02 (t, J=6.0 Hz, 1H), 7.88 (d, J=9.0 Hz, 2H), 7.53 (d, J=9.0 Hz, 2H), 6.94 (s, 2H), 6.71 (s, 1H), 5.95 (d, J=9.0 Hz, 1H), 4.71 (t, J=4.5 Hz, 1H), 4.56 (d, J=6.0 Hz, 2H), 4.3 (m, 1H), 3.44 (m, 2H), 3.18 (s, 3H), 1.14 (d, J=6.0 Hz, 3H); MS (APCI) m/z 404 [M+H]⁺, 402 [M−H]⁻.

EXAMPLE 281

4-amino-5-cyano-6-ethoxy-N-[2-(6-methoxy-1H-indol-3-yl)ethyl]pyridine-2-carboxamide The titled compound was prepared according to the procedure described in Example 104B, substituting 6-methoxytryptamine for 2,5-dimethoxybenzylamine used in Example 104B. ¹H NMR (300 MHz, DMSO-d₆) δ 10.62 (s, 1H), 8.40 (t, J=5.9 Hz, 1H), 7.45 (d, J=8.5 Hz, 1H), 7.30 (s, 2H), 7.05 (broad s, 2H), 6.84 (d, J=2.0 Hz, 1H), 6.63 (dd, J=8.7, 2.2 Hz, 1H), 4.34 (q, J=7.0 Hz, 2H), 3.35 (s, 3H), 3.53 (q, J=6.8 Hz, 2H), 2.89 (t, J=7.3 Hz, 2H), 1.28 (t, J=7.0 Hz, 3H). MS (m/e) positive mode: 380 (M+H)⁺; negative mode: 378 (M−H)⁻.

EXAMPLE 282

4-azido-5-cyano-6-isopropoxy-N-[4-(methylsulfonyl)benzyl]pyridine-2-carboxamide

The titled compound was prepared according to the procedure described in Example 104B, substituting 4-methanesulfonyl-benzylamine hydrochloride for 2,5-dimethoxybenzylamine and substituting the acid from Example 102B for the acid from Example 104A. ¹H NMR (300 MHz, DMSO-d₆) δ 9.48 (t, J=6.4 Hz, 1H), 7.89 (d, J=8.1 Hz, 2H), 7.56 (d, J=8.1 Hz, 2H), 7.58 (s, 1H), 5.77 (septet, J=6.1 Hz, 1H), 4.62 (d, J=6.4 Hz, 2H), 3.18 (s, 3H), 1.35 (d, J=6.1 Hz, 6H). MS (m/e) positive mode: 437 (M+Na)⁺; negative mode: 413 (M−H)⁻.

EXAMPLE 283

4-amino-3-cyano-N²-isopropyl-N⁶-[4-(methylsulfonyl)benzyl]pyridine-2,6-dicarboxamide

Example 283A

4-Amino-3-cyano-6-(4-methanesulfonylbenzylcarbomoyl)-pyridine-2-carboxylic acid

Step A:

Example 181F (1.62 g, 4.4 mmol) was esterified by carbon monoxide (60 psi) at 100° C. for 16 hours in methyl alcohol, using the procedure as described in Example 181D to give 4-amino-3-cyano-6-(4-methanesulfonylbenzylcarbomoyl)-pyridine-2-carboxylic acid methyl ester in 50% yield.

Step B:

This intermediate from step A was hydrolyzed by 3N aq. NaOH (5 mL) in methanol (20 mL) at room temperature for 1 hour. The reaction mixture was filtered and the filtrate was adjusted to pH 2~3. The white precipitate was collected and dried. The titled compound was obtained (45% for the two steps). ¹H NMR (300 MHz, DMSO-d₆) δ 13.11 (s, 1H), 9.74 (t, J=6.10 Hz, 1H), 7.89 (d, J=8.48 Hz, 2H), 7.60 (s, 1H), 7.58 (s, 2H), 7.57 (d, J=8.48 Hz, 2H), 4.62 (d, J=6.44 Hz, 2H), 3.18 (s, 3H); MS (APCI) m/z 375 [M+H]⁺, 373 [M−H]⁻.

Example 283B 4-amino-3-cyano-N²-isopropyl-N⁶-[4-(methylsulfonyl)benzyl]pyridine-2,6-dicarboxamide Example 283A (37.4 mg, 0.1 mmol) was stirred with isopropylamine (17.7 mg, 0.3 mmol), O-benzotriazol-1-yl-N,N,N',N'-tetramethyluronium tetrafluoroborate (39 mg, 0.12 mmol) in N,N-dimethylformamide (0.5 ml) at room temperature for 1 hour. The reaction mixture was purified on HPLC (10 mM ammonium acetate and 5% CH₃CN in H₂O/CH₃CN) to give the titled compound (35.3 mg, 85%). ¹H NMR (300 MHz, DMSO-d₆) δ 9.74 (t, J=6.44 Hz, 1H), 8.75 (d, J=8.48 Hz, 1H), 7.90 (d, J=8.48 Hz, 2H), 7.57 (s, 1H), 7.56 (d, J=8.48 Hz, 2H), 7.40 (s, 2H), 4.67 (d, J=6.44 Hz, 2H), 4.05-4.22 (m, 1H), 3.18 (s, 3H), 1.23 (d, J=6.78 Hz, 6H); MS (APCI) m/z 416 [M+H]⁺, 414 [M−H]⁻.

EXAMPLE 284

N-(4-amino-5-cyano-6-ethoxypyridin-2-yl)-2-[2-methoxy-5-(methylsulfinyl)phenyl]acetamide To a solution of 18 mg (0.048 mmol) of Example 170F in 1 mL of trifluoroacetic acid was added 100 (L (0.05 mmol) of 0.5 M $H_2O_2$ in trifluoroacetic acid (prepared from 30% $H_2O_2$ (aq.)). The solution was stirred at ambient temperature for 30 min, concentrated in vacuo. The residue was taken up in 5 mL of saturated $NaHCO_3$(aq.), and extracted with ethyl acetate (2×5 mL). The combined ethyl acetate layers were back extracted with brine (1×5 mL), dried over $MgSO_4$, filtered, and concentrated in vacuo to a solid. This was recrystallized from 2 mL of CH3CN in a capped 4 mL vial to give 10 mg (54%) of the titled compound as white crystals. $^1$H NMR (300 MHz, DMSO-$d_6$) 610.25 (s, 1H), 7.56 (m, 2H), 7.17 (d, J=8.1 Hz, 1H), 7.13 (s, 1H), 6.88 (s, 2H), 4.35 (q, J=6.9 Hz, 2H), 3.82 (s, 3H), 3.78 (s, 2H), 2.69 (s, 3H), 1.31 (t, J=7.1 Hz, 3H); MS (ESI+) m/z=389 [M+H]$^+$. Anal. Calc'd for $C_{18}H_{20}N_4O_4S.0.17H_2O$: C, 55.22; H, 5.24; N, 14.31. Found: C, 55.59; H, 5.25; N, 13.91.

EXAMPLE 285

4-amino-5-cyano-6-ethoxy-N-[3-(1H-imidazol-2-yl)propyl]pyridine-2-carboxamide

The title compound was prepared according to the procedure described in Example 104B, substituting 3-(1H-Imidazol-2-yl)-propylamine for 2,5-dimethoxybenzylamine. $^1$H NMR (300 MHz, DMSO-$d_6$) δ 8.54 (t, J=6.27 Hz, 1H), 7.64 (s, 1H), 7.30 (s, 2H), 7.19 (t, J=1.19 Hz, 1H), 7.05 (s, 1H), 6.88 (t, J=1.02 Hz, 1H), 4.49 (q, J=7.12 Hz, 2H), 3.98 (t, J=6.95 Hz, 2H), 3.24 (q, J=7.01 Hz, 2H), 1.94 (dt, J=13.99, 7.08 Hz, 2H), and 1.32 (t, J=7.12 Hz, 3H); MS (ESI) m/e positive ion 337 [M+Na]$^+$, 315 [M+H]$^+$; negative ion 313 [M–H]$^-$.

EXAMPLE 286

4-amino-6-ethoxy-5-formyl-N-[4-(methylsulfonyl)benzyl]pyridine-2-carboxamide

To a suspension of Example 176 (73 mg, 0.2 mmol) in HCOOH (5 ml, 98%) was added $AlNi_3$ (84 mg, 0.6 mmol). The mixture was refluxed for overnight and filtered after cooled down to r.t. The filtrate was concentrated and the remainder was purified on HPLC (10 mM ammonium acetate, 5% acetonitrile in $H_2O/CH_3CN$) to yield the titled compound (25 mg, 36%). $^1$H NMR (300 MHz, DMSO-$d_6$) δ 10.23 (s, 1H), 9.20 (t, J=6.44 Hz, 1H) 8.46 (s, 1H), 7.95 (s, 1H), 7.88 (d, J=8.48 Hz, 1H), 7.55 (d, J=8.48 Hz, 2H), 7.08 (s, 1H) 4.57 (d, J=8.48 Hz, 2H), 4.54 (d, J=6.44 Hz, 2H), 3.18 (s, 3H), 1.35 (q, J=6.44 Hz, 3H); MS (APCI) m/z 378 [M+H]$^+$, 376 [M–H]$^-$.

EXAMPLE 287

4-amino-5-cyano-6-ethoxy-N-({1-[(isopropylamino)carbonyl]piperidin-4-yl}methyl)pyridine-2-carboxamide To Example 194A (20 mg, 0.07 mmol) in tetrahydrofuran (0.5 mL) was added isopropyl isocyanate (8.5 mg, 0.07 mmol). The mixture was stirred at r.t for 1 h and purified by silica gel flash column eluting with 100% ethyl acetate to give the title compound (13 mg, 48%). $^1$H NMR (400 MHz, DMSO-$d_6$) δ 8.46 (t, J=6.0 Hz, 1H), 7.28 (broad s, 2H), 7.04 (s, 1H), 6.03 (d, J=7.6 Hz, 1H), 4.48 (q, J=7.2 Hz, 2H), 3.92 (broad d, J=13.2 Hz, 2H), 3.74 (septet, J=7.6 Hz, 1H), 3.15 (t, J=6.4 Hz, 2H), 2.56 (t, J=12 Hz, 2H), 1.70 (m, 1H), 1.55 (d, J=10.8 Hz, 2H), 1.32 (d, J=7.2 Hz, 3H), 1.03 (d, J=7.8 Hz, 2H), and 0.98 (m, 2H). MS (m/e) positive mode: 389 (M+H)$^+$; negative mode: 387 (M–H)$^-$.

EXAMPLE 288

4-amino-5-cyano-6-ethoxy-N-{[(3S)-1-(methylsulfonyl)pyrrolidin-3-yl]methyl}pyridine-2-carboxamide

Example 288A tert-butyl(3S)-3-({[(4-amino-5-cyano-6-ethoxypyridin-2-yl)carbonyl]amino}methyl)pyrrolidine-1-carboxylate The titled compound was prepared according to the procedure described in Example 104B, substituting (3S)-3-aminomethyl-pyrrolidine-1-carboxylic acid tert-butyl ester for 2,5-dimethoxybenzylamine.

Example 288B 4-amino-5-cyano-6-ethoxy-N-{[(3S')-1-(methylsulfonyl)pyrrolidin-3-yl]methyl}pyridine-2-carboxamide Step A
Example 288A (25 mg, 0.064 mmol) was taken up in 1 mL of dichloromethane/trifluoroacetic acid (1:1, v/v) and left at room temperature for 30 min. The volatile solvent and reagent were removed in vacuo.

Step B
The residue from step A was then taken up in dichloromethane and treated with triethylamine (50 μL, 0.36 mmol) and methanesulfonyl chloride (15 μL, 0.19 mmol). After 2 h, the reaction mixture was concentrated in vacuo and the residue was purified on a reverse phase Gilson HPLC (0-70% $CH_3CN$ in 10 mM aq. ammonium acetate) to give the titled compound (10 mg, 43%). $^1$H NMR (300 MHz, DMSO-$d_6$) δ 8.62 (t, J=6.3 Hz, 1H), 7.30 (s, 2H), 7.05 (s, 1H), 4.49 (q, J=7.1 Hz, 2H), 3.21 (m, 2H), 3.00 (dd, J=10, 6.6 Hz, 1H), 2.88 (s, 3H), 1.94 (m, 2H), 1.65 (m, 2H), 1.32 (m, J=7.1 Hz, 3H). MS (m/e) positive mode: 368 (M+H)$^+$.

EXAMPLE 289

Trans-tert-butyl 4-({[(4-amino-5-cyano-6-ethoxypyridin-2-yl)carbonyl]amino}methyl)cyclohexylcarbamate Step A
Example 275 (51 mg, 0.14 mmol) was hydrolyzed in methanol/tetrahydrofuran (1:1, v/v) with 1N LiOH (0.25 mL) at room temperature. After 30 min, the volatile solvent was removed in vacuo. The residue was acidified with 3N HCl and the resulting solid was collected through filtration to give 40 mg of the acid.

Step B
This intermediate from step A (40 mg, 0.12 mmol) was suspended in 1.0 mL of toluene with triethylamine (20 μL, 0.14 mmol) and diphenylphosphine azide (30 μL, 0.14 mmol). The resulting mixture was refluxed for 1 h before 0.5 mL of tert-butanol was added. The resulting mixture was refluxed for another 2 h before it was cooled down and partitioned between ethyl acetate and brine. The organic layer was dried over $Na_2SO_4$, filtered and evaporated in vacuo. The crude residue was purified on an Alltech silica gel Sep-Pak eluting with 30-50% ethyl acetate/hexane to give the titled compound (25 mg, 50% yield). $^1$H NMR (300 MHz, DMSO-$d_6$) δ 8.46 (t, J=6.44 Hz, 1H), 7.29 (s, 2H), 7.03 (s, 1H), 4.48 (q, J=7.1 Hz, 2H), 3.42 (m, 1H), 3.11 (t, J=6.6 Hz, 1H), 1.99 (m, 2H), 1.67 (m, 2H), 1.52 (m, 1H), 1.32 (t, J=7.1 Hz, 3H), 0.99 (s, 9H), 0.98 (m, 2H). MS (m/e) positive mode: 418 $(M+H)^+$.

EXAMPLE 290

N-[4-amino-5-cyano-6-(2,2,2-trifluoro-1-methyl-ethoxy)pyridin-2-yl]acetamide

Example 290A 4,6-Diamino-3-cyano-2-(2,2,2-trifluoro-1-methyl) ethoxypyridine To a sealable tube suitable for microwave heating was added a solution of 228 mg (2.00 mmol) of 1,1,1-trifluoro-2-propanol in 1 mL of N-methylpyrrolidinone. Next 60 mg (1.5 mmol) of 60% NaH in mineral oil was added. The reaction was stirred at ambient temperature until all the NaH had reacted, the 212 mg (1.00 mmol) of 2-bromo-4,6-diamino-3-cyanopyridine was added. The tube was sealed, placed in the reactor, heated at 200° C. for 30 min, then cooled to ambient temperature. The reaction was poured into 15 mL of water and 5 mL of saturated $NaHCO_{3(aq.)}$, then extracted with ethyl acetate (3×5 mL), filtering through celite to break an emulsion. The combined organic layers were back extracted with brine (1×5 mL), dried over $MgSO_4$, filtered, and concentrated in vacuo to an oil. This was purified via silica gel chromatography, eluting with a 5-50% ethyl acetate:hexanes gradient to give 74 mg (30%) of the titled compound as a colorless oil.

Example 290B

N-[4-amino-5-cyano-6-(2,2,2-trifluoro-1-methyl-ethoxy)pyridin-2-yl]acetamide

To a solution of 74 mg (0.30 mmol) of Example 290A in 1 mL of pyridine and 1 mL of dichloromethane at −78° C. was added 200 μL (2.81 mmol) of acetyl chloride. The reaction was warmed to 0° C., and stirred for 20 min, then 3 mL of water was added. The solvents were removed in vacuo, and the residue was taken up in 10 mL of 1 M $HCl_{(aq.)}$. The suspension was extracted with ethyl acetate (3×5 mL), then the combined ethyl acetate layers were back extracted with 1 M HCl (1×5 mL), saturated $NaHCO_{3(aq)}$ (2×5 mL) and brine (1×5 mL), dried over $MgSO_4$, filtered, and concentrated in vacuo to a solid. This was purified via silica gel chromatography, eluting with a 5-50% ethyl acetate:hexanes gradient to give 67 mg (77%) of the titled amide. $^1$H NMR (300 MHz, DMSO-$d_6$) δ ppm 10.20 (s, 1H), 7.25 (s, 1H), 7.11 (s, 2H), 5.82 (m, 1H), 2.07 (s, 3H), 1.46 (d, J=6.8 Hz, 3H); MS (ESI+) m/z=289 $[M+H]^+$. Anal. Calc'd for $C_{11}H_{11}F_3N_4O_2$: C, 45.84; H, 3.85; N, 19.44. Found: C, 45.77; H, 3.61; N, 19.19.

EXAMPLE 291

4-amino-5-cyano-6-ethoxy-N-[3-(methylsulfonyl) propyl]pyridine-2-carboxamide

Example 291A

4-Amino-5-cyano-6-ethoxy-pyridine-2-carboxylic acid (3-methylsulfanyl-propyl)-amide To a solution of 100 mg (0.48 mmol) of Example 104A in 3.0 mL of N,N-dimethylformamide was added 186 mg (0.58 mmol) O-benzotriazol-1-yl-N,N,N',N'-tetramethyluronium tetrafluoroborate. To the reaction mixture 0.05 mL (0.48 mmol) of 3-(methylthio)-propylamine and 0.2 mL (1.45 mmol) or triethylamine were added. The reaction stirred at room temperature for 18 h. It was diluted with 2M NaOH and the resulting precipitate was filtered and rinsed with $H_2O$. The crude solid was recrystallized from methanol to give 25 mg (0.084 mmol) of a white solid (17% yield). $^1$H NMR (300 MHz, $d_6$-DMSO) δ 8.53-8.57 (t, J=6.11 Hz, 1H), 7.29 (s, 2H), 7.04 (s, 1H), 4.45-4.52 (q, J=7.12 Hz, 2H), 3.29-3.36 (m, 2H), 2.46-2.50 (m, 2H), 2.05 (s, 3H), 1.72-1.82 (m, 2H), 1.29-1.34 (t, J=7.12 Hz, 3H); MS (ESI) m/e=295 $(M+H)^+$, 293 $(M-H)^-$.

Example 291B 4-amino-5-cyano-6-ethoxy-N-[3-(methylsulfonyl) propyl]pyridine-2-carboxamide To a solution of 20 mg (0.07 mmol) of 4-amino-5-cyano-6-ethoxy-pyridine-2-carboxylic acid (3-methylsulfanyl-propyl)-amide in 0.5 mL of trifluoroacetic acid was added 0.4 mL (0.2 mmol) of 0.5M $H_2O_2$ in trifluoroacetic acid. The reaction stirred at room temperature for 10 min. It was quenched with 5% aqueous $NaHSO_3$ solution and concentrated in vacuo. The residue was taken up in 5 mL saturated $NaHCO_3$ solution and extracted with ethyl acetate (2×5 mL). The combined organic layers were washed with brine (5 mL), dried over $MgSO_4$ and concentrated. The crude solid was triturated with methanol and filtered to give 8 mg of a white solid (36% yield). $^1$H NMR (300 MHz, $d_6$-DMSO) δ 8.61-8.65 (t, J=6.11 Hz, 1H), 7.30 (s, 2H), 7.06 (s, 1H), 4.46-4.53 (q, J=7.12 Hz, 2H), 3.34-3.15 (m, 2H), 2.97 (s, 3H), 1.91-1.99 (m, 2H), 1.30-1.34 (t, J=7.12 Hz, 3H); MS (ESI) m/e=327 $(M+H)^+$, 325 $(M-H)^-$.

EXAMPLE 292

N-(4-amino-5-cyano-6-ethoxypyridin-2-yl)-2-(4-cyanopiperidin-1-yl)acetamide

Example 292A tert-butyl 4-(aminocarbonyl)piperidine-1-carboxylate

To a solution of 1.28 g (10.0 mmol) of isonipecotamide in 10 mL of tetrahydrofuran and 10 mL of 2M $NaOH_{(aq.)}$ was added 2.18 g (10.0 mmol) of (di-tert-butyl)dicarbonate. The mixture was stirred at ambient temperature for 1 h, then the solvents were removed in vacuo. The residue was taken up in 10 mL of water, and 25 mL of 1 M $HCl_{(aq)}$ was added. The mixture was extracted with ethyl acetate (3×10 mL), then the combined ethyl acetate layers were back extracted with brine (1×10 mL), dried over MgSO$_4$, filtered, and concentrated in vacuo to 1.61 g (71%) of the titled compound as a white solid.

Example 292B

4-Cyano-piperidine-1-carboxylic acid tert-butyl ester

To a solution of 1.61 g (7.04 mmol) of Example 292A in 20 mL of pyridine was added 479 mg (7.04 mmol) of imidazole. After all the imidazole had dissolved, the reaction was cooled with an ice bath, then 1.3 mL (14.1 mmol) of phosphorus oxychloride was added dropwise to control the exothermic addition. The reaction was stirred at 0° C. for 1.5 h, then concentrated in vacuo. The residue was taken up in 20 mL of 1 M HCl$_{(aq.)}$, and extracted with ethyl acetate (3×10 mL). The combined ethyl acetate layers were back extracted with water (1×10 mL), and brine (1×10 mL), dried over MgSO$_4$, filtered, and concentrated in vacuo to an oil. The product was purified via silica gel chromatography, eluting with 30% ethyl acetate: hexanes to give 1.14 g (77%) of the titled nitrile.

Example 292C 4-cyanopiperidine trifluoroacetate salt

To 210 mg (1.00 mmol) of Example 292B was added 1 mL of trifluoroacetic acid. The solution was swirled at ambient temperature for 1 min, then concentrated in vacuo to give 228 mg (100%) of the trifluoroacetic acid salt of the title compound as a white solid.

Example 292D

N-(4-amino-5-cyano-6-ethoxypyridin-2-yl)-2-(4-cyanopiperidin-1-yl)acetamide

To a solution of 55 mg (0.25 mmol) of Example 292C and 60 mg (0.20 mmol) of Example 254A in 1 mL of N,N-dimethylformamide was added 120 µL (0.70 mmol) of N,N-diisopropyl-N-ethylamine. The reaction was stirred at ambient temperature for 30 min, and 10 mL of water was added. The precipitate was collected, washed with water, and dried on the filter to give 44 mg (67%) of the titled compound as a colorless solid. $^1$H NMR (300 MHz, DMSO-d$_6$) δ ppm 9.59 (s, 1H), 7.18 (s, 1H), 6.96 (s, 2H), 4.31 (q, J=7.1 Hz, 2H), 3.18 (s, 2H), 2.90 (m, 1H), 2.66 (m, 2H), 2.45 (m, 2H), 1.87 (m, 2H), 1.74 (m, 2H), 1.30 (t, J=7.0 Hz, 3H); MS (ESI$^+$) m/z=329 [M+H]$^+$. Anal. Calc'd for C$_{16}$H$_{20}$N$_6$O$_2$: C, 58.52; H, 6.14; N, 25.59. Found: C, 58.15; H, 6.05; N, 25.30.

EXAMPLE 293

4-amino-N-[2-(4-benzylpiperazin-1-yl)ethyl]-5-cyano-6-ethoxypyridine-2-carboxamide In a 20 mL vial a solution of Example 104A (32.5 mg, 0.16 mmol) dissolved in N,N-dimethylacetamide (0.8 mL) was added, followed by the addition of O-benzotriazol-1-yl-N,N,N',N'-tetramethyluronium tetrafluoroborate (50.4 mg, 0.16 mmol) dissolved in N,N-dimethylacetamide (0.8 mL). Then, 2-(4-benzylpiperazino)ethan-1-amine (41.3 mg, 0.19 mmol) dissolved in N,N-dimethylacetamide (0.6 mL) was added followed by the addition of diisopropyl ethyl amine (57.9 uL, 0.31 mmol) dissolved in N,N-dimethylacetamide (0.8 mL). The mixture was shaken at room temperature overnight. The reaction was checked by LC/MS and concentrated to dryness. The residue was dissolved in 1:1 dimethyl sulforxide/methanol and purified by reverse phase HPLC (0-70% CH$_3$CN in 10 mM aq. ammonium acetate) to give the titled compound. $^1$H NMR (500 MHz, DMSO-d$_6$) δ ppm 1.33 (t, 3H) 2.19-2.51 (m, 9H) 3.14-3.20 (m, 1H) 3.35 (t, 2H) 3.42-3.49 (m, 2H) 4.41-4.49 (m, 2H) 6.97-7.11 (m, 1H) 7.19-7.44 (m, 5H); MS (ESI) positive ion 409 (M+H).

EXAMPLE 294

4-amino-5-cyano-6-ethoxy-N-({6-[4-(methylsulfonyl)piperazin-1-yl]pyridin-3-yl}methyl)pyridine-2-carboxamide Step A:
6-(4-Methanesulfonyl-piperazin-1-yl)-nicotinonitrile was prepared according to literature procedure (M. Teruyuki, et al. *Chem. Pharm. Bull.* 1987, 35, 2280-2285).

Step B:
6-(4-Methanesulfonyl-piperazin-1-yl)-nicotinonitrile from Step A (53 mg, 0.2 mmol) and Raney Ni (35 mg, prewashed with methanol) was mixed in 30 mL of ammonia (20% solution in methanol). The heavy walled reaction vessel was charged with H$_2$ (40 psi) and the reaction was shaken at room temperature for 4 h. The mixture was filtered to remove the catalyst, the filtrate was then concentrated to give 45 mg of a white solid.

Step C:
The intermediate obtained from step B was suspended in 1 mL of anhydrous N,N-dimethylformamide, followed by the addition of Example 104A (21 mg, 0.1 mmol), O-benzotriazol-1-yl-N,N,N',N'-tetramethyluronium tetrafluoroborate (47 mg, 0.15 mmol), and N,N-diisopropylamine (26 µL, 0.15 mmol). The mixture was stirred at room temperature for 20 h, after which 2 mL of water was added. The precipitate was filtered, then washed with water and methanol to give 40 mg (87%) of the titled compound. $^1$H NMR (300 MHz, DMSO-d$_6$) δ ppm 1.31 (t, J=7.1 Hz, 3H), 2.90 (s, 3H), 3.16-3.25 (m, 4H), 3.58-3.69 (m, 4H), 4.35 (d, J=6.4 Hz, 2H), 4.48 (q, J=7.0 Hz, 2H), 7.00-7.08 (m, 2H), 7.32 (bs, 2H), 7.68 (d, J=6.0 Hz, 1H), 8.06 (d, J=2.4 Hz, 1H), 9.00 (t, J=6.0 Hz, 1H). MS (ESI+) m/e=460 (M+H)$^+$.

EXAMPLE 295

N-(4-amino-5-chloro-6-ethoxypyridin-2-yl)-2-[2,5-dimethoxy-4-(methylsulfonyl)phenyl]acetamide Example 295A 4-Amino-5-cyano-6-ethoxy-pyridine-2-carboxylic acid amide To 231 mg (1.00 mmol) of 4-amino-5-cyano-6-ethoxy-pyridine-2-carboxylic acid methyl ester from Example 104A was added 5 mL of 7 M NH$_3$ in methanol. The reaction was stirred at ambient temperature for 5 h, and concentrated in vacuo to 214 mg (100%) of the titled compound as a solid.

Example 295B 4,6-Diamino-3-chloro-2-ethoxypyridine

To a suspension of 186 mg (0.866 mmol) of Example 295A in 3 mL of 2-propanol was added 2.6 mL of 2 M NaOH$_{(aq)}$, then 2 mL of 0.82 M NaOCl$_{(aq.)}$. The amide dissolved upon addition of the NaOCl solution. The reaction was stirred at ambient temperature for 2 h, then concentrated in vacuo. The residue was taken up in 5 mL of water and filtered through a plug of diatomaceous earth to remove a small amount of insoluble material. The filter plug was washed with water (3×1 mL), then the combined filtrate and washings were acidified with 1 M HCl$_{(aq.)}$. The aqueous solution was made basic by addition of 2 M NaON$_{(aq.)}$. The alkaline aqueous suspension was extracted with ethyl acetate (3×5 mL), then the combined ethyl acetate layers were back extracted with brine (1×5 mL), dried over MgSO$_4$, filtered, and concentrated in vacuo to 93 mg (57% crude) of a soft solid. The diaminopyridine was used without further purification.

Example 295C

N-(4-amino-5-chloro-6-ethoxypyridin-2-yl)-2-[2,5-dimethoxy-4-(methylsulfonyl)phenyl]acetamide To a solution of 50 mg (0.27 mmol) of Example 295B in 1 mL of dichloromethane and 0.3 mL of pyridine at −78° C. was added a solution of 50 mg (0.18 mmol) of Example 197G in 1 mL of dichloromethane. The reaction was stirred at −78° C. for 20 min, then 2 mL of water was added, and the mixture was warmed until the ice had melted. The solvents were removed in vacuo, then the residue was taken up in 20 mL of diethyl ether. The ether solution was extracted with water (1×5 mL), 1 M HCl$_{(aq.)}$ (2×5 mL), saturated NaHCO$_{3(aq.)}$ (2×5 mL), and brine (1×5 mL), dried over MgSO$_4$, filtered, and concentrated in vacuo to a solid. This was recrystallized from methanol in a capped 4 mL vial to give 30 mg (38%) of the titled compound as a white crystalline solid. $^1$H NMR (300 MHz, DMSO-d$_6$) δ ppm 9.98 (s, 1H), 7.30 (s, 1H), 7.26 (s, 1H), 7.14 (s, 1H), 6.20 (s, 2H), 4.31 (q, J=7.1 Hz, 2H), 3.89 (s, 3H), 3.79 (s, 2H), 3.77 (s, 3H), 3.24 (s, 3H), 1.31 (t, J=7.1 Hz, 3H); MS (ESI+) m/z=444 [M+H]$^+$. Anal. Calc'd for C$_{18}$H$_{22}$ClN$_3$O$_6$S: C, 48.70; H, 5.00; N, 9.47. Found: C, 48.84; H, 5.27; N, 9.17.

EXAMPLE 296

N-[4-({[(4-amino-5-cyano-6-ethoxypyridin-2-yl)carbonyl]amino}methyl)phenyl]glycine To a solution of Example 115 (63 mg, 0.2 mmol) and N,N-diisopropylamine (40 µL, 0.22 mmol) in 0.5 mL of anhydrous N,N-dimethylformamide, was added tert-butyl bromoacetate (40 µL, 0.3 mmol). The resulting mixture was stirred at room temperature overnight, after which water was added, and the precipitate filtered. The solid was dissolved in 1 mL of trifluoroacetic acid, then stirred at room temperature for an additional hour. The mixture was concentrated, and purified via reverse phase HPLC (0-70% CH$_3$CN in 10 mM aq. ammonium acetate) to give 35 mg (41%, 2 steps) of the titled compound. $^1$H NMR (400 MHz, DMSO-d$_6$) δ ppm 1.30 (t, J=7.1 Hz, 3H), 3.46 (s, 2H), 4.30 (d, J=6.1 Hz, 2H), 4.46 (q, J=7.3 Hz, 2H), 6.46 (d, J=8.5 Hz, 2H), 7.02 (d, J=8.3 Hz, 2H), 7.07 (s, 1H), 7.28 (bs, 2H), 8.76 (t, J=6.2 Hz, 1H). MS (ESI+) m/e=370 (M+H)$^+$.

EXAMPLE 297

[4-({[(4-amino-5-cyano-6-ethoxypyridin-2-yl)carbonyl]amino}methyl)piperidin-1-yl](oxo)acetic acid To Example 194A (30 mg, 0.10 mmol) in dichloromethane (0.5 mL, not soluble) was added triethylamine and ethyl oxallyl chloride (14 mg, 0.1 mmol) at −78° C. The mixture was then stirred at r.t for 1 h and the volatiles were removed. LiOH (1N in ethanol/water 5:3) was added and the mixture was stirred for 1 h at room temperature and acidified by HCl(aq). The crude material was purified by revered-phase HPLC (0-70% CH$_3$CN in 10 mM aq. ammonium acetate) to give the title compound (15 mg, 40% over 2 steps). $^1$H NMR (400 MHz, DMSO-d$_6$) δ 8.51 (t, J=6.4 Hz, 1H), 7.28 (broad s, 2H), 7.05 (s, 1H), 4.48 (q, J=6.8 Hz, 2H), 4.20 (broad d, J=13.2 Hz, 1H), 3.54 (broad d, J=13.2 Hz, 1H), 3.18 (t, J=6.4 Hz, 2H), 3.11 (dt, J=2.4, 13.2 Hz, 1H), 2.56 (dt, J=2.8, 12.4 Hz, 1H), 1.86 (m, 1H), 1.69 (broad d, J=13.6 Hz, 2H), 1.32 (d, J=7.2 Hz, 3H), and 1.08 (m, 2H). MS (m/e) positive mode: 376 (M+H)$^+$; negative mode: 374 (M−H)$^−$.

EXAMPLE 298

4-amino-N-{2-[4-(aminosulfonyl)phenyl]ethyl}-5-cyano-6-ethoxypyridine-2-carboxamide The titled compound was prepared according to the procedure described in Example 104B, substituting 4-(2-aminoethyl)-benzenesulfonamide for 2,5-dimethoxybenzylamine used in Example 104B. $^1$H NMR (300 MHz, DMSO-d$_6$) δ 8.49 (t, J=5.9 Hz, 1H), 7.75 (d, J=8.1 Hz, 2H), 7.43 (d, J=8.5 Hz, 2H), 7.29 (broad s, 3H), 7.03 (s, 1H), 4.44 (q, J=7.0 Hz, 2H), 3.52 (m, 2H), 2.91 (t, J=7.0 Hz, 2H), 1.31 (t, J=7.0 Hz, 3H). MS (m/e) positive mode: 390 (M+H)$^+$; negative mode: 388 (M−H)$^−$.

What is claimed:

1. A compound of the formula (I), or a pharmaceutically acceptable salt, or a combination thereof,

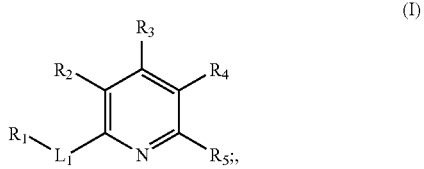

(I)

wherein

L$_1$ is selected from the group consisting of —C(O)—NH—, and —NH—C(O)—;

R$_1$ is selected from the group consisting of alkenyl, alkenyloxyalkyl, alkoxyalkoxyalkyl, alkoxyalkyl, alkoxycarbonylalkyl, alkyl, alkylcarbonylalkyl, alkylsulfinylalkyl, alkylsulfonylalkyl, alkylthioalkyl, alkynyl, alkynylalkyl, alkynylalkoxyalkyl, aryl, arylalkenyl, arylalkenyloxyalkyl, arylalkoxyalkyl, arylalkyl, arylalkylsulfonylalkyl, arylalkylthioalkyl, arylcarbonylalkyl, aryloxyalkyl, arylthioalkyl, arylsulfinylalkyl, arylsulfonylalkyl, carboxyalkyl, cyanoalkyl, cycloakenyl, cycloalkenylalkoxyalkyl, cycloalkenylalkyl, cycloalkenylalkylthioalkyl, cycloalkenyloxy, cycloalkenyloxyalkyl, cycloalkenylsulfinylalkyl, cycloalkenylsulfonylalkyl, cycloalkenylthioalkyl, cycloalkyl, cycloalkylalkoxyalkyl, cycloalkylalkyl, cycloalkylalkylthioalkyl, cycloalkylcarbonylalkyl, cycloalkyloxyalkyl, cycloalkylsulfinylalkyl, cycloalkylsulfonylalkyl, cycloalkylthioalkyl, haloalkyl, heteroaryl, heteroarylalkoxyalkyl, heteroarylalkyl, heteroarylalkylsulfonylalkyl, heteroarylalkylthioalkyl, heteroarylcarbonylalkyl, heteroaryloxy, heteroaryloxyalkyl, heteroarylsulfinylalkyl, heteroarylsulfonylalkyl, heteroarylthioalkyl, heterocycle, heterocyclealkoxyalkyl, heterocycleakyl, heteroarylalkylsulfonylalkyl, heterocyclealkylthioalkyl, heterocyclecarbonylalkyl, heterocyclecarbonylalkenyl, heterocyclesuloxyalkyl, heterocyclesulfinylalkyl, heterocyclesulfonylalkyl, heterocyclethioalkyl, hydroxyalkyl, $(R_aR_b N)$alkyl, $(R_aR_b N)$carbonylalkenyl, $(R_aR_b N)$carbonylalkyl and $(R_aR_b N)$sulfonylalkyl;

$R_2$ is selected from the group consisting of hydrogen, alkyl, alkylcarbonyl, alkylsulfonyl, alkenyl, alkynyl, aryl, arylcarbonyl, arylsulfonyl, cycloalkyl, cycloalkylcarbonyl, cycloalkylsulfonyl, cycloalkenyl, cyano, haloalkyl, heteroaryl, heterocycle, nitro, formyl and alkynylalkenyl;

$R_4$ is selected from the group consisting of alkyl, alkylcarbonyl, alkylsulfonyl, alkenyl, alkynyl, aryl, arylcarbonyl, arylsulfonyl, cycloalkyl, cycloalkylcarbonyl, cycloalkylsulfonyl, cycloalkenyl, cyano, halo, haloalkyl, heteroaryl, heterocycle, nitro, formyl and alkynylalkenyl;

$R_3$ is selected from the group consisting of azido and $R_cR_dN—$;

$R_5$ is selected from the group consisting of alkenyl, alkoxy, alkoxyalkoxy, alkoxyalkoxyalkyl, alkoxyalkyl, alkyl, alkylcarbonylalkyl, alkylsulfonylalkyl, alkylthioalkyl, alkynyl, aryl, arylalkoxy, arylalkoxyalkyl, arylalkyl, aryloxy, aryloxyalkyl, arylthioalkyl, cyanoalkyl, cycloalkenyl, cycloalkenylalkoxy, cycloalkenylalkoxyalkyl, cycloalkenylalkyl, cycloalkyl, cycloalkylalkoxy, cycloalkylalkoxyalkyl, cycloalkylalkyl, cycloalkylalkylthioalkyl, cycloalkyloxy, cycloalkyloxyalkyl, cycloalkylthioalkyl, haloalkoxy, haloalkyl, heteroaryl, heteroarylalkoxy, heteroarylalkoxyalkyl, heteroarylalkyl, heteroarylalkylthioalkyl, heteroaryloxy, heteroaryloxyalkyl, heteroarylthioalkyl, heterocycle, heterocyclealkoxy, heterocyclealkoxyalkyl, heterocyclealkyl, heterocyclealkylthioalkyl, heterocycleoxy, heterocycleoxyalkyl, heterocyclethioalkyl, hydroxyalkyl, hydroxyalkoxy, $R_eR_fN—$, $(R_eR_fN)$alkyl, $(R_eR_fN)$alkoxy, -alkenyl-C(O)OH and —C(O)$R_eR_fN$, $R_a$ and $R_b$ are independently selected from the group consisting of hydrogen, alkoxyalkyl, alkoxyalkylcarbonyl, alkoxycarbonyl, alkyl, alkylcarbonyl, alkylsulfonyl, alkylthioalkyl, alkylthioalkylcarbonyl, alkylthiocarbonyl, aryl, arylalkoxyalkyl, arylalkyl, arylcarbonyl, cycloalkyl, cycloalkylalkyl, cycloalkylalkoxyalkyl, cycloalkylcarbonyl, formyl, heteroaryl, heteroarylalkyl, heteroarylcarbonyl, heterocycle, heterocyclealkyl, heterocyclealkoxyalkyl, heterocyclecarbonyl, $(R_gR_hN)$alkyl and $(R_gR_hN)$carbonyl;

$R_c$ and $R_d$ are independently selected from the group consisting of hydrogen, alkyl, alkoxyalkyl, alkylcarbonyl, alkylsulfonyl, aryl, arylalkyl, arylalkylcarbonyl, arylalkylsulfonyl, arylcarbonyl, arylsulfonyl, cycloalkyl, cycloalkylcarbonyl, cycloalkylsulfonyl, formyl, heteroaryl, heteroarylalkyl, heteroarylcarbonyl, heteroarylsulfonyl, heterocycle, heterocyclealkyl, heterocyclecarbonyl and heterocyclesulfonyl;

$R_e$ and $R_f$ are independently selected from the group consisting of hydrogen, alkoxyalkyl, alkoxyalkylcarbonyl, alkoxycarbonyl, alkoxysulfonyl, alkyl, alkylcarbonyl, alkylsulfonyl, alkylthioalkyl, alkylthioalkylcarbonyl, alkylthiocarbonyl, aryl, arylalkoxyalkyl, arylalkyl, arylcarbonyl, cycloalkyl, cycloalkylalkoxyalkyl, cycloalkylalkyl, cycloalkylcarbonyl, formyl, heteroaryl, heteroarylalkoxyalkyl, heteroarylalkyl, heterocycle, heterocyclealkoxyalkyl, heterocyclealkyl, heterocyclecarbonyl, hydroxyalkyl, $(R_jR_kN)$alkyl and $(R_jR_kN)$carbonyl;

$R_g$ and $R_h$ are independently selected from the group consisting of hydrogen, alkoxycarbonyl, alkyl, alkylcarbonyl, alkoxysulfonyl, alkylsulfonyl, aryl, arylalkyl, arylcarbonyl, cycloalkyl, cycloalkylalkyl, cycloalkylcarbonyl, formyl, heteroaryl, heteroarylalkyl, heteroarylcarbonyl, heterocycle, heterocyclealkyl and heterocyclecarbonyl;

$R_j$ and $R_k$ are independently selected from the group consisting of hydrogen, alkoxycarbonyl, alkyl, alkylcarbonyl, alkylsulfonyl, aryl, arylalkyl, arylcarbonyl, cycloalkyl, cycloalkylalkyl, cycloalkylcarbonyl, formyl, heteroaryl, heteroarylalkyl, heteroarylcarbonyl, heterocycle, heterocyclealkyl and heterocyclecarbonyl.

2. The compound of claim 1, or a pharmaceutically acceptable salt, or a combination thereof, wherein
$L_1$ is selected from the group consisting of —C(O)—NH— and —NH—C(O)—;
$R_3$ is selected from the group consisting of azido and $R_cR_dN—$;
$R_2$ is hydrogen; and
$R_4$ is cyano or halo.

3. The compound of claim 1, or a pharmaceutically acceptable salt, or a combination thereof, wherein
$L_1$ is selected from the group consisting of —C(O)—NH— and —NH—C(O)—;
$R_3$ is selected from the group consisting of azido and $R_cR_dN—$;
$R_2$ is hydrogen;
$R_4$ is cyano or halo;
$R_5$ is selected from the group consisting of alkenyl, alkoxy, alkoxyalkoxy, alkoxyalkyl, alkyl, aryl, arylalkoxy, aryloxy, cycloalkyl, cycloalkylalkoxy, cycloalkyloxy, haloalkoxy, haloalkyl, heteroaryl, heteroarylalkoxy, heteroaryloxy, heterocycle, heterocyclealkoxy, heterocycleoxy, hydroxyalkyl, hydroxyalkoxy, $R_eR_fN$, $(R_eR_fN)$alkyl, $(R_eR_fN)$alkoxy, -alkenyl-COOH and —C(O)$NR_eR_f$; and
$R_1$ is selected from the group consisting of alkoxyalkyl, alkoxycarbonylalkyl, alkyl, alkylsulfonylalkyl, aryl, arylalkenyl, arylalkoxyalkyl, arylalkyl, aryloxyalkyl, arylsulfonylalkyl, carboxyalkyl, cyanoalkyl, cycloalkyl, cycloalkylalkyl, haloalkyl, heteroaryl, hetemarylalkyl, heteroaryloxyalkyl, heterocycle, heterocyclealkyl, heterocycleoxyalkyl, hydroxyalkyl and $(R_aR_bN)$alkyl.

4. The compound of claim 1, or a pharmaceutically acceptable salt, or a combination thereof, wherein
$L_1$ is selected from the group consisting of —C(O)—NH— and —NH—C(O)—;
$R_3$ is selected from the group consisting of azido and $R_cR_dN—$
$R_2$ is hydrogen;
$R_4$ is cyano or halo;
$R_5$ is selected from the group consisting of alkenyl, alkoxy, alkoxyalkoxy, alkyl, aryl, aryloxy, cycloalkylalkoxy, haloalkoxy, heteroaryl, hydroxyalkoxy, $R_eR_bN$, -alkenyl-COOH and —C(O)$NR_eR_b$, and
$R_1$ is selected from the group consisting of alkoxyalkyl, alkyl, alkylsulfonylalkyl, aryl, arylalkyl, arylsulfonylalkyl, cycloalkyl, cycloalkylalkyl, heterocyclealkyl, heteroarylalkyl and $(R_aR_bN)$alkyl-.

5. The compound of claim 4 selected from the group consisting of
N-(4-Amino-5-cyano-6-ethoxy-pyridin-2-yl)-acetamide;
N-(4-amino-5-cyano-6-ethoxypyridin-2-yl)cyclopentanecarboxamide;
N-(4-amino-5-cyano-6-ethoxypyridin-2-yl)pentanamide;
N-(4-amino-5-cyano-6-ethoxypyridin-2-yl)benzamide;

N-(4-amino-5-cyano-6-ethoxypyridin-2-yl)cyclobutanecarboxamide;
N-(4-amino-5-cyano-6-ethoxypyridin-2-yl)butanamide;
N-(4-amino-5-cyano-6-ethoxypyridin-2-yl)-3-methylbutanamide;
N-(4-amino-5-cyano-6-ethoxypyridin-2-yl)hexamide;
N-(4-amino-6-butoxy-5-cyanopyridin-2-yl)acetamide;
N-(4-amino-5-cyano-6-methoxypyridin-2-yl)acetamide;
N-(4-amino-5-cyano-6-ethoxypyridin-2-yl)-2-phenylacetamide;
N-(4-amino-5-cyano-6-ethoxypyridin-2-yl)-3-phenylpropanamide;
N-(4-amino-5-cyano-6-ethoxypyridin-2-yl)propanamide;
N-(4-amino-5-cyano-6-ethoxypyridin-2-yl)-2-methyl; propanamide;
N-(4-amino-5-cyano-6-ethoxypyridin-2-yl)-2,2-dimethylpropanamide;
N-(4-amino-5-cyano-6-phenoxypyridin-2-yl)acetamide;
N-(4-amino-5-cyano-6-isopropoxypyridin-2-yl)acetamide;
N-(4-amino-5-cyano-6-ethoxypyridin-2-yl)-2-methyoxyacetamide;
N-(4-amino-5-cyano-6-ethoxypyridin-2-yl)-2-(3-methoxyphenyl)acetamide;
N-(4-amino-5-cyano-6-ethoxypyridin-2-yl)-2-(4-methoxyphenyl)acetamide;
N-(4-amino-5-cyano-6-ethoxypyridin-2-yl)-2-(2-fluorophenyl)acetamide;
N-(4-amino-5-cyano-6-ethoxypyridin-2-yl)-2-(4-fluorophenyl)acetamide;
N-(4-amino-5-cyano-6-ethoxypyridin-2-yl)-2-(2-chlorophenyl)acetamide;
N-(4-amino-5-cyano-6-ethoxypyridin-2-yl)-2-(4-chlorophenyl)acetamide;
N-(4-amino-5-cyano-6-ethoxypyridin-2-yl)-2-(2-bromophenyl)acetamide;
N-(4-amino-5-cyano-6-ethoxypyridin-2-yl)-2-(3-bromophenyl)acetamide;
N-(4-amino-5-cyano-6-ethoxypyridin-2-yl)-2-(4-bromophenyl)acetamide;
N-(4-amino-5-cyano-6-ethoxypyridin-2-yl)-2-(2-methylphenyl)acetamide;
N-(4-amino-5-cyano-6-ethoxypyridin-2-yl)-2-(3-methylphenyl)acetamide;
N-(4-amino-5-cyano-6-ethoxypyridin-2-yl)-2-(4-methylphenyl)acetamide;
N-(4-amino-5-cyano-6-ethoxypyridin-2-yl)-2-(2-methoxyphenyl)acetamide;
N-(4-amino-5-cyano-6-ethoxypyridin-2-yl)-2-(2,5-difluorophenyl)acetamide;
N-(4-amino-5-cyano-6-ethoxypyridin-2-yl)-2-(3-fluorophenyl)acetamide;
N-(4-amino-5-cyano-6-ethoxypyridin-2-yl)-2-(3-chlorophenyl)acetamide;
N-(4-amino-5-cyano-6-ethoxypyridin-2-yl)-2-(2-nitrophenyl)acetamide;
N-(4-amino-5-cyano-6-ethoxypyridin-2-yl)-2-(2,4-dichlorophenyl)acetamide;
N-(4-amino-5-cyano-6-ethoxypyridin-2-yl)-2-(3-nitrophenyl)acetamide;
N-(4-amino-5-cyano-6-ethoxypyridin-2-yl)-2-(4-nitrophenyl)acetamide;
N-(4-amino-5-cyano-6-ethoxypyridin-2-yl)-2-[3-(trifluoromethyl)phenyl]acetamide;
N-(4-amino-5-cyano-6-ethoxypyridin-2-yl)-2-[4-(benzyloxy)phenyl]acetamide;
N-(4-amino-5-cyano-6-ethoxypyridin-2-yl)-2-(1-naphthyl)acetamide;
N-(4-amino-5-cyano-6-ethoxypyridin-2-yl)-2-(2-naphthyl)acetamide;
N-(4-amino-5-cyano-6-ethoxypyridin-2-yl)-2-(2,5-dimethylphenyl)acetamide;
N-(4-amino-5-cyano-6-ethoxypyridin-2-yl)-2-(3,5-dimethylphenyl)acetamide;
N-(4-amino-5-cyano-6-ethoxypyridin-2-yl)-2-(2,4-dimethoxyphenyl)acetamide;
N-(4-amino-5-cyano-6-ethoxypyridin-2-yl)-2-(2,5-dimethoxyphenyl)acetamide;
N-(4-amino-5-cyano-6-ethoxypyridin-2-yl)-2-(3,4-dimethoxyphenyl)acetamide;
N-(4-amino-5-cyano-6-ethoxypyridin-2-yl)-2-(3,5-dimethoxyphenyl)acetamide;
N-(4-amino-5-cyano-6-ethoxypyridin-2-yl)-2-(1,3-benxodioxol-5-yl)acetamide;
N-(4-amino-5-cyano-6-ethoxypyridin-2-yl)-2-(2,3-difluorophenyl)acetamide;
N-(4-amino-5-cyano-6-ethoxypyridin-2-yl)-2-(1,1'-biphenyl-4-yl)acetamide;
N-(4-amino-5-cyano-6-ethoxypyridin-2-yl)-2-[4-(dimethylamino)phenyl]acetamide;
N-(4-amino-5-cyano-6-ethoxypyridin-2-yl)-2-[4-(trifluoromethyl)phenyl]acetamide;
N-(4-amino-5-cyano-6-ethoxypyridin-2-yl)-2-[4-(trifluoromethoxy)phenyl]acetamide;
N-(4-amino-5-cyano-6-ethoxypyridin-2-yl)-2-(4-phenoxyphenyl)acetamide;
N-(4-amino-5-cyano-6-ethoxypyridin-2-yl)-2-(3,4,5-trimethoxyphenyl)acetamide;
N-(4-amino-5-cyano-6-ethoxypyridin-2-yl)-3,3-dimethylbutanamide;
N-(4-amino-5-cyano-6-ethoxypyridin-2-yl)-2-(2,3-dimethyoxyphenyl)acetamide;
N-(4-amino-5-cyano-6-ethoxypyridin-2-yl)-2-thien-2-ylacetamide;
N-(4-amino-5-cyano-6-isopropoxypyridin-2-yl)-2-(2,5-dimethoxyphenyl)acetamide;
N-[4-amino-5-cyano-6-(2-methoxyethoxy)pyridin-2-yl]-2-(2,5-dimethyoxyphenyl)acetamide;
N-[4-amino-5-cyano-6-(2-hydroxyethoxy)pyridin-2-yl]-2-(2,5-dimethoxyphenyl)acetamide;
N-(4-amino-5-cyano-6-ethoxypyridin-2-yl)-2-cyclohexylacetamide;
N-(4-amino-5-cyano-6-ethoxypyridin-2-yl)-2-cyclopentylacetamide;
N-(4-amino-5-cyano-6-phenylpyridin-2-yl)acetamide;
N-(4-amino-5-cyano-6-propylpyridin-2-yl)acetamide;
N-(4-amino-5-cyano-6-isobutylpyridin-2-yl)-2-(3-methoxyphenyl)acetamide;
N-(4-amino-5-cyano-6-propylpyridin-2-yl)-2-(2,5-dimethoxyphenyl)acetamide;
N-(4-amino-5-cyano-6-phenylpyridin-2-yl)-2-(2,5-dimethoxyphenyl)acetamide;
N-[4-amino-5-cyano-6-(4-methylphenoxy)pyridin-2-yl]acetamide;
N-[4-amino-5-cyano-6-(4-phenoxyphenoxy)pyridin-2-yl]acetamide;
N-{4-amino-5-cyano-6-[4-(1H-pyrrol-1-yl)phenoxy]pyridin-2-yl}acetamide;
N-[4-amino-6-(4-benzylphenoxy)-5-cyanopyridin-2-yl]acetamide;
N-[4-amino-6-(4-tert-butylphenoxy)-5-cyanopyridin-2-yl]acetamide;

N-(4-{[6-(acetylamino)-4-amino-3-cyanopyridin-2-yl]oxy}phenyl)acetamide;
N-[4-amino-5-cyano-6-(4-propoxyphenoxy)pyridin-2-yl]acetamide;
N-[4-amino-5-cyano-6-(4-ethoxyphenoxy)pyridin-2-yl]acetamide;
N-[4-amino-5-cyano-6-(3-methylphenyl)pyridin-2-yl]acetmide;
methyl 4-[6-(acetylamino)-4-amino-3-cyanopyridin-2-yl]benzoate;
N-[4-amino-5-cyano-6-(3-methoxyphenyl)pyridin-2-yl]acetamide;
N-[4-amino-5-cyano-6-(4-methoxyphenyl)pyridin-2-yl]acetamide;
N-[4-amino-6-(3-chlorophenyl)-5-cyanopyridin-2-yl]acetamide;
N-[4-amino-6-(4-chlorophenyl)-5-cyanopyridin-2-yl]acetamide;
N-[4-amino-5-cyano-6-(3-cyanophenyl)pyridin-2-yl]acetamide;
N-[4-amino-5-cyano-6-(4-cyanophenyl)pyridin-2-yl]acetamide;
N-[6-(3-acetylphenyl)-4-amino-5-cyanopyridin-2-yl]acetamide;
N-[4-amino-5-cyano-6-(4-phenoxyphenyl)pyridin-2-yl]acetamide;
N-[6-(4-acetylphenyl)-4-amino-5-cyanopyridin-2-yl]acetamide;
N-{4-amino-5-cyano-6-[4-(trifluoromethoxy)phenyl]pyridin-2-yl}acetamide;
N-[4-amino-5-cyano-6-(3,4-dimethylphenyl)pyridin-2-yl]acetamide;
N-[4-amino-5-cyano-6-(3,5-dimethylphenyl)pyridin-2-yl]acetamide;
N-[4-amino-5-cyano-6-(2,4-dimethoxyphenyl)pyridin-2-yl]acetamide;
N-(4-amino-5-cyano-6-thien-2-ylpyridin-2-yl)acetamide;
N-(4-amino-5-cyano-6-thien-3-ylpyridin-2-yl)acetamide;
N-[4-amino-6-(1-benzofuran-2-yl)-5-cyanopyridin-2-yl]acetamide;
N-[6-(5-acetylthien-2-yl)-4-amino-5-cyanopyridin-2-yl]acetamide;
N-[4-amino-5-cyano-6-(2-naphthyl)pyridin-2-yl]acetamide;
N-(4-amino-3-cyano-2,3'-bipyridin-6-yl)acetamide;
N-[4-amino-5-cyano-6-(3,4-dihydro-2H-1,5-benzodioxepin-7-yl)pyridin-2-yl]acetamide;
N-{4-amino-5-cyano-6-[4-(methylsulfonyl)phenyl]pyridin-2-yl}acetamide;
N-(4-amino-5-cyano-6-ethylpyridin-2-yl)acetamide;
4-azido-5-cyano-N-(2,5-dimethoxybenzyl)-6-isopropoxypyridine-2-carboxmide;
4-amino-5-cyano-N-(2,5-dimethoxybenzyl)-6-isopropoxypyridine-2-carboxamide;
4-amino-5-cyano-N-(2,5-dimethoxybenzyl)-6-ethoxypyridine-2-carboxamide;
4-amino-5-cyano-6-ethoxy-N-(1-phenylethyl)pyridine-2-carboxamide;
4-amino-5-cyano-6-ethoxy-N-(pyridin-4-ylmethyl)pyridine-2-carboxamide;
4-amino-5-cyano-6-ethoxy-N-(pyridin-3-ylmethyl)pydine-2-carboxamide;
4-amino-5-cyano-6-ethoxy-N-(pyridin-2-ylmethyl)pydine-2-carboxamide;
4-amino-N-benzyl-5-cyano-6-ethoxypyridine-2-carboxamide;
4-amino-5-cyano-6-ethoxy-N-(2-methylbenzyl)pyridine-2-carboxamide;
4-amino-5-cyano-6-ethoxy-N-(3-methylbenzyl)pyridine-2-carboxamide;
4-amino-5-cyano-6-ethoxy-N-(4-methylbenzyl)pyridine-2-carboxamide;
4-amino-N-(2-aminobenzyl)-5-cyano-6-ethoxypyridine-2-carboxamide;
4-amino-N-(3-aminobenzyl)-5-cyano-6-ethoxypyridine-2-carboxamide;
4-amino-N-(4-aminobenzyl)-5-cyano-6-ethoxypyridine-2-carboxamide;
4-amino-5-cyano-6-ethoxy-N-{4-[(trifluoromethyl)thio]benzyl}pyridine-2-carboxamide;
4-amino-5-cyano-6-ethoxy-N-[3-fluoro-5-(trifluoromethyl)benzyl]pyridine-2-carboxamide;
methyl 4-({[(4-amino-5-cyano-6-ethoxypyridin-2-yl)carbonyl]amino}methyl)benzoate;
4-amino-5-cyano-6-ethoxy-N-(2-methoxybenzyl)pyridine-2-carboxamide;
4-amino-5-cyano-6-ethoxy-N-(3-methoxybenzyl)pyridine-2-carboxamide;
4-amino-5-cyano-6-ethoxy-N-(4-methoxybenzyl)pyridine-2-carboxamide;
4-amino-5-cyano-6-ethoxy-N-(2-fluorobenzyl)pyridine-2-carboxamide;
4-amino-5-cyano-6-ethoxy-N-(3-fluorobenzyl)pyridine-2-carboxamide;
4-amino-5-cyano-6-ethoxy-N-(4-fluorobenzyl)pyridine-2-carboxamide;
4-amino-N-(2-chlorobenzyl)-5-cyano-6-ethoxypyridine-2-carboxamide;
4-amino-N-(3-chlorobenzyl)-5-cyano-6-ethoxypyridine-2-carboxamide;
4-amino-N-(4-chlorobenzyl)-5-cyano-6-ethoxypyridine-2-carboxamide;
4-amino-N-(2-bromobenzyl)-5-cyano-6-ethoxypyridine-2-carboxamide;
4-amino-N-(3-bromobenzyl)-5-cyano-6-ethoxypyridine-2-carboxamide;
4-Amino-5-cyano-6-ethoxy-pyridine-2-carboxylic acid 3-nitro-benzylamide;
4-Amino-5-cyano-6-ethoxy-pyridine-2-carboxylic acid 4-nitro-benzylamide;
4-amino-5-cyano-6-ethoxy-N-[4-(trifluoromethoxy)benzyl]pyridine-2-carboxamide;
4-amino-5-cyano-N-[4-(dimethylamino)benzyl]6-ethoxypyridine-2-carboxamide;
4-amino-5-cyano-6-ethoxy-N-[3-(trifluoromethyl)benzyl]pyridine-2-carboxamide;
4-amino-5-cyano-6-ethoxy-N-[4-(trifluoromethyl)benzyl]pyridine-2-carboxamide;
4-amino-5-cyano-6-ethoxy-N-[3-(trifluoromethoxy)benzyl]pyridine-2-carboxamide;
4-amino-5-cyano-6-ethoxy-N-(1-naphthylmethyl)pyridine-2-carboxamide;
4-amino-N-(4-tert-butylbenzyl)-5-cyano-6-ethoxypyridine-2-carboxamide;
4-amino-5-cyano-N-(2,3-dimethylbenzyl)-6-ethoxypyridine-2-carboxamide;
4-amino-5-cyano-N-(2,4-dimethylbenzyl)-6-ethoxypyridine-2-carboxamide;
4-amino-5-cyano-N-(2,5-dimethylbenzyl)-6-ethoxypyridine-2-carboxamide;
4-amino-5-cyano-N-(3,4-dimethylbenzyl)-6-ethoxypyridine-2-carboxamide;

4-amino-5-cyano-N-(3,5-dimethylbenzyl)-6-ethoxypyridine-2-carboxamide;
4-amino-5-cyano-N-(2,3-dimethoxybenzyl)-6-ethoxypyridine-2-carboxamide;
4-amino-5-cyano-N-(2,4-dimethoxybenzyl)-6-ethoxypyridine-2-carboxamide;
4-amino-5-cyano-N-(3,4-dimethoxybenzyl)-6-ethoxypyridine-2-carboxamide;
4-amino-5-cyano-N-(3,5-dimethoxybenzyl)-6-ethoxypyridine-2-carboxamide;
4-amino-N-(1,3-bentodioxol-5-ylmethyl)-5-cyano-6-ethoxypyridine-2-carboxamide;
4-amino-5-cyano-6-ethoxy-N-(3,4,5-trimethoxybenzyl)pyridine-2-carboxmide;
4-amino-5-cyano-N-(2,3-dichlorobenzyl)-6-ethoxypyridine-2-carboxamide;
4-amino-5-cyano-N-(2,4-dichlorobenzyl)-6-ethoxypyridine-2-carboxamide;
4-amino-5-cyano-N-(2,5-dichlorobenzyl)-6-ethoxypyridine-2-carboxamide;
4-amino-5-cyano-N-(3,5-dichlorobenzyl)-6-ethoxypyridine-2-carboxamide;
5-cyano-N-(2,5-dimethoxybenzyl)-6-ethoxypyridine-2-carboxamide;
4-amino-N-[2-(aminosulfonyl)benzyl]-5-cyano-6-ethoxypyridine-2-carboxamide;
4-amino-5-cyano-N-{2-[(dimethylamino)sulfonyl]benzyl}6-ethoxypyridine-2-carboxamide;
methyl 3-[5-({[(4-amino-5-cyano-6-ethoxypyridin-2-yl)carbonyl]amino}methyl)pyridin-2-yl]benzoate;
4-amino-5-cyano-6-ethoxy-N-[4-(phenylsulfinyl)benzyl]pyridine-2-carboxamide;
4-amino-5-cyano-6-ethoxy-N-[(6-{4-[(methylamino)carbonyl]phenyl}pyridin-3-ylmethyl]pyridine-2-carboxamide;
4-amino-5-cyano-6-isopropoxy-N-[4-(methylsulfonyl)benzyl]pyridine-2-carboxamide;
methyl 4-[5-({[(4-amino-5-cyano-6-ethoxypyridin-2-yl)carbonyl]amino}methypyridin-2-yl]benzoate;
4-amino-N-[2-(aminosulfonyl)benzyl]-5-chloro-6-ethoxypyridine-2-carboxmide;
4-amino-5-cyano-6-ethoxy-N-[4-(1,2,3-thiadiazol-5-yl)benzyl]pyridine-2-carboxamide;
4-amino-5-cyano-N-(4-cyanobenzyl)-6-ethoxypyridine-2-carboxamide;
N-(4-amino-5-cyano-6-ethoxypyridin-2-yl)-2-(4-amino-2,5-dimethoxyphenyl)acetamide;
4-amino-5-cyano-6-ethoxy-N-[(6-methoxypyridin-3-yl)methyl]pyridine-2-carboxamide;
N-(4-amino-5-cyano-6-ethoxypyridin-2-yl)-2-[2-methoxy-5-(methylthio)phenyl]acetamide;
4-amino-5-cyano-6-ethoxy-N-{4-[(2-hydroxyethyl)sulfonyl]benzyl}pyridine-2-carboxamide;
4-amino-N-[2-(aminosulfonyl)benzyl]-5-chloro-6-isopropoxypyridine-2-carboxamide;
4-amino-5-cyano-6-ethoxy-N-[4-(phenylsulfonyl)benzyl]pyridine-2-carboxmide;
4-amino-5-cyano-6-ethoxy-N-[(6-piperidin-1-1ypyridin-3-yl)methyl]pyridine-2-carboxamide;
4-amino-5-cyano-6-ethoxy-N-[4-(isopropylsulfonyl)benzyl]pyridine-2-carboxamide;
4-amino-5-cyano-6-ethoxy-N-[4-(methylsulfonyl)benzyl]pyridine-2-carboxamide;
2-[4-(acetylamino)-2,5-dimethoxyphenyl]-N-(4-amino-5-cyano-6-ethoxypyridin-2-yl)acetamide;
4-amino-5-cyano-N-[(dimethylamino)sulfonyl]benzyl]-6-ethoxypyridine-2-carboxamide;
4-amino-5-cyano-N-[6-(3,5-dimethoxyphenyl)pyridin-3-yl]methyl)-6-ethoxypyridine-2-carboxamide;
4-amino-5-cyano-6-ethoxy-N-[4-(methylsulfonyl)-3-(trifluoromethyl)benzyl]pyridine-2-carboxamide;
4-amino-5-cyano-6-(cyclopentylmethoxy)-N-[4-(methylsulfonyl)benzyl]pyridine-2-arboxamide;
4-amino-5-cyano-6-(isopropylamino)-N-[4-(methylsulfonyl)benzyl]pyridine-2-carboxamide;
4-amino-5-cyano-6-ethoxy-N-[4-(ethylsulfonyl)benzyl]pyridine-2-carboxmide;
4-amino-5-chloro-6-ethoxy-N-[4-(methylsulfonyl)benzyl]pyridine-2-carboxamide;
4-amino-N-[(6-chloropyridin-3-yl)methyl]-5-cyano-6-ethoxypyridine-2-carboxmide;
4-amino-5-cyano-6-(cyclopropylmethoxy)-N-[4-(methylsulfonyl)benzyl]pyridine-2-carboxamide;
4-amino-5-chloro-6-isopropoxy-N-[4-(methylsulfonyl)benzyl]pyridine-2-carboxamide;
4-amino-5-cyano-6-ethoxy-N-{4-[2-(methylamino)-2-oxoethoxy]benzyl)pyridine-2-carboxamide;
4-amino-5-cyano-6-(cyclopent ylamino)-N-[4-(methylsulfonyl)benzyl]pyridine-2-carboxamide;
4-amino-N-(1H-benzimidazol-2-ylmethyl)-5-cyano-6-ethoxypyridine-2-carboxamide;
4-amino-5-cyano-6-ethoxy-N-(4-molpholin-4-ylbenzyl)pyridine-2-carboxamide;
4-amino-5-cyano-N-[4-(methylsulfonyl)benzyl]-6-thien-3-ylpyridine-2-carboxamide;
4-amino-5-cyano-6-(cyclobutylamino)-N-[4-(methylsulfonyl)benzyl]pyridine-2-carboxamide;
methyl 4-{[4-({[(4-amino-5-cyano-6-ethoxypyridin-2-yl)carbonyl]amino}methyl)piperidin-1-yl]carbonyl}benzoate;
4-amino-5-cyano-6-ethoxy-N-[6-(trifluoromethyl)pyridin-3-yl]methyl}pyridine-2-carboxamide;
methyl 1-[5-({[(4-amino-5-cyano-6-ethoxypyridin-2-yl)carbonyl]amino}methyl)pyridin-2-yl]piperidine-4-carboxylate;
N-(4-amino-5-cyano-6-isopropoxypyridin-2-yl)-2-[2,5-d]methoxy-4-(methylsulfonyl)phenyl]acetamide;
4-amino-5-cyano-6-ethoxy-N-(4-fluoro-3-methoxybenzyl)pyridine-2-carboxamide;
4-amino-5-cyano-6-ethoxy-N-[4-({[4-(methylsulfonyl)phenyl]amino}methyl)benzyl]pyridine-2-carboxamide;
N-[4-({[(4-amino-5-cyano-6-ethoxypyridin-2-yl)carbonyl]amino}methyl)phenyl]glycinamide;
4-amino-5-cyano-6-isobutoxy-N-[4-(methylsulfonyl)benzyl]pyridine-2-carboxamide;
N-[4-(acetylamino)benzyl]-4-amino-5-cyano-6-ethoxypyridine-2-carboxamide;
4-amino-5-cyano-6-ethoxy-N-[2-methoxy-4-(methylsulfonyl)benzyl]pyridine-2-carboxamide;
4-amino-N-[4-(aminosulfonyl)benzyl]-5-cyano-6-ethoxypyridine-2-carboxamide;
4-amino-5-cyano-6-ethoxy-N-{2-[(5-nitropyridin-2-yl)amino]ethyl}pyridine-2-carboxamide;
4-amino-5-cyano-6-ethoxy-N-({6-[3-(methylsulfonyl)phenyl]pyridin-3-yl}methyl)pyridine-2-carboxamide;
4-amino-5-cyano-6-ethoxy-N-[2-(methylthio)benzyl]pyridine-2-carboxamide;
methyl N-{[4-({[(4-amino-5-cyano-6-ethoxypyridin-2-yl)carbonyl]amino}methyl)phenyl]sulfonyl}glycinate;
4-amino-5-cyano-6-ethoxy-N-(4-hydroxybenzyl)pyridine-2-carboxamide;
4-amino-5-cyano-6-ethoxy-N-[(1-pyrimidin-2-ylpiperidin-4-yl)methyl]pyridine-2-carboxamide;

4-amino-5-cyano-6-ethoxy-(N{[6-(methylsulfonyl)pyridin-3-yl]methyl}pyridine-2-carboxamide;
4-amino-5-cyano-6-ethoxy-N-{[6-(methylthio)pyridin-3-yl]methyl}pyridine-2-carboxamide;
4-amino-5-cyano-6-ethoxy-N-[4-(isopropylsulfinyl)benzyl]pyridine-2-carboxamide;
4-amino-5-cyano-N-[4-(methylsulfonyl)benzyl]-6-[(1E)-prop-1-enyl]pyridine-2-carboxamide;
tert-butyl N-{[4-({[(4-amino-5cyano-6-ethoxypyridin-2-yl)carbonyl]amino}methyl)phenyl]sulfonyl}-β-alaninate;
4-amino-5-cyano-6-ethoxy-N-[(6-methylpyridin-3-yl)methyl]pyridine-2-carboxamide;
4-amino-N-{2-[(tent-butylamino)sulfonyl]benzyl}-5-cyano-6-ethoxypyridine-2-carboxamide;
N-(4-amino-5-cyano-6-ethoxypyridin-2-yl)-2{2,5-dimethoxy-4-[(methylsulfonyl)amino]phenyl}acetamide;
4-amino-5-cyano-6-ethoxy-N-[2-(methylsulfonyl)benzyl]pyridine-2-carboxmide;
4-amino-5-cyano-6-ethoxy-N-(4-propionylbenzyl)pyridine-2-carboxmide;
4-amino-5-cyano-6-ethoxy-N-[(5-methylpyridin-3-yl)methyl]pyridine-2-carboxamide;
4-amino-5-cyano-N-{4-[2-(dimethylamino)-2-oxoethoxy]benzyl}-6-ethoxypyridine-2-carboxamide;
4-amino-5-cyano-N-[4-(phenylsulfonyl)benzyl]-6-thien-3-ylpyridine-2-carboxamide;
4-amino-5-bromo-6-ethoxy-N-[4-(methylsulfonyl)benzyl]pyridine-2-carboxamide;
4-amino-5-cyano-6-ethoxy-N-(3-hydroxybenzyl)pyridine-2-carboxamide;
4-amino-N-[4-(2-amino-2-oxoethoxy)benzyl]-5-cyano-6-ethoxypyridine-2-carboxamide;
N-(4-amino-5-cyano-6-ethoxypyridin-2-yl)-2-[2-methoxy-5-(methylsulfonyl)phenyl]acetamide;
4-amino-5-cyano-6-ethoxy-N-[3-(methylsulfonyl)benzyl]pyridine-2-carboxmide;
benzyl 4-({[(4-amino-5-cyano-6-ethoxypyridin-2-yl)carbonyl]amino}methyl)pipendine-1-carboxylate;
4-amino-5-cyano-6-ethoxy-N-(4-ethoxybenzyl)pyridine-2-carboxamide;
4-amino-5-cyano-6-ethoxy-N-{4-[(methylamino)carbonyl]benzyl}pyridine-2-carboxamide;
4-[5-({[(4-amino-5-cyano-6-ethoxypyridin-2-yl)carbonyl]amino}methyl)pyridin-2-yl]benzoic acid;
4-amino-5-cyano-6-ethoxy-N-[(6-{3-[(methylamino)carbonyl]phenyl}pyridin-3-yl)methyl]pyridine-2-carboxamide;
4-amino-5-cyano-6-ethoxy-N-[(6-phenylpyridin-3-yl)methyl]pyridine-2-carboxamide;
4-amino-5-cyano-6-ethoxy-N-({6-[4-(methylsulfonyl)phenyl]pyridin-3-yl}methyl)pyridine-2-carboxamide;
methyl 3-{[4-({[(4-amino-5-cyano-6-ethoxypyridin-2-yl)carbonyl]amino}methyl)piperidin-1-yl]carbonyl}benzoate;
4-amino-N-[(5-chlorothien-2-yl)methyl]-5-cyano-6-ethoxypyridine-2-carboxmide;
4-amino-5-cyano-6-(cyclopropylamino)-N-[4-(methylsulfonyl)benzyl]pyridine-2-carboxamide;
4-amino-6-ethoxy-5-iodo-N-[4-(methylsulfonyl)benzyl]pyridine-2-carboxamide;
tent-butyl 3-{[4-amino-3-cyano-6-({[4-(methylsulfonyl)benzyl]amino}carbonyl)pyridin-2-yl]amino}pyrrolidine-1-carboxylate;
4-amino-5-cyano-6-ethoxy-N-(2-hydroxybenzyl)pyridine-2-carboxmide;
4-amino-5-cyano-6-ethoxy-N-(4-pentanoylbenzyl)pyridine-2-carboxamide;
4-amino-5-cyano-6-ethoxy-N-[3-methoxy-4-(methylsulfonyl)benzyl]pyridine-2-carboxamide;
4-amino-5-cyano-6-ethoxy-N-[(5-pyridin-2-ylthien-2-yl)methyl]pyridine-2-carboxamide;
4-amino-5-cyano-6-ethoxy-N-[(6-fluoropyridin-3-yl)methyl]pyridine-2-carboxamide;
4-amino-N-[(1-benzylpiperidin-4-yl)methyl]-5-cyano-6-ethoxypyridine-2-carboxamide;
4-amino-N-[(2-chloropyridin-3-yl)methyl]-5-cyano-6-ethoxypyridine-2-carboxamide;
N-(4-amino-5-cyano-6-ethoxypyridin-2-yl)-2-[2,5-dimethoxy-4-(methylsulfonyl)phenyl]acetamide;
4-amino-5-cyano-6-ethoxy-N-[4-(morpholin-4-ylcarbonyl)benzyl]pyridine-2-carboxamide;
ethyl 2-[5-({[(4-amino-5-cyano-6-ethoxypyridin-2-yl)carbonyl]amino}methyl)pyridin-2-yl]benzoate;
trans-4-amino-5-cyano-6-ethoxy-N-({4-(methylsulfonyl)amino]cyclohexyl}methyl)pyridine-2-carboxamide;
isobutyl 4-({[(4-amino-5-cyano-6-ethoxypyridin-2-yl)carbonyl]amino}methyl)piperidine-1-carboxylate;
2-(4-acetyl-4-phenylpiperidin-1-yl)-N-(4-amino-5-cyano-6-ethoxypyridin-2-yl)acetamide;
4-amino-5-cyano-6-ethoxy-N-[(1-pyridin-2-ylpiperidin-4-yl)methyl]pyridine-2-carboxamide;
4-amino-5-cyano-6-ethoxy-N-{4-[(methylamino)sulfonyl]benzyl}pyridine-2-carboxamide;
methyl 1-{2-[(4-amino-5-cyano-6-ethoxypyridin-2-yl)amino]-2-oxoethyl}piperidine-4-carboxylate;
4-amino-5-cyano-6-ethoxy-N-(4-heptanoylbenzyl)pyridine-2-carboxamide;
4-amino-5-cyano-6-ethoxy-N-[4-(pyridin-2-yloxy)benzyl]pyridine-2-carboxamide;
4-amino-5-cyano-6-ethoxy-N-(1,3-thiazol-5-ylmethyl)pyridine-2-carboxamide;
N-(4-amino-5-cyano-6-ethoxypyridin-2-yl)-2-[2-(meythylthio)phenyl]acetamide;
4-amino-5-cyano-6-(3-methoxyphenyl)-N-[4-(methylsulfonyl)benzyl]pyridine-2-carboxamide;
methyl trans-N-{[4-({[(4-amino-5-cyano-6-ethoxypyridin-2-yl)carbonyl]amino}methyl)cyclohexyl]carbonyl-L-norleucinate;
4-amino-5-cyano-6-ethoxy-N-[(4-methyl-1H-imidazol-2-yl)methyl]pyridine-2-carboxamide;
4-amino-5-cyano-N-(pyridin-3-ylmethyl)-6-thien-3-ylpyridine-2-carboxamide;
methyl 4-({[(4-amino-5-cyano-6-ethoxypyridin-2-yl)carbonyl]amino}methyl)pipendine-1-carboxylate;
4-amino-5-bromo-N-(2,5-dimethoxybenzyl)-6-ethoxypyridine-2-carboxamide;
4-amino-5-cyano-6-ethoxy-N-[(2-fluoropyridin-3-yl)methyl]pyridine-2-carboxamide;
4-amino-6-ethoxy-5-fluoro-N-[4-(methylsulfonyl)benzyl]pyridine-2-carboxamide;
N-(4-amino-5-cyano-6-ethoxypyridin-2-yl)-2-[4-(methysulfonyl) phenyl]acetamide;
4-amino-5-cyano-6-ethoxy-N-[2-(methylsulfonyl)ethyl]pyridine-2-carboxamide;
4-amino-5-cyano-N-[4-(methylsulfonyl)benzyl]-6-{[3-(methylthio)propyl]amino}pyridine-2-carboxamide;
methyl trans-4-({[(4-amino-5-cyano-6-ethoxypyridin-2-yl)carbonyl]amino}methyl)cyclohexanecarboxylate;
1-{2-[(4-amino-5-cyano-6-isopropoxypyridin-2-yl)amino]-2-oxoethyl}pipendine-4-carboxamide;
4-amino-5-cyano-6-ethoxy-N-{4-[(trifluoromethyl)sulfonyl]benzyl}pyridine-2-carboxamide;

4-amino-5-cyano-6-ethoxy-N-{3-[(4-methylphenyl)sulfonyl]propyl}pyridine-2-carboxamide;
(2E)-3-[4-amino-3-cyano-6-({[4-(methylsulfonyl)benzyl]amino}carbonyl)pyridin-2-yl]acrylic acid;
4-amino-5-cyano-6-{[(1R)-2-hydroxy-1-methylethyl]amino}-N-[4-(methylsulfonyl)benzyl]pyridine-2-carboxamide;
4-amino-5-cyano-6-ethoxy-N-[2-(6-methoxy-1-indol-3-yl)ethyl]pyridine-2-carboxamide;
4-azido-5-cyano-6-isopropoxy-N-[4-(methylsulfonyl)benzyl]pyridine-2-carboxamide;
4-amino-3-cyano-$N^2$-isopropyl-$N^6$-[4-(methyl sulfonyl)$_b$ enzyl]pyridine-2,6-dicarboxamide;
N-(4-amino-5-cyano-6-ethoxypyridin-2-yl)-2-[2-methoxy-5-(methylsulfinyl)phenyl]acetamide;
4-amino-5-cyano-6-ethoxy-N-[3-(1H-imidazol-2-yl)propyl]pyridine-2-carboxamide;
4-amino-5-cyano-6-ethoxy-N-({1-[(isopropylamino)carbonyl]piperidin-4-yl}methyl)pyridine-2-carboxamide;
4-amino-5-cyano-6-ethoxy-N-{[(3S)-1-(methylsulfonyl)pyrrolidin-3-yl]methyl}pyridine-2-carboxamide;
trans-tent-butyl 4-({[(4-amino-5-cyano-6-ethoxypyridin-2-yl)carbonyl]amino methyl}cyclohexylcarbamate;
N-[4-amino-5-cyano-6-(2,2,2-trifluoro-1-methylethoxy)pyridin-2-yl]acetamide;
4-amino-5-cyano-6-ethoxy-N-[3-(methylsulfonyl)propyl]pyridine-2-carboxamide;
N-(4-amino-5-cyano-6-ethoxypyridin-2-yl)-2-(4-cyanopiperadin-1-yl)acetamide;
4-amino-N-[2-(4-benzylpiperazin-1-yl)ethyl]-5-cyano-6-ethoxypyridine-2-carboxamide;
4-amino-5-cyano-6-ethoxy-N-({6-[4-(methylsulfonyl)piperazin-1-yl]pyridin-3-yl}methyl)pyridine-2-carboxamide;
N-(4-amino-5-chloro-6-ethoxypyridin-2-yl)-2-[2,5-dimethoxy-4-(methylsulfonyl)phenyl]acetamide;
N-[4-({[(4-amino-5-cyano-6-ethoxypyridin-2-yl)carbonyl]amino}methyl)phenyl]glycine;
[4-({[(4-amino-5-cyano-6-ethoxypyridin-2-yl)carbonyl}methyl)piperidin-1-yl](oxo)acetic acid; and
4-amino-N-{2-[4-(aminosulfonyl)phenyl]ethyl}-5-cyano-6-ethoxypyridine-2-carboxamide; or
a pharmaceutically acceptable salt, or a combination thereof.

6. The compound of claim 1, or a pharmaceutically acceptable salt, or a combination thereof, wherein
$L_1$ is selected from the group consisting of —C(O)—NH— and —NH—C(O)—;
$R_3$ is selected from the group consisting of azido and $R_cR_dN$—;
$R_1$ is hydrogen;
$R_4$ is heteroaryl, formyl or alkynylalkenyl;
$R_5$ is selected from the group consisting of alkenyl, alkoxy, alkoxyalkoxy, alkyl, aryl, aryloxy, cycloalkylalkoxy, haloalkoxy, heteroaryl, hydroxyalkoxy, $R_eR_fN$, -alkenyl-COOH and —C(O)NR$_e$,R$_f$; and
$R_1$ is selected from the group consisting of alkoxyalkyl, alkyl, alkylsulfonylalkyl, aryl, arylalkyl, arylsulfonylalkyl, cycloalkyl, cycloalkylalkyl, heterocyclealkyl, heteroarylalkyl and (R$_a$R$_b$N)alkyl-.

7. The compound of claim 6 selected from the group consisting of
4'-amino-2'ethoxy-N-[4-methylsulfonyl)benzyl]-2,3'-bipyridine-6'-carboxamide;
4-amino-5-[(1E)-but-1-en-3-ynyl]-6-ethoxy-N-[4-methylsulfonyl)benzyl]pyridine-2-carboxamide; and 4-amino-6-ethoxy-5-formyl-N-[4-(methylsulfonyl)benzyl]pyridine-2-carboxamide; or a pharmaceutically acceptable salt, or a combination thereof.

8. The compound of claim 1, or a pharmaceutically acceptable salt, or a combination thereof, wherein
$L_1$ is selected from the group consisting of —C(O)—NH— and —NH—C(O)—;
$R_2$ is hydrogen;
$R_4$ is cyano or halo;
$R_5$ is selected from the group consisting of alkenyl, alkoxy, alkoxyalkoxy, alkyl, aryl, aryloxy, cycloalkylalkoxy, haloalkoxy, heteroaryl, hydroxyalkoxy, $R_eR_fN$, -alkenyl-COOH and —C(O)NR$_e$,R$_f$; and
$R_1$ is selected from the group consisting of alkoxyalkyl, alkyl, alkylsulfonylalkyl, aryl, arylalkyl, arylsulfonylalkyl, cycloalkyl, cycloalkylalkyl, heterocycleallyl, heteroarylalkyl and (R$_a$R$_b$N)alkyl-.

9. The compound of claim 8 selected from the group consisting of
5-cyano-N-(2,5-dimethoxybenzyl)-6-isopropoxypyridine-2-carboxamide; and
5-chloro-6-ethoxy-N-[4-(methylsulfonyl)benzyl]pyridine-2-carboxamide; or a
pharmaceutically acceptable salt, or a combination thereof.

10. A compound of the formula (I), or a pharmaceutically acceptable salt, or a combination thereof, (I)

wherein
$L_1$ is selected from the group consisting of —C(O)—NH—, and —NH—C(O)—;
$R_1$ is selected from the group consisting of alkoxyalkyl, alkyl, alkylsulfinylalkyl, aryl, arylalkyl, arylsulfinylalkyl, cycloalkyl, cycloalkylalkyl, heteroarylalkyl, and heterocyclealkyl;
$R_1$ is selected from the group consisting of hydrogen, cyano, and heteroaryl;
$R_4$ is selected from the group consisting of cyano, halo, and heteroaryl;
$R_3$ is selected from the group consisting of azido, and $R_cR_dN$—;
$R_5$ is selected from the group consisting of alkenyl, alkoxy, alkoxyalkoxy, alkyl, aryl, aryloxy,cycloalkyloxy, haloalkoxy, heteroaryl, heterocycle, hydroxyalkoxy, and $R_eR_fN$—;
$R_c$ and $R_d$ are hydrogen; and
$R_e$ and $R_f$ are independently selected from the group consisting of hydrogen, alkylthioalkyl, and cycloalkyl.

11. A pharmaceutical composition comprising a therapeutically effective amount of a compound of formula (I) according to claim 1, or a pharmaceutically acceptable salt, or a combination thereof, in combination with a pharmaceutically suitable carrier.

12. A method of treating a disorder regulated by c-jun N-terminal kinase 1, (JNK1) in a mammal, which method comprises administering a therapeutically effective amount of a compound of formula (I) according to claim 1, or a pharmaceutically acceptable salt, or a combination thereof.

13. The method according to claim 12 wherein the disorder is selected from the group consisting of impaired glucose tolerance, insulin resistance, Type 2 diabetes, obesity, and diabetes mellitus.

14. The method according to claim 12 wherein the disorder is selected from the group consisting of hypercalcemia, osteoporosis, osteoarthritis, bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obstructive pulmonary disorder, contact dermatitis, Paget's disease, asthma, ischemic or reperfusion injury, allergic disease, atopic dermatitis, allergic rhinitis, Crohn's disease, and psoriasis.

15. The method according to claim 12 wherein the disorder is selected from the group consisting of Alzheimer's disease, Huntington's, Parkinson's, AIDS associated dementia, amyotrophic lateral sclerosis (AML), epilepsy, stroke, multiple sclerosis (MS), schizophrenia, cardiomycete hypertrophy, and baldness.

16. A method of treating a disorder regulated by c-jun N-terminal kinase 2 (JNK2) in a mammal, which method comprises administering a therapeutically effective amount of a compound of formula (I) according to claim 1, or a pharmaceutically acceptable salt, or a combination thereof.

17. The method according to claim 16 wherein the disorder is selected from the group consisting of impaired glucose tolerance, insulin resistance, Type 2 diabetes, obesity, and diabetes mellitus.

18. The method according to claim 16 wherein the disorder is selected from the group consisting of hypercalcemia, osteoporosis, osteoarthritis, bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obstructive pulmonary disorder, contact dermatitis, Paget's disease, asthma, ischemic or reperfusion injury, allergic disease, atopic dermatitis, allergic rhinitis, Crohn's disease, and psoriasis.

19. The method according to claim 16 wherein the disorder is selected from the group consisting of Alzheimer's disease, Huntington's, Parkinson's, AIDS associated dementia, amyotrophic lateral sclerosis (AML), epilepsy, stroke, multiple sclerosis (MS), schizophrenia, cardiomycete hypertrophy, and baldness.

20. A method of treating a disorder regulated by c-jun N-terminal kinase 3 (JNK3) in a mammal, which method comprises administering a therapeutically effective amount of a compound of formula (I) according to claim 1, or a pharmaceutically acceptable salt, or a combination thereof.

21. The method according to claim 19 wherein the disorder is selected from the group consisting of impaired glucose tolerance, insulin resistance, Type 2 diabetes, obesity, and diabetes mellitus.

22. The method according to claim 19 wherein the disorder is selected from the group consisting of hypercalcemia, osteoporosis, osteoarthritis, bone metastasis, rheumatoid arthritis, inflammatory bowel disease, multiple sclerosis, psoriasis, lupus, graft vs. host disease, T-cell mediated hypersensitivity disease, Hashimoto's thyroiditis, Guillain-Barre syndrome, chronic obstructive pulmonary disorder, contact dermatitis, Paget's disease, asthma, ischemic or reperfusion injury, allergic disease, atopic dermatitis, allergic rhinitis, Crohn's disease, and psoriasis.

23. The method according to claim 19 wherein the disorder is selected from the group consisting of Alzheimer's disease, Huntington's, Parkinson's, AIDS associated dementia, amyotrophic lateral sclerosis (AML), epilepsy, stroke, multiple sclerosis (MS), schizophrenia, cardiomycete hypertrophy, and baldness.

* * * * *